US008940741B2

(12) United States Patent
Berthel et al.

(10) Patent No.: US 8,940,741 B2
(45) Date of Patent: Jan. 27, 2015

(54) INHIBITORS OF BRUTON'S TYROSINE KINASE

(71) Applicant: Hoffmann-La Roche Inc., Nutley, NJ (US)

(72) Inventors: Steven Joseph Berthel, Mendham Township, NJ (US); Roland Joseph Billedeau, Santa Clara, CA (US); Christine E. Brotherton-Pleiss, Sunnyvale, CA (US); Fariborz Firooznia, Florham Park, NJ (US); Stephen Deems Gabriel, Morristown, NJ (US); Xiaochun Han, Cedar Grove, NJ (US); Ramona Hilgenkamp, Montclair, NJ (US); Saul Jaime-Figueroa, Morris Plains, NJ (US); Buelent Kocer, Shanghai (CN); Francisco Javier Lopez-Tapia, Honolulu, HI (US); Yan Lou, Pleasanton, CA (US); Lucja Orzechowski, Kinnelon, NJ (US); Timothy D. Owens, San Carlos, CA (US); Jenny Tan, New Providence, NJ (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/781,815

(22) Filed: Mar. 1, 2013

(65) Prior Publication Data

US 2013/0178461 A1    Jul. 11, 2013

Related U.S. Application Data

(62) Division of application No. 13/207,481, filed on Aug. 11, 2011, now Pat. No. 8,481,540.

(60) Provisional application No. 61/372,887, filed on Aug. 12, 2010, provisional application No. 61/497,093, filed on Jun. 15, 2011.

(51) Int. Cl.
*A01N 43/58* (2006.01)
*A61K 31/50* (2006.01)
*C07D 237/02* (2006.01)

(52) U.S. Cl.
USPC .......................... 514/247; 544/224

(58) Field of Classification Search
USPC .......................... 514/247; 544/224
See application file for complete search history.

(56) References Cited

U.S. PATENT DOCUMENTS

| 7,683,064 B2 | 3/2010 | Dewdney et al. |
|---|---|---|
| 2008/0153834 A1 | 6/2008 | Blomgren et al. |
| 2009/0306041 A1 | 12/2009 | Dewdney et al. |
| 2009/0318448 A1 | 12/2009 | Dewdney et al. |

FOREIGN PATENT DOCUMENTS

| WO | 2004/022562 | 3/2004 |
|---|---|---|
| WO | 2005/014599 | 2/2005 |
| WO | 2006/099075 | 9/2006 |
| WO | 2006/124731 | 11/2006 |
| WO | 2007/021795 | 2/2007 |
| WO | 2007/027594 | 3/2007 |
| WO | 2007/027729 | 3/2007 |
| WO | 2007027528 | 3/2007 |
| WO | 2007/136465 | 11/2007 |
| WO | 2008/033854 | 3/2008 |
| WO | 2008/033857 | 3/2008 |
| WO | 2008/033858 | 3/2008 |
| WO | 2009/053269 | 4/2009 |
| WO | 2009/077334 | 6/2009 |
| WO | 2009/098144 | 8/2009 |
| WO | 2009/156284 | 12/2009 |
| WO | 2010/000633 | 1/2010 |
| WO | 2010/100070 | 9/2010 |

OTHER PUBLICATIONS

Ellmeier et al., J. Exp. Med. 192:1611-1623 ( 2000).
Rosen et al., New Eng. J. Med.(333):431 ( 1995).
Patani, G et al., Chemical Reviews (XP000652176), 96(8):3147-3176 (Jan. 1, 1996).

(Continued)

*Primary Examiner* — Paul V. Ward

(57) ABSTRACT

This application discloses 6-(2-Hydroxymethyl-phenyl)-2-methyl-2H-pyridazin-3-one derivatives according to generic Formula I:

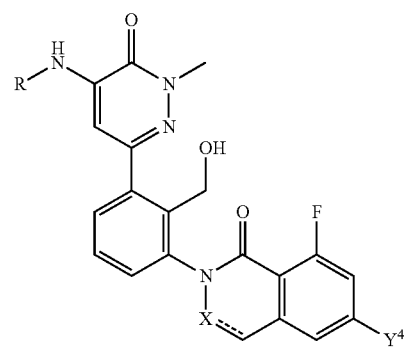

wherein, variables X, R, and $Y^4$, are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation, such as rheumatoid arthritis. Also disclosed are compositions containing compounds of Formula I and at least one carrier, diluent or excipient.

19 Claims, No Drawings

(56) References Cited

OTHER PUBLICATIONS

Rastetter et al., Annu. Rev. Med. 55:477-503 ( 2004).
Vassilev et al., J. Biol. Chem. 274:1646-1656 ( 1998).
Feldhahn et al., J. Exp. Med. 201:1837-1852 ( 2005).
Pan et al., Chem. Med. Chem. 2:58-61 ( 2007).
Islam et al., Immunol. Rev. 178:49-63 ( 2000).
Khan et al., Immunity 3:283-299 ( 1995).
Jansson et al., Clin. Exp. Immunol. 94:459-465 ( 1993).
Iwaki et al., J. Biol. Chem. 280:40261-40270 ( 2005).
Hunter, T., Cell 50:823-829 ( 1987).
(International Search Report for PCT/EP2011/063657 Oct. 28, 2011).
Horwood et al., J. Exp. Med. 197:1603-1611 ( 2003).
Lindvall et al., Immunol. Rev. 203:200-215 ( 2005).
The English translation of the Korean Office Action, issued on Aug. 26, 2014, in the corresponding Korean application No. 2013-7006162.

INHIBITORS OF BRUTON'S TYROSINE KINASE

CROSS-REFERENCE TO RELATED APPLICATIONS

This application is a divisional application of U.S. Ser. No. 13/207,481, filed Aug. 11, 2011. This application is entitled to the benefit of U.S. provisional patent application Ser. No. 61/372,887 filed on Aug. 12, 2010 and U.S. provisional patent application Ser. No. 61/497,093, filed on Jun. 15, 2011, the disclosures of which are incorporated herein by reference.

FIELD OF THE INVENTION

The present invention relates to the use of novel derivatives which inhibit Btk and are useful for the treatment of autoimmune and inflammatory diseases caused by aberrant B-cell activation. The novel 6-(2-Hydroxymethyl-phenyl)-2-methyl-2H-pyridazin-3-one derivatives described herein are useful for the treatment of arthritis.

Protein kinases constitute one of the largest families of human enzymes and regulate many different signaling processes by adding phosphate groups to proteins (T. Hunter, *Cell* 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. J Exp Med 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837,).

SUMMARY OF THE INVENTION

The present application provides the Btk inhibitor compounds of Formula I, methods of use thereof, as described herein below:

The application provides a compound of Formula I,

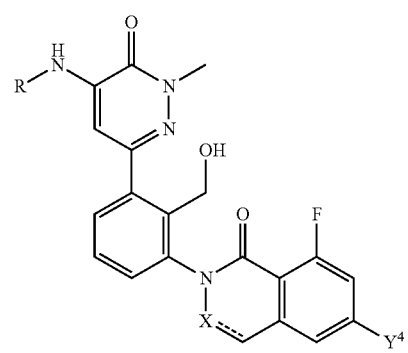

I wherein:
⁚⁚ is either a single or double bond;
X is either CH, or $CH_2$, or N;
R is H, $-R^1$, $-R^1-R^2-R^3$, $-R^1-R^3$, or $-R^2-R^3$;
$R^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
$R^2$ is $-C(=O)$, $-C(=O)O$, $-C(=O)NR^{2'}$, $-NHC(=O)$ $O$, $-C(R^{2'})_2$, $-O$, $-S$, $-C(=NH)NR^{2'}$, or $-S(=O)_2$;
  each $R^{2'}$ is independently H or lower alkyl;
$R^3$ is H or $R^4$;

$R^4$ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano, and lower alkoxy;

$Y^{4c}$ is lower cycloalkyl, optionally substituted with one or more substituents selected from the group consisting of lower alkyl, lower haloalkyl, halogen, hydroxy, amino, cyano, and lower alkoxy; and $Y^{4d}$ is amino, optionally substituted with one or more lower alkyl, alkoxy lower alkyl, or hydroxy lower alkyl;

or a pharmaceutically acceptable salt thereof.

The application provides a method for treating an inflammatory and/or autoimmune condition comprising administering to a patient in need thereof a therapeutically effective amount of the Btk inhibitor compound of Formula I.

The application provides a pharmaceutical composition comprising the Btk inhibitor compound of any one of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

$MeC(\!=\!O)OR^4$ wherein

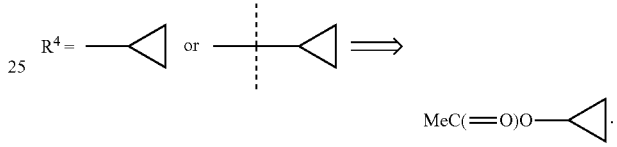

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "aryl" denotes a monovalent aromatic carbocyclic mono- or bicyclic ring system comprising 6 to 10 carbon ring atoms. Examples of aryl moieties include phenyl and naphthyl.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" or "lower cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Heteroaryl may be optionally substituted as defined directly below. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

The present application discloses 6-(2-Hydroxymethyl-phenyl)-2-methyl-2H-pyridazin-3-one derivatives according to generic Formula I, wherein the variables are defined as described herein:

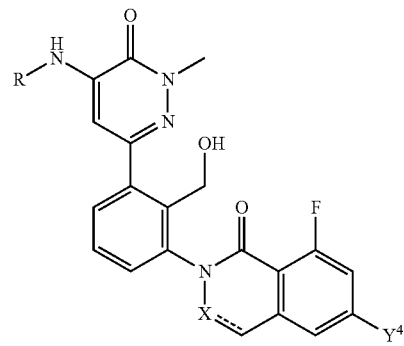

I

The phrase "as defined herein" refers to the broadest definition for each group as provided in the Summary of the Invention, the Detailed Description, or the broadest claim. In all other aspects, variations and embodiments provided, substituents which can be present in each embodiment and which are not explicitly defined retain the broadest definition provided in the Summary of the Invention, the Detailed Description, or the broadest claim.

The compounds of generic Formula I inhibit Bruton's tyrosine kinase (Btk). Activation of Btk by upstream kinases results in activation of phospholipase-Cγ which, in turn, stimulates release of pro-inflammatory mediators. The compounds of generic Formula I, incorporating side chains of the

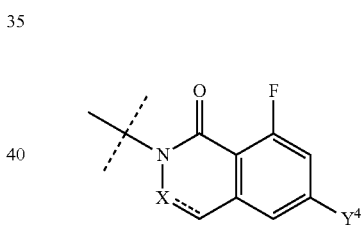

ring systems, exhibit unexpectedly enhanced inhibitory activity compared to analogues with other side chains. Notably, fluorine substitution on the unsaturated side chains produces an unexpected approximately 5-10-fold increase in potency in human whole blood. Furthermore, the fluorinated sidechain provides the increase in potency while, in conjunction with the pyridazinone core of the molecules, the molecules generally have unexpectedly improved safety profiles compared to those with pyridinone cores. Specifically, the pyridazinone core molecules do not undergo unacceptable levels of covalent binding due to reactive metabolites during metabolism. Compounds of Formula I are useful in the treatment of arthritis and other anti-inflammatory and auto-immune diseases. Compounds according to Formula I are, accordingly, useful for the treatment of arthritis. Compounds of Formula I are useful for inhibiting Btk in cells and for modulating B-cell development. The present invention further comprises pharmaceutical compositions containing compounds of Formula I admixed with pharmaceutically acceptable carrier, excipients or diluents.

The application provides a compound of Formula I,

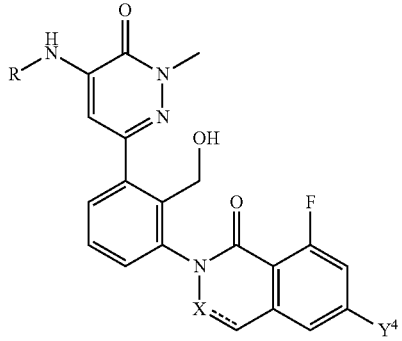

wherein:
⚌ is either a single or double bond;
X is either CH, CH$_2$, or N;
R is H, —R$^1$, —R$^1$—R$^2$—R$^3$, —R$^1$—R$^3$, or —R$^2$—R$^3$;
R$^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
R$^2$ is —C(═O), —C(═O)O, —C(═O)NR$^{2'}$, —NHC(═O)O, —C(R$^{2'}$)$_2$, —O, —S, —C(═NH)NR$^{2'}$, or —S(═O)$_2$;
each R$^{2'}$ is independently H or lower alkyl;
R$^3$ is H or R$^4$;
R$^4$ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;
Y$^4$ is Y$^{4a}$, Y$^{4b}$, Y$^{4c}$, or Y$^{4d}$;
Y$^{4a}$ is H or halogen;
Y$^{4b}$ is lower alkyl, optionally substituted with one or more substituents selected from the group consisting of lower haloalkyl, halogen, hydroxy, amino, cyano, and lower alkoxy;
Y$^{4c}$ is lower cycloalkyl, optionally substituted with one or more substituents selected from the group consisting of lower alkyl, lower haloalkyl, halogen, hydroxy, amino, cyano, and lower alkoxy; and
Y$^{4d}$ is amino, optionally substituted with one or more lower alkyl, alkoxy lower alkyl, or hydroxy lower alkyl;
or a pharmaceutically acceptable salt thereof.

Further it is to be understood that every embodiment relating to a specific residue R, X and Y$^4$ as disclosed herein may be combined with any other embodiment relating to another residue R, X and Y$^4$ as disclosed herein.

The application provides a compound of Formula I, wherein
⚌ is a double bond; and
X is N.

The application provides a compound of Formula I, wherein
⚌ is a single bond; and
X is CH$_2$.

The application provides a compound of Formula I, wherein
⚌ is a double bond;
X is N;
R is —R$^1$—R$^2$—R$^3$;
R$^1$ is pyridyl;
R$^2$ is —S(═O)$_2$,
R$^3$ is R$^4$; and
R$^4$ is lower alkyl.

The application provides a compound of Formula I, wherein
⚌ is a double bond;
X is N;
R is —R$^1$—R$^2$—R$^3$;
R$^1$ is pyridyl;
R$^2$ is —C(CH$_3$)$_2$;
R$^3$ is R$^4$; and
R$^4$ is lower alkyl amino, lower dialkyl amino, or heterocycloalkyl optionally substituted with one or more lower alkyl.

The application provides a compound of Formula I, wherein
⚌ is a double bond;
X is N;
R is —R$^1$—R$^2$—R$^3$;
R$^1$ is phenyl or pyridyl;
R$^2$ is —C(═O);
R$^3$ is R$^4$; and
R$^4$ is morpholine or piperazine, optionally substituted with one or more lower alkyl.

The application provides a compound of Formula I, wherein
⚌ is a double bond;
X is N; and
Y$^4$ is tert-butyl.

The application provides a compound of Formula I, wherein
⚌ is a double bond;
X is CH; and
Y$^4$ is

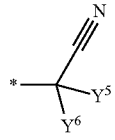

wherein, Y$^5$ and Y$^6$ are independently H, lower alkyl, or lower haloalkyl.

The application provides a compound of Formula I, wherein
⚌ is a double bond;
X is N; and
Y$^4$ is

wherein, Y$^5$ is H, halogen, lower alkyl or lower haloalkyl.

The application provides a compound of Formula I, wherein
═ is a double bond;
X is N; and
Y⁴ is

wherein, Y⁵ and Y⁶ are independently H or lower alkyl.

The application provides a compound of Formula I, wherein
═ is a double bond;
X is N;
Y⁴ is tert-butyl;
R is —R¹—R³;
R¹ is pyridyl or pyrazolopyrazine;
R³ is R⁴; and
R⁴ is optionally substituted lower alkyl, heterocycloalkyl, or alkyl heterocycloalkyl.

The application provides a compound of Formula I, wherein
═ is a double bond;
X is N;
Y⁴ is tert-butyl;
R is —R¹—R²—R³;
R¹ is pyridyl;
R² is —C(CH₃)₂;
R³ is R⁴; and
R⁴ is lower alkyl amino, lower dialkyl amino, or heterocycloalkyl optionally substituted with one or more lower alkyl.

The application provides a compound of Formula I, wherein
═ is a double bond;
X is N;
Y⁴ is tert-butyl;
R is —R¹—R²—R³;
R¹ is pyridyl;
R² is —C(═O);
R³ is R⁴; and
R⁴ is optionally substituted heterocycloalkyl or bicyclic spiroheterocycloalkyl.

The application provides a compound of Formula I, wherein
═ is a double bond;
X is N;
Y⁴ is tert-butyl;
R is —R¹—R²—R³;
R¹ is pyridyl;
R² is —C(═O);
R³ is R⁴; and
R⁴ is optionally substituted morpholine or piperazine.

The application provides a compound of Formula I selected from the group consisting of:

6-tert-Butyl-2-(3-{5-[5-(1-ethylamino-1-methyl-ethyl)-pyridin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one;

6-tert-Butyl-8-fluoro-2-{3-hydroxymethyl-3-[5-(5-methanesulfonyl-pyridin-2-ylamino)-1-methyl-6-oxo-1,6-dihydro-pyridazin-3-yl]-phenyl}-2H-phthalazin-1-one;

6-tert-Butyl-8-fluoro-2-(2-hydroxymethyl-3-{5-[5-(3-methoxy-azetidin-1-ylmethyl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(8-methyl-3,8-diaza-bicyclo[3.2.1]oct-3-ylmethyl)-pyridin-2-ylamino]-6-oxo-1,6-dihydro-pyridazin-3-yl}-phenyl)-2H-phthalazin-1-one;

6-tert-Butyl-2-(3-{5-[5-(2-dimethylamino-1,1-dimethyl-ethoxy)-pyridin-2-ylamino]-1-methyl-6-oxo-1,6-dihydro-pyridazin-3-yl}-2-hydroxymethyl-phenyl)-8-fluoro-2H-phthalazin-1-one;

2-{3-[5-(5-Azetidin-1-ylmethyl-pyridin-2-ylamino)-1-methyl-6-oxo-1,6-dihydro-pyridazin-3-yl]-2-hydroxymethyl-phenyl}-6-tert-butyl-8-fluoro-2H-phthalazin-1-one;

6-tert-Butyl-2-{3-[5-(5-dimethylaminomethyl-pyridin-2-ylamino)-1-methyl-1-6-oxo-1,6-dihydro-pyridazin-3-yl]-2-hydroxymethyl-phenyl}-8-fluoro-2H-phthalazin-1-one;

6-tert-Butyl-2-(3-{5-[(1R,5S)-5-(3,8-diaza-bicyclo[3.2.1]oct-8-yl)-pyridin-2-ylamino]-1-methyl-6-oxo-1,6-dihydro-pyridazin-3-yl}-2-hydroxymethyl-phenyl)-8-fluoro-2H-phthalazin-1-one;

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide;

6-tert-Butyl-8-fluoro-2-{2-hydroxymethyl-3-[1-methyl-6-oxo-5-(5-trifluoromethyl-pyrazin-2-ylamino)-1,6-dihydro-pyridazin-3-yl]-phenyl}-2H-phthalazin-1-one;

6-tert-Butyl-8-fluoro-2-(3-{5-[5-(2-hydroxy-1,1-dimethyl-ethoxy)-pyridin-2-ylamino]-1-methyl-6-oxo-1,6-dihydro-pyridazin-3-yl}-2-hydroxymethyl-phenyl)-2H-phthalazin-1-one;

2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one;

6-tert-Butyl-8-fluoro-2-(2-hydroxymethyl-3-{5-[5-(2-hydroxy-2-methyl-propoxy)-pyridin-2-ylamino]-1-methyl-6-oxo-1,6-dihydro-pyridazin-3-yl}-phenyl)-2H-phthalazin-1-one;

2-[8-Fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile;

6-tert-Butyl-8-fluoro-2-(3-{5-[5-((S)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one;

6-tert-Butyl-8-fluoro-2-(3-{5-[5-((R)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one;

6-tert-Butyl-8-fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-((R)-1-methyl-pyrrolidin-2-yl)-pyridin-2-ylamino]-6-oxo-1,6-dihydro-pyridazin-3-yl}-phenyl)-2H-phthalazin-1-one;

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide;

6-tert-Butyl-8-fluoro-2-(2-hydroxymethyl-3-{5-[5-(4-hydroxy-4-methyl-piperidine-1-carbonyl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(6-methyl-2,6-diaza-spiro[3.3]hept-2-yl)-pyridin-2-ylamino]-6-oxo-1,6-dihydro-pyridazin-3-yl}-phenyl)-2H-phthalazin-1-one;

6-tert-Butyl-2-{3-[5-(5-ethanesulfonyl-pyridin-2-ylamino)-1-methyl-6-oxo-1,6-dihydro-pyridazin-3-yl]-2-hydroxymethyl-phenyl}-8-fluoro-2H-phthalazin-1-one;

6-tert-Butyl-8-fluoro-2-(2-hydroxymethyl-3-{1-methyl-6-oxo-5-[5-(propane-2-sulfonyl)-pyridin-2-ylamino]-1,6-dihydro-pyridazin-3-yl}-phenyl)-2H-phthalazin-1-one;

6-tert-Butyl-8-fluoro-2-(3-{5-[5-(2-hydroxy-ethylsulfanyl)-pyridin-2-ylamino]-1-methyl-6-oxo-1,6-dihydro-pyridazin-3-yl}-2-hydroxymethyl-phenyl)-2H-phthalazin-1-one;

6-tert-Butyl-8-fluoro-2-(3-{5-[5-(2-hydroxy-ethanesulfonyl)-pyridin-2-ylamino]-1-methyl-6-oxo-1,6-dihydro-pyridazin-3-yl}-2-hydroxymethyl-phenyl)-2H-phthalazin-1-one;

6-tert-Butyl-8-fluoro-2-(2-hydroxymethyl-3-{5-[5-(4-isopropyl-piperazin-1-yl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one;

6-tert-Butyl-8-fluoro-2-{2-hydroxymethyl-3-[5-(1'-isopropyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one;

6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-8-fluoro-2H-phthalazin-1-one;

6-tert-Butyl-2-{3-[5-(1,5-dimethyl-1H-pyrazol-3-ylamino)-1-methyl-6-oxo-1,6-dihydro-pyridazin-3-yl]-2-hydroxymethyl-phenyl}-8-fluoro-2H-phthalazin-1-one;

6-tert-Butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one;

6-tert-Butyl-8-fluoro-2-{2-hydroxymethyl-3-[1-methyl-5-(4-methyl-3,4,5,6-tetrahydro-2H-[1,2']bipyrazinyl-5'-ylamino)-6-oxo-1,6-dihydro-pyridazin-3-yl]-phenyl}-2H-phthalazin-1-one;

6-tert-Butyl-2-{3-[5-(5-cyclobutylaminomethyl-pyrazin-2-ylamino)-1-methyl-6-oxo-1,6-dihydro-pyridazin-3-yl]-2-hydroxymethyl-phenyl}-8-fluoro-2H-phthalazin-1-one;

6-tert-Butyl-2-(3-{5-[5-(2-dimethylamino-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{1-methyl-5-[5-(4-methyl-piperazin-1-ylmethyl)-pyrazin-2-ylamino]-6-oxo-1,6-dihydro-pyridazin-3-yl}-phenyl)-2H-phthalazin-1-one;

6-tert-Butyl-2-(3-{5-[5-(2-dimethylamino-1,1-dimethyl-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-2-(3-{5-[6-(2-dimethylamino-1,1-dimethyl-ethoxy)-pyridazin-3-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{1-methyl-5-[6-(1-methyl-piperidin-4-yl)-pyridazin-3-ylamino]-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(4-methyl-piperazin-1-ylmethyl)-pyridin-2-ylamino]-6-oxo-1,6-dihydro-pyridazin-3-yl}-phenyl)-2H-phthalazin-1-one;

6-tert-Butyl-8-fluoro-2-[2-hydroxymethyl-3-(5-{5-[(2-methoxy-ethylamino)-methyl]-pyridin-2-ylamino}-1-methyl-6-oxo-1,6-dihydro-pyridazin-3-yl)-phenyl]-2H-phthalazin-1-one;

6-tert-Butyl-8-fluoro-2-(2-hydroxymethyl-3-{1-methyl-5-[5-((1S,4S)-5-methyl-2,5-diaza-bicyclo[2.2.1]hept-2-ylmethyl)-pyridin-2-ylamino]-6-oxo-1,6-dihydro-pyridazin-3-yl}-phenyl)-2H-phthalazin-1-one;

6-tert-Butyl-8-fluoro-2-{2-hydroxymethyl-3-[5-(5-{[(2-methoxy-ethyl)-methyl-amino]-methyl}-pyridin-2-ylamino)-1-methyl-6-oxo-1,6-dihydro-pyridazin-3-yl]-phenyl}-2H-phthalazin-1-one;

6-tert-Butyl-8-fluoro-2-(2-hydroxymethyl-3-{1-methyl-5-[6-(4-methyl-piperazin-1-yl)-pyridazin-3-ylamino]-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[6-((1S,4S)-5-methyl-2,5-diaza-bicyclo[2.2.1]hept-2-yl)-pyridazin-3-ylamino]-6-oxo-1,6-dihydro-pyridazin-3-yl}-phenyl)-2H-phthalazin-1-one;

2-(3-{5-[5-(Azetidine-1-carbonyl)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one;

6-tert-Butyl-2-(3-{5-[5-(1,1-dioxo-1λ6-thiomorpholine-4-carbonyl)-pyridin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(6-methyl-2,6-diaza-spiro[3.3]heptane-2-carbonyl)-pyridin-2-ylamino]-6-oxo-1,6-dihydro-pyridazin-3-yl}-phenyl)-2H-phthalazin-1-one;

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-dimethylamino-ethyl)-nicotinamide;

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-hydroxy-ethyl)-N-methyl-nicotinamide;

1-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridine-3-carbonyl)-azetidine-3-carbonitrile;

6-tert-Butyl-8-fluoro-2-(2-hydroxymethyl-3-{5-[5-(3-hydroxy-pyrrolidine-1-carbonyl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{5-[5-(4-hydroxy-piperidine-1-carbonyl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(4-methyl-piperazin-1-yl)-pyridin-2-ylamino]-6-oxo-1,6-dihydro-pyridazin-3-yl}-phenyl)-2H-phthalazin-1-one;

6-tert-Butyl-2-(3-{5-[5-((S)-1,2-dihydroxy-ethyl)-pyrazin-2-ylamino]-1-methyl-6-oxo-1,6-dihydro-pyridazin-3-yl}-2-hydroxymethyl-phenyl)-8-fluoro-2H-phthalazin-1-one;

2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-8-fluoro-2H-phthalazin-1-one;

6-tert-Butyl-8-fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one;

6-tert-Butyl-8-fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-2H-phthalazin-1-one;

6-tert-Butyl-8-fluoro-2-{3-[5-(1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one;

6-tert-Butyl-8-fluoro-2-{2-hydroxymethyl-3-[5-(1'-methanesulfonyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one;

2-{3-[5-(1'-Acetyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-6-tert-butyl-8-fluoro-2H-phthalazin-1-one;

6-tert-Butyl-8-fluoro-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridazin-3-yl]-phenyl}-2H-phthalazin-1-one;

6-tert-Butyl-8-fluoro-2-{2-hydroxymethyl-3-[5-(4-hydroxy-3,4,5,6-tetrahydro-2H-[1,3']bipyridinyl-6'-ylamino)-1-methyl-6-oxo-1,6-dihydro-pyridazin-3-yl]-phenyl}-2H-phthalazin-1-one;

6-tert-Butyl-8-fluoro-2-(2-hydroxymethyl-3-{1-methyl-5-[5-((1R,5S)-3-methyl-3,8-diaza-bicyclo[3.2.1]oct-8-yl)-pyridin-2-ylamino]-6-oxo-1,6-dihydro-pyridazin-3-yl}-phenyl)-2H-phthalazin-1-one;

6-tert-Butyl-8-fluoro-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one;

6-tert-Butyl-2-(3-{5-[1-((R)-2,3-dihydroxy-propyl)-1H-pyrazol-3-ylamino]-1-methyl-6-oxo-1,6-dihydro-pyridazin-3-yl}-2-hydroxymethyl-phenyl)-8-fluoro-2H-phthalazin-1-one;

6-tert-Butyl-2-(3-{5-[5-(4-ethyl-piperazin-1-yl)-pyridin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{5-[1-(2-hydroxy-2-methyl-propyl)-1H-pyrazol-3-ylamino]-1-methyl-6-oxo-1,6-dihydro-pyridazin-3-yl}-phenyl)-2H-phthalazin-1-one;

2-(8-Fluoro-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-isoquinolin-6-yl)-2-methyl-propionitrile;

2-(2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile;

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2-dihydro-isoquinolin-6-yl]-2-methyl-propionitrile;

2-(8-Fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile;

6-(6-{3-[6-(Cyano-dimethyl-methyl)-8-fluoro-1-oxo-1H-isoquinolin-2-yl]-2-hydroxymethyl-phenyl}-2-methyl-3-oxo-2,3-dihydro-pyridazin-4-ylamino)-N,N-dimethyl-nicotinamide;

2-[8-Fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile;

2-[8-Fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile;

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile;

2-(8-Fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile;

6-tert-Butyl-8-fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one;

2-(8-Fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-isoquinolin-6-yl)-2-methyl-propionitrile;

6-tert-Butyl-2-{3-[5-(5-ethyl-4,5,6,7-tetrahydro-pyrazolo[1,5-a]pyrazin-2-ylamino)-1-methyl-6-oxo-1,6-dihydro-pyridazin-3-yl]-2-hydroxymethyl-phenyl}-8-fluoro-2H-phthalazin-1-one;

2-(2-{3-[5-(5-Ethyl-4,5,6,7-tetrahydro-pyrazolo[1,5-a]pyrazin-2-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile;

6-tert-Butyl-2-[3-(5-{5-[((1S,4S)-1-(2,5-diaza-bicyclo[2.2.1]hept-2-yl)methyl]-pyridin-2-ylamino}-1-methyl-6-oxo-1,6-dihydro-pyridazin-3-yl)-2-hydroxymethyl-phenyl]-8-fluoro-2H-phthalazin-1-one;

6-tert-Butyl-8-fluoro-2-(2-hydroxymethyl-3-{5-[5-(4-hydroxy-4-methyl-piperidin-1-ylmethyl)-pyridin-2-ylamino]-1-methyl-6-oxo-1,6-dihydro-pyridazin-3-yl}-phenyl)-2H-phthalazin-1-one;

4-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridin-3-yl)-piperazine-1-carboxylic acid ethyl ester;

8-Fluoro-6-(2-fluoro-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one;

6-tert-Butyl-8-fluoro-2-(2-hydroxymethyl-3-{1-methyl-5-[5-((4S,4S)-5-methyl-2,5-diaza-bicyclo[2.2.1]hept-2-yl)-pyrazin-2-ylamino]-6-oxo-1,6-dihydro-pyridazin-3-yl}-phenyl)-2H-phthalazin-1-one;

2-[8-Fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile; and 6-tert-Butyl-8-fluoro-2-(2-hydroxymethyl-3-{1-methyl-6-oxo-5-[1'-(2,2,2-trifluoro-ethyl)-1',2',3',4',5',6'-hexahydro-[3,4']bipyridinyl-6-ylamino]-1,6-dihydro-pyridazin-3-yl}-phenyl)-2H-phthalazin-1-one.

The application provides a method for treating an inflammatory and/or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides the use of a compound as described above for the treatment of inflammatory and/or autoimmune condition.

The application provides the use of a compound as described above for the treatment of rheumatoid arthritis.

The application provides the use of a compound as described above for the treatment of asthma.

The application provides a compound as described above for use in the treatment of inflammatory and/or autoimmune condition.

The application provides a compound as described above for use in the treatment of rheumatoid arthritis.

The application provides a compound as described above for use in the treatment of asthma.

The application provides a compound, method, or composition as described herein.

The application provides a compound of Formula I', wherein:
R is H, $-R^1$, $-R^1-R^2-R^3$, $-R^1-R^3$, or $-R^2-R^3$;
$R^1$ is aryl, heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
$R^2$ is $-C(=O)$, $-C(=O)O$, $-C(=O)NR^{2'}$, $-NHC(=O)O$, $-C(R^{2'})_2$, $-O$, $-C(=NH)NR^{2'}$, or $-S(=O)_2$;
each $R^{2'}$ is independently H or lower alkyl;
$R^3$ is H or $R^4$;
$R^4$ is lower alkyl, lower haloalkyl, lower alkoxy, amino, lower alkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, or spiroheterocycloalkyl, each of which is optionally substituted with one or more lower alkyl, halo, lower alkyl amino, lower dialkyl amino, hydroxy, hydroxy lower alkyl, lower alkoxy, halo, nitro, amino, amido, acyl, cyano, oxo, guanidino, hydroxyl amino, carboxy, carbamoyl, carbamate, halo lower alkoxy, or halo lower alkyl, wherein two lower alkyl groups may together form a ring;
$Y^4$ is $Y^{4a}$, $Y^{4b}$, $Y^{4c}$, or $Y^{4d}$;
$Y^{4a}$ is H or halogen;
$Y^{4b}$ is lower alkyl, optionally substituted with one or more substituents selected from the group consisting of lower haloalkyl, halogen, hydroxy, amino, cyano, and lower alkoxy;
$Y^{4c}$ is lower cycloalkyl, optionally substituted with one or more substituents selected from the group consisting of lower alkyl, lower haloalkyl, halogen, hydroxy, amino, cyano, and lower alkoxy; and
$Y^{4d}$ is amino, optionally substituted with one or more lower alkyl, alkoxy lower alkyl, or hydroxy lower alkyl;
or a pharmaceutically acceptable salt thereof.

In one variation of Formula I', $Y^4$ is tert-butyl, dimethyl amino, cyclopropyl, or iso-propyl.
In one variation of Formula I', $Y^4$ is tert-butyl.
In one variation of Formula I', $Y^4$ is dimethyl amino.
In one variation of Formula I', $Y^4$ is cyclopropyl.
In one variation of Formula I', $Y^4$ is iso-propyl.
In one variation of Formula I', R is $-R^1-R^3$;
$R^1$ is pyridyl;
$R^3$ is $R^4$; and
$R^4$ is heterocycloalkyl, optionally substituted with lower alkyl.
In one variation of Formula I', R is $-R^1-R^2-R^3$;
$R^1$ is pyridyl;
$R^2$ is $-C(CH_3)_2$;
$R^3$ is $R^4$; and
$R^4$ is lower alkyl amino, lower dialkyl amino, or heterocycloalkyl optionally substituted with one or more lower alkyl.
In one variation of Formula I',
R is $-R^1-R^2-R^3$;
$R^1$ is phenyl or pyridyl;
$R^2$ is $-C(=O)$;
$R^3$ is $R^4$; and
$R^4$ is morpholine or piperazine, optionally substituted with one or more lower alkyl.
In one variation of Formula I', $R^1$ is pyridyl;
$R^3$ is $R^4$; and
$R^4$ is $-S(=O)_2R^{4'}$, wherein $R^{4'}$ is lower alkyl.
In one variation of Formula I', $Y^4$ is wherein, $Y^5$ is H, halogen, lower alkyl or lower haloalkyl.

In one variation of Formula I', Y⁴ is

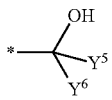

wherein, Y⁵ and Y⁶ are independently H, lower alkyl, or lower haloalkyl.

In one variation of Formula I', Y⁴ is

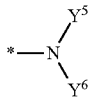

wherein, Y⁵ and Y⁶ are independently H or lower alkyl.

In one variation of Formula I', Y⁴ is

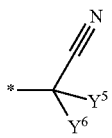

wherein, Y⁵ and Y⁶ are independently H, lower alkyl, or lower haloalkyl.

In one variation of Formula I', Y⁴ is tert-butyl;
R is —R¹—R³;
R¹ is pyridyl;
R³ is R⁴; and
R⁴ is —S(=O)₂R⁴', wherein R⁴' is lower alkyl.

In one variation of Formula I', Y⁴ is tert-butyl;
R is —R¹—R²—R³;
R¹ is pyridyl;
R² is —C(CH₃)₂;
R³ is R⁴; and
R⁴ is lower alkyl amino, lower dialkyl amino, or heterocycloalkyl optionally substituted with one or more lower alkyl.

In one variation of Formula I', Y⁴ is tert-butyl;
R is —R¹—R²—R³;
R¹ is pyridyl;
R² is —C(=O);
R³ is R⁴; and
R⁴ is morpholine or piperazine, optionally substituted with one or more lower alkyl.

In one variation of Formula I', Y⁴ is tert-butyl;
R is —R¹—R³;
R¹ is pyridyl;
R³ is R⁴; and
R⁴ is heterocycloalkyl, optionally substituted with lower alkyl.

The application provides the compounds of Formula I' selected from the group consisting of:

6-tert-Butyl-2-(3-{5-[5-(1-ethylamino-1-methyl-ethyl)-pyridin-2-ylamino]-1-methyl-6-oxo-1,6-dihydro-pyridazin-3-yl}-2-hydroxymethyl-phenyl)-8-fluoro-2H-phthalazin-1-one;

6-tert-Butyl-8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one;

6-tert-Butyl-8-fluoro-2-{2-hydroxymethyl-3-[5-(5-methanesulfonyl-pyridin-2-ylamino)-1-methyl-6-oxo-1,6-dihydro-pyridazin-3-yl]-phenyl}-2H-phthalazin-1-one;

6-tert-Butyl-8-fluoro-2-(2-hydroxymethyl-3-{5-[5-(3-methoxy-azetidin-1-ylmethyl)-pyridin-2-ylamino]-1-methyl-6-oxo-1,6-dihydro-pyridazin-3-yl}-phenyl)-2H-phthalazin-1-one;

6-tert-Butyl-8-fluoro-2-(2-hydroxymethyl-3-{1-methyl-5-[5-(8-methyl-3,8-diaza-bicyclo[3.2.1]oct-3-ylmethyl)-pyridin-2-ylamino]-6-oxo-1,6-dihydro-pyridazin-3-yl}-phenyl)-2H-phthalazin-1-one;

6-tert-Butyl-2-(3-{5-[5-(2-dimethylamino-1,1-dimethyl-ethoxy)-pyridin-2-ylamino]-1-methyl-6-oxo-1,6-dihydro-pyridazin-3-yl}-2-hydroxymethyl-phenyl)-8-fluoro-2H-phthalazin-1-one;

2-{3-[5-(5-Azetidin-1-ylmethyl-pyridin-2-ylamino)-1-methyl-6-oxo-1,6-dihydro-pyridazin-3-yl]-2-hydroxymethyl-phenyl}-6-tert-butyl-8-fluoro-2H-phthalazin-1-one;

6-tert-Butyl-2-{3-[5-(5-dimethylaminomethyl-pyridin-2-ylamino)-1-methyl-1-6-oxo-1,6-dihydro-pyridazin-3-yl]-2-hydroxymethyl-phenyl}-8-fluoro-2H-phthalazin-1-one;

6-tert-Butyl-2-(3-{5-[(1R,5S)-5-(3,8-diaza-bicyclo[3.2.1]oct-8-yl)-pyridin-2-ylamino]-1-methyl-6-oxo-1,6-dihydro-pyridazin-3-yl}-2-hydroxymethyl-phenyl)-8-fluoro-2H-phthalazin-1-one;

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide; and 6-tert-Butyl-8-fluoro-2-{2-hydroxymethyl-3-[1-methyl-6-oxo-5-(5-trifluoromethyl-pyrazin-2-ylamino)-1,6-dihydro-pyridazin-3-yl]-phenyl}-2H-phthalazin-1-one.

The application provides a method for treating an inflammatory and/or autoimmune condition comprising administering to a patient in need thereof a therapeutically effective amount of the Btk inhibitor compound of Formula I'.

The application provides a method for treating arthritis comprising administering to a patient in need thereof a therapeutically effective amount of the Btk inhibitor compound of Formula I'.

The application provides a method for treating asthma comprising administering to a patient in need thereof a therapeutically effective amount of the Btk inhibitor compound of Formula I'.

The application provides a method of inhibiting B-cell proliferation comprising administering to a patient in need thereof a therapeutically effective amount of the Btk inhibitor compound of Formula I'.

The application provides a method for inhibiting Btk activity comprising administering the Btk inhibitor compound of any one of Formula I', wherein the Btk inhibitor compound exhibits an IC₅₀ of 50 micromolar or less in an in vitro biochemical assay of Btk activity.

In one variation of the above method, the Btk inhibitor compound exhibits an IC₅₀ of 100 nanomolar or less in an in vitro biochemical assay of Btk activity.

In another variation of the above method, the compound exhibits an IC₅₀ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of Formula I'.

The application provides a method for treating arthritis comprising co-administering to a patient in need thereof a therapeutically effective amount of an anti-inflammatory compound in combination with the Btk inhibitor compound of Formula I'.

The application provides a method for treating a lymphoma or a BCR-ABL1⁺ leukemia cells by administering to a patient in need thereof a therapeutically effective amount of the Btk inhibitor compound of Formula I'.

The application provides a pharmaceutical composition comprising the Btk inhibitor compound of Formula I', admixed with at least one pharmaceutically acceptable carrier, excipient or diluent.

The application provides a use of the compound of formula I' in the manufacture of a medicament for the treatment of an inflammatory disorder.

The application provides a use of the compound of formula I' in the manufacture of a medicament for the treatment of an autoimmune disorder.

The application provides a compound, method, or composition as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to generic Formula I:

TABLE I

| Compound | Nomenclature | Structure |
|----------|--------------|-----------|
| I-1 | 6-tert-Butyl-2-(3-{5-[5-(1-ethylamino-1-methyl-ethyl)-pyridin-2-ylamino]-1-methyl-6-oxo-1,6-dihydro-pyridazin-3-yl}-2-hydroxymethyl-phenyl)-8-fluoro-2H-phthalazin-1-one | 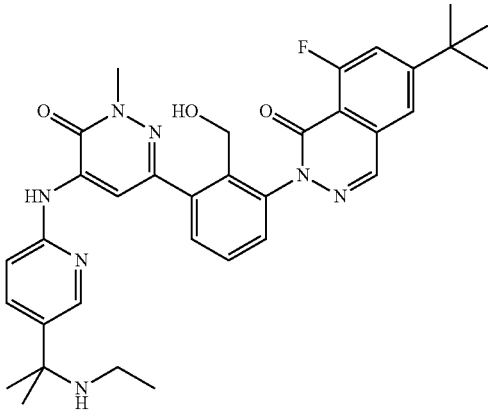 [SMILES: CCNC(C)(C)c1ccc(Nc2cc(-c3cccc(-n4ncc5cc(C(C)(C)C)cc(F)c5c4=O)c3CO)nn(C)c2=O)nc1] |
| I-2 | 6-tert-Butyl-8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one | 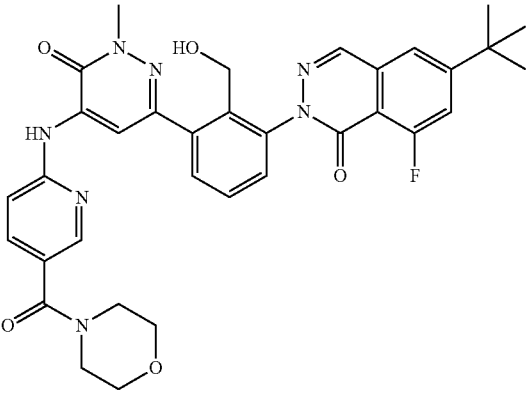 [SMILES: Cn1nc(-c2cccc(-n3ncc4cc(C(C)(C)C)cc(F)c4c3=O)c2CO)cc(Nc2ccc(C(=O)N3CCOCC3)cn2)c1=O] |

TABLE I-continued

| Compound | Nomenclature | Structure |
|---|---|---|
| I-3 | 6-tert-Butyl-8-fluoro-2-{2-hydroxymethyl-3-[5-(5-methanesulfonyl-pyridin-2-ylamino)-1-methyl-6-oxo-1,6-dihydro-pyridazin-3-yl]-phenyl}-2H-phthalazin-1-one | 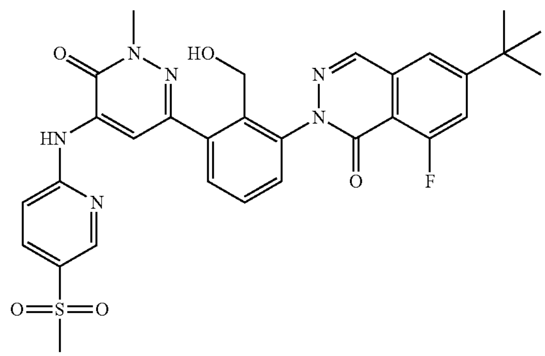 [SMILES: Cn1nc(-c2cccc(-n3ncc4cc(C(C)(C)C)cc(F)c4c3=O)c2CO)cc(Nc2ccc(S(C)(=O)=O)cn2)c1=O] |
| I-4 | 6-tert-Butyl-8-fluoro-2-(2-hydroxymethyl-3-{5-[5-(3-methoxy-azetidin-1-ylmethyl)-pyridin-2-ylamino]-1-methyl-6-oxo-1,6-dihydro-pyridazin-3-yl}-phenyl)-2H-phthalazin-1-one | 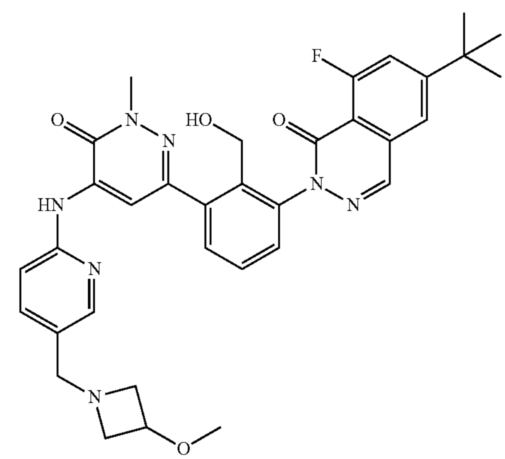 [SMILES: COC1CN(Cc2ccc(Nc3cc(-c4cccc(-n5ncc6cc(C(C)(C)C)cc(F)c6c5=O)c4CO)nn(C)c3=O)nc2)C1] |
| I-5 | 6-tert-Butyl-8-fluoro-2-(2-hydroxymethyl-3-{1-methyl-5-[5-(8-methyl-3,8-diaza-bicyclo[3.2.1]oct-3-ylmethyl)-pyridin-2-ylamino]-6-oxo-1,6-dihydro-pyridazin-3-yl}-phenyl)-2H-phthalazin-1-one | 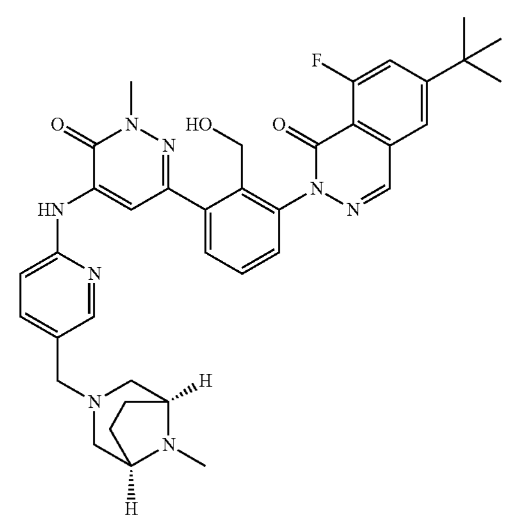 [SMILES: CN1[C@@H]2CC[C@H]1CN(Cc1ccc(Nc3cc(-c4cccc(-n5ncc6cc(C(C)(C)C)cc(F)c6c5=O)c4CO)nn(C)c3=O)nc1)C2] |

TABLE I-continued

| Compound | Nomenclature | Structure |
|---|---|---|
| I-6 | 6-tert-Butyl-2-(3-{5-[5-(2-dimethylamino-1,1-dimethyl-ethoxy)-pyridin-2-ylamino]-1-methyl-6-oxo-1,6-dihydro-pyridazin-3-yl}-2-hydroxymethyl-phenyl)-8-fluoro-2H-phthalazin-1-one | 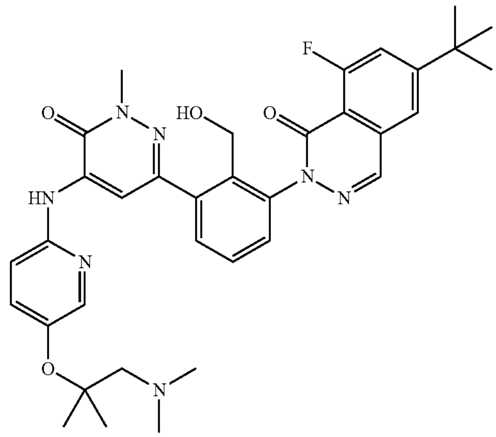 [SMILES: CN(C)CC(C)(C)Oc1ccc(Nc2cc(-c3cccc(-n4ncc5cc(C(C)(C)C)cc(F)c5c4=O)c3CO)nn(C)c2=O)nc1] |
| I-7 | 2-{3-[5-(5-Azetidin-1-ylmethyl-pyridin-2-ylamino)-1-methyl-6-oxo-1,6-dihydro-pyridazin-3-yl]-2-hydroxymethyl-phenyl}-6-tert-butyl-8-fluoro-2H-phthalazin-1-one | 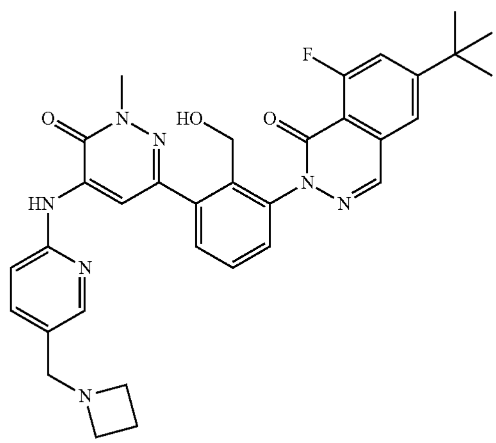 [SMILES: Cn1nc(-c2cccc(-n3ncc4cc(C(C)(C)C)cc(F)c4c3=O)c2CO)cc(Nc2ccc(CN3CCC3)cn2)c1=O] |
| I-8 | 6-tert-Butyl-2-{3-[5-(5-dimethylaminomethyl-pyridin-2-ylamino)-1-methy-1-6-oxo-1,6-dihydro-pyridazin-3-yl]-2-hydroxymethyl-phenyl}-8-fluoro-2H-phthalazin-1-one | 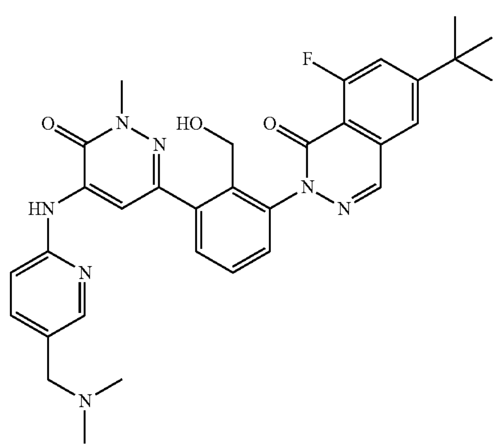 [SMILES: CN(C)Cc1ccc(Nc2cc(-c3cccc(-n4ncc5cc(C(C)(C)C)cc(F)c5c4=O)c3CO)nn(C)c2=O)nc1] |

TABLE I-continued

| Compound | Nomenclature | Structure |
| --- | --- | --- |
| I-9 | 6-tert-Butyl-2-(3-{5-[(1R,5S)-5-(3,8-diaza-bicyclo[3.2.1]oct-8-yl)-pyridin-2-ylamino]-1-methyl-6-oxo-1,6-dihydro-pyridazin-3-yl}-2-hydroxymethyl-phenyl)-8-fluoro-2H-phthalazin-1-one | 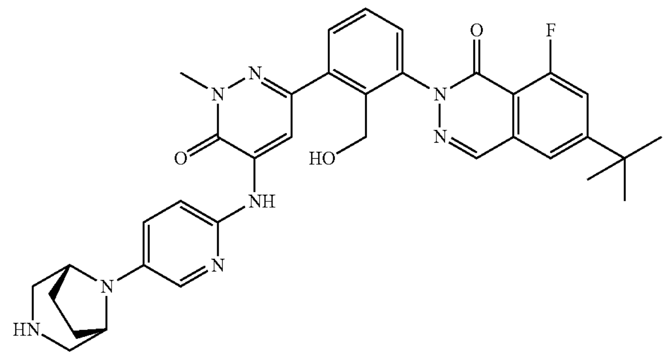 [SMILES: Cn1nc(-c2cccc(-n3ncc4cc(C(C)(C)C)cc(F)c4c3=O)c2CO)cc(Nc2ccc(N3[C@@H]4CC[C@H]3CNC4)cn2)c1=O] |
| I-10 | 6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide | 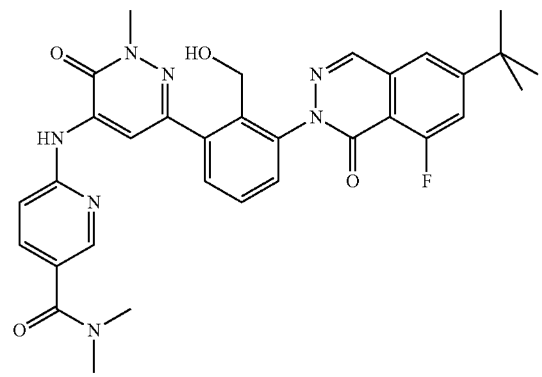 [SMILES: CN(C)C(=O)c1ccc(Nc2cc(-c3cccc(-n4ncc5cc(C(C)(C)C)cc(F)c5c4=O)c3CO)nn(C)c2=O)nc1] |
| I-11 | 6-tert-Butyl-8-fluoro-2-{2-hydroxymethyl-3-[1-methyl-6-oxo-5-(5-trifluoromethyl-pyrazin-2-ylamino)-1,6-dihydro-pyridazin-3-yl]-phenyl}-2H-phthalazin-1-one | 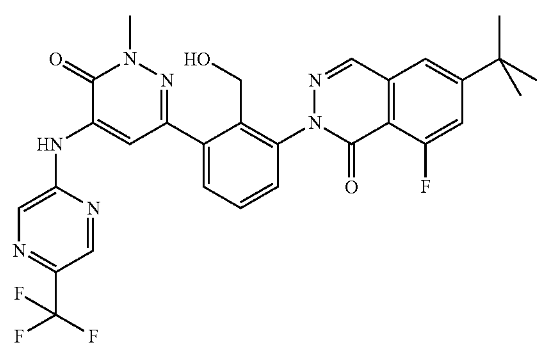 [SMILES: Cn1nc(-c2cccc(-n3ncc4cc(C(C)(C)C)cc(F)c4c3=O)c2CO)cc(Nc2cnc(C(F)(F)F)cn2)c1=O] |
| I-12 | 6-tert-Butyl-8-fluoro-2-(3-{5-[5-(2-hydroxy-1,1-dimethyl-ethoxy)-pyridin-2-ylamino]-1-methyl-6-oxo-1,6-dihydro-pyridazin-3-yl}-2-hydroxymethyl-phenyl)-2H-phthalazin-1-one | 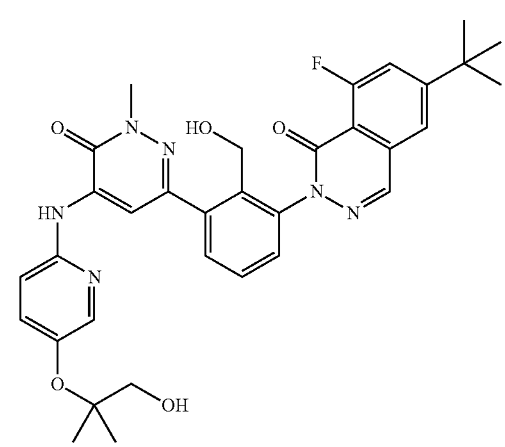 [SMILES: Cn1nc(-c2cccc(-n3ncc4cc(C(C)(C)C)cc(F)c4c3=O)c2CO)cc(Nc2ccc(OC(C)(C)CO)cn2)c1=O] |

TABLE I-continued

| Compound | Nomenclature | Structure |
|---|---|---|
| I-13 | 2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one | 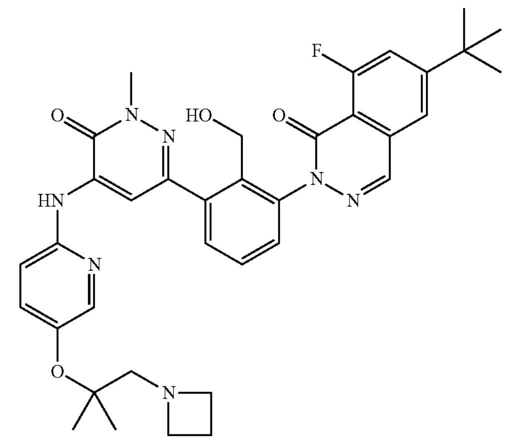 [SMILES: Cn1nc(-c2cccc(-n3ncc4cc(C(C)(C)C)cc(F)c4c3=O)c2CO)cc(Nc2ccc(OC(C)(C)CN3CCC3)cn2)c1=O] |
| I-14 | 6-tert-Butyl-8-fluoro-2-(2-hydroxymethyl-3-{5-[5-(2-hydroxy-2-methyl-propoxy)-pyridin-2-ylamino]-1-methyl-6-oxo-1,6-dihydro-pyridazin-3-yl}-phenyl)-2H-phthalazin-1-one | 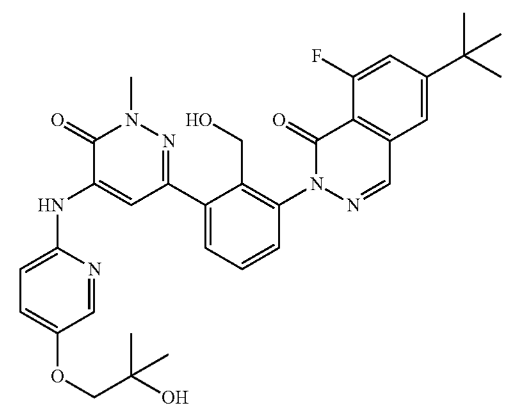 [SMILES: Cn1nc(-c2cccc(-n3ncc4cc(C(C)(C)C)cc(F)c4c3=O)c2CO)cc(Nc2ccc(OCC(C)(C)O)cn2)c1=O] |
| I-15 | 2-[8-Fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile | 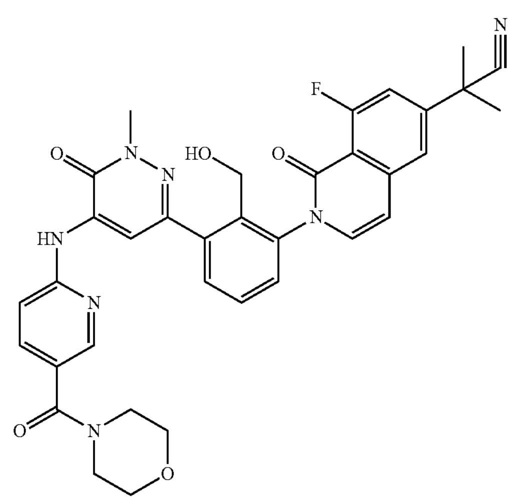 [SMILES: Cn1nc(-c2cccc(-n3ccc4cc(C(C)(C)C#N)cc(F)c4c3=O)c2CO)cc(Nc2ccc(C(=O)N3CCOCC3)cn2)c1=O] |

TABLE I-continued

| Compound | Nomenclature | Structure |
|---|---|---|
| I-16 | 6-tert-Butyl-8-fluoro-2-(3-{5-[5-((S)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one | 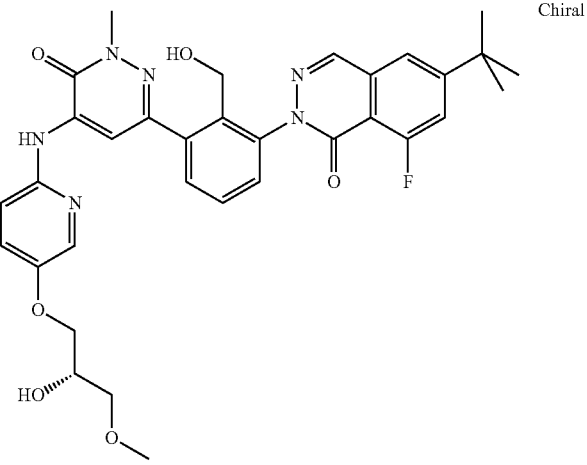 [SMILES: COC[C@H](O)COc1ccc(Nc2cc(-c3cccc(-n4ncc5cc(C(C)(C)C)cc(F)c5c4=O)c3CO)nn(C)c2=O)nc1] Chiral |
| I-17 | 6-tert-Butyl-8-fluoro-2-(3-{5-[5-((R)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one | 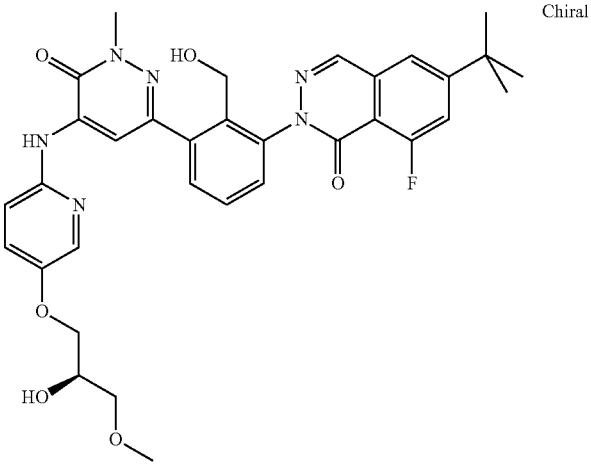 [SMILES: COC[C@@H](O)COc1ccc(Nc2cc(-c3cccc(-n4ncc5cc(C(C)(C)C)cc(F)c5c4=O)c3CO)nn(C)c2=O)nc1] Chiral |
| I-18 | 6-tert-Butyl-8-fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one | 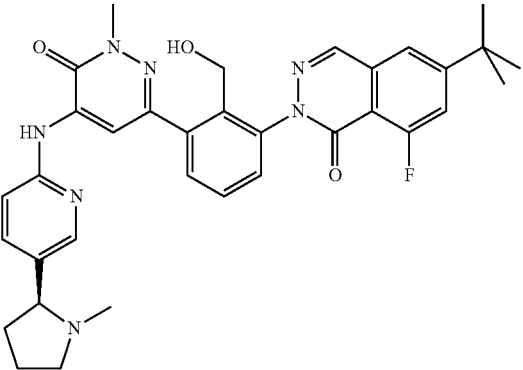 [SMILES: CN1CCC[C@H]1c1ccc(Nc2cc(-c3cccc(-n4ncc5cc(C(C)(C)C)cc(F)c5c4=O)c3CO)nn(C)c2=O)nc1] |

TABLE I-continued

| Compound | Nomenclature | Structure |
|---|---|---|
| I-19 | 6-tert-Butyl-8-fluoro-2-(2-hydroxymethyl-3-{1-methyl-5-[5-((R)-1-methyl-pyrrolidin-2-yl)-pyridin-2-ylamino]-6-oxo-1,6-dihydro-pyridazin-3-yl}-phenyl)-2H-phthalazin-1-one | 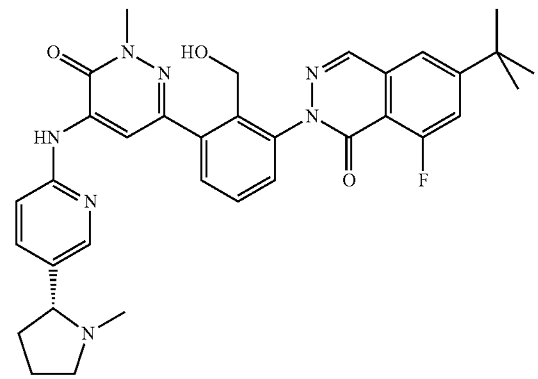 [SMILES: CN1CCC[C@@H]1c1ccc(Nc2cc(-c3cccc(-n4ncc5cc(C(C)(C)C)cc(F)c5c4=O)c3CO)nn(C)c2=O)nc1] |
| I-20 | 6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide | 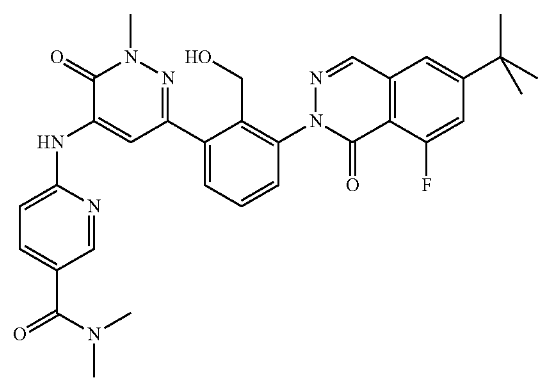 [SMILES: CN(C)C(=O)c1ccc(Nc2cc(-c3cccc(-n4ncc5cc(C(C)(C)C)cc(F)c5c4=O)c3CO)nn(C)c2=O)nc1] |
| I-21 | 6-tert-Butyl-8-fluoro-2-(2-hydroxymethyl-3-{5-[5-(4-hydroxy-4-methyl-piperidine-1-carbonyl)-pyridin-2-ylamino]-1-methyl-6-oxo-1,6-dihydro-pyridazin-3-yl}-phenyl)-2H-phthalazin-1-one | 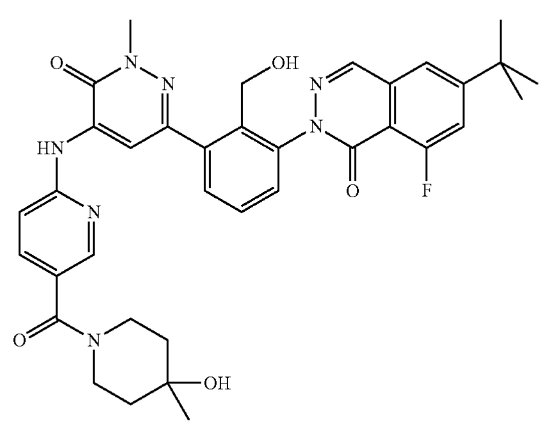 [SMILES: Cn1nc(-c2cccc(-n3ncc4cc(C(C)(C)C)cc(F)c4c3=O)c2CO)cc(Nc2ccc(C(=O)N3CCC(C)(O)CC3)cn2)c1=O] |

TABLE I-continued

| Compound | Nomenclature | Structure |
|---|---|---|
| I-22 | 6-tert-Butyl-8-fluoro-2-(2-hydroxymethyl-3-{1-methyl-5-[5-(6-methyl-2,6-diaza-spiro[3.3]hept-2-yl)-pyridin-2-ylamino]-6-oxo-1,6-dihydro-pyridazin-3-yl}-phenyl)-2H-phthalazin-1-one | 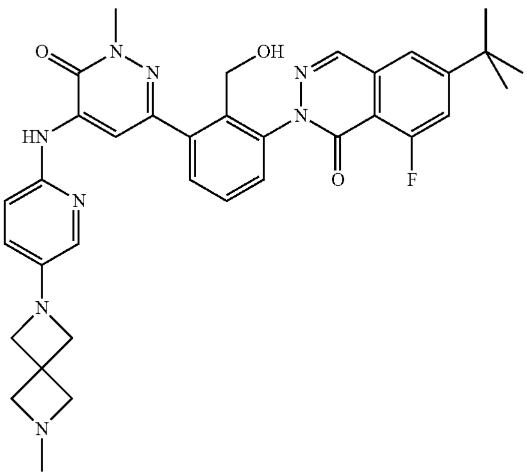 [SMILES: CN1CC2(C1)CN(c1ccc(Nc3cc(-c4cccc(-n5ncc6cc(C(C)(C)C)cc(F)c6c5=O)c4CO)nn(C)c3=O)nc1)C2] |
| I-23 | 6-tert-Butyl-2-{3-[5-(5-ethanesulfonyl-pyridin-2-ylamino)-1-methyl-6-oxo-1,6-dihydro-pyridazin-3-yl]-2-hydroxymethyl-phenyl}-8-fluoro-2H-phthalazin-1-one | 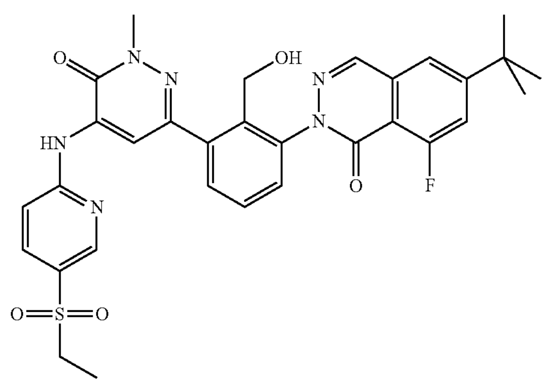 [SMILES: CCS(=O)(=O)c1ccc(Nc2cc(-c3cccc(-n4ncc5cc(C(C)(C)C)cc(F)c5c4=O)c3CO)nn(C)c2=O)nc1] |
| I-24 | 6-tert-Butyl-8-fluoro-2-(2-hydroxymethyl-3-{1-methyl-6-oxo-5-[5-(propane-2-sulfonyl)-pyridin-2-ylamino]-1,6-dihydro-pyridazin-3-yl}-phenyl)-2H-phthalazin-1-one | 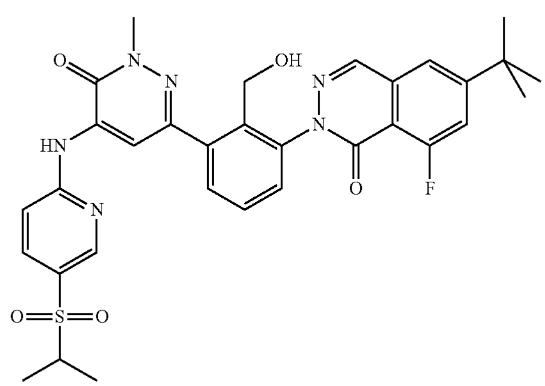 [SMILES: CC(C)S(=O)(=O)c1ccc(Nc2cc(-c3cccc(-n4ncc5cc(C(C)(C)C)cc(F)c5c4=O)c3CO)nn(C)c2=O)nc1] |

TABLE I-continued

| Compound | Nomenclature | Structure |
|---|---|---|
| I-25 | 6-tert-Butyl-8-fluoro-2-(3-{5-[5-(2-hydroxy-ethylsulfanyl)-pyridin-2-ylamino]-1-methyl-6-oxo-1,6-dihydro-pyridazin-3-yl}-2-hydroxymethyl-phenyl)-2H-phthalazin-1-one | 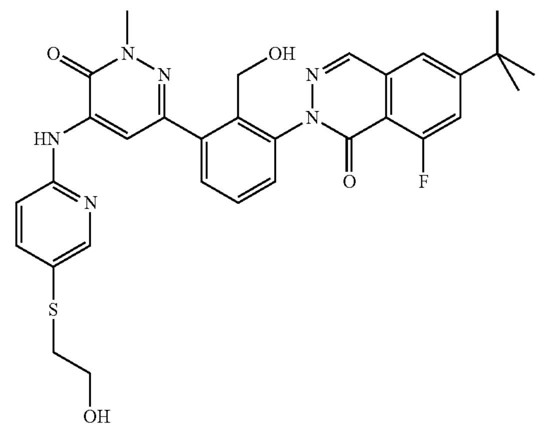 [SMILES: Cn1nc(-c2cccc(-n3ncc4cc(C(C)(C)C)cc(F)c4c3=O)c2CO)cc(Nc2ccc(SCCO)cn2)c1=O] |
| I-26 | 6-tert-Butyl-8-fluoro-2-(3-{5-[5-(2-hydroxy-ethanesulfonyl)-pyridin-2-ylamino]-1-methyl-6-oxo-1,6-dihydro-pyridazin-3-yl}-2-hydroxymethyl-phenyl)-2H-phthalazin-1-one | 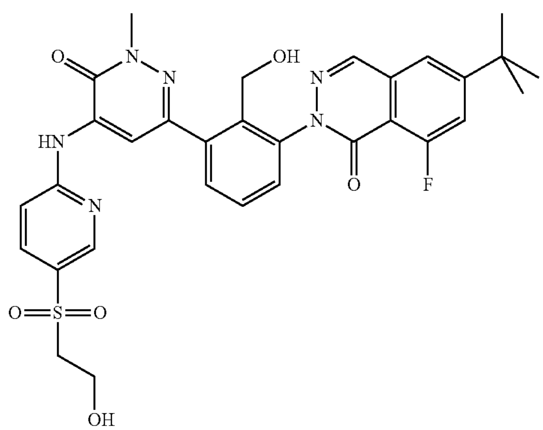 [SMILES: Cn1nc(-c2cccc(-n3ncc4cc(C(C)(C)C)cc(F)c4c3=O)c2CO)cc(Nc2ccc(S(=O)(=O)CCO)cn2)c1=O] |
| I-27 | 6-tert-Butyl-8-fluoro-2-(2-hydroxymethyl-3-{5-[5-(4-isopropyl-piperazin-1-yl)-pyridin-2-ylamino]-1-methyl-6-oxo-1,6-dihydro-pyridazin-3-yl}-phenyl)-2H-phthalazin-1-one | ClH |

TABLE I-continued

| Compound | Nomenclature | Structure |
|---|---|---|
| I-28 | 6-tert-Butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one | 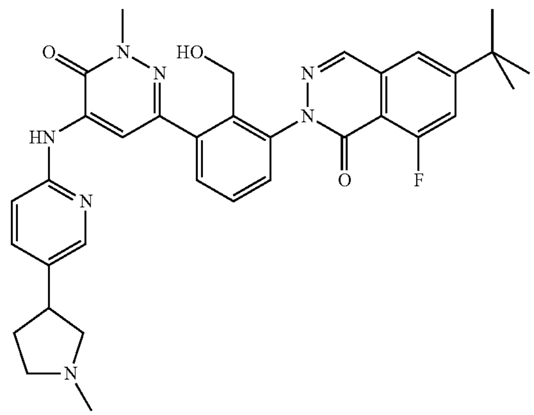 [SMILES: CN1CCC(c2ccc(Nc3cc(-c4cccc(-n5ncc6cc(C(C)(C)C)cc(F)c6c5=O)c4CO)nn(C)c3=O)nc2)C1] |
| I-29 | 6-tert-Butyl-8-fluoro-2-{2-hydroxymethyl-3-[5-(1'-isopropyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one | 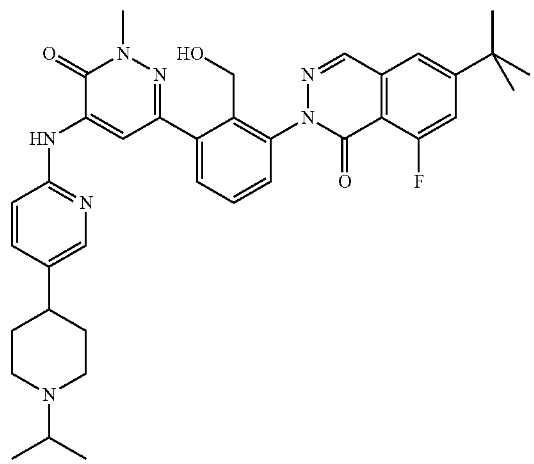 [SMILES: CC(C)N1CCC(c2ccc(Nc3cc(-c4cccc(-n5ncc6cc(C(C)(C)C)cc(F)c6c5=O)c4CO)nn(C)c3=O)nc2)CC1] |
| I-30 | 6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-8-fluoro-2H-phthalazin-1-one | 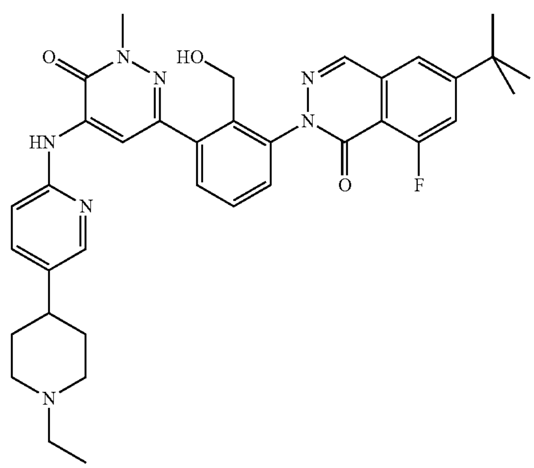 [SMILES: CCN1CCC(c2ccc(Nc3cc(-c4cccc(-n5ncc6cc(C(C)(C)C)cc(F)c6c5=O)c4CO)nn(C)c3=O)nc2)CC1] |
| I-31 | 6-tert-Butyl-2-{3-[5-(1,5-dimethyl-1H-pyrazol-3-ylamino)-1-methyl-6-oxo-1,6-dihydro-pyridazin-3-yl]-2-hydroxymethyl-phenyl}-8-fluoro-2H-phthalazin-1-one | 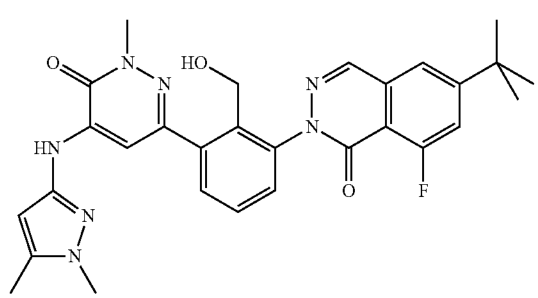 [SMILES: Cc1cc(Nc2cc(-c3cccc(-n4ncc5cc(C(C)(C)C)cc(F)c5c4=O)c3CO)nn(C)c2=O)nn1C] |

TABLE I-continued

| Compound | Nomenclature | Structure |
|---|---|---|
| I-32 | 6-tert-Butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one | 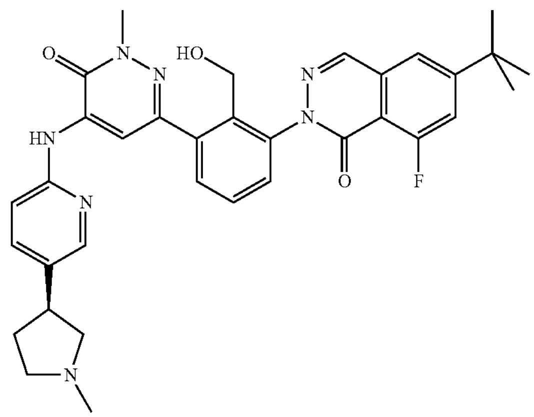 [SMILES: CN1CC[C@@H](c2ccc(Nc3cc(-c4cccc(-n5ncc6cc(C(C)(C)C)cc(F)c6c5=O)c4CO)nn(C)c3=O)nc2)C1] |
| I-33 | 6-tert-Butyl-8-fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one | 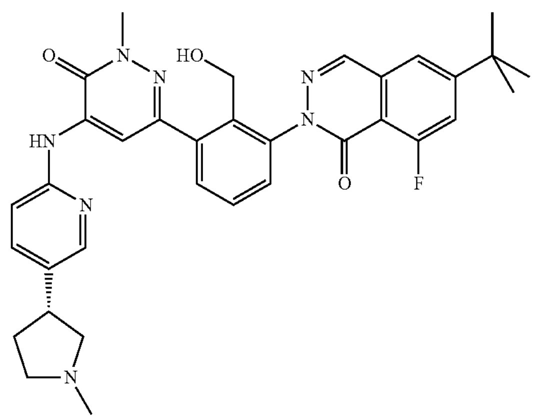 [SMILES: CN1CC[C@H](c2ccc(Nc3cc(-c4cccc(-n5ncc6cc(C(C)(C)C)cc(F)c6c5=O)c4CO)nn(C)c3=O)nc2)C1] |
| I-34 | 6-tert-Butyl-8-fluoro-2-{2-hydroxymethyl-3-[1-methyl-5-(4-methyl-3,4,5,6-tetrahydro-2H-[1,2']bipyrazinyl-5'-ylamino)-6-oxo-1,6-dihydro-pyridazin-3-yl]-phenyl}-2H-phthalazin-1-one | 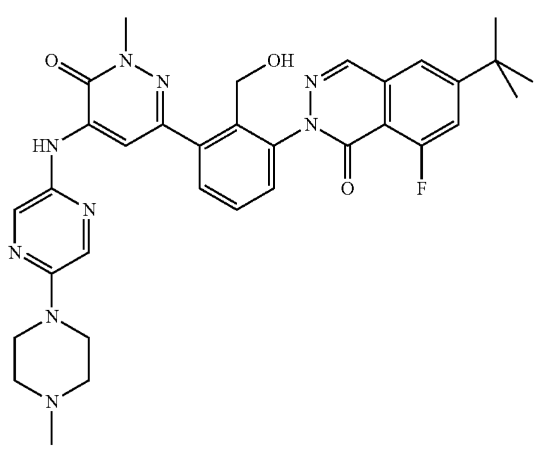 [SMILES: CN1CCN(c2cnc(Nc3cc(-c4cccc(-n5ncc6cc(C(C)(C)C)cc(F)c6c5=O)c4CO)nn(C)c3=O)cn2)CC1] |

TABLE I-continued

| Compound | Nomenclature | Structure |
| --- | --- | --- |
| I-35 | 6-tert-Butyl-2-{3-[5-(5-cyclobutylaminomethyl-pyrazin-2-ylamino)-1-methyl-6-oxo-1,6-dihydro-pyridazin-3-yl]-2-hydroxymethyl-phenyl}-8-fluoro-2H-phthalazin-1-one | 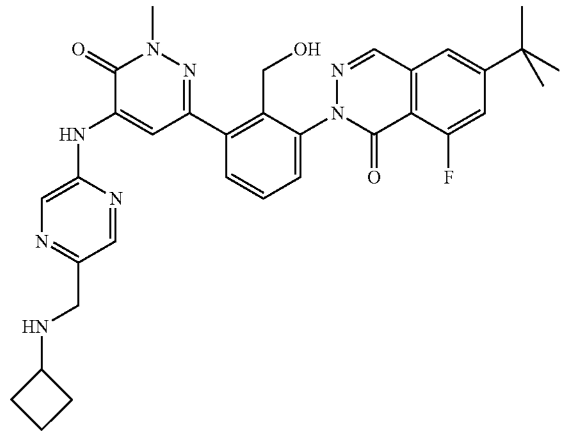 [SMILES: Cn1nc(-c2cccc(-n3ncc4cc(C(C)(C)C)cc(F)c4c3=O)c2CO)cc(Nc2cnc(CNC3CCC3)cn2)c1=O] |
| I-36 | 6-tert-Butyl-2-(3-{5-[5-(2-dimethylamino-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one | 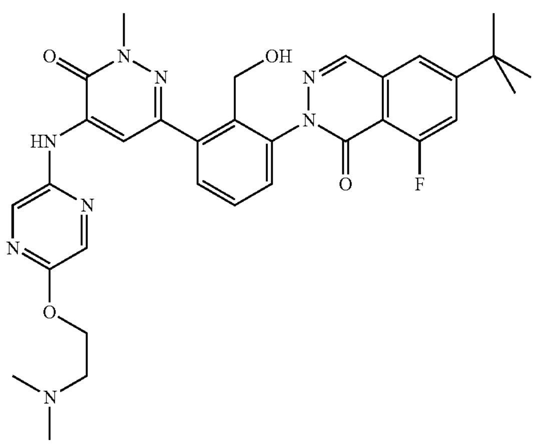 [SMILES: CN(C)CCOc1cnc(Nc2cc(-c3cccc(-n4ncc5cc(C(C)(C)C)cc(F)c5c4=O)c3CO)nn(C)c2=O)cn1] |
| I-37 | 6-tert-Butyl-8-fluoro-2-(2-hydroxymethyl-3-{1-methyl-5-[5-(4-methyl-piperazin-1-ylmethyl)-pyrazin-2-ylamino]-6-oxo-1,6-dihydro-pyridazin-3-yl}-phenyl)-2H-phthalazin-1-one | 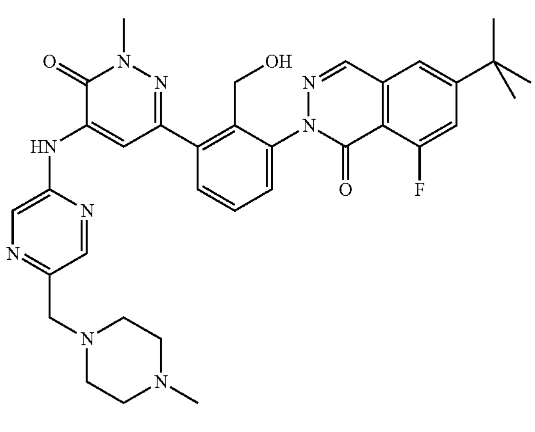 [SMILES: CN1CCN(Cc2cnc(Nc3cc(-c4cccc(-n5ncc6cc(C(C)(C)C)cc(F)c6c5=O)c4CO)nn(C)c3=O)cn2)CC1] |

TABLE I-continued

| Compound | Nomenclature | Structure |
|---|---|---|
| I-38 | 6-tert-Butyl-2-(3-{5-[5-(2-dimethylamino-1,1-dimethyl-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one | 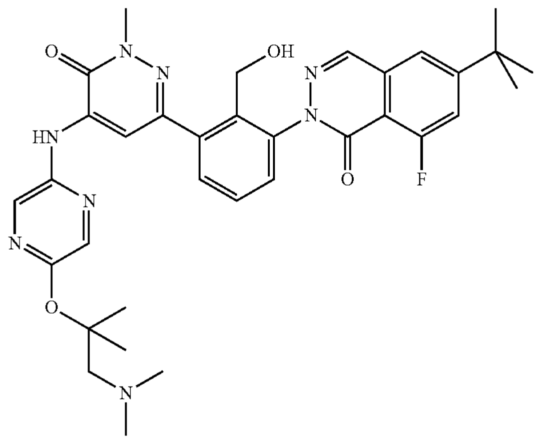 [SMILES: CN(C)CC(C)(C)Oc1cnc(Nc2cc(-c3cccc(-n4ncc5cc(C(C)(C)C)cc(F)c5c4=O)c3CO)nn(C)c2=O)cn1] |
| I-39 | 6-tert-Butyl-2-(3-{5-[6-(2-dimethylamino-1,1-dimethyl-ethoxy)-pyridazin-3-ylamino]-1-methyl-6-oxo-1,6-dihydro-pyridazin-3-yl}-2-hydroxymethyl-phenyl)-8-fluoro-2H-phthalazin-1-one | 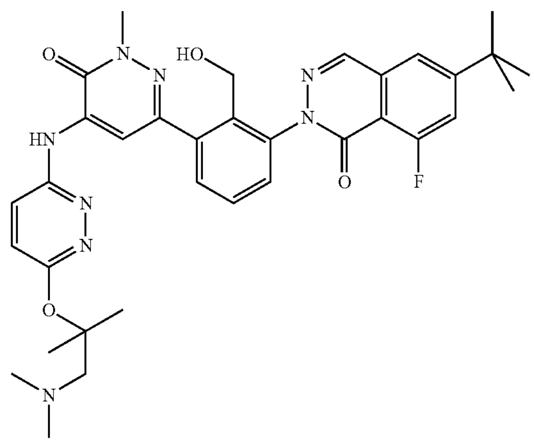 [SMILES: CN(C)CC(C)(C)Oc1ccc(Nc2cc(-c3cccc(-n4ncc5cc(C(C)(C)C)cc(F)c5c4=O)c3CO)nn(C)c2=O)nn1] |
| I-40 | 6-tert-Butyl-8-fluoro-2-(2-hydroxymethyl-3-{1-methyl-5-[6-(1-methyl-piperidin-4-yl)-pyridazin-3-ylamino]-6-oxo-1,6-dihydro-pyridazin-3-yl}-phenyl)-2H-phthalazin-1-one | 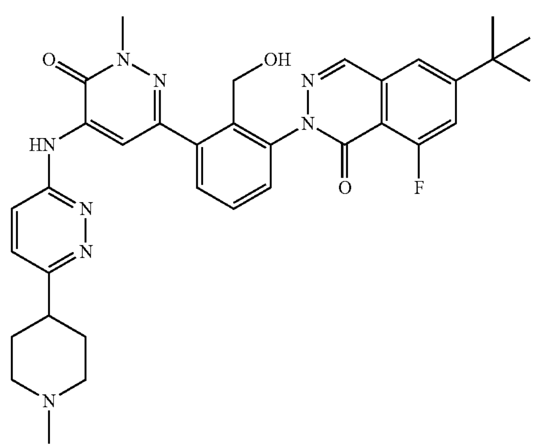 [SMILES: CN1CCC(c2ccc(Nc3cc(-c4cccc(-n5ncc6cc(C(C)(C)C)cc(F)c6c5=O)c4CO)nn(C)c3=O)nn2)CC1] |

TABLE I-continued

| Compound | Nomenclature | Structure |
|---|---|---|
| I-41 | 6-tert-Butyl-8-fluoro-2-(2-hydroxymethyl-3-{1-methyl-5-[5-(4-methyl-piperazin-1-ylmethyl)-pyridin-2-ylamino]-6-oxo-1,6-dihydro-pyridazin-3-yl}-phenyl)-2H-phthalazin-1-one | 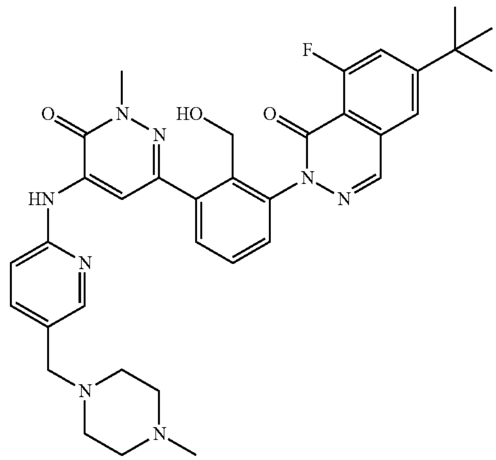 [SMILES: CN1CCN(Cc2ccc(Nc3cc(-c4cccc(-n5ncc6cc(C(C)(C)C)cc(F)c6c5=O)c4CO)nn(C)c3=O)nc2)CC1] |
| I-42 | 6-tert-Butyl-8-fluoro-2-[2-hydroxymethyl-3-(5-{5-[(2-methoxy-ethylamino)-methyl]-pyridin-2-ylamino}-1-methyl-6-oxo-1,6-dihydro-pyridazin-3-yl)-phenyl]-2H-phthalazin-1-one | 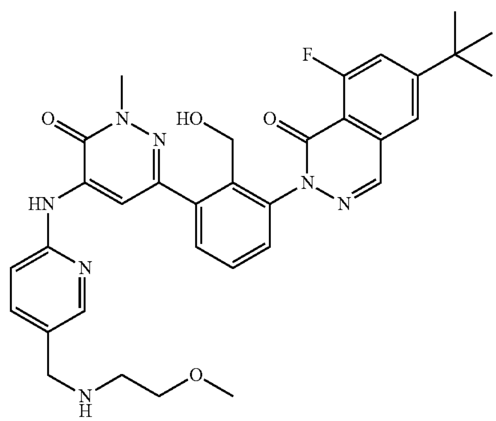 [SMILES: COCCNCc1ccc(Nc2cc(-c3cccc(-n4ncc5cc(C(C)(C)C)cc(F)c5c4=O)c3CO)nn(C)c2=O)nc1] |
| I-43 | 6-tert-Butyl-8-fluoro-2-(2-hydroxymethyl-3-{1-methyl-5-[5-((1S,4S)-5-methyl-2,5-diaza-bicyclo[2.2.1]hept-2-ylmethyl)-pyridin-2-ylamino]-6-oxo-1,6-dihydro-pyridazin-3-yl}-phenyl)-2H-phthalazin-1-one | 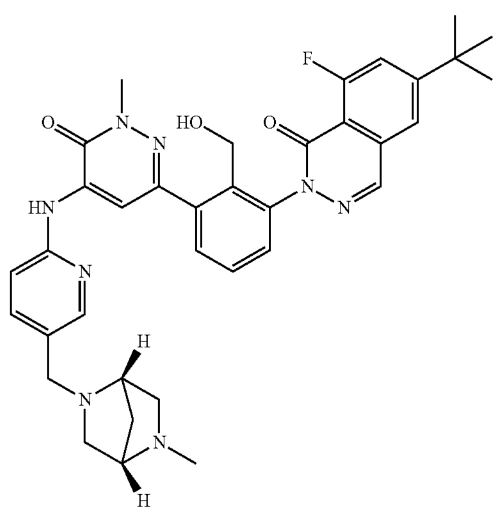 [SMILES: CN1C[C@@H]2C[C@H]1CN2Cc1ccc(Nc2cc(-c3cccc(-n4ncc5cc(C(C)(C)C)cc(F)c5c4=O)c3CO)nn(C)c2=O)nc1] |

TABLE I-continued

| Compound | Nomenclature | Structure |
|---|---|---|
| I-44 | 6-tert-Butyl-8-fluoro-2-{2-hydroxymethyl-3-[5-(5-{[(2-methoxy-ethyl)-methyl-amino]-methyl}-pyridin-2-ylamino)-1-methyl-6-oxo-1,6-dihydro-pyridazin-3-yl]-phenyl}-2H-phthalazin-1-one | 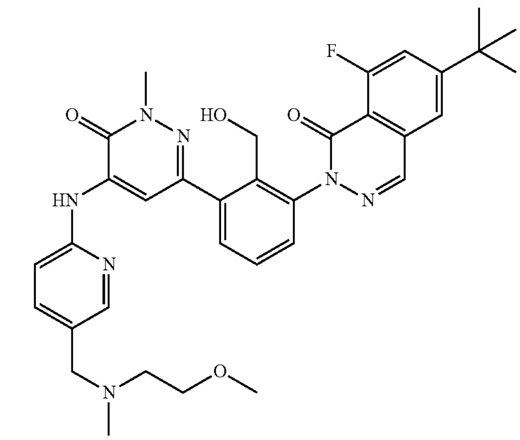 [SMILES: COCCN(C)Cc1ccc(Nc2cc(-c3cccc(-n4ncc5cc(C(C)(C)C)cc(F)c5c4=O)c3CO)nn(C)c2=O)nc1] |
| I-45 | 6-tert-Butyl-8-fluoro-2-(2-hydroxymethyl-3-{1-methyl-5-[6-(4-methyl-piperazin-1-yl)-pyridazin-3-ylamino]-6-oxo-1,6-dihydro-pyridazin-3-yl}-phenyl)-2H-phthalazin-1-one | 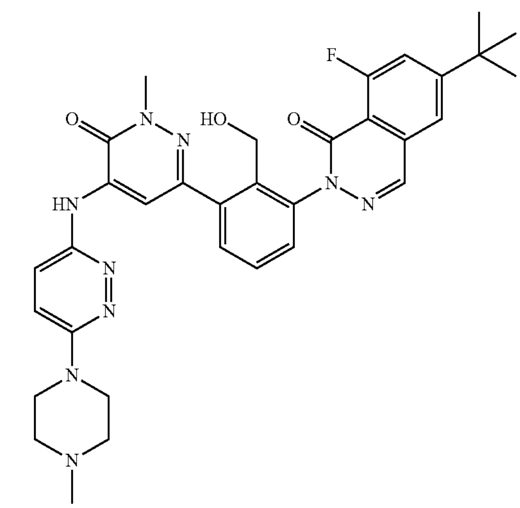 [SMILES: CN1CCN(c2ccc(Nc3cc(-c4cccc(-n5ncc6cc(C(C)(C)C)cc(F)c6c5=O)c4CO)nn(C)c3=O)nn2)CC1] |
| I-46 | 6-tert-Butyl-8-fluoro-2-(2-hydroxymethyl-3-{1-methyl-5-[6-((1S,4S)-5-methyl-2,5-diaza-bicyclo[2.2.1]hept-2-yl)-pyridazin-3-ylamino]-6-oxo-1,6-dihydro-pyridazin-3-yl}-phenyl)-2H-phthalazin-1-one | 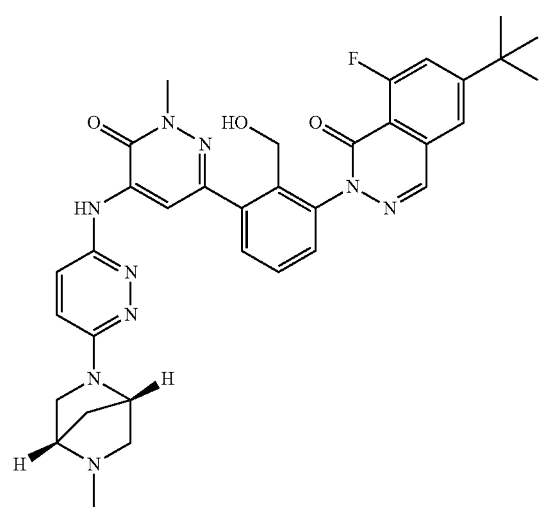 [SMILES: CN1C[C@@H]2C[C@H]1CN2c1ccc(Nc2cc(-c3cccc(-n4ncc5cc(C(C)(C)C)cc(F)c5c4=O)c3CO)nn(C)c2=O)nn1] |

TABLE I-continued

| Compound | Nomenclature | Structure |
|---|---|---|
| I-47 | 2-(3-{5-[5-(Azetidine-1-carbonyl)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one | 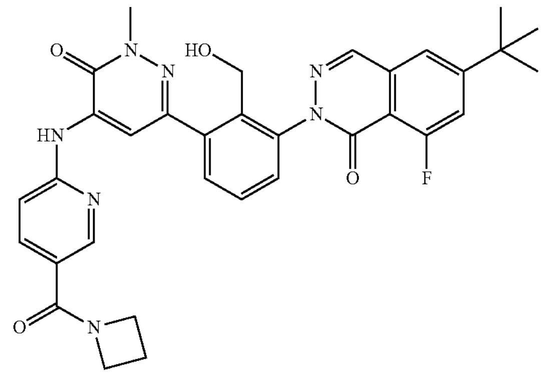 [SMILES: Cn1nc(-c2cccc(-n3ncc4cc(C(C)(C)C)cc(F)c4c3=O)c2CO)cc(Nc2ccc(C(=O)N3CCC3)cn2)c1=O] |
| I-48 | 6-tert-Butyl-2-(3-{5-[5-(1,1-dioxo-1λ6-thiomorpholine-4-carbonyl)-pyridin-2-ylamino]-1-methyl-6-oxo-1,6-dihydro-pyridazin-3-yl}-2-hydroxymethyl-phenyl)-8-fluoro-2H-phthalazin-1-one | 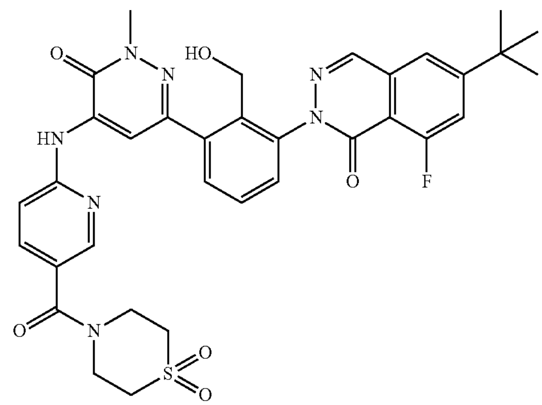 [SMILES: Cn1nc(-c2cccc(-n3ncc4cc(C(C)(C)C)cc(F)c4c3=O)c2CO)cc(Nc2ccc(C(=O)N3CCS(=O)(=O)CC3)cn2)c1=O] |
| I-49 | 6-tert-Butyl-8-fluoro-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridazin-3-yl}-phenyl)-2H-phthalazin-1-one | 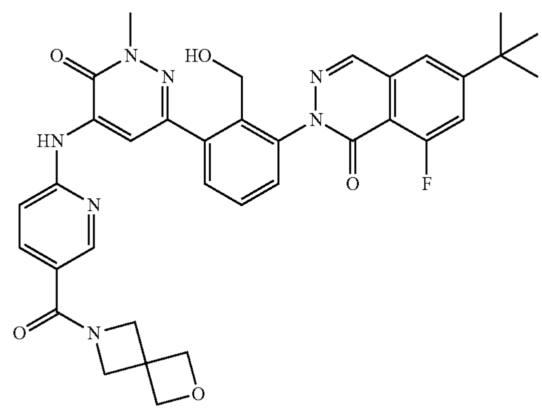 [SMILES: Cn1nc(-c2cccc(-n3ncc4cc(C(C)(C)C)cc(F)c4c3=O)c2CO)cc(Nc2ccc(C(=O)N3CC4(COC4)C3)cn2)c1=O] |
| I-50 | 6-tert-Butyl-8-fluoro-2-(2-hydroxymethyl-3-{1-methyl-5-[5-(6-methyl-2,6-diaza-spiro[3.3]heptane-2-carbonyl)-pyridin-2-ylamino]-6-oxo-1,6-dihydro-pyridazin-3-yl}-phenyl)-2H-phthalazin-1-one | 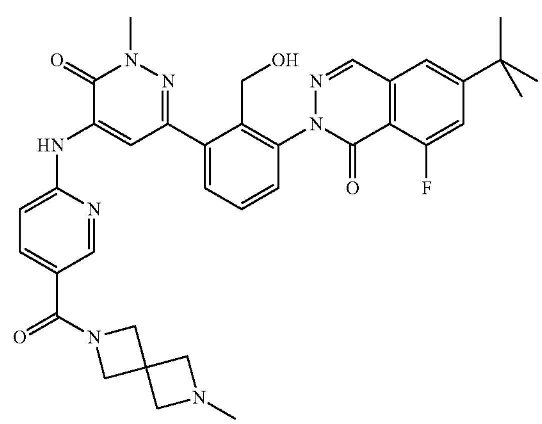 [SMILES: CN1CC2(C1)CN(C(=O)c1ccc(Nc3cc(-c4cccc(-n5ncc6cc(C(C)(C)C)cc(F)c6c5=O)c4CO)nn(C)c3=O)nc1)C2] |

TABLE I-continued

| Compound | Nomenclature | Structure |
|---|---|---|
| I-51 | 6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-dimethylamino-ethyl)-nicotinamide | 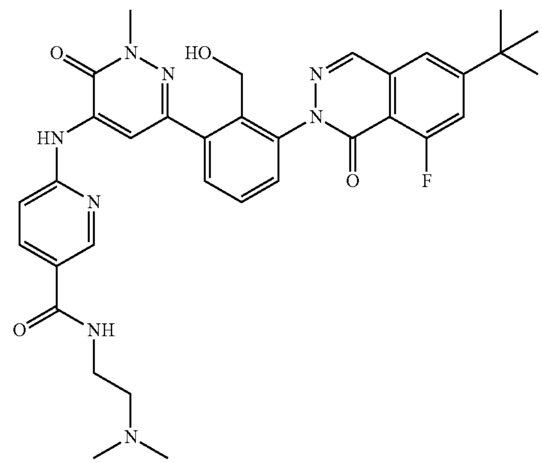 [SMILES: CN(C)CCNC(=O)c1ccc(Nc2cc(-c3cccc(-n4ncc5cc(C(C)(C)C)cc(F)c5c4=O)c3CO)nn(C)c2=O)nc1] |
| I-52 | 6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-hydroxy-ethyl)-N-methyl-nicotinamide | 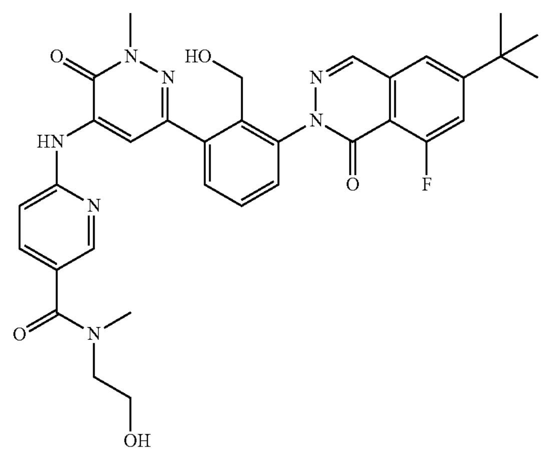 [SMILES: CN(CCO)C(=O)c1ccc(Nc2cc(-c3cccc(-n4ncc5cc(C(C)(C)C)cc(F)c5c4=O)c3CO)nn(C)c2=O)nc1] |
| I-53 | 1-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridine-3-carbonyl)-azetidine-3-carbonitrile | 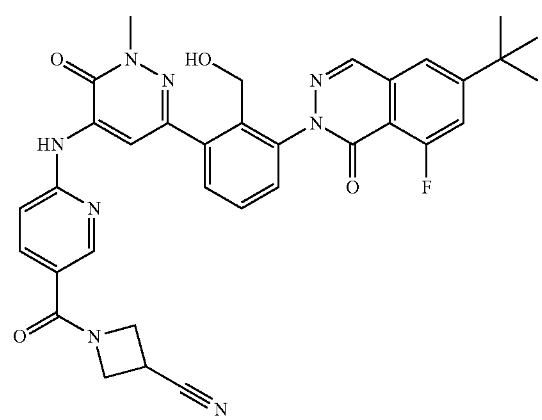 [SMILES: Cn1nc(-c2cccc(-n3ncc4cc(C(C)(C)C)cc(F)c4c3=O)c2CO)cc(Nc2ccc(C(=O)N3CC(C#N)C3)cn2)c1=O] |

TABLE I-continued

| Compound | Nomenclature | Structure |
|---|---|---|
| I-54 | 6-tert-Butyl-8-fluoro-2-(2-hydroxymethyl-3-{5-[5-(3-hydroxy-pyrrolidine-1-carbonyl)-pyridin-2-ylamino]-1-methyl-6-oxo-1,6-dihydro-pyridazin-3-yl}-phenyl)-2H-phthalazin-1-one | 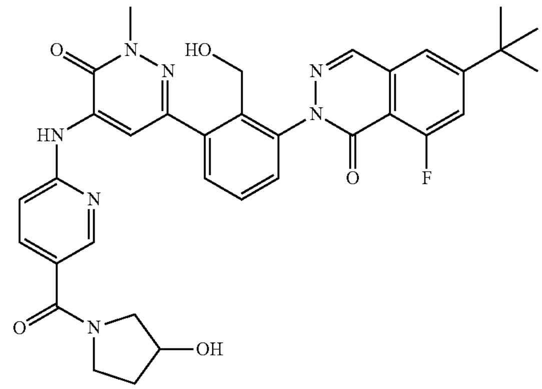 [SMILES: Cn1nc(-c2cccc(-n3ncc4cc(C(C)(C)C)cc(F)c4c3=O)c2CO)cc(Nc2ccc(C(=O)N3CCC(O)C3)cn2)c1=O] |
| I-55 | 6-tert-Butyl-8-fluoro-2-(2-hydroxymethyl-3-{5-[5-(4-hydroxy-piperidine-1-carbonyl)-pyridin-2-ylamino]-1-methyl-6-oxo-1,6-dihydro-pyridazin-3-yl}-phenyl)-2H-phthalazin-1-one | 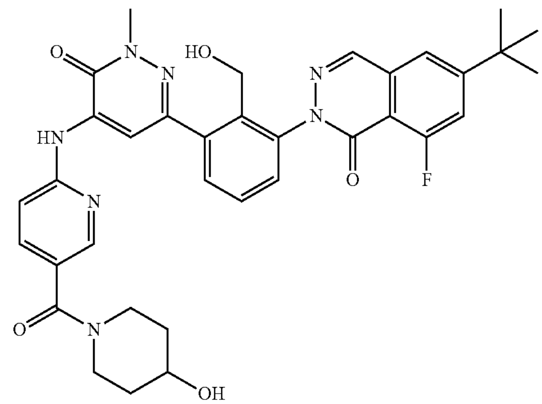 [SMILES: Cn1nc(-c2cccc(-n3ncc4cc(C(C)(C)C)cc(F)c4c3=O)c2CO)cc(Nc2ccc(C(=O)N3CCC(O)CC3)cn2)c1=O] |
| I-56 | 6-tert-Butyl-8-fluoro-2-(2-hydroxymethyl-3-{1-methyl-5-[5-(4-methyl-piperazin-1-yl)-pyridin-2-ylamino]-6-oxo-1,6-dihydro-pyridazin-3-yl}-phenyl)-2H-phthalazin-1-one | 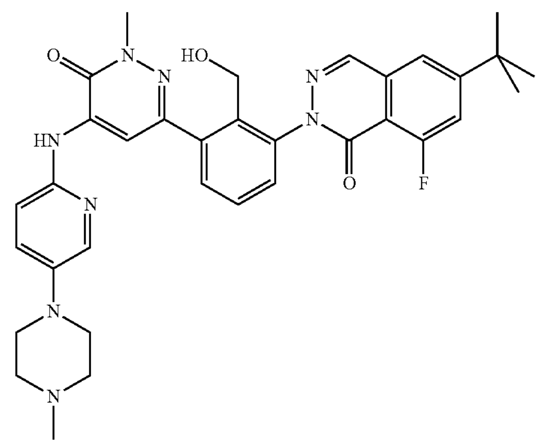 [SMILES: CN1CCN(c2ccc(Nc3cc(-c4cccc(-n5ncc6cc(C(C)(C)C)cc(F)c6c5=O)c4CO)nn(C)c3=O)nc2)CC1] |
| I-57 | 6-tert-Butyl-2-(3-{5-[5-((S)-1,2-dihydroxy-ethyl)-pyrazin-2-ylamino]-1-methyl-6-oxo-1,6-dihydro-pyridazin-3-yl}-2-hydroxymethyl-phenyl)-8-fluoro-2H-phthalazin-1-one | 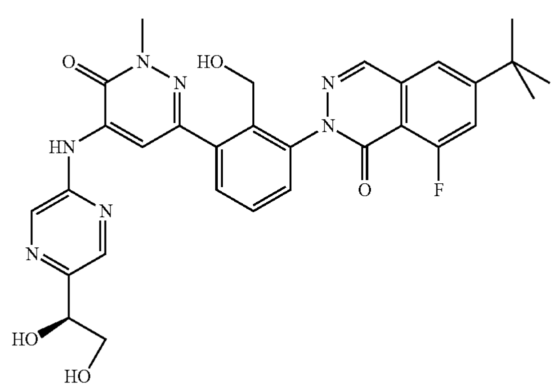 [SMILES: Cn1nc(-c2cccc(-n3ncc4cc(C(C)(C)C)cc(F)c4c3=O)c2CO)cc(Nc2cnc([C@H](O)CO)cn2)c1=O] |

TABLE I-continued

| Compound | Nomenclature | Structure |
|---|---|---|
| I-58 | 2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-6-tert-butyl-8-fluoro-2H-phthalazin-1-one | 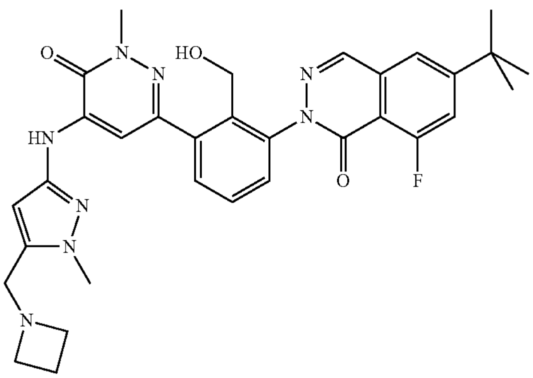 [SMILES: Cn1nc(Nc2cc(-c3cccc(-n4ncc5cc(C(C)(C)C)cc(F)c5c4=O)c3CO)nn(C)c2=O)cc1CN1CCC1] |
| I-59 | 6-tert-Butyl-8-fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-2H-phthalazin-1-one | 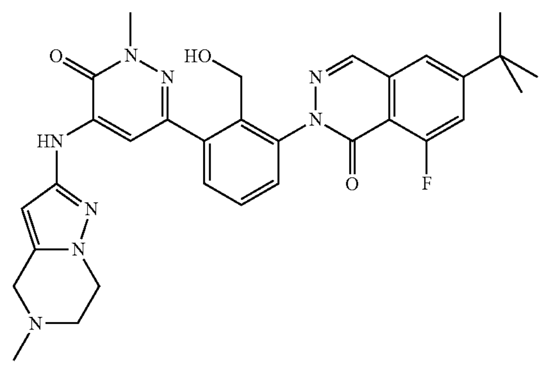 [SMILES: CN1CCn2nc(Nc3cc(-c4cccc(-n5ncc6cc(C(C)(C)C)cc(F)c6c5=O)c4CO)nn(C)c3=O)cc2C1] |
| I-60 | 6-tert-Butyl-8-fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-2H-phthalazin-1-one | 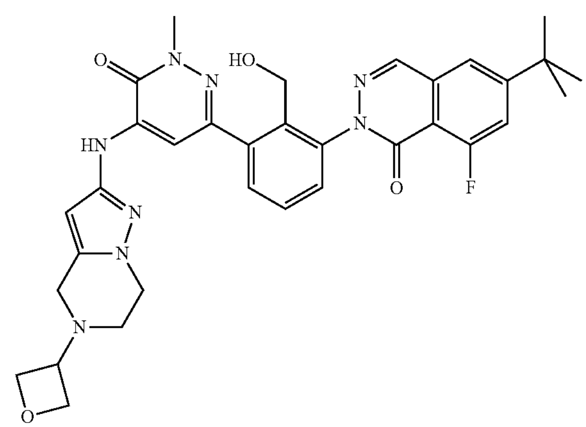 [SMILES: Cn1nc(-c2cccc(-n3ncc4cc(C(C)(C)C)cc(F)c4c3=O)c2CO)cc(Nc2cc3n(n2)CCN(C2COC2)C3)c1=O] |
| I-61 | 6-tert-Butyl-8-fluoro-2-{3-[5-(1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-2H-phthalazin-1-one | 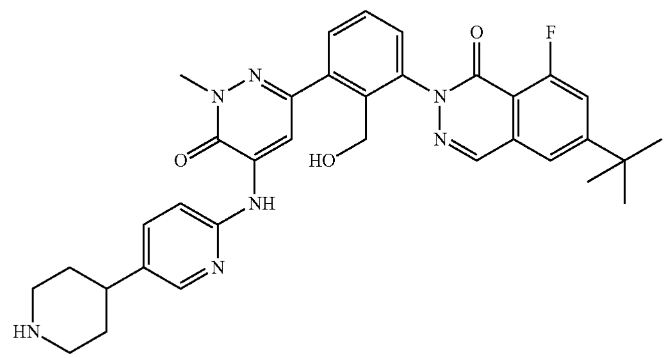 [SMILES: Cn1nc(-c2cccc(-n3ncc4cc(C(C)(C)C)cc(F)c4c3=O)c2CO)cc(Nc2ccc(C3CCNCC3)cn2)c1=O] |

TABLE I-continued

| Compound | Nomenclature | Structure |
|---|---|---|
| I-62 | 6-tert-Butyl-8-fluoro-2-{2-hydroxymethyl-3-[5-(1'-methanesulfonyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one | 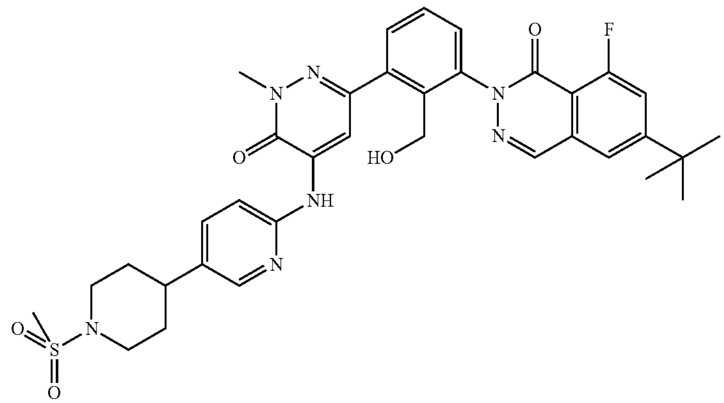 [SMILES: Cn1nc(-c2cccc(-n3ncc4cc(C(C)(C)C)cc(F)c4c3=O)c2CO)cc(Nc2ccc(C3CCN(S(C)(=O)=O)CC3)cn2)c1=O] |
| I-63 | 2-{3-[5-(1'-Acetyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-6-tert-butyl-8-fluoro-2H-phthalazin-1-one | 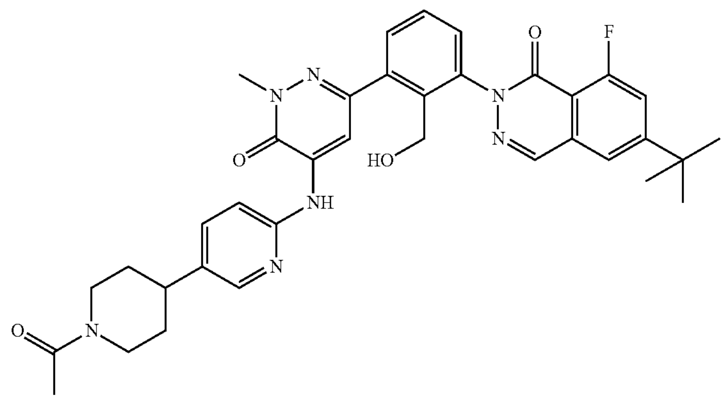 [SMILES: CC(=O)N1CCC(c2ccc(Nc3cc(-c4cccc(-n5ncc6cc(C(C)(C)C)cc(F)c6c5=O)c4CO)nn(C)c3=O)nc2)CC1] |
| I-64 | 6-tert-Butyl-8-fluoro-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridazin-3-yl]-phenyl}-2H-phthalazin-1-one | 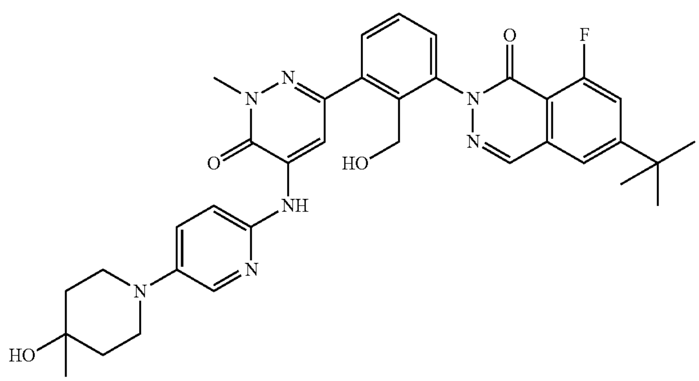 [SMILES: Cn1nc(-c2cccc(-n3ncc4cc(C(C)(C)C)cc(F)c4c3=O)c2CO)cc(Nc2ccc(N3CCC(C)(O)CC3)cn2)c1=O] |
| I-65 | 6-tert-Butyl-8-fluoro-2-{2-hydroxymethyl-3-[5-(4-hydroxy-3,4,5,6-tetrahydro-2H-[1,3']bipyridinyl-6'-ylamino)-1-methyl-6-oxo-1,6-dihydro-pyridazin-3-yl]-phenyl}-2H-phthalazin-1-one | 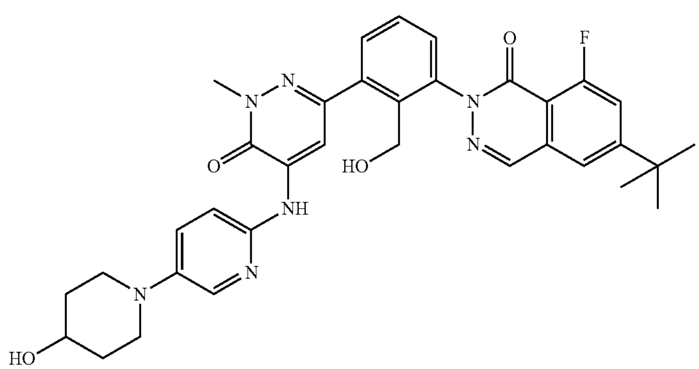 [SMILES: Cn1nc(-c2cccc(-n3ncc4cc(C(C)(C)C)cc(F)c4c3=O)c2CO)cc(Nc2ccc(N3CCC(O)CC3)cn2)c1=O] |

TABLE I-continued

| Compound | Nomenclature | Structure |
|---|---|---|
| I-66 | 6-tert-Butyl-8-fluoro-2-(2-hydroxymethyl-3-{1-methyl-5-[5-((1R,5S)-3-methyl-3,8-diaza-bicyclo[3.2.1]oct-8-yl)-pyridin-2-ylamino]-6-oxo-1,6-dihydro-pyridazin-3-yl}-phenyl)-2H-phthalazin-1-one | 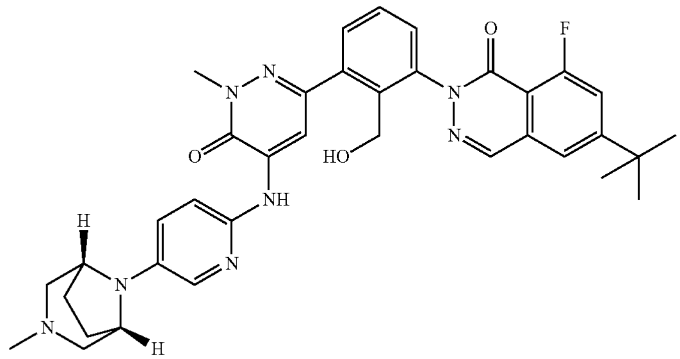 [SMILES: CN1C[C@H]2CC[C@@H](C1)N2c1ccc(Nc2cc(-c3cccc(-n4ncc5cc(C(C)(C)C)cc(F)c5c4=O)c3CO)nn(C)c2=O)nc1] |
| I-67 | 6-tert-Butyl-8-fluoro-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one | 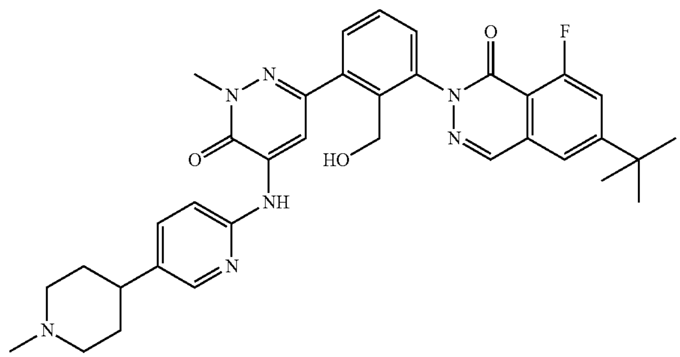 [SMILES: CN1CCC(c2ccc(Nc3cc(-c4cccc(-n5ncc6cc(C(C)(C)C)cc(F)c6c5=O)c4CO)nn(C)c3=O)nc2)CC1] |
| I-68 | 6-tert-Butyl-2-(3-{5-[1-((R)-2,3-dihydroxy-propyl)-1H-pyrazol-3-ylamino]-1-methyl-6-oxo-1,6-dihydro-pyridazin-3-yl}-2-hydroxymethyl-phenyl)-8-fluoro-2H-phthalazin-1-one | 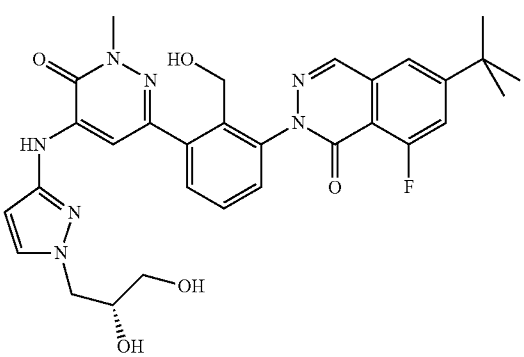 [SMILES: Cn1nc(-c2cccc(-n3ncc4cc(C(C)(C)C)cc(F)c4c3=O)c2CO)cc(Nc2ccn(C[C@@H](O)CO)n2)c1=O] |
| I-69 | 6-tert-Butyl-2-(3-{5-[5-(4-ethyl-piperazin-1-yl)-pyridin-2-ylamino]-1-methyl-6-oxo-1,6-dihydro-pyridazin-3-yl}-2-hydroxymethyl-phenyl)-8-fluoro-2H-phthalazin-1-one | 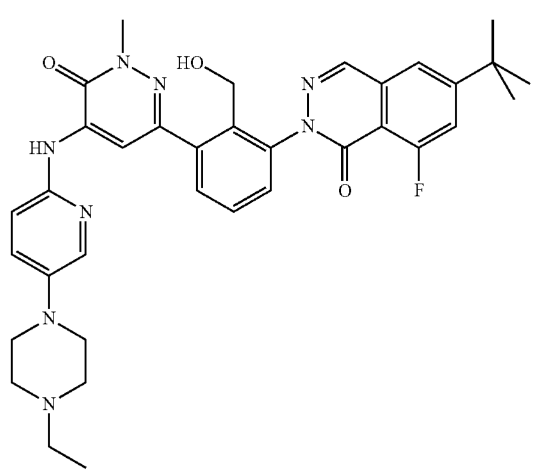 [SMILES: CCN1CCN(c2ccc(Nc3cc(-c4cccc(-n5ncc6cc(C(C)(C)C)cc(F)c6c5=O)c4CO)nn(C)c3=O)nc2)CC1] |

TABLE I-continued

| Compound | Nomenclature | Structure |
|---|---|---|
| I-70 | 6-tert-Butyl-8-fluoro-2-(2-hydroxymethyl-3-{5-[1-(2-hydroxy-2-methyl-propyl)-1H-pyrazol-3-ylamino]-1-methyl-6-oxo-1,6-dihydro-pyridazin-3-yl}-phenyl)-2H-phthalazin-1-one | 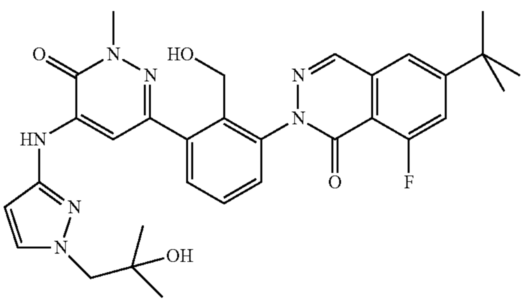 [SMILES: Cn1nc(-c2cccc(-n3ncc4cc(C(C)(C)C)cc(F)c4c3=O)c2CO)cc(Nc2ccn(CC(C)(C)O)n2)c1=O] |
| I-71 | 2-(8-Fluoro-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-isoquinolin-6-yl)-2-methyl-propionitrile | 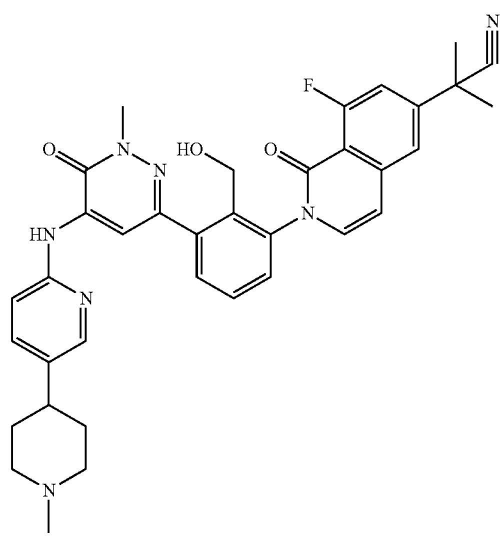 [SMILES: CN1CCC(c2ccc(Nc3cc(-c4cccc(-n5ccc6cc(C(C)(C)C#N)cc(F)c6c5=O)c4CO)nn(C)c3=O)nc2)CC1] |
| I-72 | 2-(2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile | 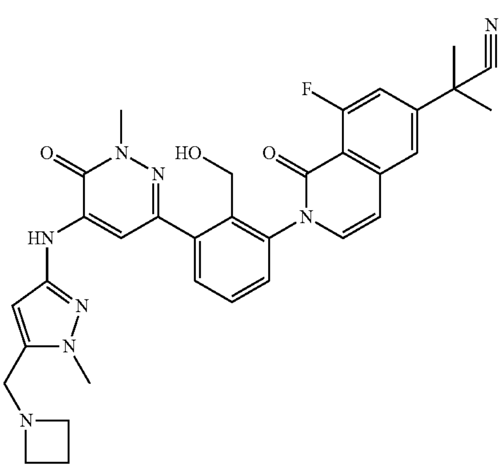 [SMILES: Cn1nc(Nc2cc(-c3cccc(-n4ccc5cc(C(C)(C)C#N)cc(F)c5c4=O)c3CO)nn(C)c2=O)cc1CN1CCC1] |

TABLE I-continued

| Compound | Nomenclature | Structure |
|---|---|---|
| I-73 | 2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2-dihydro-isoquinolin-6-yl]-2-methyl-propionitrile | 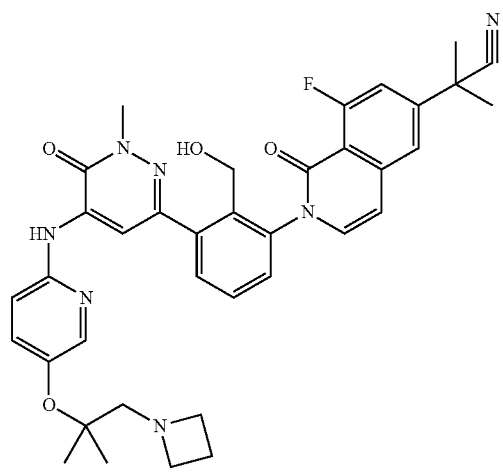 [SMILES: Cn1nc(-c2cccc(-n3ccc4cc(C(C)(C)C#N)cc(F)c4c3=O)c2CO)cc(Nc2ccc(OC(C)(C)CN3CCC3)cn2)c1=O] |
| I-74 | 2-(8-Fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile | 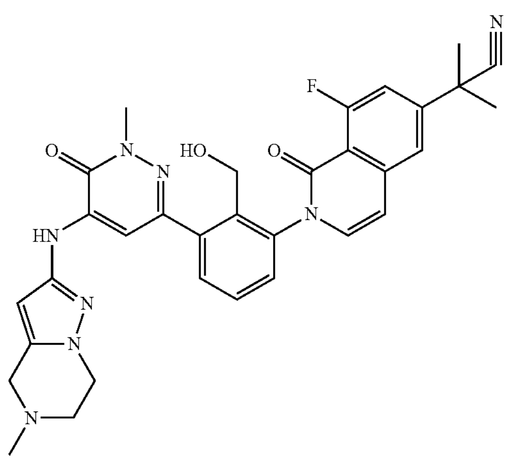 [SMILES: CN1CCn2nc(Nc3cc(-c4cccc(-n5ccc6cc(C(C)(C)C#N)cc(F)c6c5=O)c4CO)nn(C)c3=O)cc2C1] |
| I-75 | 6-(6-{3-[6-(Cyano-dimethyl-methyl)-8-fluoro-1-oxo-1H-isoquinolin-2-yl]-2-hydroxymethyl-phenyl}-2-methyl-3-oxo-2,3-dihydro-pyridazin-4-ylamino)-N,N-dimethyl-nicotinamide | 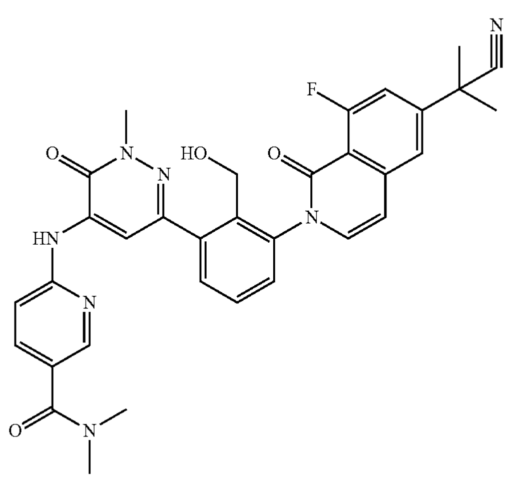 [SMILES: CN(C)C(=O)c1ccc(Nc2cc(-c3cccc(-n4ccc5cc(C(C)(C)C#N)cc(F)c5c4=O)c3CO)nn(C)c2=O)nc1] |

TABLE I-continued

| Compound | Nomenclature | Structure |
|---|---|---|
| I-76 | 2-[8-Fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile | 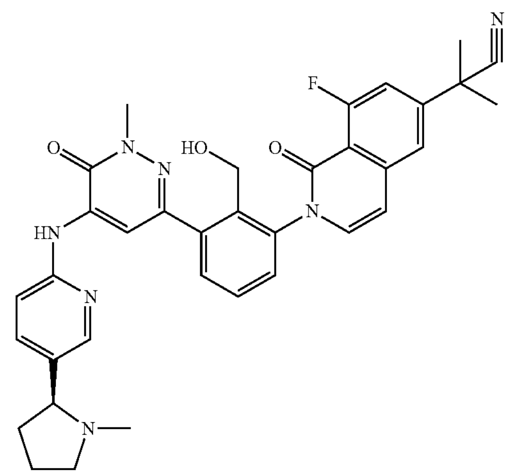 [SMILES: CN1CCC[C@H]1c1ccc(Nc2cc(-c3cccc(-n4ccc5cc(C(C)(C)C#N)cc(F)c5c4=O)c3CO)nn(C)c2=O)nc1] |
| I-77 | 2-[8-Fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile | 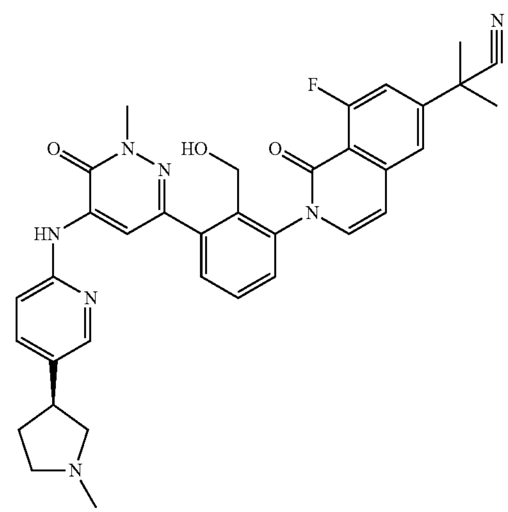 [SMILES: CN1CC[C@@H](c2ccc(Nc3cc(-c4cccc(-n5ccc6cc(C(C)(C)C#N)cc(F)c6c5=O)c4CO)nn(C)c3=O)nc2)C1] |
| I-78 | 2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile | 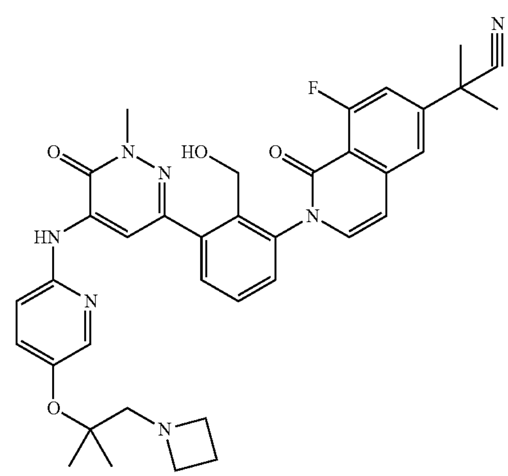 [SMILES: Cn1nc(-c2cccc(-n3ccc4cc(C(C)(C)C#N)cc(F)c4c3=O)c2CO)cc(Nc2ccc(OC(C)(C)CN3CCC3)cn2)c1=O] |

TABLE I-continued

| Compound | Nomenclature | Structure |
|---|---|---|
| I-79 | 2-(8-Fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile | 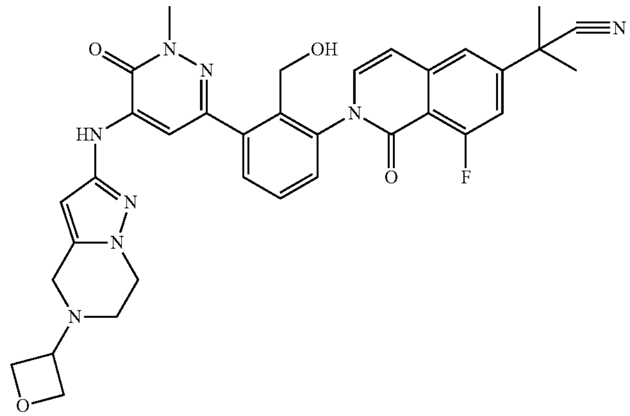 [SMILES: Cn1nc(-c2cccc(-n3ccc4cc(C(C)(C)C#N)cc(F)c4c3=O)c2CO)cc(Nc2cc3n(n2)CCN(C2COC2)C3)c1=O] |
| I-80 | 6-tert-Butyl-8-fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one | 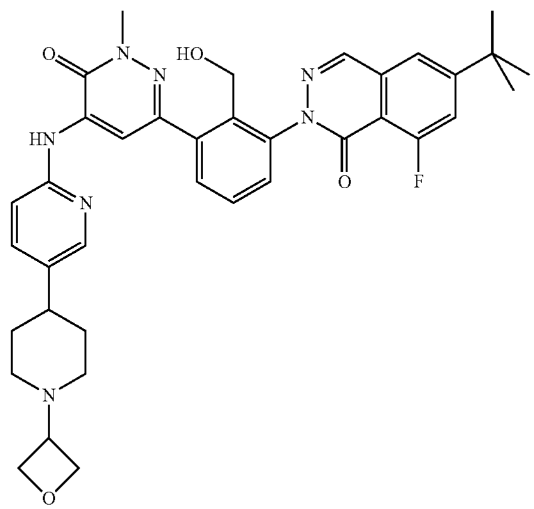 [SMILES: Cn1nc(-c2cccc(-n3ncc4cc(C(C)(C)C)cc(F)c4c3=O)c2CO)cc(Nc2ccc(C3CCN(C4COC4)CC3)cn2)c1=O] |
| I-81 | 2-(8-Fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-1-oxo-1,2-dihydro-isoquinolin-6-yl)-2-methyl-propionitrile | 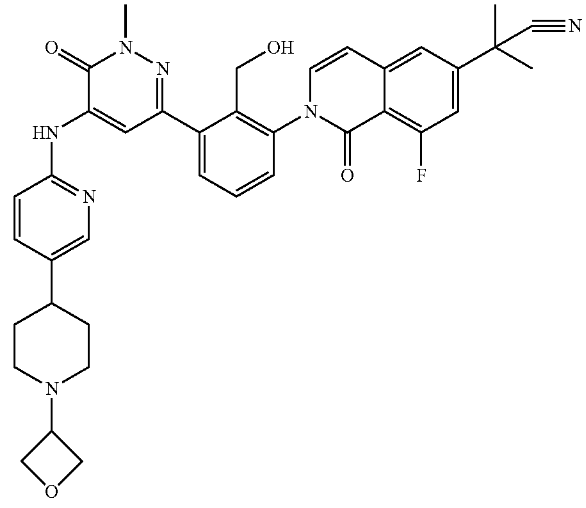 [SMILES: Cn1nc(-c2cccc(-n3ccc4cc(C(C)(C)C#N)cc(F)c4c3=O)c2CO)cc(Nc2ccc(C3CCN(C4COC4)CC3)cn2)c1=O] |

TABLE I-continued

| Compound | Nomenclature | Structure |
|---|---|---|
| I-82 | 6-tert-Butyl-2-{3-[5-(5-ethyl-4,5,6,7-tetrahydro-pyrazolo[1,5-a]pyrazin-2-ylamino)-1-methyl-6-oxo-1,6-dihydro-pyridazin-3-yl]-2-hydroxymethyl-phenyl}-8-fluoro-2H-phthalazin-1-one | 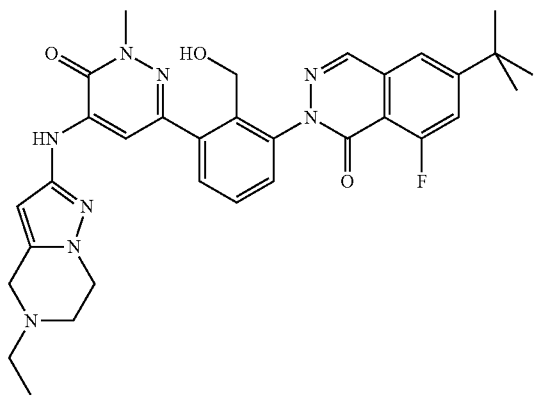 [SMILES: CCN1CCn2nc(Nc3cc(-c4cccc(-n5ncc6cc(C(C)(C)C)cc(F)c6c5=O)c4CO)nn(C)c3=O)cc2C1] |
| I-83 | 2-(2-{3-[5-(5-Ethyl-4,5,6,7-tetrahydro-pyrazolo[1,5-a]pyrazin-oxo-1,6-dihydro-pyridazin-3-yl]-2-hydroxymethyl-phenyl}-8-fluoro-1-oxo-1,2-dihydro-isoquinolin-6-yl)-2-methyl-propionitrile | 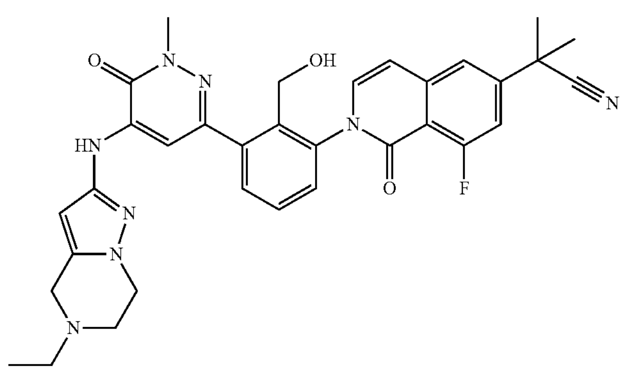 [SMILES: CCN1CCn2nc(Nc3cc(-c4cccc(-n5ccc6cc(C(C)(C)C#N)cc(F)c6c5=O)c4CO)nn(C)c3=O)cc2C1] |
| I-84 | 6-tert-Butyl-2-[3-(5-{5-[(1S,4S)-1-(2,5-diaza-bicyclo[2.2.1]hept-2-yl)methyl]-pyridin-2-ylamino}-1-methyl-6-oxo-1,6-dihydro-pyridazin-3-yl)-2-hydroxymethyl-phenyl]-8-fluoro-2H-phthalazin-1-one | 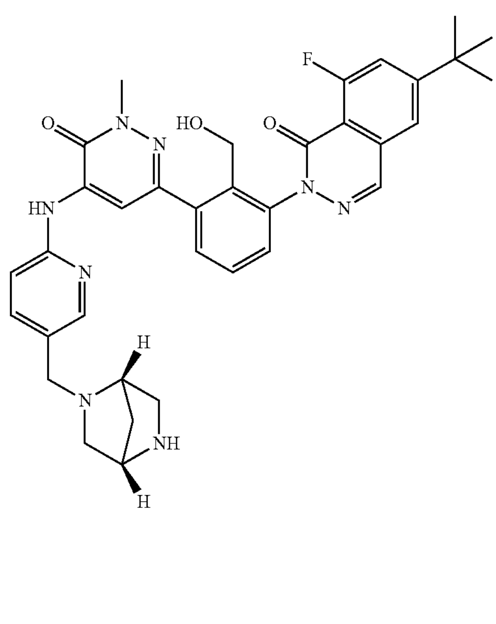 [SMILES: Cn1nc(-c2cccc(-n3ncc4cc(C(C)(C)C)cc(F)c4c3=O)c2CO)cc(Nc2ccc(CN3C[C@@H]4C[C@H]3CN4)cn2)c1=O] |

TABLE I-continued

| Compound | Nomenclature | Structure |
|---|---|---|
| I-85 | 6-tert-Butyl-8-fluoro-2-(2-hydroxymethyl-3-{5-[5-(4-hydroxy-4-methyl-piperidin-1-ylmethyl)-pyridin-2-ylamino]-1-methyl-6-oxo-1,6-dihydro-pyridazin-3-yl}-phenyl)-2H-phthalazin-1-one | 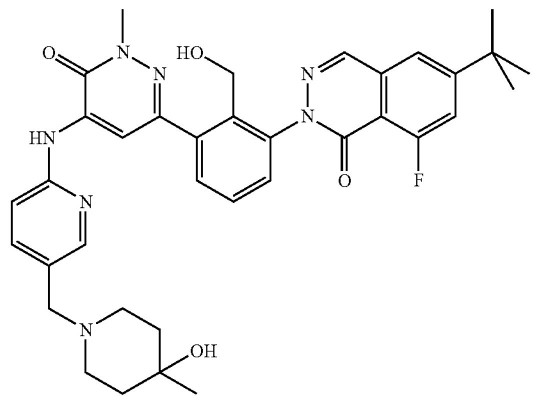 [SMILES: Cn1nc(-c2cccc(-n3ncc4cc(C(C)(C)C)cc(F)c4c3=O)c2CO)cc(Nc2ccc(CN3CCC(C)(O)CC3)cn2)c1=O] |
| I-86 | 4-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridin-3-yl)-piperazine-1-carboxylic acid ethyl ester | 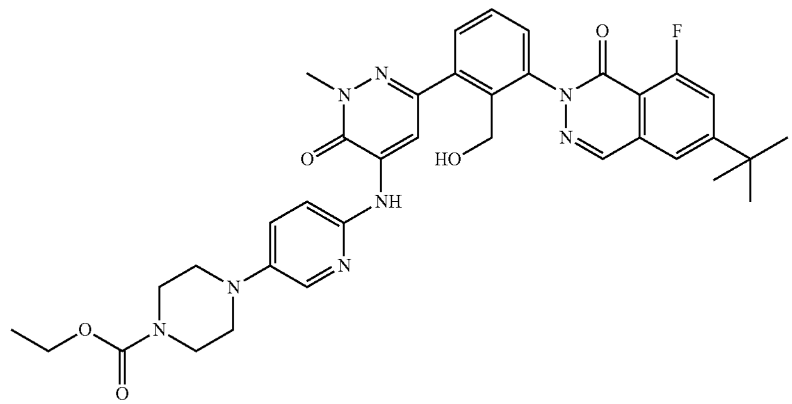 [SMILES: CCOC(=O)N1CCN(c2ccc(Nc3cc(-c4cccc(-n5ncc6cc(C(C)(C)C)cc(F)c6c5=O)c4CO)nn(C)c3=O)nc2)CC1] |
| I-87 | 8-Fluoro-6-(2-fluoro-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one | 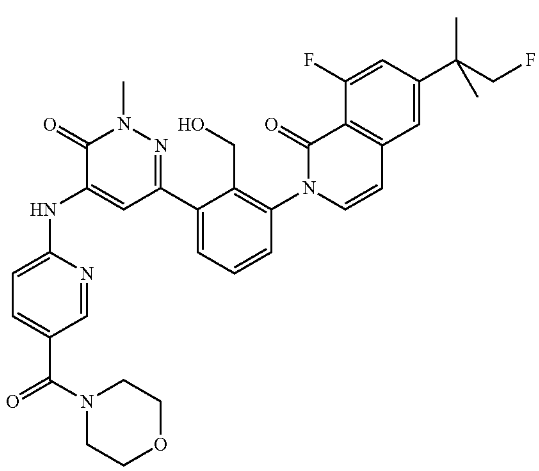 [SMILES: Cn1nc(-c2cccc(-n3ccc4cc(C(C)(C)CF)cc(F)c4c3=O)c2CO)cc(Nc2ccc(C(=O)N3CCOCC3)cn2)c1=O] |

TABLE I-continued

| Compound | Nomenclature | Structure |
|---|---|---|
| I-88 | 6-tert-Butyl-8-fluoro-2-(2-hydroxymethyl-3-{1-methyl-5-[5-((1S,4S)-5-methyl-2,5-diaza-bicyclo[2.2.1]hept-2-yl)-pyrazin-2-ylamino]-6-oxo-1,6-dihydro-pyridazin-3-yl}-phenyl)-2H-phthalazin-1-one | 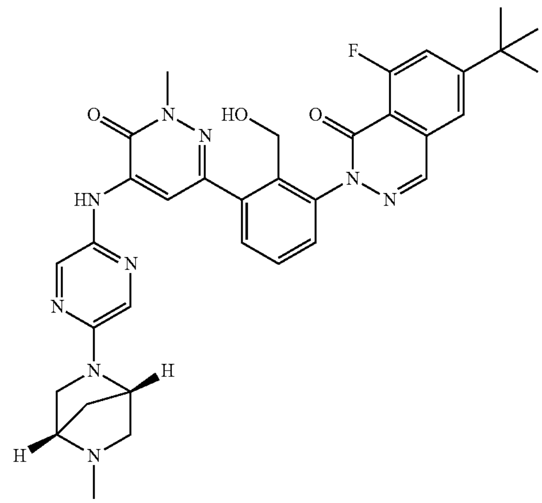 [SMILES: CN1C[C@@H]2C[C@H]1CN2c1cnc(Nc2cc(-c3cccc(-n4ncc5cc(C(C)(C)C)cc(F)c5c4=O)c3CO)nn(C)c2=O)cn1] |
| I-89 | 2-[8-Fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile | 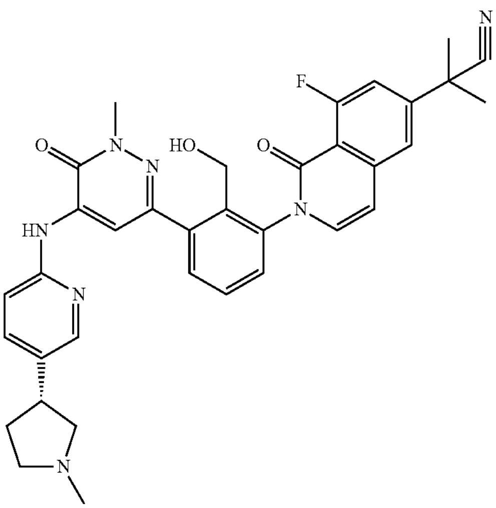 [SMILES: CN1CC[C@H](c2ccc(Nc3cc(-c4cccc(-n5ccc6cc(C(C)(C)C#N)cc(F)c6c5=O)c4CO)nn(C)c3=O)nc2)C1] |
| I-90 | 6-tert-Butyl-8-fluoro-2-(2-hydroxymethyl-3-{1-methyl-6-oxo-5-[1'-(2,2,2-trifluoro-ethyl)-1',2',3',4',5',6'-hexahydro-[3,4']bipyridinyl-6-ylamino]-1,6-dihydro-pyridazin-3-yl}-phenyl)-2H-phthalazin-1-one | 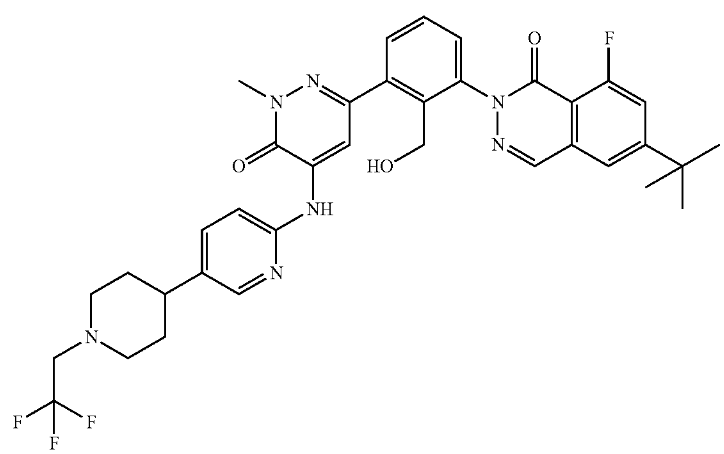 [SMILES: Cn1nc(-c2cccc(-n3ncc4cc(C(C)(C)C)cc(F)c4c3=O)c2CO)cc(Nc2ccc(C3CCN(CC(F)(F)F)CC3)cn2)c1=O] |

Synthesis

General Synthetic Schemes

This application is related to U.S. patent application Ser. No. 12/711,312, filed on Feb. 24, 2010, the disclosure of which is incorporated herein by reference in its entirety.

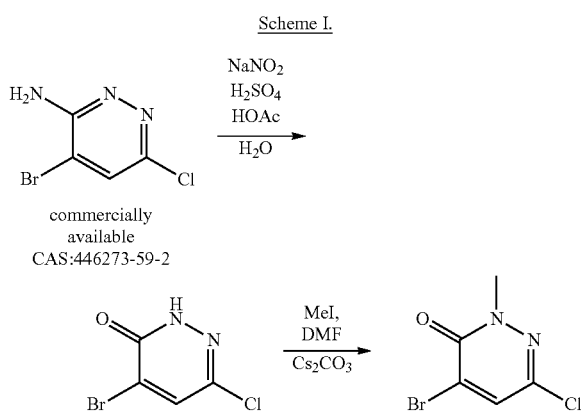

Scheme I.

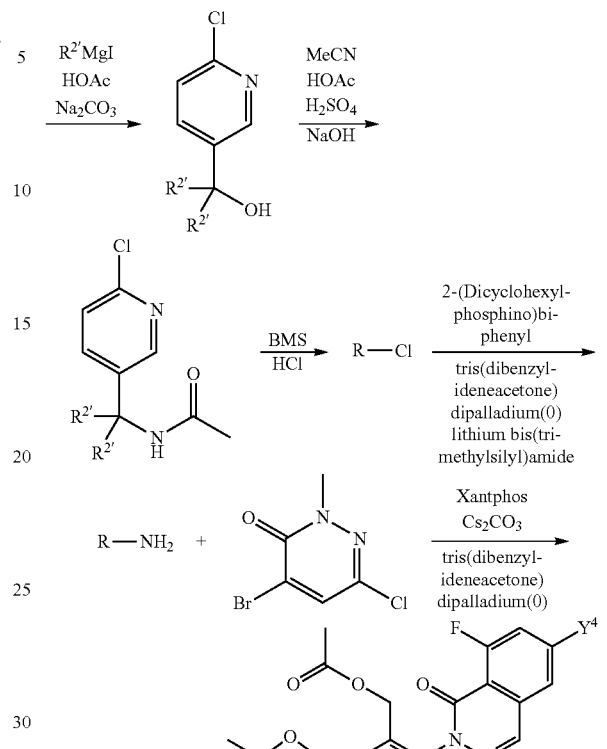

Scheme III.

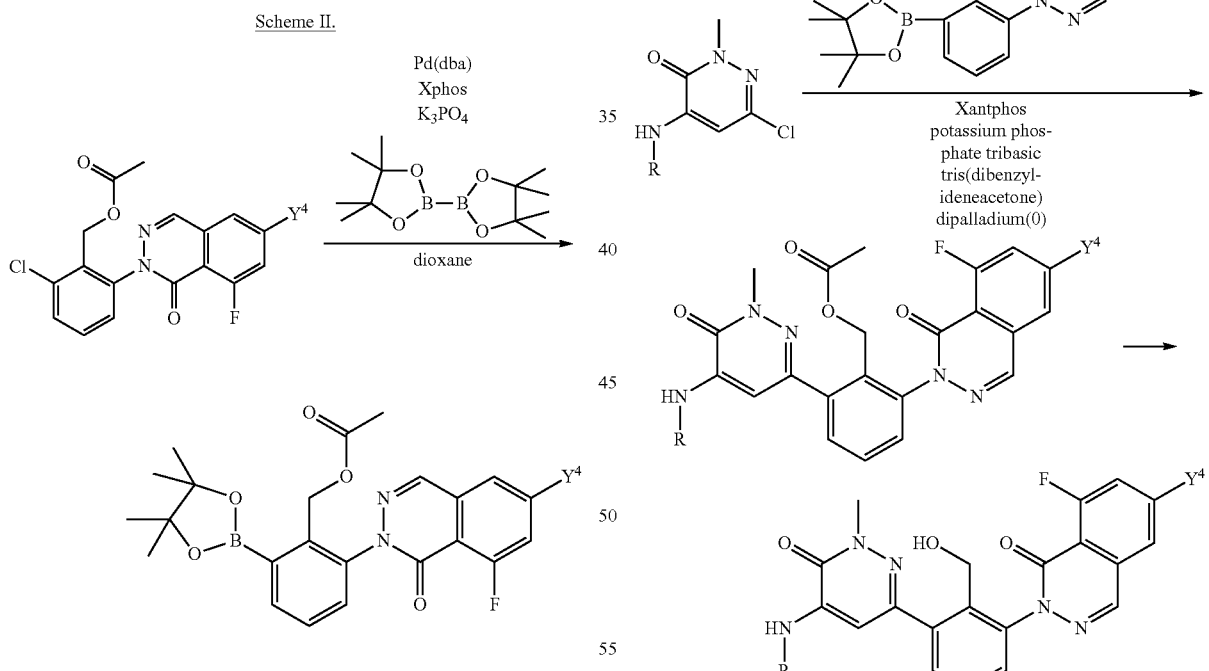

Scheme II.

Wherein $Y^4$ can be $Y^{4a}$, $Y^{4b}$, $Y^{4c}$, or $Y^{4d}$; $Y^{4a}$ can be H or halogen; $Y^{4b}$ can be lower alkyl, optionally substituted with one or more substituents selected from the group consisting of lower haloalkyl, halogen, hydroxy, amino, cyano, and lower alkoxy; $Y^{4c}$ can be lower cycloalkyl, optionally substituted with one or more substituents selected from the group consisting of lower alkyl, lower haloalkyl, halogen, hydroxy, amino, cyano, and lower alkoxy; and $Y^{4d}$ can be amino, optionally substituted with one or more lower alkyl, alkoxy lower alkyl, or hydroxy lower alkyl.

Wherein R can be H, —$R^1$, —$R^1$—$R^2$—$R^3$, —$R^1$—$R^3$, or —$R^2$—$R^3$; $R^1$ can be aryl, heteroaryl, bicyclic heteroaryl, cycloalkyl, or heterocycloalkyl, each of which can be optionally substituted with one or more lower alkyl, hydroxy, hydroxy lower alkyl, lower alkoxy, halo, nitro, amino, amido, cyano, oxo, or lower haloalkyl; $R^2$ can be —C(=O), —C(=O)O, —C(=O)NR$^{2'}$, —NHC(=O)O, —C(R$^{2'}$)$_2$, —O, —S, —C(=NH)NR$^{2'}$, or —S(=O)$_2$; each $R^{2'}$ can be independently H or lower alkyl; $R^3$ can be H or $R^4$; $R^4$ can be lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl each of which can be optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring.

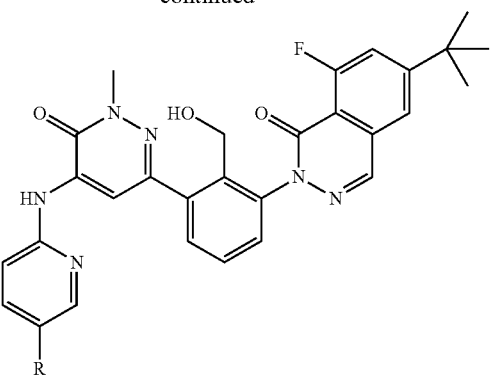

Wherein R can be —$R^2$—$R^3$ or —$R^3$; $R^2$ can be —C(=O), —C(=O)O, —C(=O)$NR^{2'}$, —NHC(=O)O, —C($R^{2'}$)$_2$, —O, —S, —C(=NH)$NR^{2'}$, or —S(=O)$_2$; each $R^{2'}$ can be independently H or lower alkyl; $R^3$ can be H or $R^4$; $R^4$ can be lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl or bicyclic spiroheterocycloalkyl, each of which can be optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring.

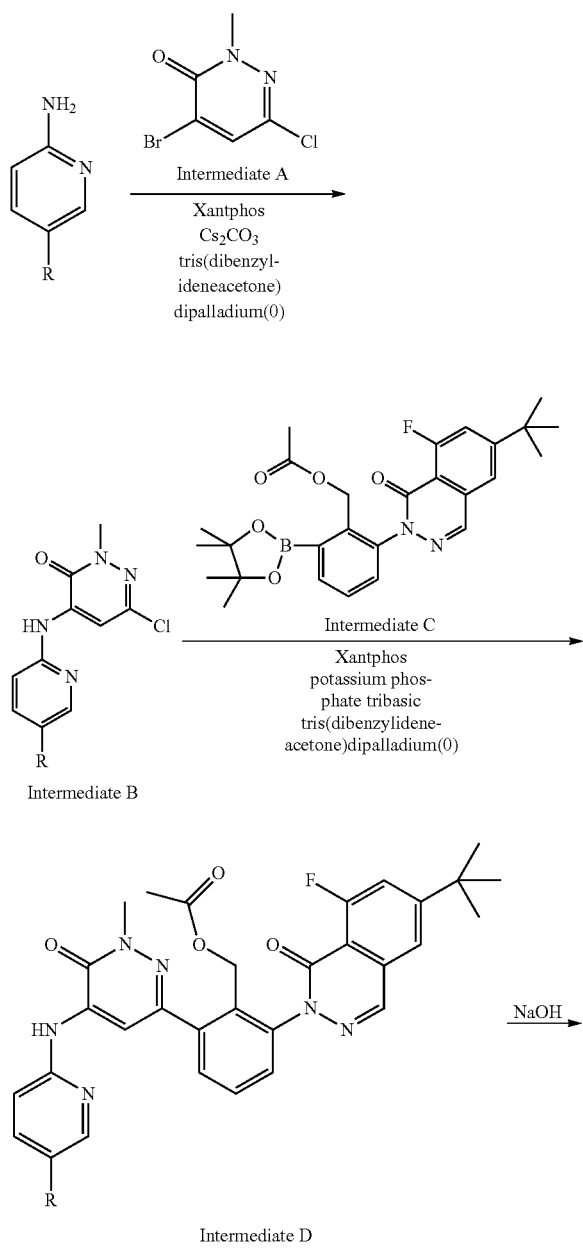

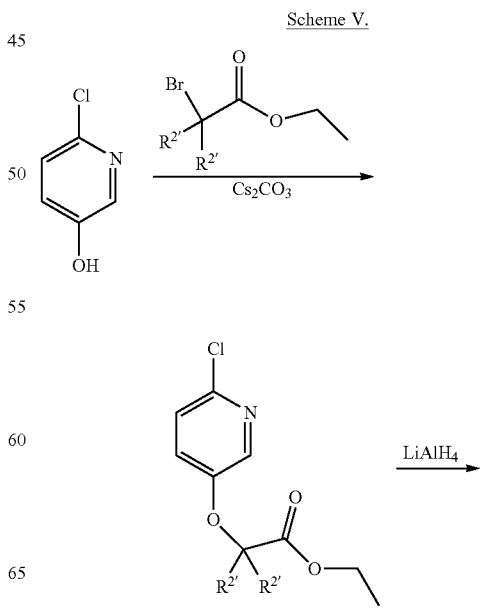

-continued

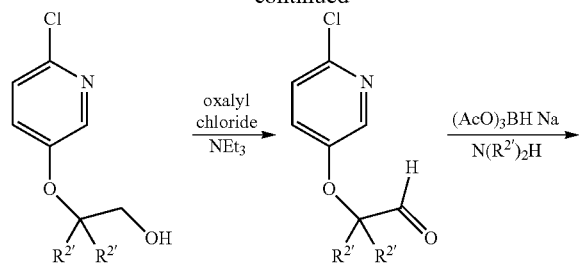

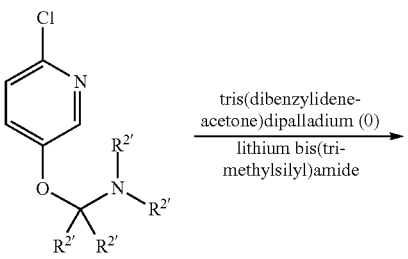

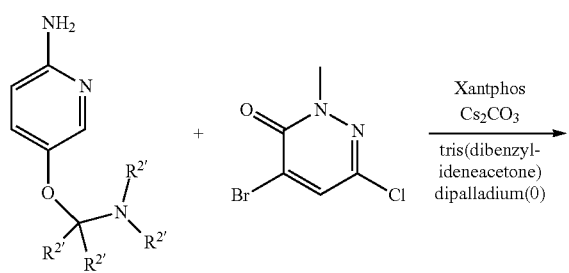

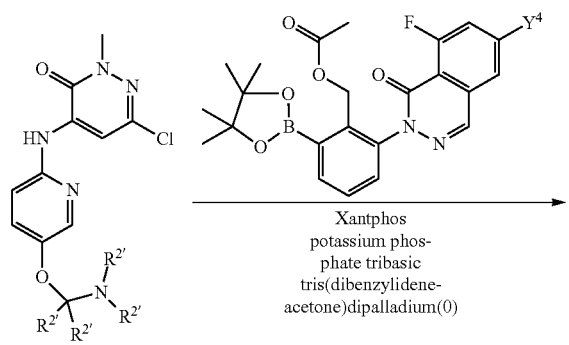

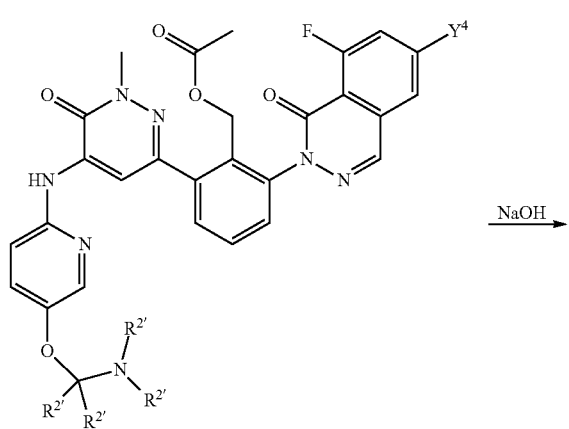

-continued

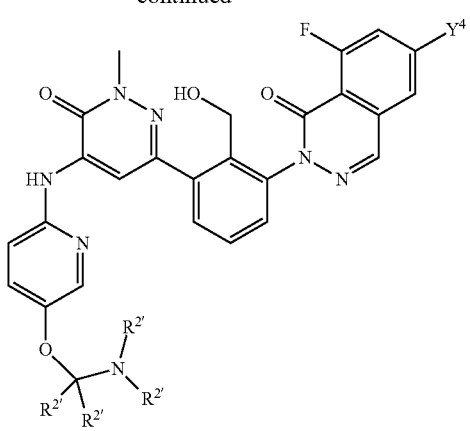

Wherein each $R^{2'}$ can be independently H or lower alkyl; $Y^4$ can be $Y^{4a}$, $Y^{4b}$, $Y^{4c}$, or $Y^{4d}$; $Y^{4a}$ can be H or halogen; $Y^{4b}$ can be lower alkyl, optionally substituted with one or more substituents selected from the group consisting of lower haloalkyl, halogen, hydroxy, amino, cyano, and lower alkoxy; $Y^{4c}$ can be lower cycloalkyl, optionally substituted with one or more substituents selected from the group consisting of lower alkyl, lower haloalkyl, halogen, hydroxy, amino, cyano, and lower alkoxy; and $Y^{4d}$ can be amino, optionally substituted with one or more lower alkyl, alkoxy lower alkyl, or hydroxy lower alkyl.

Scheme VI.

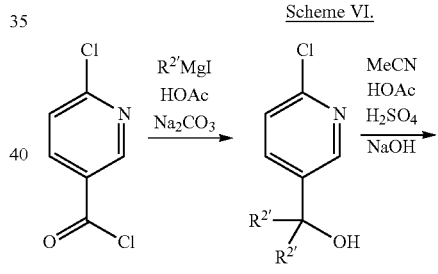

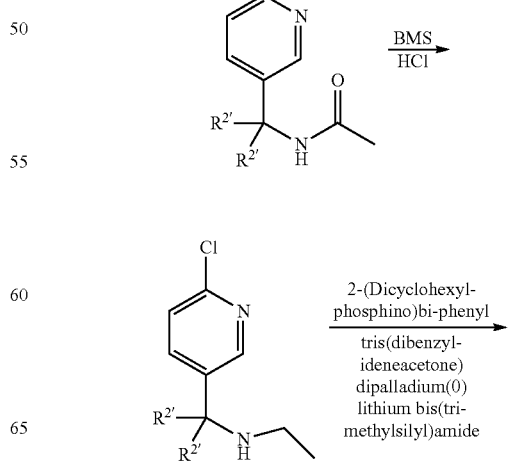

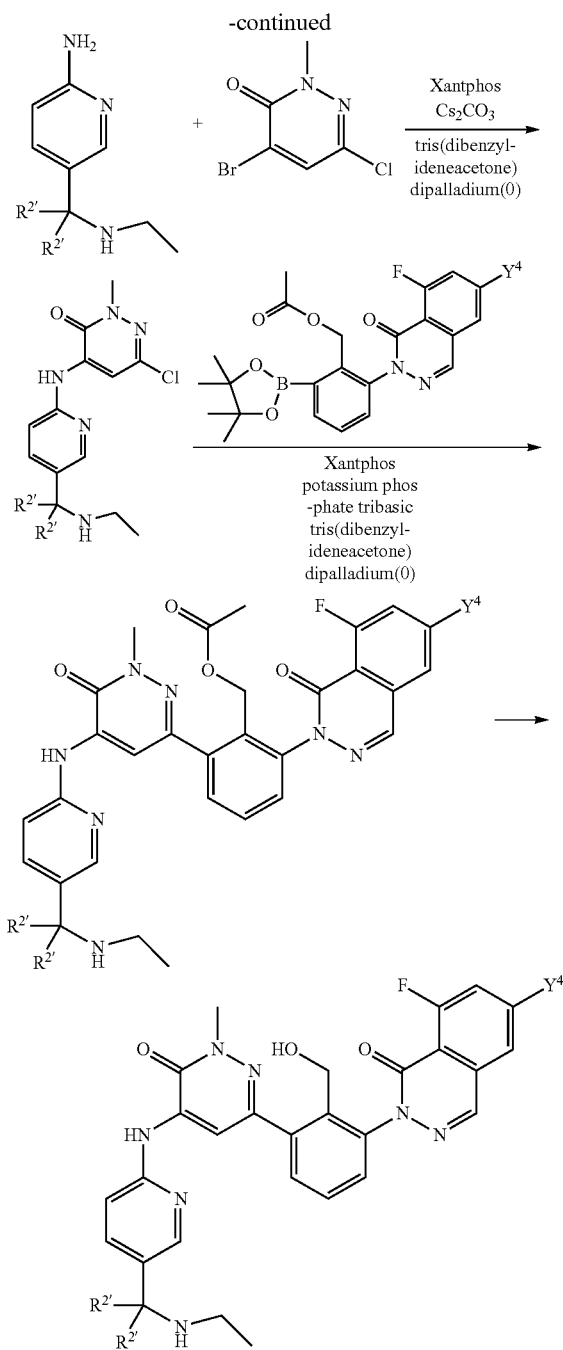

Wherein each R[2'] can be independently H or lower alkyl; Y[4] can be Y[4a], Y[4b], Y[4c], or Y[4d]; Y[4a] can be H or halogen; Y[4b] can be lower alkyl, optionally substituted with one or more substituents selected from the group consisting of lower haloalkyl, halogen, hydroxy, amino, cyano, and lower alkoxy; Y[4c] can be lower cycloalkyl, optionally substituted with one or more substituents selected from the group consisting of lower alkyl, lower haloalkyl, halogen, hydroxy, amino, cyano, and lower alkoxy; and Y[4d] can be amino, optionally substituted with one or more lower alkyl, alkoxy lower alkyl, or hydroxy lower alkyl.

Pharmacological Activity

The pyridazinone derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11): 1837-1852)

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLES

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), hexanes (hex), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$-(mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-$BuMe_2Si$ (TBDMS), tetra-n-butylammonium fluoride (TBAF), triethylamine (TEA or $Et_3N$), 2,2,6,6-tetramethylpiperidine 1-oxyl (TEMPO), triflate or $CF_3SO_2$-(Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Preparation of I-1

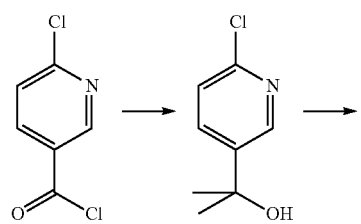

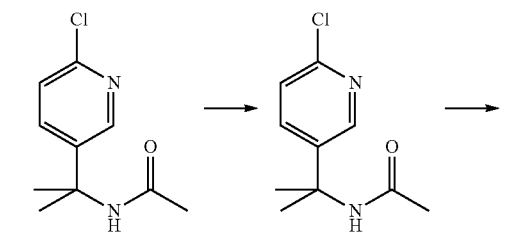

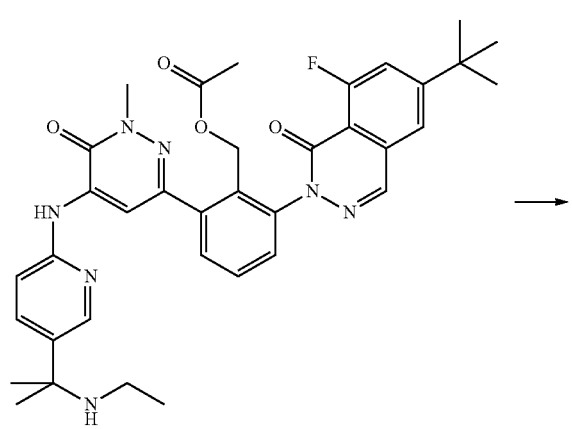

I-1

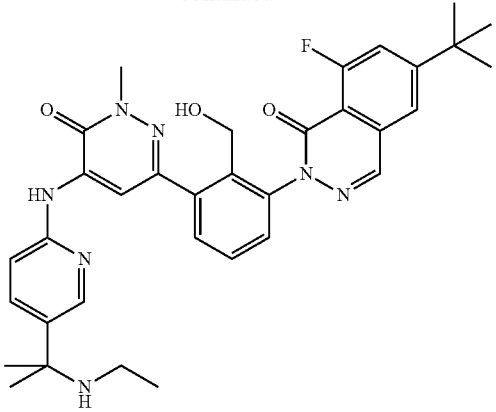

Step 1. Preparation of 2-(6-chloropyridin-3-yl)propan-2-ol

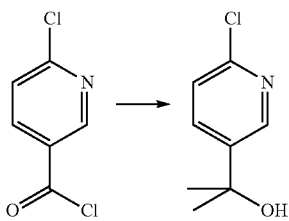

A solution of 6-chloronicotinoyl chloride (38.037 g, 216 mmol, Eq: 1.00) in anhydrous diethyl ether (200 ml) was added dropwise to a stirred 3 M methylmagnesium iodide solution (158 ml, 475 mmol, Eq: 2.2) at room temperature. After the addition the reaction mixture was refluxed for 3 hours. Reaction was quenched by pouring it to a stirred mixture of ice/200 ml acetic acid; sodium bicarbonate was added until pH 8; extracted with diethyl ether; washed with brine; dried over sodium sulfate; filtered; concentrated to give a yellow solid (30.15 g, 0.175 mol) MS (H+)=172.1

Step 2. Preparation of N-(2-(6-chloropyridin-3-yl)propan-2-yl)acetamide

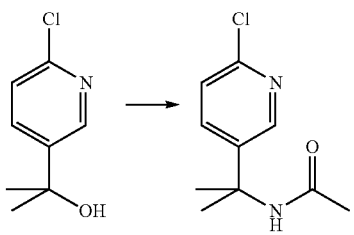

2-(6-chloropyridin-3-yl)propan-2-ol (637 mg, 3.71 mmol, Eq: 1.00) was dissolved in acetonitrile (5 ml). Acetic acid (2.9 g, 2.76 ml, 48.3 mmol, Eq: 13) was added at room temperature and cooled after the addition to 0° C. Sulfuric acid, concentrated (5.1 g, 2.77 ml, 52.0 mmol, Eq: 14) was added dropwise to the solution, then allowed to warm up to room temperature and stirred over night. The reaction mixture was poured into ice, concentrated NaOH solution was added until pH was basic; extracted with ethyl acetate; org. phase was washed with brine; dried with sodium sulfate; filtered to give a yellow solid. This residue was triturated with ethyl acetate and a little bit hexane. Resulting precipitate was filtered off to give a white solid (338 mg, 1.59 mmol).

MS (H+)=213.1

Step 3. Preparation of 2-(6-chloropyridin-3-yl)-N-ethylpropan-2-amine

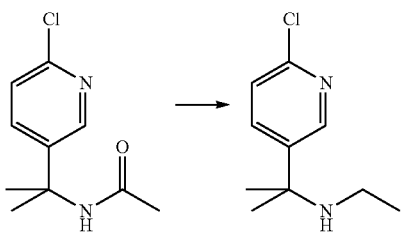

N-(2-(6-chloropyridin-3-yl)propan-2-yl)acetamide (11.3 g, 53.1 mmol, Eq: 1.00) was dissolved in anhydrous THF (350 ml) and refluxed. BMS (2M in THF) (53.1 ml, 106 mmol, Eq: 2) was added dropwise to the solution and refluxed over night. Conc. HCl solution (15 ml) was gently added to the refluxed reaction mixture and stirred for 1 hr. The reaction mixture was concentrated in vacuo.

The crude material was dissolved in dichloromethane/1 M HCl solution. Water phase was collected and treated with saturated sodium carbonate solution; extracted with dichloromethane; org. phase was dried with sodium sulfate; filtered; concentrated. Crude product was purified by silica gel chromatography to give a yellow gum (8.03 g, 40.4 mmol). It was used as is for the next step.

Step 4. Preparation of 5-(1-Ethylamino-1-methyl-ethyl)-pyridin-2-ylamine

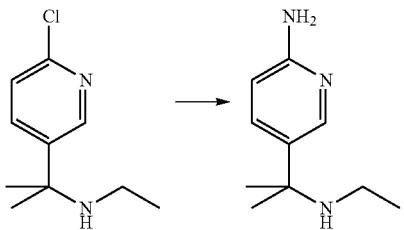

2-(6-chloropyridin-3-yl)-N-ethylpropan-2-amine (5 g, 25.2 mmol, Eq: 1.00) was dissolved in tetrahydrofuran (130 ml). 2-(Dicyclohexylphosphino)biphenyl (1.76 g, 5.03 mmol, Eq: 0.2), then tris(dibenzylideneacetone)dipalladium (0) (2.3 g, 2.52 mmol, Eq: 0.1) were added under an argon atmosphere. Finally 1 M lithium bis(trimethylsilyl)amide in THF (75.5 ml, 75.5 mmol, Eq: 3) was added dropwise. The reaction mixture was stirred in a sealed flask at 90° C. overnight.

The reaction mixture was poured into sat NH4Cl (200 ml) and extracted with DCM (4×50 mL). The crude material was purified by flash chromatography (silica gel, 40 g, 0% to 15% MeOH (contains 0.5% NH4OH) in DCM to give a white solid (2.6 g, 14.5 mmol)

¹H NMR (300 MHz, CHLOROFORM-d) δ ppm 1.06 (t, J=1.00 Hz, 3H) 1.44 (s, 6H) 1.86 (s, 1H) 2.37 (q, J=1.00 Hz, 2H) 4.39 (s, 2H) 6.49 (d, J=1.00 Hz, 1H) 7.55 (d, J=1.00 Hz, 1H) 8.08 (s, 1H)

Step 5. Preparation of 6-chloro-4-[5-(1-ethylamino-1-methyl-ethyl)-pyridin-2-ylamino]-2-methyl-2H-pyridazin-3-one

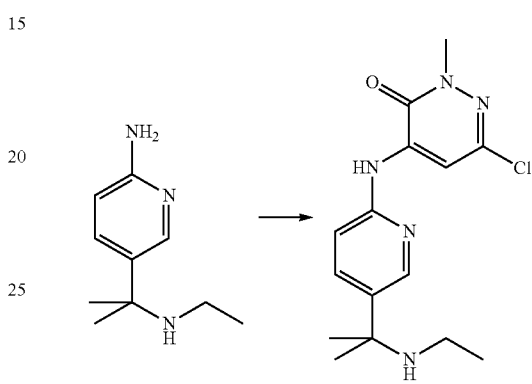

This reaction was carried out under similar conditions to those described in step 6 of the preparation of 1-6. After work up the product was purified by preparative HPLC on silica gel, using a gradient of 2% to 8% methanol/methylene chloride. This provided the desired product as a yellow powder (328 mg). (M+H)⁺=322 m/e.

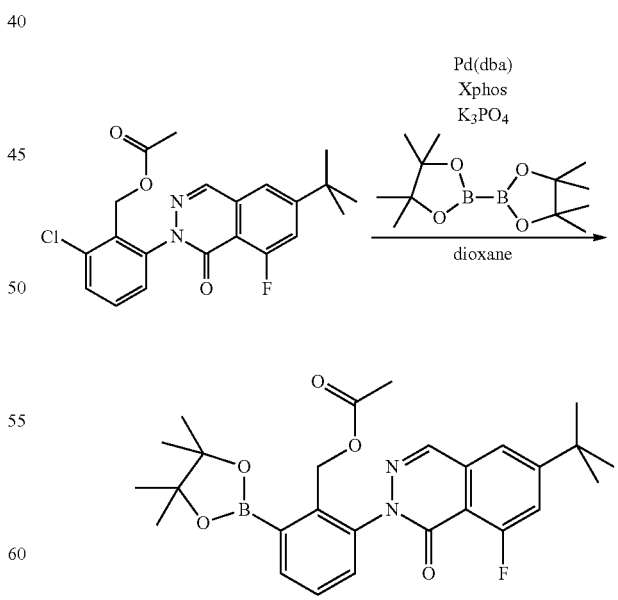

In a microwave reaction vial, added acetic acid 2-(6-tert-butyl-8-fluoro-1-oxo-1H-phthalazin-2-yl)-6-chloro-benzyl ester (329 mg, 0.818 mmol), bis-pinaco-diboron (416 mg, 1.637 mmol), KOAc (241 mg, 2.454 mmol) and Xphos (39 mg, 0.0818 mmol) and dioxane (4 mL). Bubble argon through for 15 min and then add Pd(dba)2 (24 mg, 0.0409 mmol). Seal the tube and heat it to 60° C. for 18 hrs. The reaction mixture was then diluted with EtOAc (5 mL) and washed with NaHCO₃ (concentrated) (1×10 mL) and water (10 mL). The organic phase was then concentrated and purified on silica gel column with 25% EtOAc in Hex to give acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester as an yellow oil (330 mg, 81%).

Step 6. Preparation of acetic acid 2-(6-tert-butyl-8-fluoro-1-oxo-1H-phthalazin-2-yl)-6-{5-[5-(1-ethylamino-1-methyl-ethyl)-pyridin-2-ylamino]-1-methyl-6-oxo-1,6-dihydro-pyridazin-3-yl}-benzyl ester

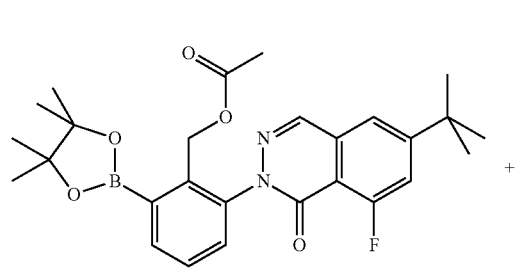

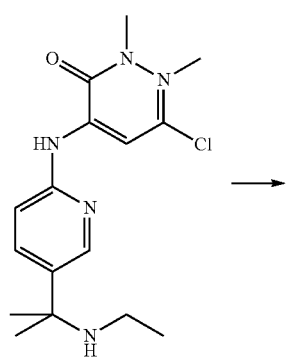

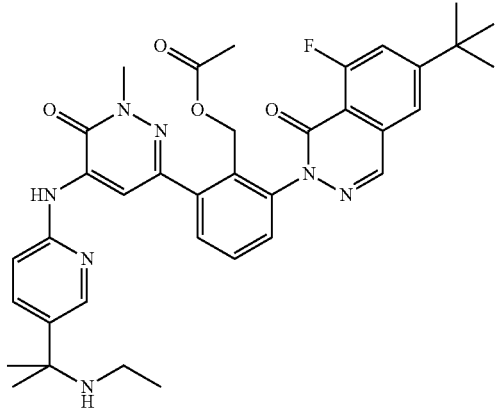

This reaction was carried out under similar conditions to those in step 7 of the preparation of I-6. After work up the product was purified by preparative TLC (3 plates), eluting with 10% methanol/methylene chloride. This provided the desired product (together with some des-acetyl product) as an orange-yellow foam (303 mg). (M+H)⁺=654 (612) m/e.

Example 1

Step 7. Preparation of 6-tert-butyl-2-(3-{5-[5-(1-ethylamino-1-methyl-ethyl)-pyridin-2-ylamino]-1-methyl-6-oxo-1,6-dihydro-pyridazin-3-yl}-2-hydroxymethyl-phenyl)-8-fluoro-2H-phthalazin-1-one

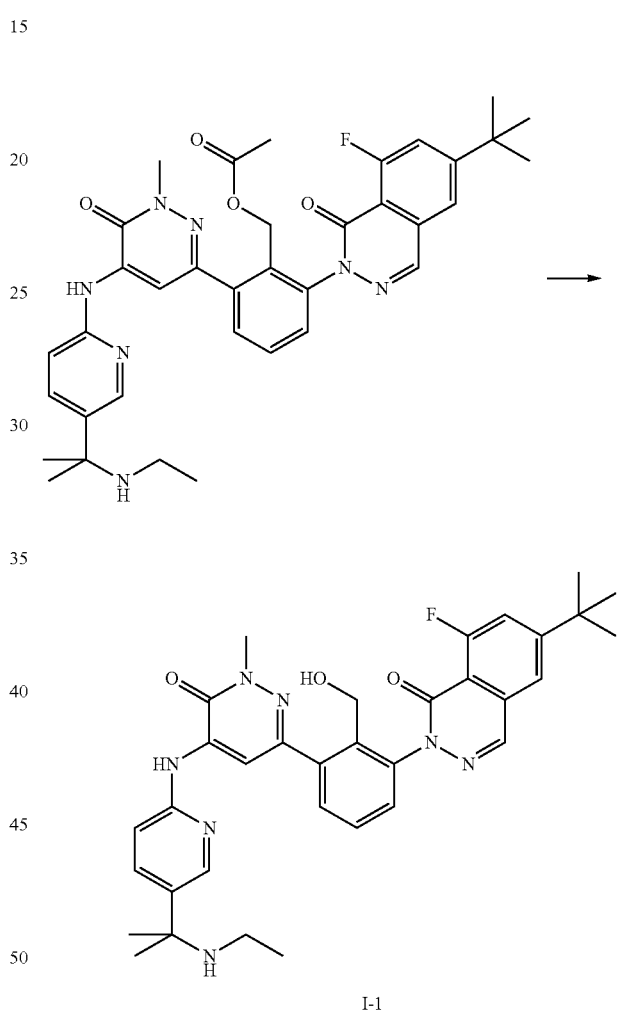

I-1

This reaction was carried out under similar conditions to those in step 8 of the preparation of I-6. After work up the product was purified by preparative HPLC on silica gel, using a gradient of 2% to 10% methanol*/methylene chloride (*methanol contains 2% ammonium hydroxide). The product was collected and further purified by crystallization from hot iso-propylacetate/hexanes. A crystalline product was collected by filtration, providing the desired product as a light yellow-white powder (341 mg). MP=229-233*C. (M+H)⁺=612 m/e. Page 079. ¹H NMR (300 MHz, CHLOROFORM-d) δ ppm 1.05 (t, J=7.18 Hz, 3H) 1.32-1.59 (m, 15H) 2.38 (q, J=7.20 Hz, 2H) 3.81-4.05 (m, 4H) 4.43 (s, 2H) 6.93 (d, J=8.31 Hz, 1H) 7.39-7.82 (m, 6H) 8.28 (d, J=2.64 Hz, 2H) 8.40 (d, J=2.27 Hz, 1H) 8.64 (s, 1H).

Preparation of I-2

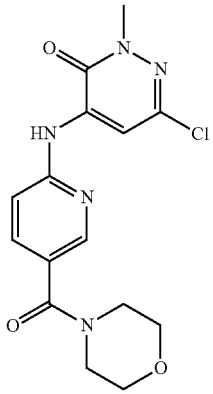 [SMILES: Cn1nc(Cl)cc(Nc2ccc(C(=O)N3CCOCC3)cn2)c1=O]

6-Chloro-2-methyl-4-[5-(morpholine-4-carbonyl)-pyridin-2-ylamino]-2H-pyridazin-3-one 6-aminopyridin-3-yl-morpholino-methanone (800 mg, 3.86 mmol, Eq: 1.00), 4-bromo-6-chloro-2-methylpyridazin-3(2H)-one (1 g, 4.48 mmol, Eq: 1.16), cesium carbonate (4.4 g, 13.5 mmol, Eq: 3.5) and xantphos (335 mg, 579 μmol, Eq: 0.15) were suspended in dioxane (40 ml). The suspension was degassed with argon. Finally $Pd_2(dba)_3$ (265 mg, 290 μmol, Eq: 0.075) was added and the reaction mixture was stirred at 90° C. over night under an argon atmosphere. The reaction mixture was allowed to cool to room temperature, and then filtered over celite. Filtrate was concentrated in vacuo to give a light brown solid. The crude material was purified by flash chromatography (silica gel, 110 g, 0% to 10% MeOH in (EtOAc 1:1 Hex) to afford a light yellow solid (408 mg, 1.17 mmol). MS ($H^+$)=350.0 $^1$H NMR (300 MHz, CHLOROFORM-d) δ ppm 3.60-3.80 (m, 8H) 3.83 (s, 3H) 6.96 (d, J=8.69 Hz, 1H) 7.77 (dd, J=8.50, 2.45 Hz, 1H) 8.35-8.44 (m, 2H) 8.47 (d, J=2.27 Hz, 1H)

Example 2

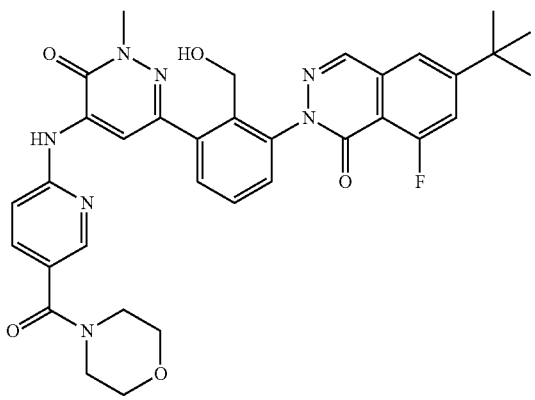

I-2

6-tert-Butyl-8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-phthalazin-1-one 6-chloro-2-methyl-4-(5-(morpholine-4-carbonyl)pyridin-2-ylamino)pyridazin-3(2H)-one (200 mg, 572 μmol, Eq: 1.00), 2-(6-tert-butyl-8-fluoro-1-oxophthalazin-2(1H)-yl)-6-(4,4,5,5-tetramethyl-1,3,2-dioxaborolan-2-yl)benzyl acetate (525 mg, 743 μmol, Eq: 1.3) and cesium carbonate (652 mg, 2.00 mmol, Eq: 3.5) were dissolved in 10% aq. dioxane solution (3.3 ml). The reaction mixture was heated to 125° C. for 35 min in the microwave. Reaction mixture was filtered over celite. Filtrate was extracted with ethyl acetate, washed with water, and then with brine. Organic phase was dried over sodium sulfate; filtered; concentrated to give 640 mg of a light brown solid. The crude material was dissolved in ethyl acetate, and treated with hexane until a precipitate was formed. Precipitate was collected by filtration to give 354 mg of an off-white solid. Solid was dissolved in dioxane (3 ml) and 1 M sodium hydroxide solution (858 μl, 858 μmol, Eq: 1.5) was added and stirred at room temperature overnight.

The reaction mixture was loaded into a 24 g column and purified by flash chromatography (silica gel, 24 g, 0-13% MeOH in (EtOAc 1:1 Hex)) to give 194 mg of an off-white solid. Drying under high vacuum afforded an off-white crystalline product (178 mg, 278 μmol)

m.p.=215-220° C. MS ($H^+$)=640.1

$^1$H NMR (300 MHz, CHLOROFORM-d) δ ppm 1.44 (s, 9H) 3.63-3.79 (m, 8H) 3.93 (s, 3H) 4.44 (s, 2H) 7.05 (d, 1H) 7.45-7.69 (m, 5H) 7.75-7.82 (d, 1H) 8.29 (d, J=2.64 Hz, 1H) 8.43 (s, 1H) 8.54 (s, 1H) 8.68 (s, 1H).

Preparation of I-3

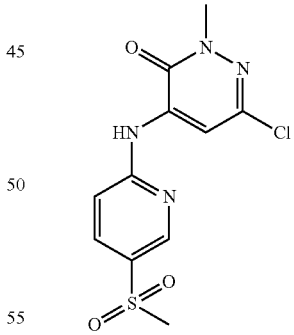

6-Chloro-4-(5-methanesulfonyl-pyridin-2-ylamino)-2-methyl-2H-pyridazin-3-one 4-bromo-6-chloro-2-methylpyridazin-3(2H)-one (1 g, 4.48 mmol, Eq: 1.00), 5-(methylsulfonyl)pyridin-2-amine (771 mg, 4.48 mmol, Eq: 1), 4,5-Bis(diphenylphosphino)-9,9-dimethylxanthene (388 mg, 671 μmol, Eq: 0.15) and cesium carbonate (5.1 g, 15.7 mmol, Eq: 3.5) were suspended in dioxane (80.0 ml). Finally tris (dibenzylideneacetone)dipalladium(0) (307 mg, 336 μmol, Eq: 0.075) was added. The reaction mixture was heated to 90° C. over night.

Reaction mixture was filtered over celite; washed with dioxane; concentrated. Crude material was triturated with dichloromethane and precipitate was collected by filtration to afford an off-white solid (70 mg, 222 μmol)

$^1$H NMR (300 MHz, DMSO-$d_6$) δ ppm 3.25 (s, 3H) 3.69 (s, 3H) 7.73 (d, J=8.69 Hz, 1H) 8.16 (dd, J=1.00 Hz, 1H) 8.42 (s, 1H) 8.83 (d, J=2.27 Hz, 1H)

Example 3

6-tert-Butyl-8-fluoro-2-{2-hydroxymethyl-3-[5-(5-methanesulfonyl-pyridin-2-ylamino)-1-methyl-6-oxo-1,6-dihydro-pyridazin-3-yl]-phenyl}-2H-phthalazin-1-one 6-Chloro-4-(5-methanesulfonyl-pyridin-2-ylamino)-2-methyl-2H-pyridazin-3-one (40 mg, 127 μmol, Eq: 1.00), 2-(6-tert-butyl-8-fluoro-1-oxophthalazin-2(1H)-yl)-6-(4,4,5,5-tetramethyl-1,3,2-dioxaborolan-2-yl)benzyl acetate (136 mg, 165 μmol, Eq: 1.3) and cesium carbonate (145 mg, 445 μmol, Eq: 3.5) were dissolved in 10% aq. dioxane solution (3.3 ml). The reaction mixture was heated to 130° C. for 30 min in the microwave. Reaction mixture was filtered over celite. Filtrate was extracted with ethyl acetate, washed with water, and then with brine. Organic phase was dried over sodium sulfate; filtered; concentrated to give light brown solid. The crude material was dissolved in ethyl acetate, and treated with hexane until a precipitate was formed. Precipitate was collected by filtration to give an off-white solid. Solid was dissolved in dioxane (2 ml) and 1 M sodium hydroxide solution (191 μl, 191 μmol, Eq: 1.5) was added and stirred at room temperature overnight+

The reaction mixture was loaded into a 12 g column and purified by flash chromatography (silica gel, 12 g, 0-13% MeOH in (EtOAc 1:1 Hex)) to give an off-white solid (39 mg, 64.5 μmol) m.p.=225-230° C. MS (H$^+$)=605.3

$^1$H NMR (400 MHz, CHLOROFORM-d) δ ppm 1.36 (s, 9H) 3.03 (s, 3H) 3.87 (s, 3H) 4.38 (s, 2H) 7.00 (d, J=1.00 Hz, 1H) 7.40-7.61 (m, 5H) 8.02 (d, J=1.00 Hz, 1H) 8.22 (s, 1H) 8.56 (br. s., 1H) 8.73 (s, 1H) 8.83 (br. s., 1H).

Preparation of I-4

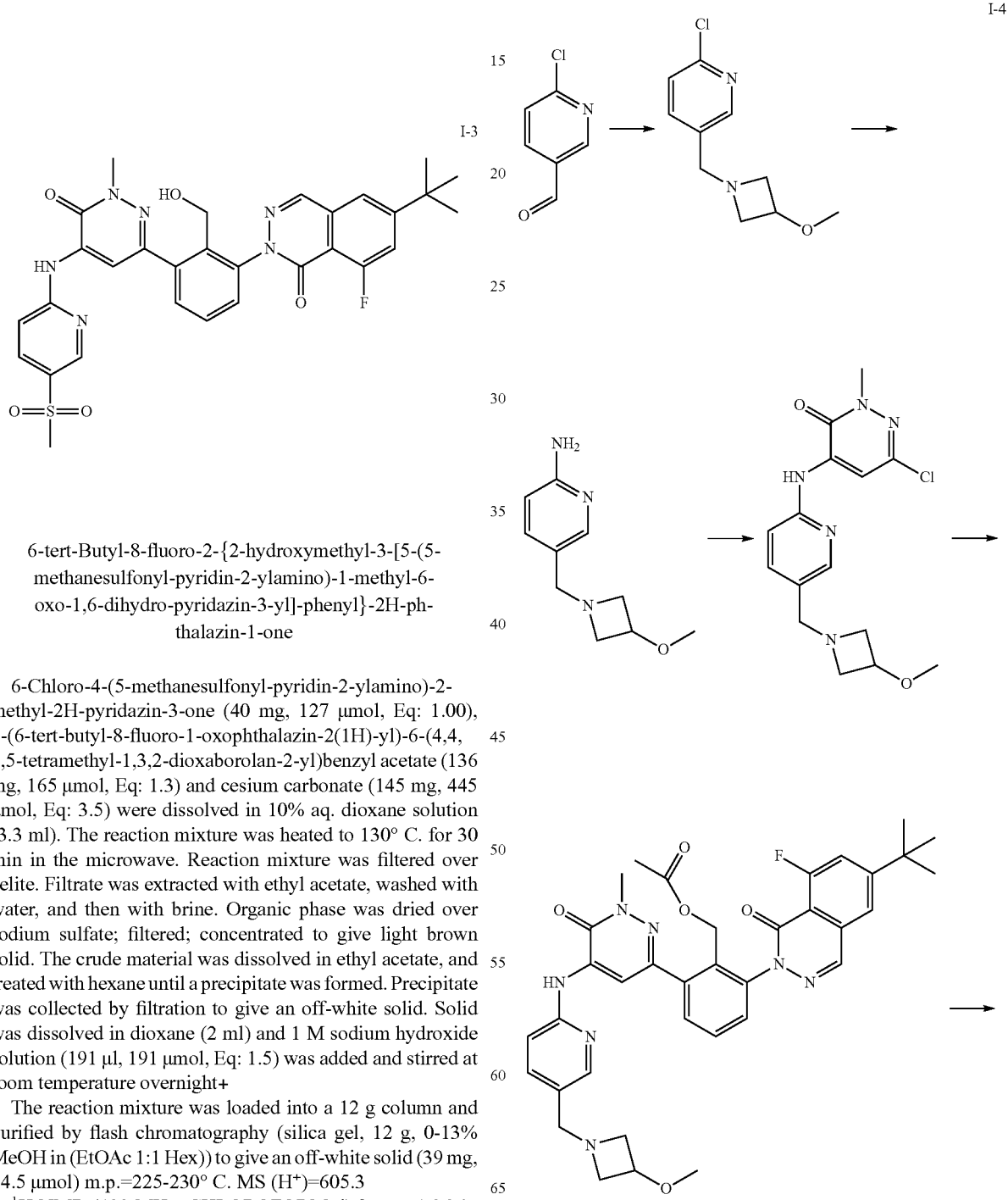

-continued

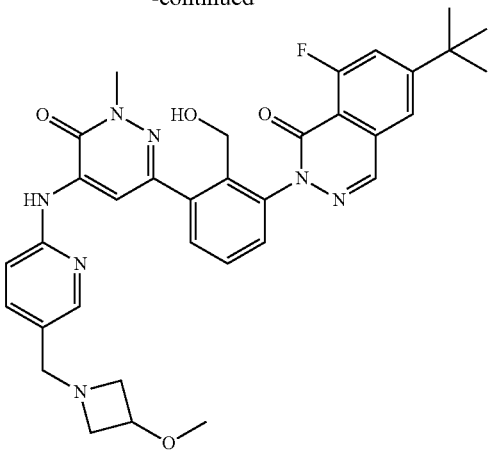

2-Chloro-5-(3-methoxy-azetidin-1-ylmethyl)-pyridine:
To a slurry of methoxy azetidine HCL salt (24.2 g, 198 mmol, Eq: 1.00) in 400 mL of methylene chloride was added triethylamine (24.0 g, 33.1 ml, 237 mmol, Eq: 1.2). The precipitate formed went back into solution. Next 6-chloronicotinaldehyde (28 g, 198 mmol, Eq: 1.00) and acetic acid (22.6 ml, 396 mmol, Eq: 2.0) was added. Finally sodium triacetoxyhydroborate (41.9 g, 198 mmol, Eq: 1.00) was added in portions. The first 11 g were added and waited for the chunks to disperse. The second 11 g were then added and an aliquot was checked by TLC. Added the remainder still in portions and continued stirring the slurry. After completion of addition, by TLC, some aldehyde seems to remain so stirring was continued. After another 30 minutes it looked essentially done. Added 400 mL of water and an additional 200 mL of methylene chloride and separated layers. The aqueous phase was made basic with ~400 mL of 1.0M NaOH and then extracted with 3 times 400 mL of methylene chloride. Concentrated to afford a thick colorless oil. Pumped down to constant weight 28.3 g (67.3%).

5-(3-Methoxy-azetidin-1-ylmethyl)-pyridin-2-ylamine:
To a round bottomed flask charged with 2-chloro-5-((3-methoxyazetidin-1-yl)methyl)pyridine (11.5 g, 54.1 mmol, Eq: 1.00), tris(dibenzylideneacetone)dipalladium(0) (1.24 g, 1.35 mmol, Eq: 0.025), and biphenyl-2-yldicyclohexylphosphine (948 mg, 2.7 mmol, Eq: 0.05) was added toluene (150 ml) followed immediately by lithium bis(trimethylsilyl)amide (81.1 ml, 81.1 mmol, Eq: 1.5) as a 1.0 M solution in THF. Brought quickly to reflux and stirred overnight under Argon. Next day, the reaction was checked by TLC (9:1 MC:MeOH) and the starting material was gone, replaced primarily by a single lower $R_f$ spot. Cooled while stirring and added 5 ml of 1.0M HCl. Stirred 20 min and filtered over celite. The filtrate was diluted with ether and washed with 200 mL of 1.0M NaOH followed by water and brine. Dried the org phase over sodium sulfate, filtered and removed solvent. Obtained a dark red oil weighing 14.4 g. Took the oil up in CH$_2$Cl$_2$ and flashed (neat MC to 90:10 MC:MeOH:0.1 Et3N). Collected 4.4 g (42.1%) of cleanest fractions as a reddish oil for next step.

6-Chloro-4-[5-(3-methoxy-azetidin-1-ylmethyl)-pyridin-2-ylamino]-2-methyl-2H-pyridazin-3-one: 5-(3-Methoxy-azetidin-1-ylmethyl)-pyridin-2-ylamine (130 mg, 0.67 mmol, Eq: 1.0), 4-bromo-6-chloro-2-methyl-2H-pyridazin-3-one (165 mg, 223 mmol, Eq: 1.1), xantphos (58 mg, 0.1 mmol, Eq: 0.15), tris(dibenzylideneacetone)dipalladium(0) (46 mg, 0.05 mmol, Eq: 0.075) and cesium carbonate (767 mg, 2.35 mmol, Eq: 3.5) were added to a microwave vial. The vial was capped and purged with argon. Degassed dioxane (4.5 ml) was added to the vial through the septum and the vial was purged again, then backfilled with argon. The reaction was heated at 90° C. overnight in a sand bath. The crude reaction mixture was filtered through celite and purified by chromatography using a gradient of 5% to 25% methanol in DCM with a little added ammonium hydroxide to give 150 mg of product (63.7%).

Acetic acid 2-(6-tert-butyl-8-fluoro-1-oxo-1H-phthalazin-2-yl)-6-{5-[5-(3-methoxy-azetidin-1-ylmethyl)-pyridin-2-ylamino]-1-methyl-6-oxo-1,6-dihydro-pyridazin-3-yl}-benzyl ester: 6-Chloro-4-[5-(3-methoxy-azetidin-1-ylmethyl)-pyridin-2-ylamino]-2-methyl-2H-pyridazin-3-one (100 mg, 0.29 mmol, Eq: 1.0), acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (247 mg, 0.5 mmol, Eq: 1.75), bis(dibenzylideneacetone)palladium (8.2 mg, 0.014 mmol, Eq: 0.05), x-phos (13.6 mg, 0.028 mmol, Eq: 0.10), and tripotassium phosphate (121 mg, 0.57 mmol, Eq: 2.0) were added to a microwave vial. The vial was capped and purged with nitrogen. Butanol (2.3 ml) and water (0.5 ml) were added and the vial was purged again, then backfilled with nitrogen. The reaction was heated at 110° C. for 2.5 hrs in a sand bath. The crude reaction was filtered through celite and purified by chromatography using a gradient of 0% to 25% methanol in DCM. Fractions containing the desired product were combined with those in which the acetate protecting group had been removed during the course of the reaction to give 175 mg of material (approximately 92%).

Example 4

6-tert-Butyl-8-fluoro-2-(2-hydroxymethyl-3-{5-[5-(3-methoxy-azetidin-1-ylmethyl)-pyridin-2-ylamino]-1-methyl-6-oxo-1,6-dihydro-pyridazin-3-yl}-phenyl)-2H-phthalazin-1-one: Acetic acid 2-(6-tert-butyl-8-fluoro-1-oxo-1H-phthalazin-2-yl)-6-{5-[5-(3-methoxy-azetidin-1-ylmethyl)-pyridin-2-ylamino]-1-methyl-6-oxo-1,6-dihydro-pyridazin-3-yl}-benzyl ester (175 mg, 0.26 mmol, Eq: 1.0) was dissolved in 2.6 ml of THF. Sodium hydroxide (1.3 ml of a 1.0M solution in water, 1.3 mmol, Eq: 5.0) was added dropwise. The reaction was stirred at room temperature overnight. Starting material was still present the next morning. The reaction was heated at 50° C. for two hours at which point no starting material remained. The reaction was diluted with ethyl acetate and water and the layers were separated. The organic layer was dried and concentrated. The residue was triturated with isopropyl acetate, filtered, washed with ether, and dried in a vacuum oven to give 75 mg (45.7%) of the desired product as a white powder. $^1$H NMR (300 MHz, DMSO-d6) δ ppm 1.37 (s, 9H) 2.79 (t, J=6.80 Hz, 2H) 3.11 (s, 3H) 3.37-3.44 (m, 2H) 3.46 (s, 2H) 3.77 (s, 3H) 3.92 (t, J=5.85 Hz, 1H) 4.40 (br.s., 2H) 4.52-4.63 (m, 1H) 7.40-7.62 (m, 5H)

7.74 (d, J=13.22 Hz, 1H) 7.86 (s, 1H) 8.15 (s, 1H) 8.48-8.55 (m, 2H) 9.36-9.44 (m, 1H). MS: (M+H)⁺=626. MP=140-142° C.

Preparation of I-5

Example 5

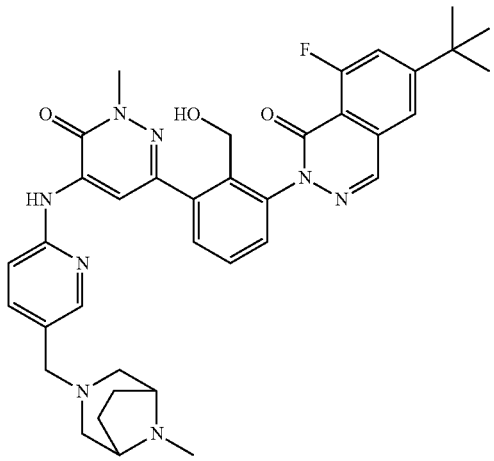

I-5

6-tert-Butyl-8-fluoro-2-(2-hydroxymethyl-3-{1-methyl-5-[5-(8-methyl-3,8-diaza-bicyclo[3.2.1]oct-3-ylmethyl)-pyridin-2-ylamino]-6-oxo-1,6-dihydro-pyridazin-3-yl}-phenyl)-2H-phthalazin-1-one was prepared using the general procedure described for preparation of compound I-4, substituting 8-methyl-3,8-diazabicyclo[3.2.1]octane dihydrochloride for methoxy azetidine HCL salt in the first step of the synthesis and using 2.5 equivalents of triethyl amine to free base the dihydrochloride salt. The resulting benzyl amine intermediate was carried through the remaining steps of the synthesis to give 65 mg of final product as a white powder. ¹H NMR (300 MHz, DMSO-d6) δ 9.38 (s, 1H), 8.48-8.54 (m, 2H), 8.10-8.17 (m, 1H), 7.86 (s, 1H), 7.74 (d, J=13.22 Hz, 1H), 7.55-7.62 (m, 1H), 7.42-7.55 (m, 4H), 4.53-4.60 (m, 1H), 4.39 (br. s., 2H), 3.77 (s, 3H), 2.93 (br. s., 2H), 2.41 (d, J=7.93 Hz, 2H), 2.15 (d, J=10.20 Hz, 2H), 2.09 (s, 3H), 1.78 (d, J=4.91 Hz, 2H), 1.62 (d, J=6.80 Hz, 2H), 1.37 (s, 9H). MS: (M+H)⁺=665. MP=162-165° C.

Preparation of I-6

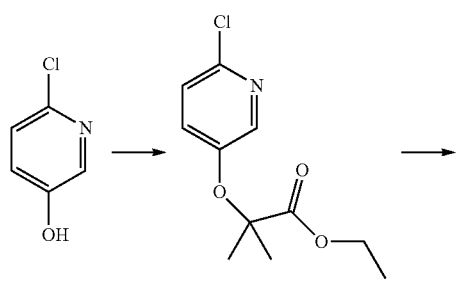

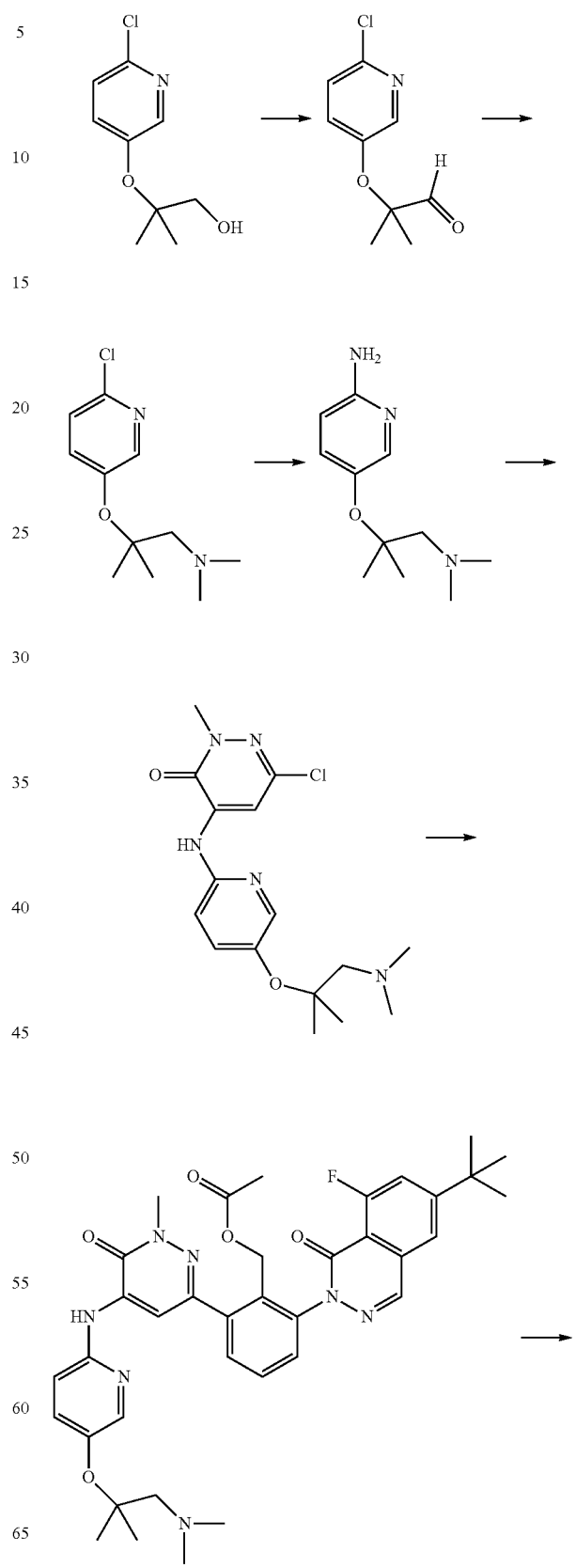

-continued

-continued

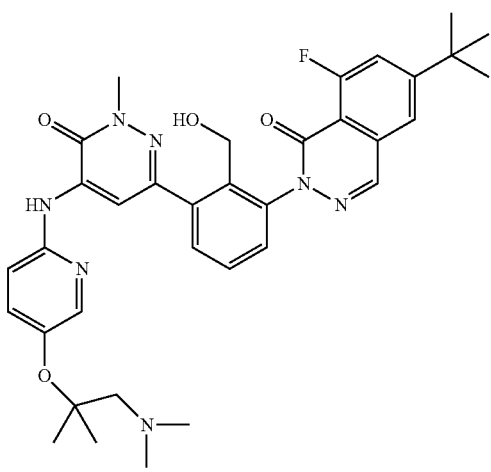 [SMILES: CN(C)CC(C)(C)Oc1ccc(Nc2cc(-c3cccc(-n4ncc5cc(C(C)(C)C)cc(F)c5c4=O)c3CO)nn(C)c2=O)nc1]

Step 1. Preparation of Ethyl 2-(6-chloropyridin-3-yloxy)-2-methylpropanoate

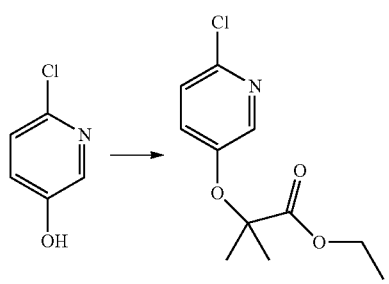 [SMILES: Oc1ccc(Cl)nc1 ; CCOC(=O)C(C)(C)Oc1ccc(Cl)nc1]

To a solution of 6-chloropyridin-3-ol (5 g, 38.6 mmol) and ethyl-2-bromo-2-methylpropanoate (6.01 ml, 40.5 mmol) in acetonitrile (50 mL) was added cesium carbonate (27 g, 83 mmol). The material was stirred vigorously for 48 hours. The mixture was taken up in water (100 ml) and ethyl acetate (100 ml) and transferred to a separatory funnel and shaken. The organic phase was collected and the aqueous phase was back extracted with ethyl acetate (2×50 mL). The organic phases were combined, dried (magnesium sulfate), filtered and stripped. The crude material was purified via preparative HPLC (silica gel; 50 g column) eluting with 5-30% ethyl acetate/hexanes to provide the desired product as light white-yellow mobile oil (6.78 g). (M+H)$^+$=244 m/e.

Step 2. Preparation of 2-(6-chloropyridin-3-yloxy)-2-methylpropan-1-ol

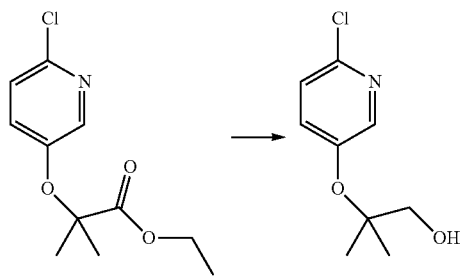 [SMILES: CCOC(=O)C(C)(C)Oc1ccc(Cl)nc1 ; CC(C)(CO)Oc1ccc(Cl)nc1]

A solution of ethyl 2-(6-chloropyridin-3-yloxy)-2-methylpropanoate (6.093 g, 25.0 mmol) in dry tetrahydrofuran (80 mL) is cooled to −20° C. (acetonitrile/dry ice bath) under nitrogen atmosphere. A solution of lithium aluminum hydride (1.0 M in THF, 35 ml) was added via drop-wise addition over 10 minutes. The mixture was stirred at −20° C. for 1 hour. The reaction was carefully quenched via addition of water (0.73 ml). The mixture was stirred for 10 minutes and then an aqueous solution of 5% sodium hydroxide (1.34 ml) was added with stirring for 10 minutes. Finally water (1.34 ml) was added and the mixture was stirred for 10 additional minutes. Magnesium sulfate was added and the material was filtered through a plug of celite, rinsing well with tetrahydrofuran. (Note that subsequent stirring of the aluminum salts in dichloromethane (50 ml) and filtering through celite provides additional product). The filtrates were stripped on the rotary evaporator, providing the desired product as a semi-viscous brown oil (4.843 g). (M+H)$^+$=202 m/e.

Step 3. Preparation of 2-(6-chloropyridin-3-yloxy)-2-methylpropanal

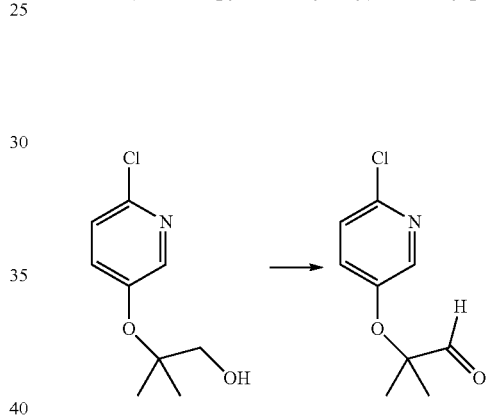

An oven dried flask (50 ml, round bottom) containing dry dichloromethane (13 ml) is cooled to −78° C. (dry ice/acetone bath) under argon atmosphere. Oxalyl chloride (0.23 ml, 2.67 mmol) is added followed by the addition of dry dimethyl sulfoxide (0.31 ml, 4.31 mmol) via drop-wise addition. The mixture is stirred for 10 minutes and then a solution of 2-(6-chloropyridin-3-yloxy)-2-methylpropan-1-ol (451 mg, 2.06 mmol) [dissolved in dichloromethane (4 ml)] is added via slow drop-wise addition. The cooled solution was stirred for 30 minutes and then triethylamine (1.15 ml, 8.2 mmol) was added and the cooling bath was removed. The mixture was stirred and warmed to ambient over 1 hour. A saturated solution of sodium bicarbonate (20 ml) was added and also dichloromethane (20 ml). The material was transferred and shaken in a reparatory funnel. The dichloromethane phase was collected and washed with brine solution (25 mL). The aqueous phase was back extracted with methylene chloride (2×20 mL) and the organic phases combined, dried over magnesium sulfate, filtered and stripped. The material was purified by filtration through a short column of silica gel (20 g), eluting with 30% ethyl acetate/hexanes, which provided the product as a light yellow oil (361 mg). (M+H)$^+$=200 m/e.

Step 4. Preparation of 2-(6-chloropyridin-3-yloxy)-N,N,2-trimethylpropan-1-amine

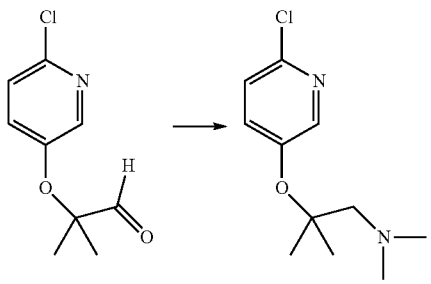

To a large capacity microwave tube containing 2-(6-chloropyridin-3-yloxy)-2-methylpropanal (354 mg, 1.77 mmol) and sodium triacetoxyborohydride (940 mg, 4.43 mmol) in dry dichloromethane (4 ml) was added glacial acetic acid (0.81 ml, 14.2 mmol) followed by a 2 M solution of dimethylamine (14.2 ml, 28.4 mmol, in tetrahydrofuran). The tube was capped and heated to 50° C. (oil bath) with vigorous stirring for 16 hours. The mixture was cooled to ambient and the contents poured into a separatory funnel containing an aqueous solution of saturated sodium bicarbonate (30 ml). Dichloromethane (30 ml) was added and the mixture was shaken. The contents were filtered through a plug of celite, washing well with dichloromethane. The filtrate was collected and washed with a brine solution (40 ml). The dichloromethane phase was collected and the aqueous phase was back extracted with methylene chloride (2×40 mL). The organic phases were combined, dried over magnesium sulfate, filtered and stripped. The material was purified by preparative thin layer chromatography (2 plates), eluting with 1.8% methanol/dichloromethane. The plates were then re-developed with 2.6% methanol/dichloromethane, and the product band was collected which provided the desired as a light yellow mobile oil, which slowly solidified on standing (255 mg). $(M+H)^+=229$ m/e.

Step 5. Preparation of 4-bromo-6-chloro-2-methylpyridazin-3(2H)-one

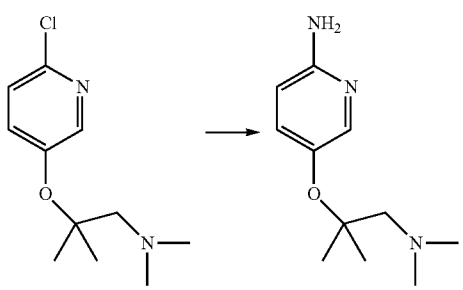

To a solution of 2-(6-chloropyridin-3-yloxy)-N,N,2-trimethylpropan-1-amine (255 mg, 1.11 mmol) in dry tetrahydrofuran (6.6 ml) was added 2-(dicyclohexylphosphino)biphenyl (78 mg, 0.22 mmol) followed by tris(dibenzylideneacetone)dipalladium (0) (102 mg, 0.11 mmol). The mixture was vacuum de-gassed and placed under argon atmosphere. A 1M solution of lithium bis(trimethylsilyl)amide (3.34 ml, in tetrahydrofuran) was added and the tube was sealed and heated to 75° C. (oil bath) with vigorous stirring overnight. The mixture was cooled to ambient and the contents poured into a separatory funnel containing a saturated aqueous solution of ammonium chloride (25 ml). Dichloromethane (30 ml) was added and the mixture was shaken. The organic phase was collected and the aqueous phase was back extracted with methylene chloride (4×50 mL). The methylene chloride phases were combined, dried over magnesium sulfate, filtered and stripped. The material was purified by preparative thin layer chromatography (2 plates), eluting with 8% methanol/dichloromethane. A polar band was collected which provided the product as a red-brown viscous oil (229 mg). Material was used "as is" in the next step.

Step 6. Preparation of 6-chloro-4-(5-(1-(dimethylamino)-2-methylpropan-2-yloxy)pyridin-2-ylamino)-2-methylpyridazin-3(2H)-one

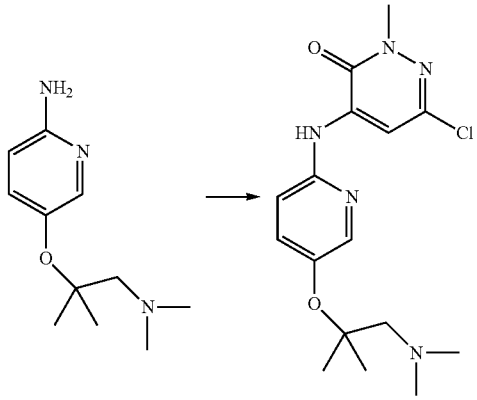 [SMILES: CN(C)CC(C)(C)Oc1ccc(N)nc1 ; CN(C)CC(C)(C)Oc1ccc(Nc2cc(Cl)nn(C)c2=O)nc1]

A solution of 4-bromo-6-chloro-2-methylpyridazin-3(2H)-one (282 mg, 1.26 mmol), 5-(1-(dimethylamino)-2-methylpropan-2-yloxy)pyridin-2-amine (203 mg, 0.97 mmol), Xantphos (84 mg, 0.15 mmol) and cesium carbonate (1.11 g, 3.39 mmol) in dry dioxane (6.6 ml) was vacuum de-gassed and place under argon atmosphere. To this mixture was added tris(dibenzylideneacetone)dipalladium (0) (67 mg, 0.073 mmol) and the vacuum de-gas cycle was repeated. The material was heated at 90° C. (oil bath) with vigorous stirring overnight. The flask was cooled to ambient and the contents were filtered through a plug of celite, rinsing well with dioxane. The volatiles were stripped and the crude was purified by preparative thin layer chromatography (4 plates), eluting first with 6% and then re-developing with 8% methanol/dichloromethane. The product band was collected which provided the desired as a light brown powder (196 mg). $(M+H)^+=352$ m/e.

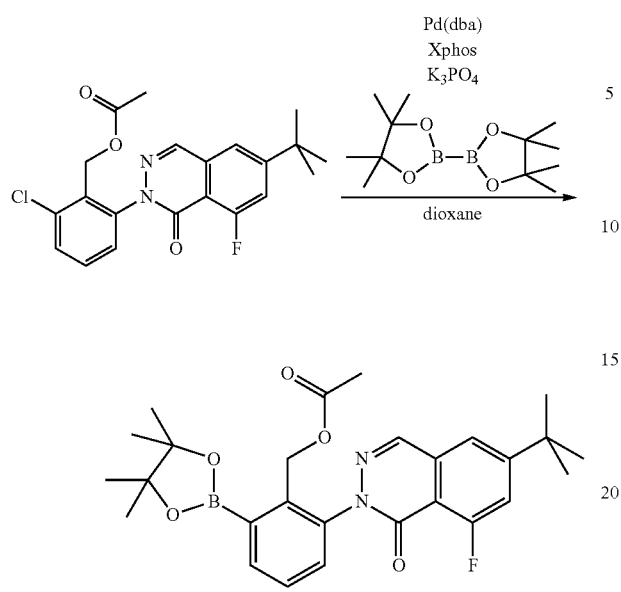

In a microwave reaction vial, added acetic acid 2-(6-tert-butyl-8-fluoro-1-oxo-1H-phthalazin-2-yl)-6-chloro-benzyl ester (329 mg, 0.818 mmol), bis-pinaco-diboron (416 mg, 1.637 mmol), KOAc (241 mg, 2.454 mmol) and Xphos (39 mg, 0.0818 mmol) and dioxane (4 mL). Bubble argon through for 15 min and then add Pd(dba)2 (24 mg, 0.0409 mmol). Seal the tube and heat it to 60° C. for 18 hrs. The reaction mixture was then diluted with EtOAc (5 mL) and washed with NaHCO$_3$ (concentrated) (1×10 mL) and water (10 mL). The organic phase was then concentrated and purified on silica gel column with 25% EtOAc in Hex to give acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester as an yellow oil (330 mg, 81%).

Step 7. Preparation of acetic acid 2-(6-tert-butyl-8-fluoro-1-oxo-1H-phthalazin-2-yl)-6-{5-[5-(2-dimethylamino-1,1-dimethyl-ethoxy)-pyridin-2-ylamino]-1-methyl-6-oxo-1,6-dihydro-pyridazin-3-yl}-benzyl ester A flask was charged with 2-(6-tert-butyl-8-fluoro-1-oxophthalazin-2(1H)-yl)-6-(4,4,5,5-tetramethyl-1,3,2-dioxaborolan-2-yl)benzyl acetate (391 mg, 0.55 mmol), 6-chloro-4-(5-(1-(dimethylamino)-2-methylpropan-2-yloxy)pyridin-2-ylamino)-2-methylpyridazin-3(2H)-one (150 mg, 0.43 mmol), X-phos (31 mg, 0.06 mmol) and potassium phosphate tribasic (199 mg, 0.94 mmol). The mixture was taken up in n-butanol (2.8 ml) and water (0.67 ml) and vacuum de-gassed and placed under argon atmosphere. To this mixture was added bis(dibenzylideneacetone)palladium (17 mg, 0.03 mmol) and the vacuum de-gas cycle was repeated. The material was heated at 110° C. (oil bath) with vigorous stirring under argon atmosphere for 2.5 hours. The flask was cooled to ambient and the contents were taken up in water (35 ml) and ethyl acetate (35 ml). The contents were transferred to a separatory funnel and shaken. The organic phase was collected and washed with water (35 ml). The aqueous phases were back extracted with ethyl acetate (2×30 ml) and the organic phases combined, dried (magnesium sulfate), filtered and stripped. The remainder was purified by preparative thin layer chromatography (3 plates), eluting with 8% methanol/dichloromethane to provide desired product (together with some des-acetyl product) as a golden brown oil (312 mg). (M+H)$^+$=684 (642) m/e.

Example 6

Step 8. Preparation of 6-tert-Butyl-2-(3-{5-[5-(2-dimethylamino-1,1-dimethyl-ethoxy)-pyridin-2-ylamino]-1-methyl-6-oxo-1,6-dihydro-pyridazin-3-yl}-2-hydroxymethyl-phenyl)-8-fluoro-2H-phthalazin-1-one

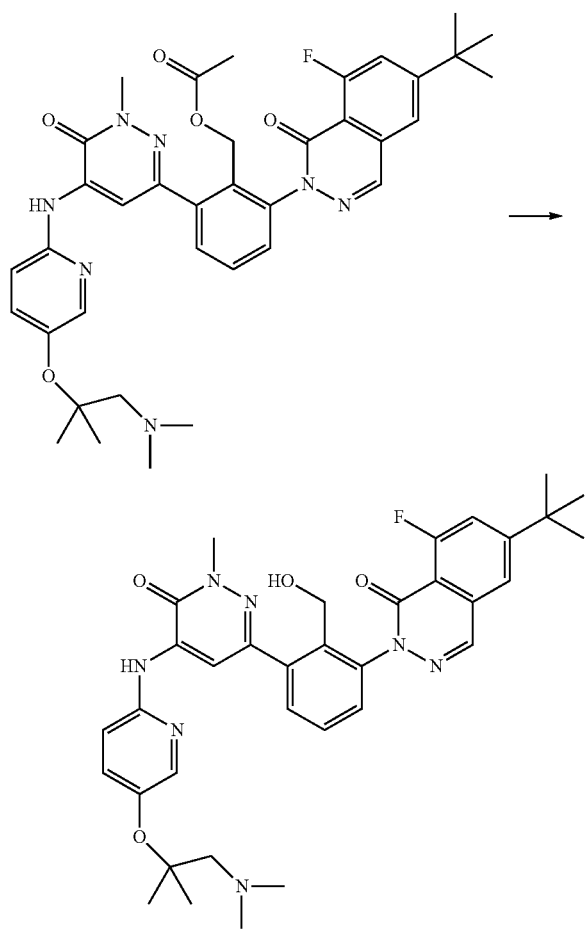

I-6

To a solution of 2-(6-tert-butyl-8-fluoro-1-oxophthalazin-2(1H)-yl)-6-(5-(5-(1-(dimethylamino)-2-methylpropan-2-yloxy)pyridin-2-ylamino)-1-methyl-6-oxo-1,6-dihydropyridazin-3-yl)-benzyl acetate (292 mg, 0.43 mmol) in dioxane (1.5 ml) was added a solution of 2N sodium hydroxide (2.5 ml, 5 mmol). The flask was heated at 50° C. (oil bath) with vigorous stirring under argon atmosphere for 3 hours. The material was cooled to ambient and the contents were taken up in water (25 ml) and methylene chloride (50 ml) and transferred to a reparatory funnel and shaken. The organic phase was collected and washed with a solution of 50% diluted brine (25 ml). The aqueous phases were back extracted with methylene chloride (2×40 ml) and the organic phases combined, dried (magnesium sulfate), filtered and stripped. The remainder was purified by preparative thin layer chromatography (3 plates), eluting with 6% methanol/dichloromethane and then re-developing the plates with first 8% and then 11% methanol/dichloromethane. The product band was collected providing the desired product as a light yellow-white solid (72 mg). MP=136-144° C.; (M+H)$^+$=642 m/e. $^1$H NMR (300 MHz, CHLOROFORM-d) δ ppm 1.28 (s, 6H) 1.42 (s, 9H) 2.40 (s, 6H) 2.51 (s, 2H) 3.90 (s, 3H) 4.42 (s, 2H) 6.90 (d, J=9.06 Hz, 1H) 7.33 (dd, J=8.69, 3.02 Hz, 1H) 7.41-7.72 (m, 5H) 8.09 (d, J=3.02 Hz, 1H) 8.20-8.35 (m, 2H) 8.53 (s, 1H).

Preparation of I-7

Example 7

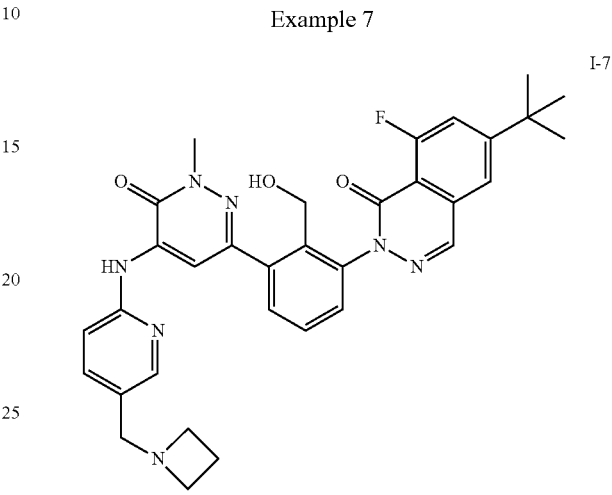

I-7

2-{3-[5-(5-Azetidin-1-ylmethyl-pyridin-2-ylamino)-1-methyl-6-oxo-1,6-dihydro-pyridazin-3-yl]-2-hydroxymethyl-phenyl}-6-tert-butyl-8-fluoro-2H-phthalazin-1-one was prepared using the general procedure described for compound I-4, substituting azetidine for methoxy azetidine HCL salt in the first step and omitting the use of triethyl amine. The resulting benzyl amine intermediate was carried through the remaining steps of the synthesis to give 35 mg of final product as an off-white powder. $^1$H NMR (300 MHz, DMSO-d6) δ 9.37 (s, 1H), 8.47-8.56 (m, 2H), 8.15 (s, 1H), 7.86 (s, 1H), 7.74 (d, J=13.22 Hz, 1H), 7.40-7.63 (m, 5H), 4.51-4.62 (m, 1H), 4.40 (br. s., 2H), 3.77 (s, 3H), 3.40 (s, 2H), 3.06 (t, J=6.80 Hz, 4H), 1.92 (quin, J=6.89 Hz, 2H), 1.37 (s, 9H). MS: (M+H)$^+$=596. MP=160-163° C.

Preparation of I-8

Example 8

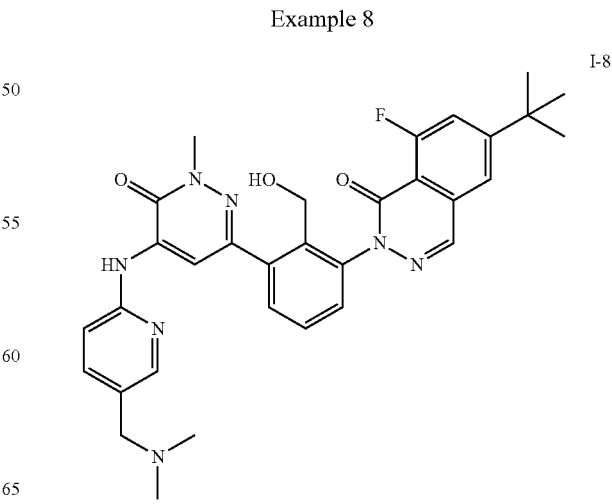

I-8

6-tert-Butyl-2-{3-[5-(5-dimethylaminomethyl-pyridin-2-ylamino)-1-methyl-6-oxo-1,6-dihydro-pyridazin-3-yl]-2-hydroxymethyl-phenyl}-8-fluoro-2H-phthalazin-1-one was prepared using the general procedure described for the preparation of compound I-4, except that the first step was omitted since (6-chloro-pyridin-3-ylmethyl)-dimethyl-amine is commercially available. This compound was carried through the remaining steps of the synthesis to give 120 mg of final product as an off-white powder. $^1$H NMR (300 MHz, DMSO-d6) δ ppm 9.40 (s, 1H) 8.47-8.57 (m, 2H) 8.15 (s, 1H) 7.86 (s, 1H) 7.74 (d, J=13.2 Hz, 1H) 7.56-7.65 (m, 1H) 7.42-7.56 (m, 4H) 4.52-4.61 (m, 1H) 4.40 (br. s., 2H) 3.77 (s, 3H) 3.34-3.40 (s, 2H, occluded by DMSO water peak) 2.10 (s, 6H) 1.37 (s, 9H). MS: $(M+H)^+$=584. MP=170-174° C.

Preparation of I-9

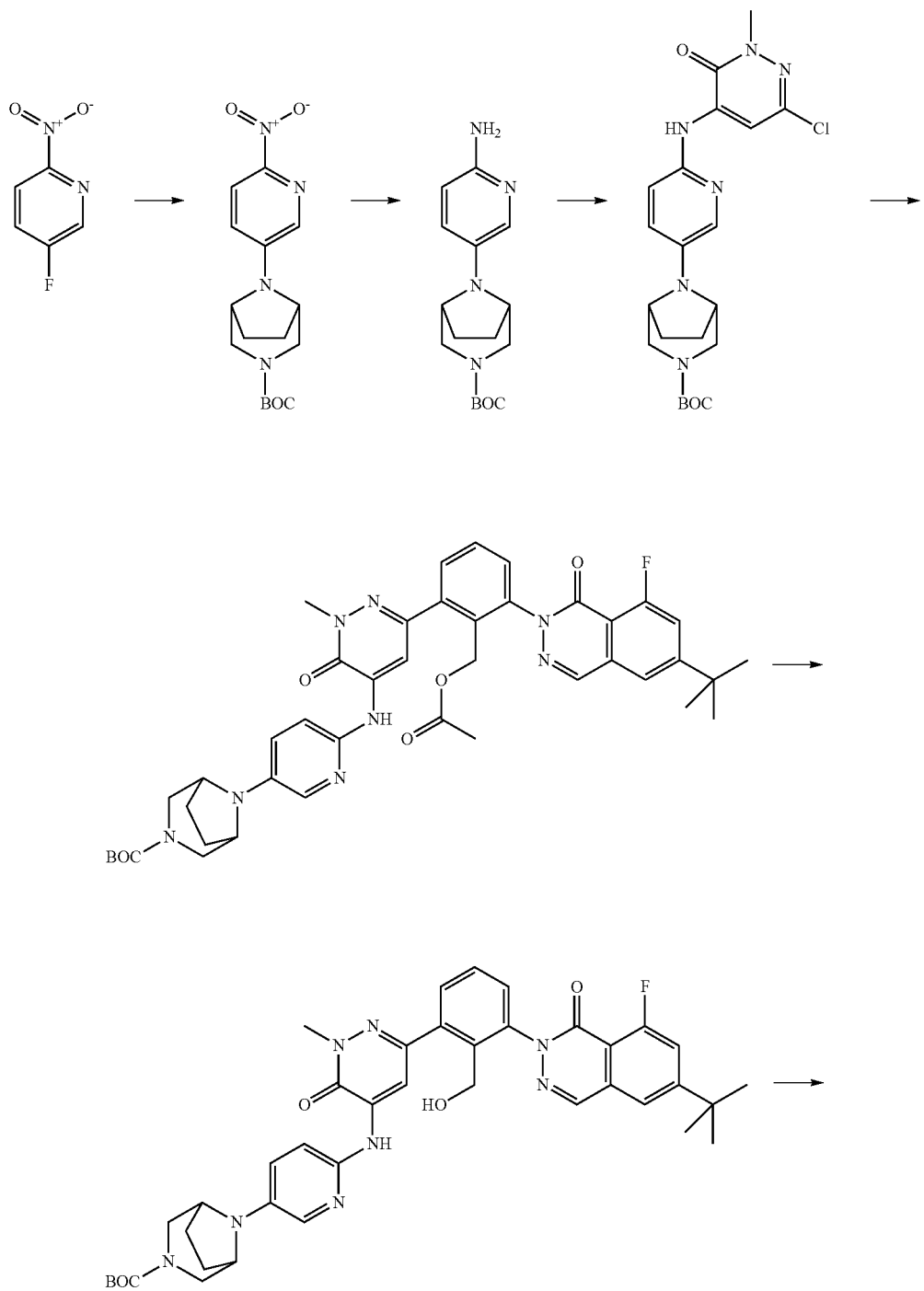

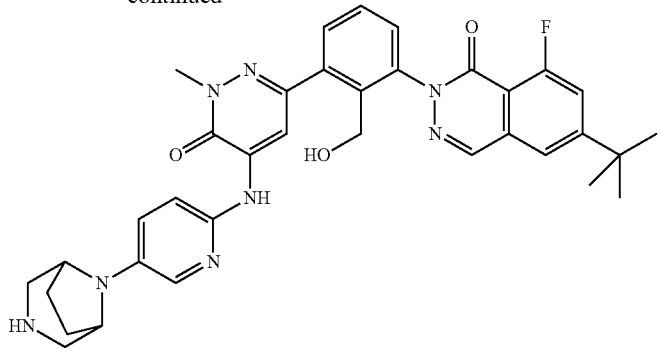

tert-butyl 8-(6-nitropyridin-3-yl)-3,8-diazabicyclo[3.2.1]octane-3-carboxylate

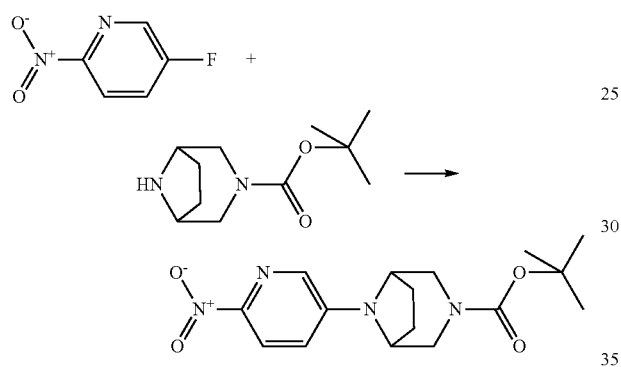

Triethylamine (6.87 mL, 49.3 mmol) was added to a stirred solution of 5-fluoro-2-nitropyridine (700 mg, 4.93 mmol) and (1R,5S)-tert-butyl 3,8-diazabicyclo[3.2.1]octane-3-carboxylate (1.05 g, 4.93 mmol) in 8 mL of DMSO at room temperature. The reaction mixture was heated to 80° C. for 2 hr. After cooling to room temperature, the reaction mixture was diluted with ethyl acetate, washed with, saturated ammonium chloride, water (3×), dried over anhydrous sodium sulfate, filtered and concentrated in vacuo to afford 1.21 g (73.5%) of tert-butyl 8-(6-nitropyridin-3-yl)-3,8-diazabicyclo[3.2.1]octane-3-carboxylate as yellow solid.

tert-butyl 8-(6-aminopyridin-3-yl)-3,8-diazabicyclo[3.2.1]octane-3-carboxylate

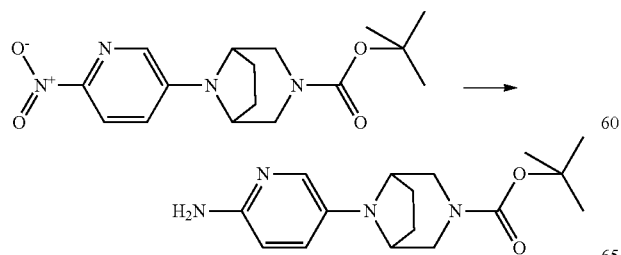

To a solution of tert-butyl 8-(6-nitropyridin-3-yl)-3,8-diazabicyclo[3.2.1]octane-3-carboxylate (330 mg, 987 umol) in 10 ml of Methanol was added 10% Palladium in carbon (10 mg. The reaction mixture was hydrogenated 2 hr under 50 psi hydrogen. The reaction mixture was filtered through pack of celite and concentrated to afford 300 mg (100%) of tert-butyl 8-(6-aminopyridin-3-yl)-3,8-diazabicyclo[3.2.1]octane-3-carboxylate as colorless oil. This product was used in subsequent steps without further purification.

(1R,5S)-tert-butyl 8-(6-(6-chloro-2-methyl-3-oxo-2,3-dihydropyridazin-4-ylamino)pyridin-3-yl)-3,8-diazabicyclo[3.2.1]octane-3-carboxylate

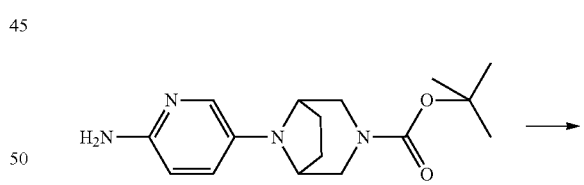

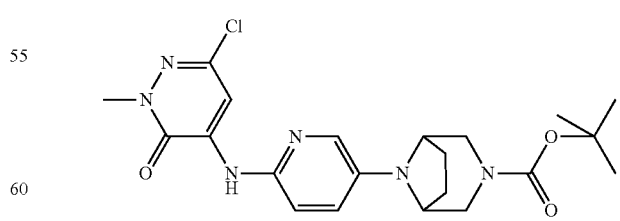

This reaction was carried out under similar conditions to those described above in step 6 of preparation of Example 6. After work up the product was purified by preparative HPLC on silica gel, using a gradient of 2% to 8% methanol/methylene chloride. This provided the desired product as a light yellow solid (275 mg 62.4%). (M+H)+=447.2 m/e.

tert-butyl 8-(6-(6-(2-(acetoxymethyl)-3-(6-tert-butyl-8-fluoro-1-oxophthalazin-2(1H)-yl)phenyl)-2-methyl-3-oxo-2,3-dihydropyridazin-4-ylamino)pyridin-3-yl)-3,8-diazabicyclo[3.2.1]octane-3-carboxylate

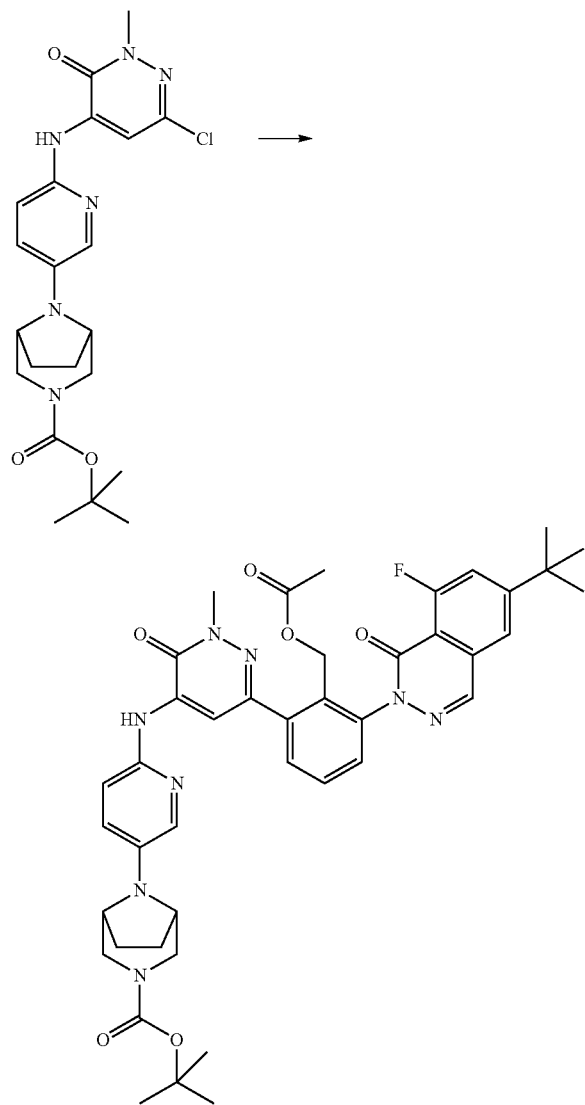

This reaction was carried out under similar conditions to those described above in step 7 of preparation of Example 6. (1R,5S)-tert-butyl 8-(6-(6-chloro-2-methyl-3-oxo-2,3-dihydropyridazin-4-ylamino)pyridin-3-yl)-3,8-diazabicyclo[3.2.1]octane-3-carboxylate (100 mg, 224 umol), 2-(6-tert-butyl-8-fluoro-1-oxophthalazin-2(1H)-yl)-6-(4,4,5,5-tetramethyl-1,3,2-dioxaborolan-2-yl)benzyl acetate (114 mg, 224 umol), xPhos (10.7 mg, 22.4 umol) and potassium phosphate (119 mg, 559 umol) in 7 ml of Dioxane/water (9:1) was degassed with nitrogen for 10 minutes and bis(dibenzylideneacetone)palladium (0) (6.42, 11.2 umol) was added. The reaction mixture was heated to 100° C. for 2 hr. After work up, the product was purified by preparative HPLC on silica gel, using a gradient of 5% to 70% ethylacetate/hexane. This provided the desired product as a light yellow solid (105 mg 60.3%). (M+H)+=779 m/e.

tert-butyl 8-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)-3,8-diazabicyclo[3.2.1]octane-3-carboxylate

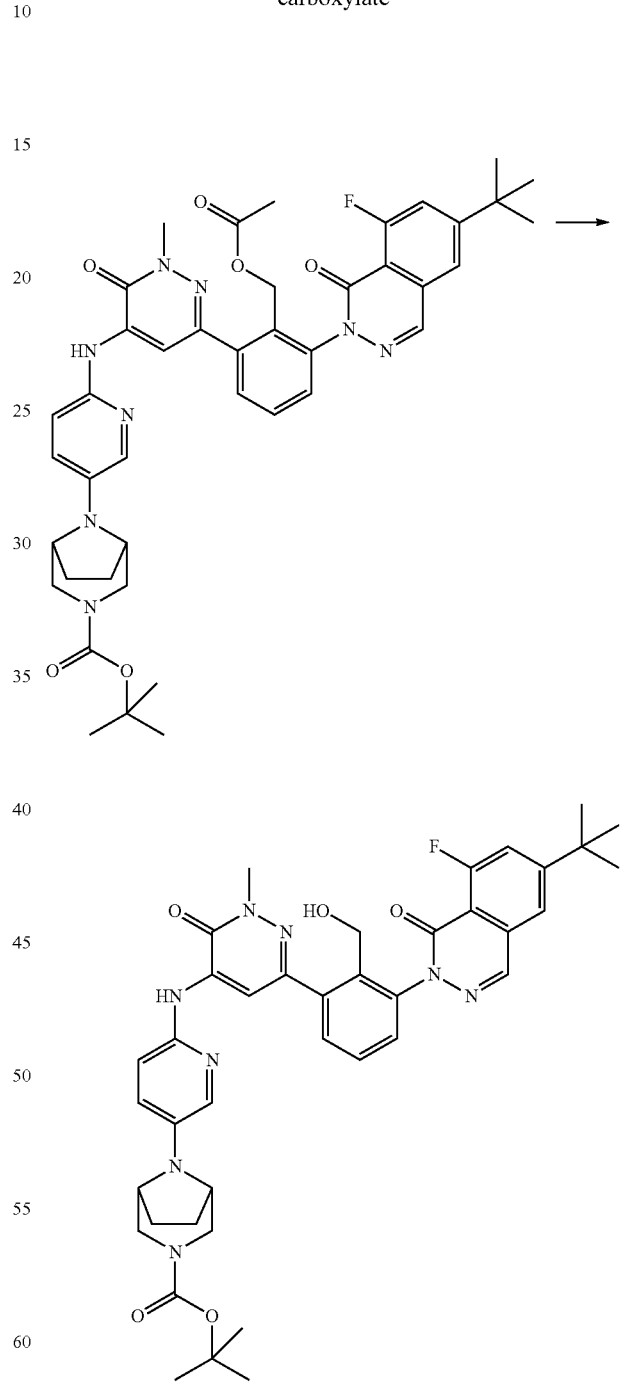

This reaction was carried out under similar conditions to those described above in step 8 of the preparation for I-6. After work up, the product was crystallized as light yellow powder (90 mg, 90.6%). (M+H)+=737 m/e.

Example 9

2-(3-(5-(5-(3,8-diazabicyclo[3.2.1]octan-8-yl)pyridin-2-ylamino)-1-methyl-6-oxo-1,6-dihydropyridazin-3-yl)-2-(hydroxymethyl)phenyl)-6-tert-butyl-8-fluorophthalazin-1(2H)-one

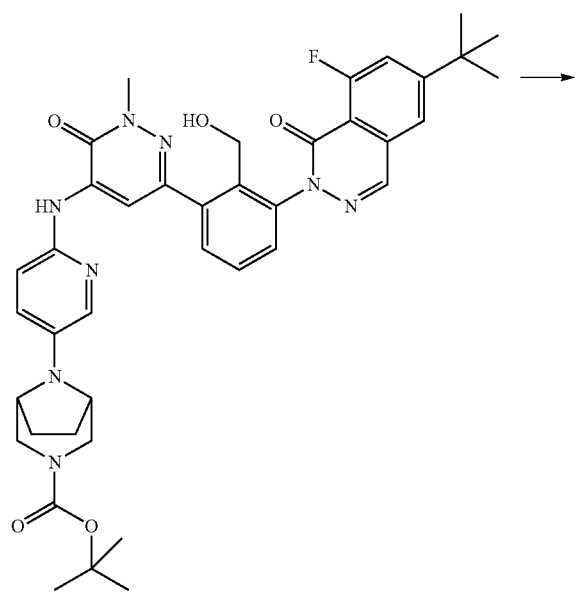

I-9 tert-butyl 8-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)-3,8-diazabicyclo[3.2.1]octane-3-carboxylate (90 mg, 122 umol) was de-BOC with 50% trifluoro acid in dichloromethane (10 mL) for 2 hr. The reaction mixture was concentrated to dryness, then partitioned between ethyl acetate and saturated sodium bicarbonate. The organic phase was dried over sodium sulfate, filtered and concentrated.

The product was collected and further purified by crystallization from hot iso-propylacetate/hexanes. A crystalline product was collected by filtration, providing the desired product as a light brown powder (53 mg, 68.1%). (M+H)$^+$=638 m/e. $^1$H NMR (500 MHz, DMSO-d$_6$) δ 9.13 (s, 1H), 8.49 (d, J=2.44 Hz, 1H), 8.31-8.35 (m, 1H), 7.90 (d, J=2.44 Hz, 1H), 7.85 (d, J=1.95 Hz, 1H), 7.73 (d, J=11.71 Hz, 1H), 7.49-7.55 (m, 1H), 7.43-7.48 (m, 2H), 7.37 (d, J=8.79 Hz, 1H), 7.27 (dd, J=2.93, 9.27 Hz, 1H), 4.48-4.56 (m, 1H), 4.38 (d, J=11.23 Hz, 3H), 4.04-4.15 (m, 2H), 3.69-3.79 (m, 3H), 2.93 (d, J=12.20 Hz, 2H), 2.42-2.46 (m, 2H), 1.82-1.93 (m, 4H), 1.36 (s, 9H)

Preparation of I-10

Step 1

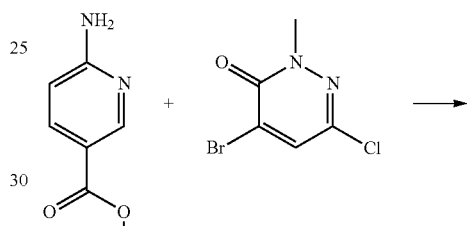

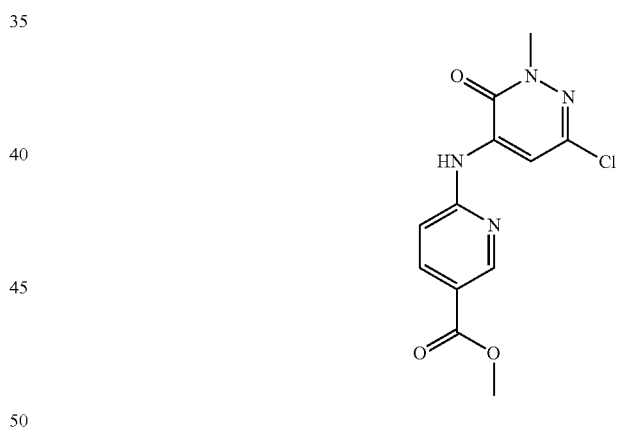

To a 15 mL microwave vial was added methyl 6-aminonicotinate (170 mg, 1.12 mmol, Eq: 1.00), 4-bromo-6-chloro-2-methylpyridazin-3(2H)-one (250 mg, 1.12 mmol, Eq: 1.00), Cs$_2$CO$_3$ (1.28 g, 3.92 mmol, Eq: 3.5) and xantphos (97.1 mg, 168 μmol, Eq: 0.15) in Dioxane (8 ml). The reaction was purged with argon and Pd$_2$(dba)$_3$ (76.8 mg, 83.9 μmol, Eq: 0.075) was added. The vial was capped and heated in the microwave at 90° C. for 30 min. LC-MS at t=30 min showed the reaction was incomplete with starting material remaining. The reaction was heated further at 120° C. for 30 mins. The sample had solidified. The crude mixture was taken up in DCM and stripped to a dark brown oily solid. The residue was taken up in DCM and washed with water. The aqueous layer was back-extracted with DCM (2×50 mL). The organic layers were combined, washed with sat NaCl (1×25 mL), dried over Na$_2$SO$_4$ and concentrated in vacuo. LC-MS of crude org phase showed mainly product.

The crude material was triturated with DCM and cooled. The tan solid was filtered and washed with a minimum amount of cold DCM. The solid was dried under vacuum to give 158 mg of a light tan solid in 48% yield. $^1$H NMR in DMSO-d6 is consistent with desired product. MS (m+1)=295.0.

Step 2

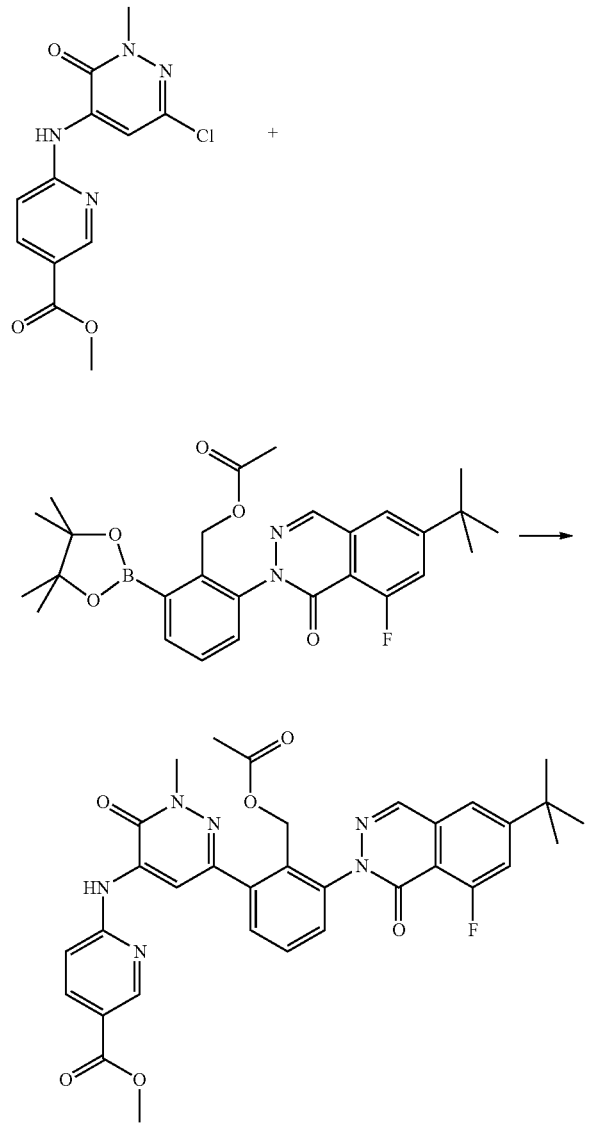

To a 15 mL microwave vial was added methyl 6-(6-chloro-2-methyl-3-oxo-2,3-dihydropyridazin-4-ylamino)nicotinate (153 mg, 519 µmol, Eq: 1.00), 2-(6-tert-butyl-8-fluoro-1-oxophthalazin-2(1H)-yl)-6-(4,4,5,5-tetramethyl-1,3,2-dioxaborolan-2-yl)benzyl acetate (334 mg, 675 µmol, Eq: 1.3) and Cs$_2$CO$_3$ (592 mg, 1.82 mmol, Eq: 3.5) in Dioxane (5 ml) and Water (0.5 ml). PdDCl2 (DPPF) (42.4 mg, 51.9 µmol, Eq: 0.1) was added and the suspension was purged with argon. The vial was capped and heated in the microwave at 120° C. for 30 min. LC-MS at t=30 min showed the reaction was complete. Diluted with DCM and filtered through celite. The yellow filtrate was stripped in vacuo to a tan solid. The material was not very soluble in DCM. The crude material was used as is in the subsequent hydrolysis.

Step 3

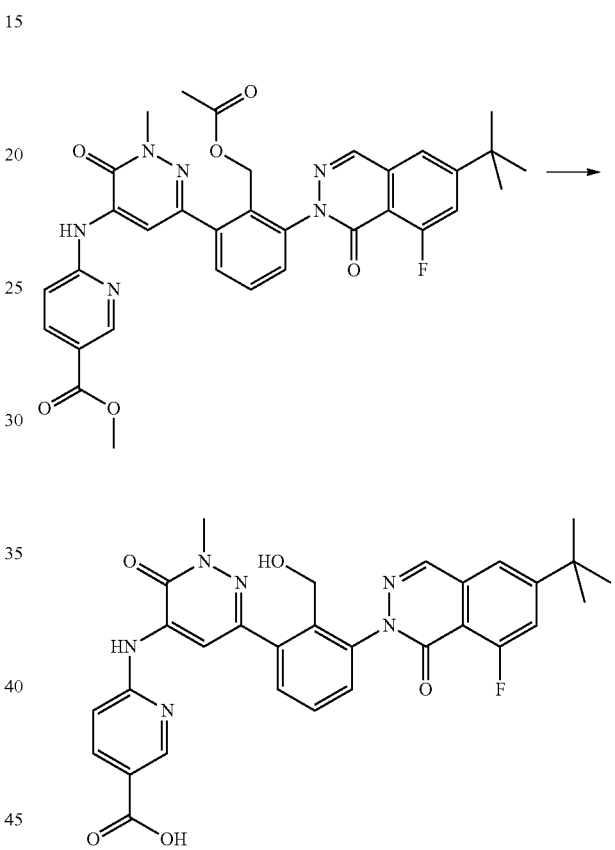

In a 250 mL round-bottomed flask, methyl 6-(6-(2-(acetoxymethyl)-3-(6-tert-butyl-8-fluoro-1-oxophthalazin-2(1H)-yl)phenyl)-2-methyl-3-oxo-2,3-dihydropyridazin-4-ylamino)nicotinate (325 mg, 519 µmol, Eq: 1.00) was combined with Dioxane (10 ml) and 1M LiOH (3 ml) to give a yellow solution containing a small amount of insoluble fine granules. The reaction mixture was stirred at 25° C. for 17 h. LC-MS at t=17 h showed the reaction was complete. Quenched with small amount of 1M HCl (acidic pH~1) and diluted with EtOAc. Separated the phases and the aqueous layer was back-extracted with EtOAc (2×25 mL). The combined organic layers were dried over Na$_2$SO$_4$ and concentrated in vacuo to a light tan solid. The solid was dried under vacuum to give 34 mg of a light tan powder in 12% yield. 1H NMR in CDCl$_3$ is consistent with desired product. MS (m−1)=569.

Example 10

6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide

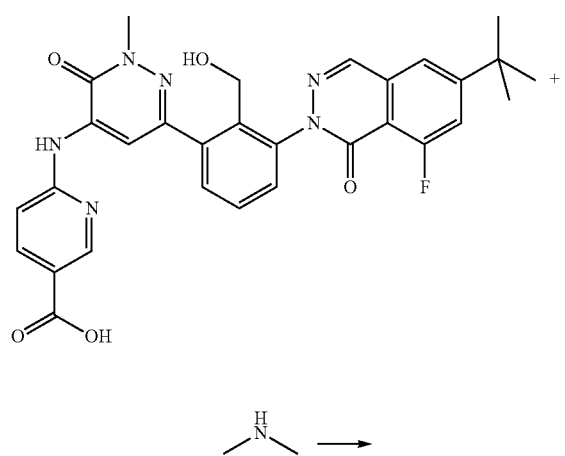

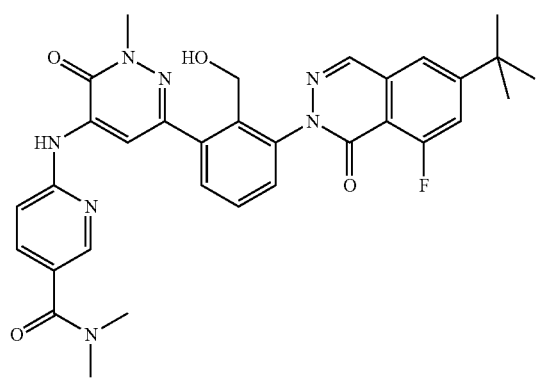

I-10

Step 4

In a 50 mL round-bottomed flask, 6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)nicotinic acid (34 mg, 59.6 µmol, Eq: 1.00), dimethylamine 2M in THF (38.7 µl, 77.5 µmol, Eq: 1.3) and Hunig's base (23.1 mg, 31.2 µl, 179 µmol, Eq: 3) were combined with DMF (1 ml) to give a yellow solution. HATU (27.2 mg, 71.5 µmol, Eq: 1.2) was added and the reaction mixture was stirred at 25° C. for 21 h. LC-MS at t=21 h showed the reaction was complete. The reaction mixture was diluted with H$_2$O and DCM. The two phase mixture was filtered and the aqueous layer was back-extracted with DCM (3×20 mL). The organic layers were combined, washed with water, dried over Na$_2$SO$_4$ and concentrated in vacuo to a peach colored solid. The crude material was purified by flash chromatography (silica gel, 25 g, 0% to 5% MeOH in DCM). The product was dried under vacuum to give 11 mg of a white crystalline solid in 31% yield. 1H NMR in CDCl$_3$ is consistent with desired product. MS (m+1)=598.

Preparation of I-11

Example 11

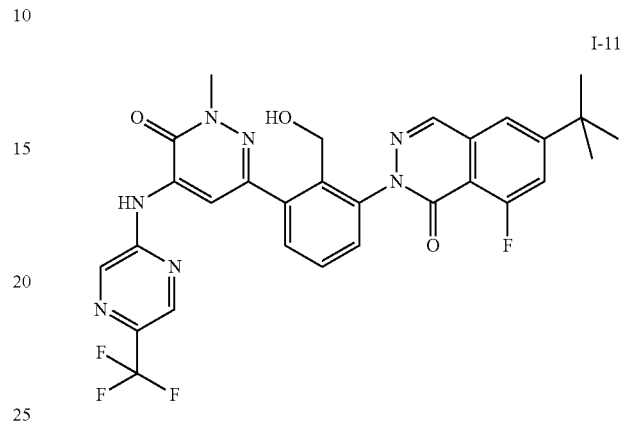

I-11

To a solution of 5-(trifluoromethyl)pyrazin-2-amine (146 mg, 0.90 mmol), 4-bromo-6-chloro-2-methylpyridazin-3(2H)-one (200 mg, 0.90 mmol), cesium carbonate (1.02 g, 3.13 mmol) and 4,5-bis(diphenylphosphino)-9,9-dimethylxanthine (77.7 mg, 0.13 mmol) in dioxane (10.0 ml) was added tris(dibenzylideneacetone)dipalladium(0) (61.5 mg, 0.07 mmol) and the reaction mixture purged with argon (3×) before being warmed to 90° C. for 18 hr. The mixture was cooled, diluted with dichloromethane and water (50 mL) and the layers separated. The aqueous phase was extracted with methylene chloride (2×25 mL). The organic phases were combined and dried over MgSO$_4$. The mixture was filtered and evaporated and the residue purified via automated flash chromatography (Analogix, SF15-24 g column, 1%-10% methanol/dichloromethane gradient) to give 6-chloro-2-methyl-4-(5-trifluoromethyl-pyrazin-2-ylamino)-2H-pyridazin-3-one (197 mg, 72%) as a yellow solid: LC/MS m/e calculated for C$_{10}$H$_7$ClF$_3$N$_5$O [M]$^+$ 305.03, observed 305.9

A solution of 6-chloro-2-methyl-4-(5-(trifluoromethyl)pyrazin-2-ylamino)pyridazin-3(2H)-one (109 mg, 0.36 mmol), 2-(6-tert-butyl-8-fluoro-1-oxophthalazin-2(1H)-yl)-6-(4,4,5,5-tetramethyl-1,3,2-dioxaborolan-2-yl)benzyl acetate (264 mg, 0.54 mmol), potassium phosphate (189 mg, 0.89 mmol) and 2-dicyclohexylphosphino-2',4',6'-triisopropylbiphenyl (17.0 mg, 0.04 mmol) in n-butanol (4 ml) and water (1 ml) was bubbled argon gas for 10 min. To this solution was added bis(dibenzylideneacetone)dipalladium (0) (10.3 mg, 0.02 mmol) was added and the resulting mixture heated to 100° C. for 2 hr. The mixture was cooled and then poured into a saturated ammonium chloride solution. The resulting mixture was extracted with methylene chloride (2×100 ml). The organic phases were combined and dried over MgSO$_4$. The mixture was filtered and evaporated and the residue dissolved in dioxane (10 mL). To this solution was slowly added a 2 M lithium hydroxide solution (0.5 mL) and the resulting mixture stirred at room temperature overnight. The resulting mixture was poured into a saturated ammonium chloride solution. The mixture was extracted with methylene chloride (2×150 ml). The organic phases were combined and dried over MgSO$_4$. The mixture was filtered and evaporated and the residue purified via automated flash chromatography (Analogix, SF15-24 g column, 1%-10% methanol/dichloromethane gradient) to give a light yellow solid which was recrystallized from methanol/dichloromethane to give 6-tert-butyl-8-fluoro-2-{2-hydroxymethyl-3-[1-methyl-6-oxo-5-(5-trifluoromethyl-pyrazin-2-ylamino)-1,6-dihydro-pyridazin-3-yl]-phenyl}-2H-phthalazin-1-one (65 mg, 31%) as a white solid: Mp 250-254° C.; LC/MS m/e calculated for $C_{29}H_{25}F_4N_7O_3$ $[M+H]^+$ 596.20, observed 596.3; $^1$H NMR (DMSO-$d_6$) δ: 10.38 (s, 1H), 8.71-9.08 (m, 2H), 8.43-8.66 (m, 2H), 7.68-8.02 (m, 2H), 7.38-7.65 (m, 3H), 4.54-4.76 (m, 1H), 4.40 (br. s., 2H), 3.82 (s, 3H), 1.38 (s, 9H).

Preparation of I-12

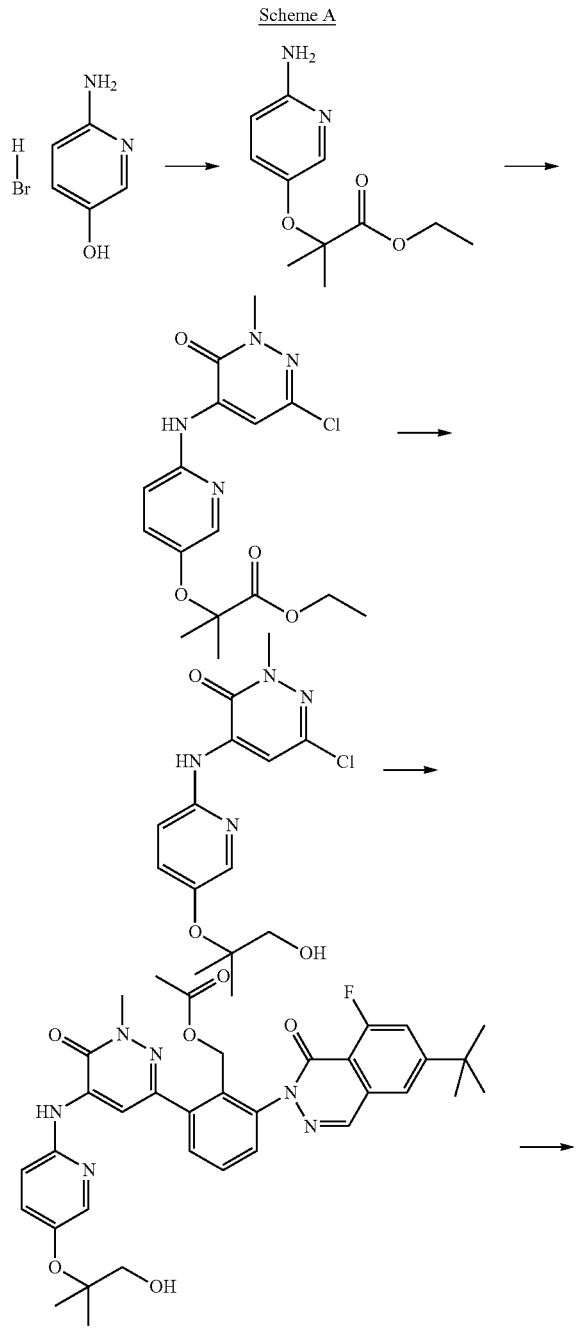

Scheme A

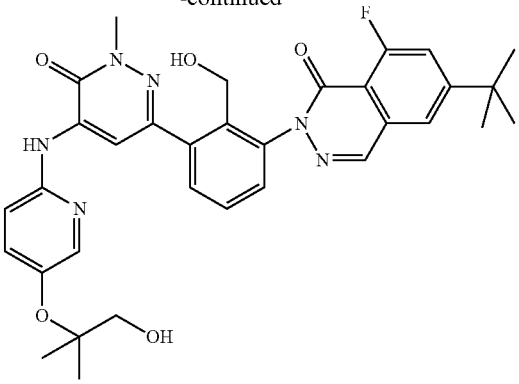

This example illustrates the synthesis of "6-tert-butyl-8-fluoro-2-(3-{5-[5-(2-hydroxy-1,1-dimethyl-ethoxy)-pyridin-2-ylamino]-1-methyl-6-oxo-1,6-dihydro-pyridazin-3-yl}-2-hydroxymethyl-phenyl)-2H-phthalazin-1-one".

Step 1. Preparation of 2-(6-amino-pyridin-3-yloxy)-2-methyl-propionic acid ethyl ester

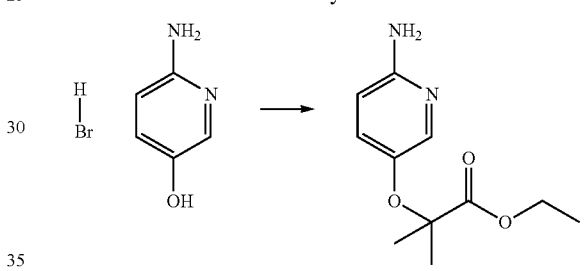

To a flask containing 6-aminopyridin-3-ol hydrobromide (2 g, 10.5 mmol) and ethyl-2-bromo-2-methylpropanate (2.04 g, 10.5 mmol) in anhydrous acetonitrile (25 ml) was added cesium carbonate (10.7 g, 33 mmol) and the material was stirred for 16 hours under argon atmosphere. Water (60 ml) and ethyl acetate (60 ml) were added and the material was shaken in a reparatory funnel. The organic phase was collected and the aqueous phase was back extracted with ethyl acetate (2×50 ml). The combined organic phases were dried over magnesium sulfate, filtered and concentrated in vacuo to provide a golden brown solid (1.626 g)(M+H)$^+$=225 m/e.

Step 2. Preparation of 2-[6-(6-chloro-2-methyl-3-oxo-2,3-dihydro-pyridazin-4-ylamino)-pyridin-3-yloxy]-2-methyl-propionic acid ethyl ester

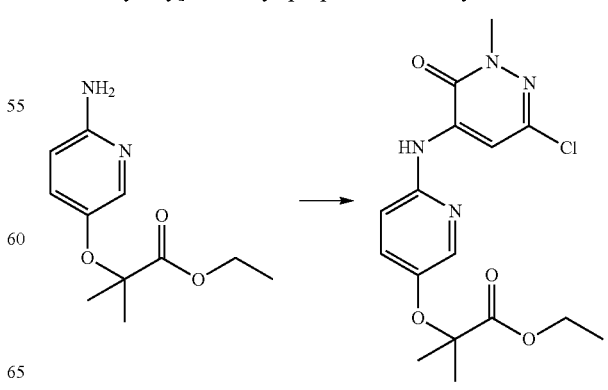

A flask containing 2-(6-amino-pyridin-3-yloxy)-2-methyl-propionic acid ethyl ester (1.365 g, 6.09 mmol), 4-bromo-6-chloro-2-methylpyridazin-3(2H)-one (1.77 g, 7.91 mmol), 4,5-bis(diphenylphosphino)-9,9-dimethylxanthene (528 mg, 0.913 mmol) and cesium carbonate (6.94 g, 21.3 mmol) in dry dioxane (60 ml) was evacuated under vacuum and back filled with argon (repeat 3 times). Tris(dibenzylideneacetone)dipalladium (0) (418 mg, 0.457 mmol) was added and the flask evacuated under vacuum and back filled with argon (repeat 3 times). The flask was place in an oil bath heated to 90° C. and stirred for 16 hours under argon atmosphere. The flask was cooled to ambient and the material was filtered through a plug of celite, rinsing well with dioxane. The volatiles were concentrated in vacuo and the residue was purified by silica gel chromatography, eluting with 5% to 25% ethyl acetate/hexane to provide the desired product as a light yellow-brown powder (2.035 g). $(M+H)^+=367$ m/e.

Step 3. Preparation of 6-chloro-4-[5-(2-hydroxy-1,1-dimethyl-ethoxy)-pyridin-2-ylamino]-2-methyl-2H-pyridazin-3-one

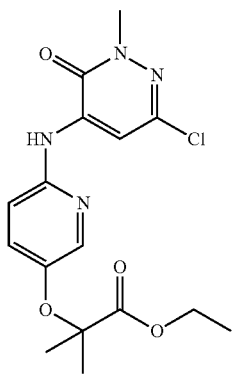
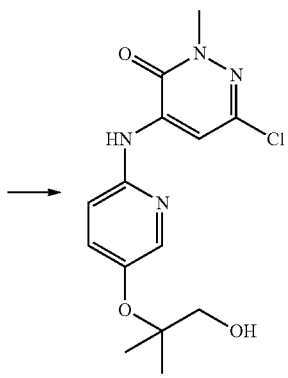

2-[6-(6-Chloro-2-methyl-3-oxo-2,3-dihydro-pyridazin-4-ylamino)-pyridin-3-yloxy]-2-methyl-propionic acid ethyl ester (1.23 g, 3.35 mmol, Eq: 1.00) was dissolved in anhydrous THF (25 ml) and cooled to −30° C. (dry ice/acetonitrile cooling bath) under nitrogen atmosphere A solution of lithium aluminum hydride (4.7 ml, 4.69 mmol, 1.0 M in THF) was added slowly, over 10 minutes via drop-wise addition. The mixture was stirred for 1 hour while maintaining the bath temperature at about −20° C. The reaction was carefully quenched by adding water (0.1 ml) and stirring for 10 minutes to ambient. Then a 5% aqueous solution of sodium hydroxide (0.19 ml) was added and the mixture stirred for 10 minutes. Water (0.19 ml) was added and stirring continued for 10 minutes. Finally magnesium sulfate was added and the material was filtered through a plug of celite, rinsing well with tetrahydrofuran. The material was concentrated on a rotary evaporator to about half the volume. Ethyl acetate (50 ml) and water (70 ml) was added and the material was shaken in a reparatory funnel. The organic phase was collected and the aqueous phase was back extracted with ethyl acetate (2×40 ml). The organics were combined, dried with magnesium sulfate, filtered and concentrated in vacuo. The residue was triturated from hot dichloromethane/hexanes to provide the desired product as a light yellow-brown solid (1.041 g). $(M+H)^+=325$ m/e.

Step 4. Preparation of acetic acid 2-(6-tert-butyl-8-fluoro-1-oxo-1H-phthalazin-2-yl)-6-{5-[5-(2-hydroxy-1,1-dimethyl-ethoxy)-pyridin-2-ylamino]-1-methyl-6-oxo-1,6-dihydro-pyridazin-3-yl}-benzyl ester

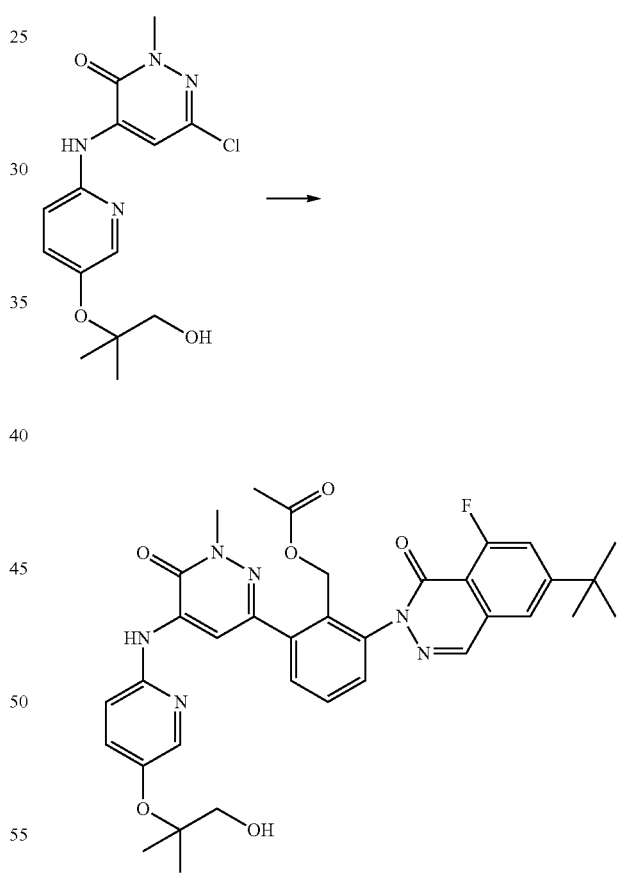

This reaction was carried out under similar conditions to those described in step 7, example I-6, but substituting 6-chloro-4-[5-(2-hydroxy-1,1-dimethyl-ethoxy)-pyridin-2-ylamino]-2-methyl-2H-pyridazin-3-one for 6-chloro-4-[5-(2-dimethylamino-1,1-dimethyl-ethoxy)-pyridin-2-ylamino]-2-methyl-2H-pyridazin-3-one. After work-up the product was purified by preparative thin layer chromatography (3 plates), eluting with 5% methanol/methylene chloride.

This provided the desired product (together with some desacetyl product) as a light brown viscous oil (400 mg). (M+H)⁺=657 m/e.

Example 12

Step 5. Preparation of 6-tert-butyl-8-fluoro-2-(3-{5-[5-(2-hydroxy-1,1-dimethyl-ethoxy)-pyridin-2-ylamino]-1-methyl-6-oxo-1,6-dihydro-pyridazin-3-yl}-2-hydroxymethyl-phenyl)-2H-phthalazin-1-one

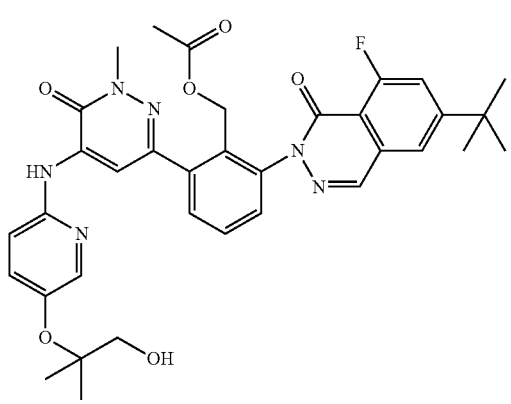

This reaction was carried out under similar conditions to those described in step 8, example I-6. After work-up the product was purified by preparative thin layer chromatography (3 plates), eluting with 2% methanol/methylene chloride. The plates were then re-developed with 3% and then 5% methanol/methylene chloride. This provided the desired product as a light yellow solid (226 mg). (M+H)⁺=615 m/e. ¹H NMR (300 MHz, CHLOROFORM-d) δ ppm 1.27 (s, 6H) 1.43 (s, 9H) 2.14 (t, J=6.42 Hz, 1H) 3.61 (d, J=6.04 Hz, 2H) 3.90 (s, 3H) 3.91-3.95 (m, 1H) 4.42 (d, J=6.80 Hz, 2H) 6.92 (d, J=8.69 Hz, 1H) 7.32 (dd, J=8.88, 2.83 Hz, 1H) 7.43-7.54 (m, 3H) 7.57 (t, J=7.90 Hz, 1H) 7.63-7.70 (m, 1H) 8.09 (d, J=3.02 Hz, 1H) 8.24-8.32 (m, 2H) 8.55 (s, 1H)

Preparation of I-13

Scheme B

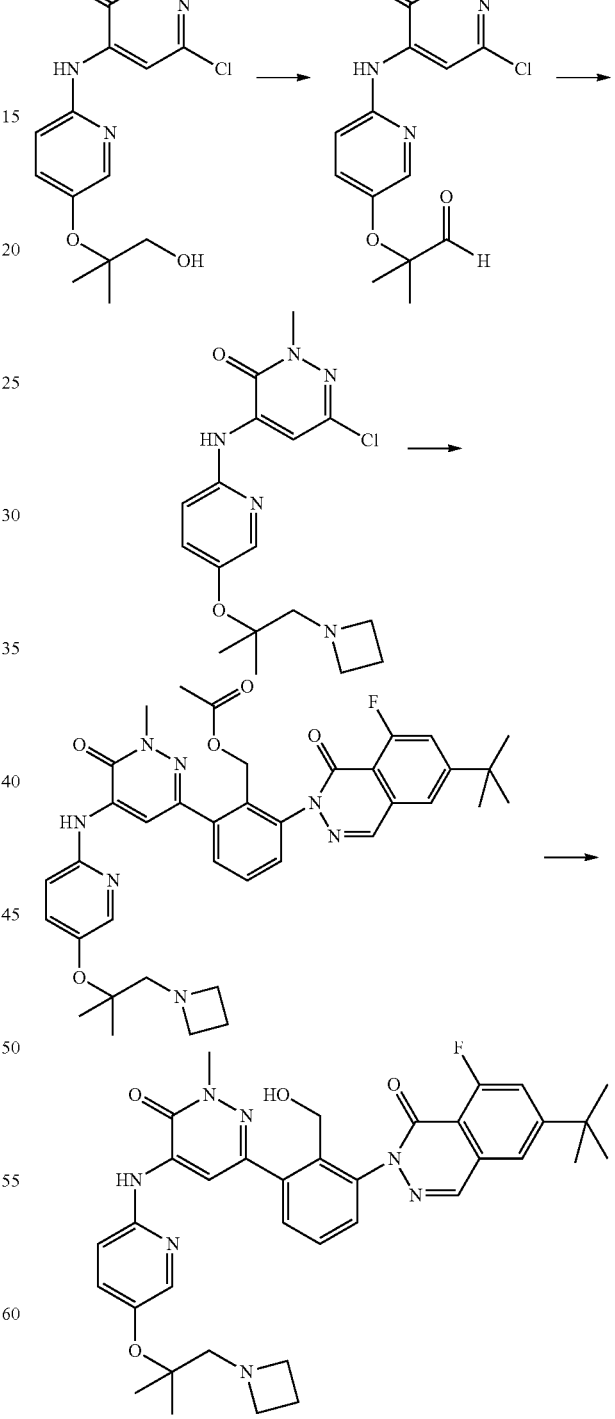

This example illustrates the synthesis of "2-(3-{5-[5-(2-Azetidin-1-yl-1,1-dimethyl-ethoxy)-pyridin-2-ylamino]-1- methyl-6-oxo-1,6-dihydro-pyridazin-3-yl}-2-hydroxymethyl-phenyl)-6-tert-butyl-8-fluoro-2H-phthalazin-1-one".

Step 1. Preparation of 2-[6-(6-chloro-2-methyl-3-oxo-2,3-dihydro-pyridazin-4-ylamino)-pyridin-3-yloxy]-2-methyl-propionaldehyde

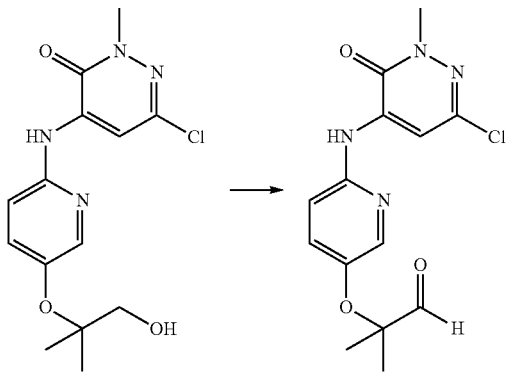 [SMILES: Cn1nc(Cl)cc(Nc2ccc(OC(C)(C)CO)cn2)c1=O ; Cn1nc(Cl)cc(Nc2ccc(OC(C)(C)C=O)cn2)c1=O]

6-Chloro-4-(5-(1-hydroxy-2-methylpropan-2-yloxy)pyridine-2-ylamino)-2-methylpyridazin-3-(2H)-one (965 mg, 2.97 mmol) was taken up in a mixture of tetrahydrofuran (25 ml) and dichloromethane (15 ml). To the suspension was added Dess-Martin Periodinane (1.64 g, 3.86 mmol) and the flask was capped and stirred for 40 minutes. An aqueous saturated solution of sodium bicarbonate (50 ml) followed by the addition of an aqueous 10% solution of sodium thiosulfate (50 ml) and the material was stirred vigorously for 15 minutes. Ethyl acetate (50 ml) was added and the contents were shaken in a separatory funnel. The organic phase was collected and washed with brine solution (50 ml). The ethyl acetate phase was collected and the aqueous phases were back extracted with dichloromethane (2×40 ml). The combined organic phases were dried over magnesium sulfate, filtered and concentrated in vacuo. The product was purified via trituration from hot dichloromethane/hexanes to provide a brown solid (688 mg) (M+H)$^+$=323 m/e.

Step 2. Preparation of 4-[5-(2-Azetidin-1-yl-1,1-dimethyl-ethoxy)-pyridin-2-ylamino]-6-chloro-2-methyl-2H-pyridazin-3-one

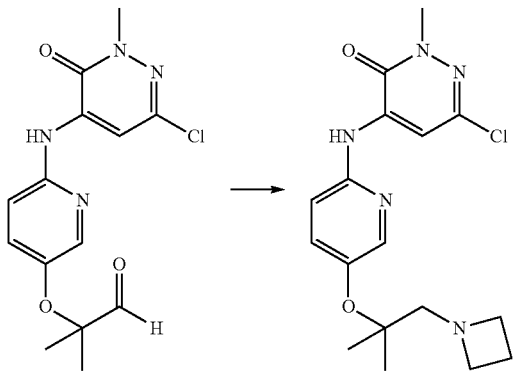 [SMILES: Cn1nc(Cl)cc(Nc2ccc(OC(C)(C)C=O)cn2)c1=O ; Cn1nc(Cl)cc(Nc2ccc(OC(C)(C)CN3CCC3)cn2)c1=O]

A pressure flask containing 2-[6-(6-chloro-2-methyl-3-oxo-2,3-dihydro-pyridazin-4-ylamino)-pyridin-3-yloxy]-2-methyl-propionaldehyde (188 mg, 0.582 mmol) was taken up in dichloromethane (2.5 ml). Sodium triacetoxyborohydride (309 mg, 1.46 mmol) and acetic acid (0.1 ml, 1.75 mmol) were added and the flask was next cooled in an ice bath under nitrogen atmosphere. Azetidine (0.24 ml, 3.49 mmol) was added and the flask was sealed. The flask was placed in an oil bath heated to 50° C. and stirred for 16 hours. The mixture was cooled to ambient and taken up in dichloromethane (50 ml) and a saturated solution of aqueous sodium bicarbonate (50 ml). The material was transferred to a separatory funnel and shaken. The organic phase was collected and washed with a solution of 50% diluted brine (50 ml). The dichloromethane phase was collected and the aqueous phases were back extracted with methylene chloride (2×40 ml). The combined organic phase was dried (magnesium sulfate), filtered and concentrated in vacuo. The crude residue was loaded onto two preparatory TLC plates and eluted with 8% methanol/dichloromethane. The product band was collected to provide the desired product as a light white-brown powder (139 mg). (M+H)$^+$=364 m/e.

Step 3. Preparation of acetic acid 2-{5-[5-(2-azetidin-1-yl-1,1-dimethyl-ethoxy)-pyridin-2-ylamino]-1-methyl-6-oxo-1,6-dihydro-pyridazin-3-yl}-6-(6-tert-butyl-8-fluoro-1-oxo-1H-phthalazin-2-yl)-benzyl ester

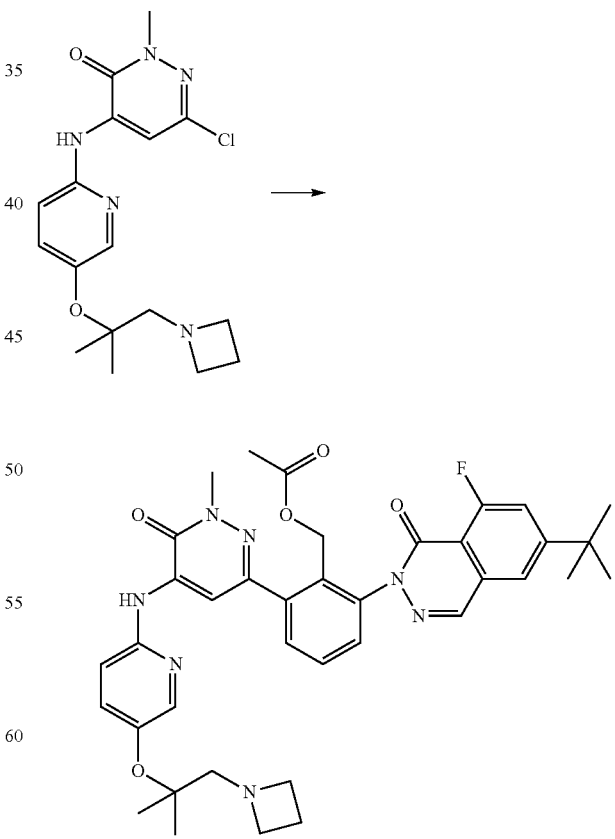

Acetic acid 2-{5-[5-(2-azetidin-1-yl-1,1-dimethyl-ethoxy)-pyridin-2-ylamino]-1-methyl-6-oxo-1,6-dihydropyridazin-3-yl}-6-(6-tert-butyl-8-fluoro-1-oxo-1H-phthalazin-2-yl)-benzyl ester was prepared using the general procedure described in step 7 for the preparation of I-6. After work up the material was purified by preparative TLC (3 plates, eluting with 8% methanol/dichloromethane to provide the desired product as a light brown viscous oil (238 mg). (M+H)$^+$=696 m/e.

Example 13

Step 4. Preparation of 2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one

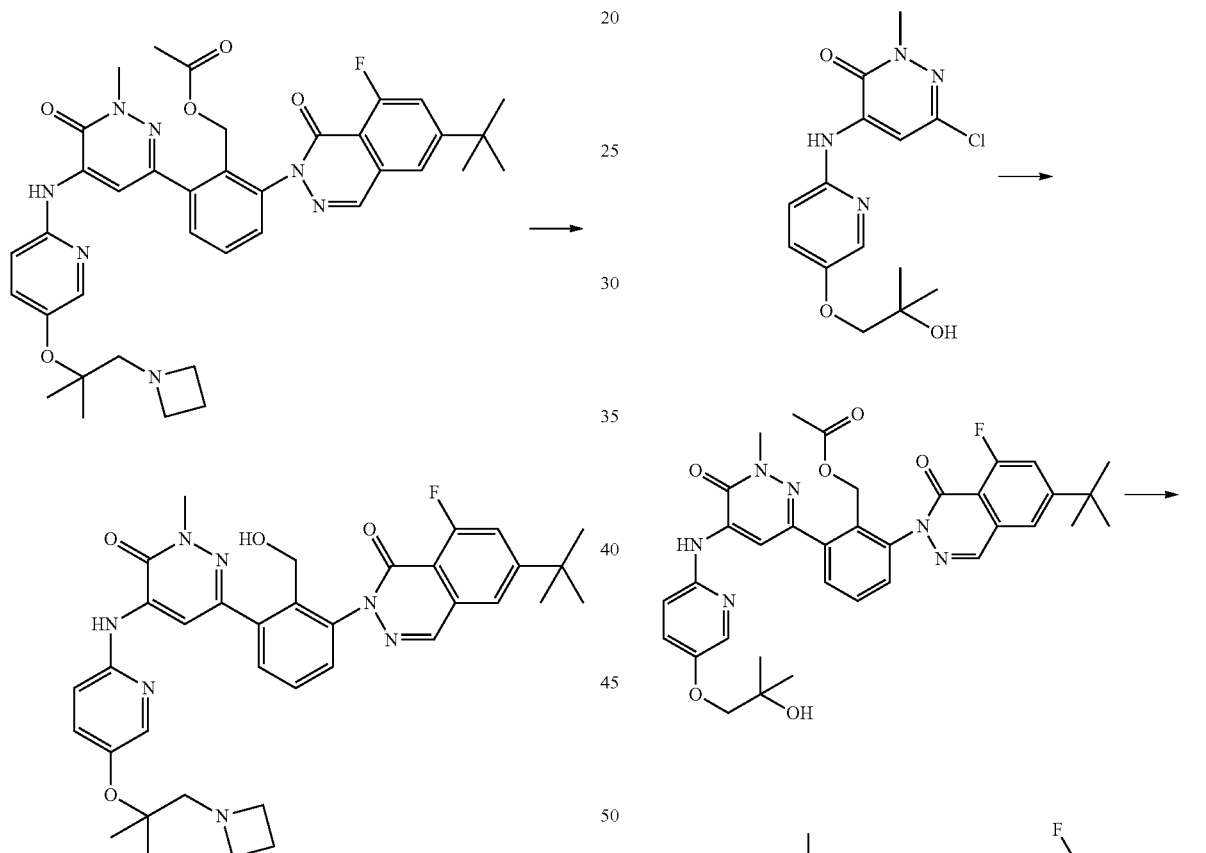

2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one was prepared using the general procedure described in step 8 of the preparation of I-6. After work up the product was purified by preparative TLC on silica gel, eluting with 3% methanol/methylene chloride and then re-developing with 5%, 8% and then finally 11% methanol/methylene chloride. This provided the desired product as a light brown powder (96 mg). (M+H)$^+$=654 m/e. $^1$H NMR (300 MHz, CHLOROFORM-d) δ ppm 1.21 (s, 6H) 1.40 (s, 9H) 2.11 (quin, J=7.20 Hz, 2H) 2.58 (s, 2H) 3.35 (t, J=6.99 Hz, 4H) 3.87 (s, 3H) 4.40 (s, 2H) 6.90 (d, J=9.06 Hz, 1H) 7.29 (dd, J=8.88, 2.83 Hz, 1H) 7.39-7.69 (m, 5H) 8.04 (d, J=2.64 Hz, 1H) 8.27 (d, J=2.64 Hz, 1H) 8.32 (s, 1H) 8.51 (s, 1H).

Preparation of I-14

This example illustrates the synthesis of "6-tert-Butyl-8-fluoro-2-(2-hydroxymethyl-3-{5-[5-(2-hydroxy-2-methylpropoxy)-pyridin-2-ylamino]-1-methyl-6-oxo-1,6-dihydro-pyridazin-3-yl}-phenyl)-2H-phthalazin-1-one".

Step 1. Preparation of 1-(6-amino-pyridin-3-yloxy)-2-methyl-propan-2-ol

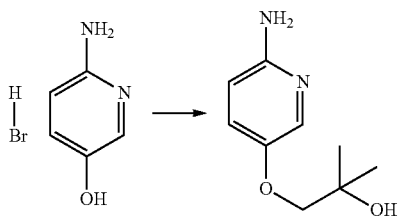

To a microwave flask containing 6-aminopyridin-3-ol hydrobromide (700 mg, 3.66 mmol) and 1-chloro-2-methyl-2-propanol (597 mg, 5.5 mmol) in anhydrous dimethylformamide (17 ml) was added cesium carbonate (3.7 g, 11.4 mmol) and the material was heated in a microwave oven at 140° C. for 3 hours. The vial was cooled to ambient and the solvent was concentrated in vacuo (rotary evaporator/mechanical pump). The residue was taken up in methylene chloride and filtered to remove insolubles, rinsing well with methylene chloride. The crude material was purified by HPLC on silica gel, eluting with a gradient of 2% to 10% methanol/methylene chloride to provide the desired product as a orange-brown viscous oil which solidified on standing (449 mg). MS (H+)=183 m/e.

Step 2. Preparation of 6-chloro-4-[5-(2-hydroxy-2-methyl-propoxy)-pyridin-2-ylamino]-2-methyl-2H-pyridazin-3-one

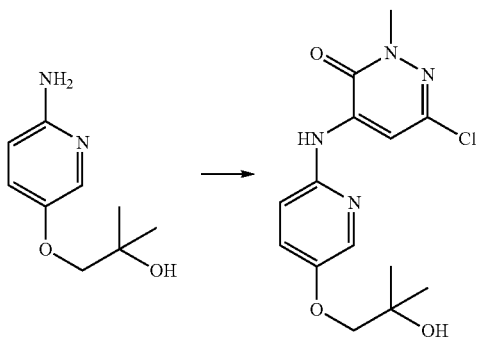 [SMILES: CC(C)(O)COc1ccc(N)nc1 ; Cn1nc(Cl)cc(Nc2ccc(OCC(C)(C)O)cn2)c1=O]

6-Chloro-4-[5-(2-hydroxy-2-methyl-propoxy)-pyridin-2-ylamino]-2-methyl-2H-pyridazin-3-one was prepared using the general procedure described in step 6 of the preparation of I-6. The crude product was purified by preparative thin layer chromatography (3 plates), eluting with 4.5% methanol/methylene chloride to provide the desired product as a light yellow powder (392 mg). (M+H)+=325 m/e.

Step 3. Preparation of acetic acid 2-(6-tert-butyl-8-fluoro-1-oxo-1H-phthalazin-2-yl)-6-{5-[5-(2-hydroxy-2-methyl-propoxy)-pyridin-2-ylamino]-1-methyl-6-oxo-1,6-dihydro-pyridazin-3-yl}-benzyl ester

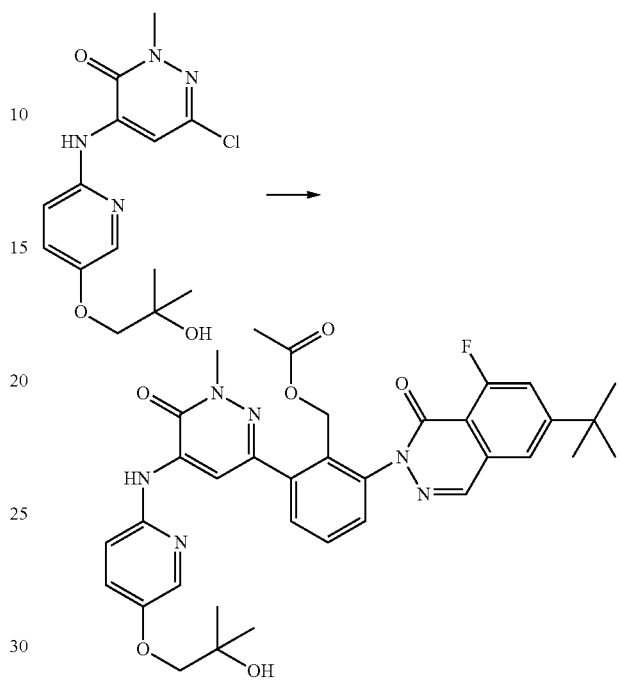

This reaction was carried out under similar conditions to those described in step 7, example I-6, but substituting 6-chloro-4-[5-(2-hydroxy-2-methyl-propoxy)-pyridin-2-ylamino]-2-methyl-2H-pyridazin-3-one for 6-chloro-4-[5-(2-dimethylamino-1,1-dimethyl-ethoxy)-pyridin-2-ylamino]-2-methyl-2H-pyridazin-3-one. After work-up the product was purified by preparative thin layer chromatography (2 plates), eluting with 5% methanol/methylene chloride. This provided the desired product (together with some desacetyl product) as a light yellow powder (284 mg).
(M+H)+=657 m/e.

Example 14

Step 4. Preparation of 6-tert-butyl-8-fluoro-2-(2-hydroxymethyl-3-{5-[5-(2-hydroxy-2-methyl-propoxy)-pyridin-2-ylamino]-1-methyl-6-oxo-1,6-dihydro-pyridazin-3-yl}-phenyl)-2H-phthalazin-1-one

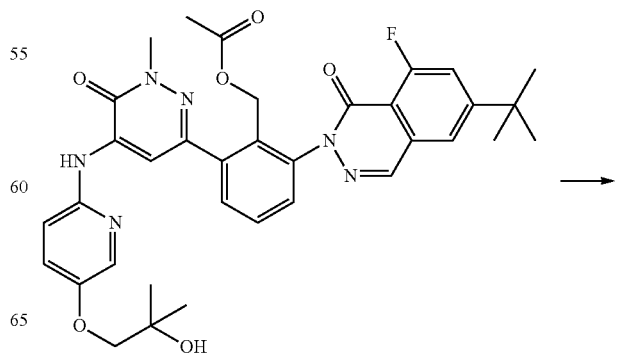

137

-continued

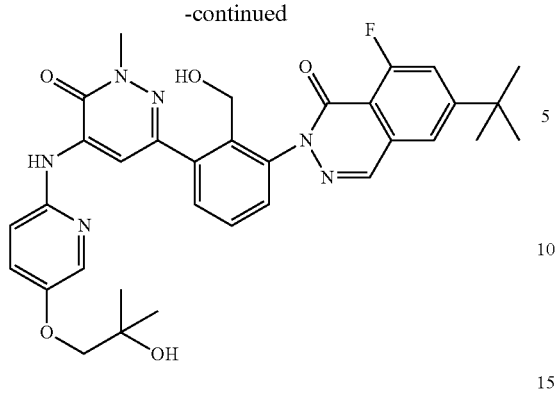

This reaction was carried out under similar conditions to those described in step 8, example I-6. After work-up the product was purified by preparative thin layer chromatography (2 plates), eluting with 3.5% methanol/methylene chloride. The plates were then re-developed with 5% methanol/methylene chloride. This provided the desired product as a light yellow solid (195 mg). (M+H)$^+$=615 m/e. $^1$H NMR (300 MHz, DMSO-d$_6$) δ ppm 1.16 (s, 6H) 1.37 (s, 9H) 3.72 (s, 2H) 3.76 (s, 3H) 4.32-4.46 (m, 2H) 4.51-4.59 (m, 1H) 4.61 (s, 1H) 7.39 (dd, J=8.69, 3.02 Hz, 1H) 7.43-7.57 (m, 4H) 7.69-7.78 (m, 1H) 7.86 (br. s, 1H) 8.02 (d, J=2.64 Hz, 1H) 8.39 (s, 1H) 8.50 (d, J=2.64 Hz, 1H) 9.31 (s, 1H).

Preparation of I-15

Scheme D

138

-continued

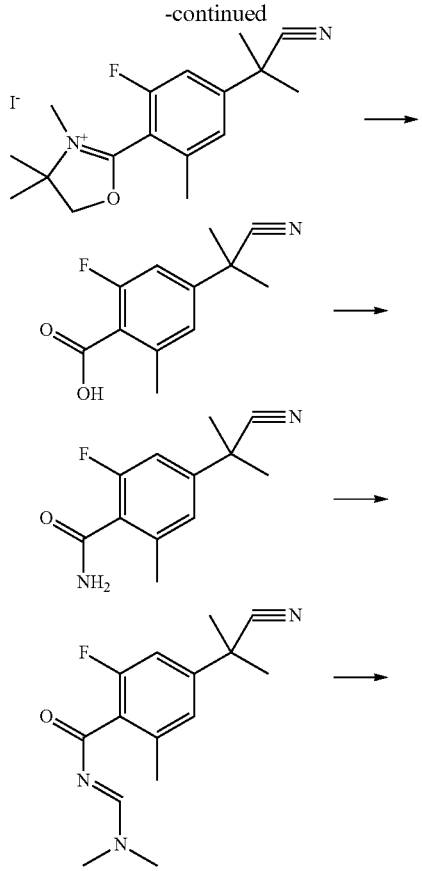

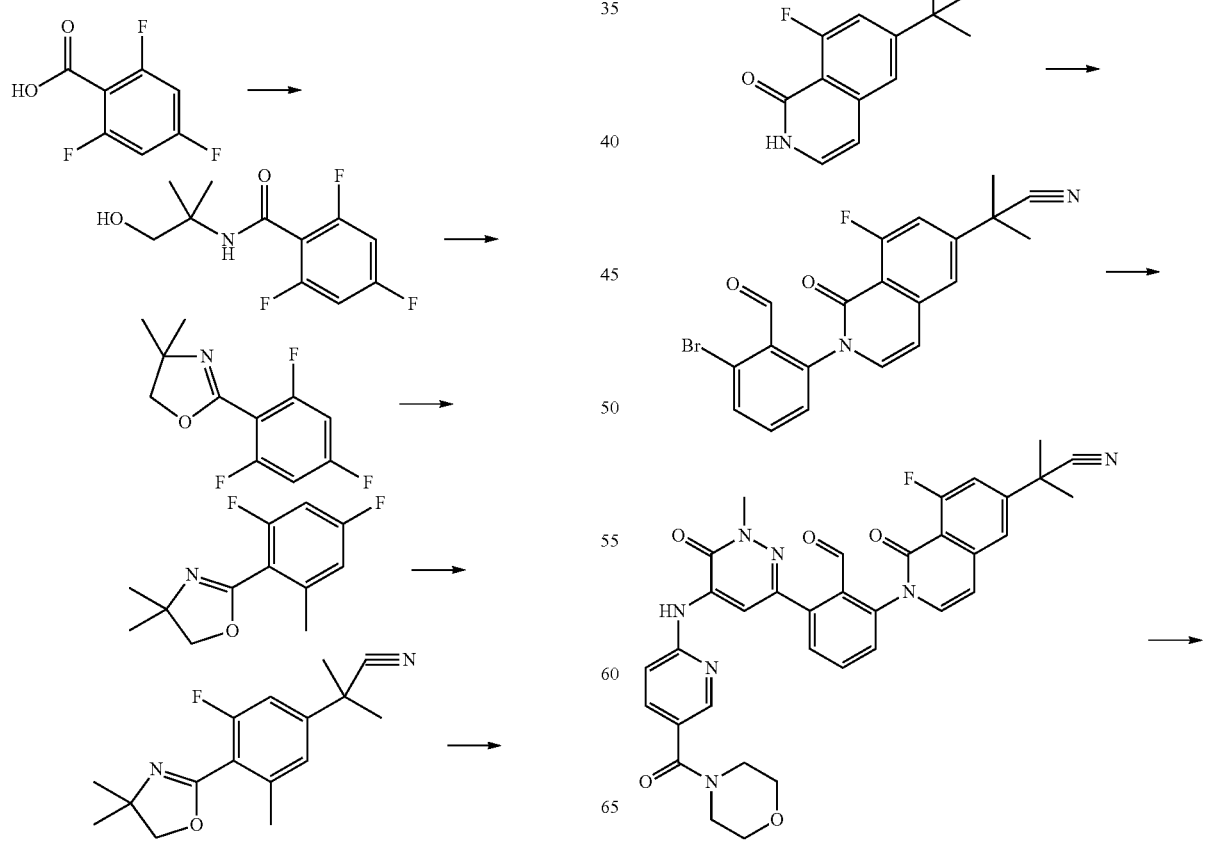

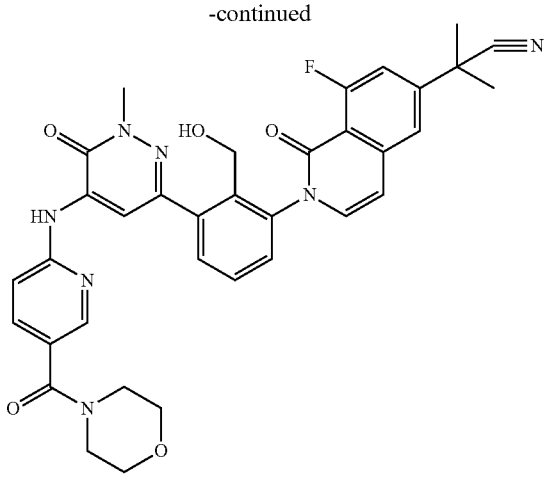

This example illustrates the synthesis of "2-[8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile".

Step 1. Preparation of 2,4,6-trifluoro-N-(2-hydroxy-1,1-dimethyl-ethyl)-benzamide

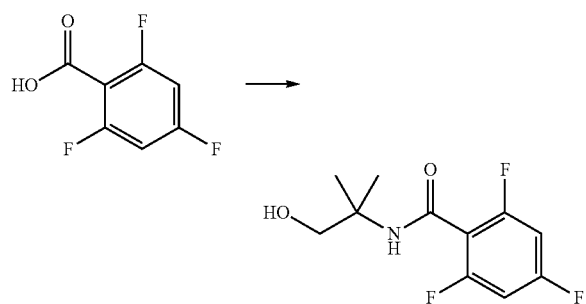

A flask, fitted with a calcium chloride drying tube, was charged with 2,4,6-trifluorobenzoic acid (25 g, 142 mmol) and taken up in dry dichloromethane (220 mL). The material was cooled to 0° C. (ice bath) and to this was added oxalyl chloride (13.2 ml; 156 mmol) via syringe. Dry dimethylformamide (104 mg; 1.42 mmol) was next added and moderate bubbling was observed. After 15 minutes the cooling bath was removed and the mixture was stirred vigorously for 5 hours. The volatiles were concentrated in vacuo. (rotary evaporator) and the residue was taken up in dry dichloromethane (150 ml) and cooled to 0° C. (ice bath). To this solution was added 2-amino-2-methyl-1-propanol (27.2 ml, 284 mmol) via slow drop-wise addition. After complete addition the cooling bath was removed and the mixture was warmed to ambient over night.

The reaction, as described above was repeated on the same scale, and the combined reaction products were worked up as follows: The non-homogeneous mixture was suction filtered, rinsing with dichloromethane (approximately 300 ml). This first filtrate was set aside and the solid was rinsed a second time with dichloromethane (500 ml) using slow gravity filtration. The dichloromethane from the second filtration was concentrated in vacuo, which provided very pure product as a white crystalline solid (22.9 g). The dichloromethane solution from the first filtration was concentrated in vacuo to provide an impure brown colored residue. This material was taken up in dichloromethane (200 ml) and water (250 ml) and shaken in a reparatory funnel. The organic phase was collected and the aqueous phase back extracted with dichloromethane (2×120 ml). The dichloromethane phases were combined, dried (magnesium sulfate), filtered and concentrated in vacuo. The crude residue was purified via trituration from hot dichloromethane/hexanes to provide additional desired product as a yellow solid (43.8 g). (M+H)$^+$=246 m/e.

Step 2. Preparation of 4,4-dimethyl-2-(2,4,6-trifluoro-phenyl)-4,5-dihydro-oxazole

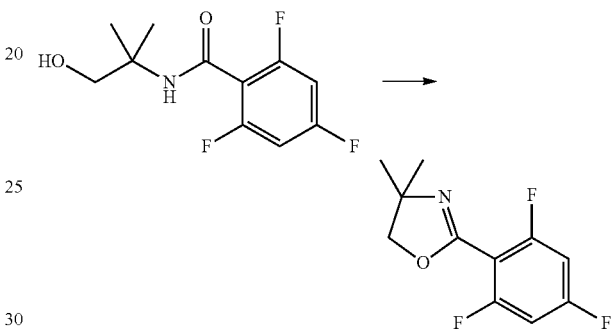

To a solution of 2,4,6-trifluoro-N-(2-hydroxy-1,1-dimethyl-ethyl)-benzamide (43.8 g, 177.1 mmol) in dry dichloromethane (400 mL) was added thionyl chloride (58.9 ml, 415 mmol) via slow drop-wise addition over 25 minutes (reaction flask was immersed in an ice bath part way through the addition to control the temperature). After complete addition the material was stirred at ambient temperature over night. The volume was reduced to 30% by concentration under vacuum. To that was added ether (200 ml) and a solid precipitate (39.94 g off-white solid) was collected by filtration. The ether filtrate was set aside and the solid material was taken up in water (120 ml) and treated with an aqueous solution of sodium hydroxide (2N, 55 ml). Ethyl acetate (120 ml) was added and the mixture was transferred to a separatory funnel and shaken. The organic phase was collected and washed with an equal volume of water. The ethyl acetate phase was collected and the aqueous phases were back extracted with ethyl acetate (2×100 ml). The combined organic phases were dried (magnesium sulfate), filtered and concentrated in vacuo to provide the desired as a pure off-white solid (33.98 g). (M+H)$^+$=230 m/e.

Step 3. Preparation of 2-(2,4-difluoro-6-methyl-phenyl)-4,4-dimethyl-4,5-dihydro-oxazole

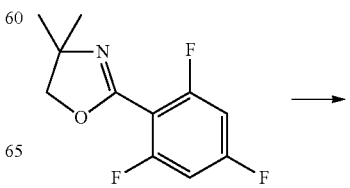

-continued

To a cooled (ice bath) solution of 4,4-dimethyl-2-(2,4,6-trifluorophenyl)-4,5-dihydrooxazole (16.8 g, 73.3 mmol) in dry tetrahydrofuran (150 ml) was added a solution of methyl magnesium bromide (73.3 ml, 3M in ether) via slow dropwise addition. The mixture was stirred for 2 hours at 0° C. and then warmed to ambient over 6 hours. The reaction was carefully quenched via the addition a saturated aqueous solution of ammonium chloride (30 ml) and the material was taken up in water (200 ml) and ethyl acetate (150 ml), transferred to a separatory funnel and the organic phase was collected. The organic phase was washed with water (200 ml) and the ethyl acetate phase collected. The aqueous phases were back extracted with ethyl acetate (2×120 ml) and the organic phases were combined, dried over magnesium sulfate, filtered and concentrated in vacuo to provide the desired product as a light yellow oil (16.31 g). $(M+H)^+=226$ m/e.

Step 4. Preparation of 2-[4-(4,4-dimethyl-4,5-dihydro-oxazol-2-yl)-3-fluoro-5-methyl-phenyl]-2-methyl-propionitrile

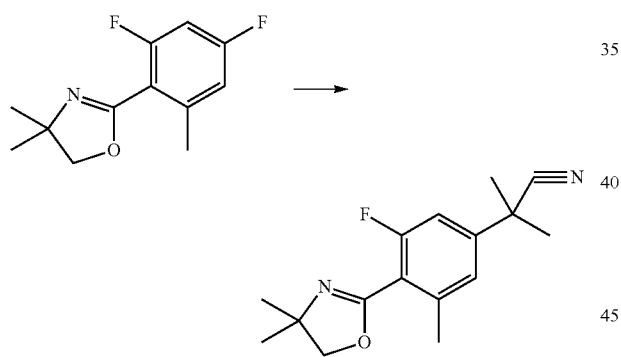

A flask containing a solution of 2-(2,4-difluoro-6-methylphenyl)-4,4-dimethyl-4,5-dihydrooxazole (14.84 g, 65.9 mmol) and isobutyronitrile (9.11 g, 132 mmol) in dry tetrahydrofuran (130 ml) was cooled to −15 to −20° C. (acetonitrile/dry ice bath) under an argon atmosphere. A solution of potassium bis(trimethylsilyl) amide (171 ml, 0.5M in toluene) was added via slow drop-wise addition. The mixture was stirred for 30 minutes at −15° C. and then gradually warmed to 15° C. over about 1.5 hours. The material was quenched via the addition of a saturated solution of aqueous ammonium chloride (100 ml). Water (80 ml) and diethyl ether (50 ml) were added and the material was transferred to a reparatory funnel and the organic phase was collected. This was washed with an equal volume of water and the organic phase was collected. The aqueous phases were back extracted with ether (2×100 ml) and the combined organic phases were dried over magnesium sulfate, filtered and concentrated in vacuo. The material was purified by chromatography on silica gel eluting with 60% ethyl acetate/hexane to provide semi-pure product as a golden yellow oil (18 g, 75% pure). This material was used "as is" in subsequent steps. $(M+H)^+=275$ m/e.

Step 5. Preparation of 2-(4-(2-cyanopropyl-2-yl)-2-fluoro-6-methylphenyl)-3,4,4-trimethyl-4,5-dihydrooxazole-3-ium iodide

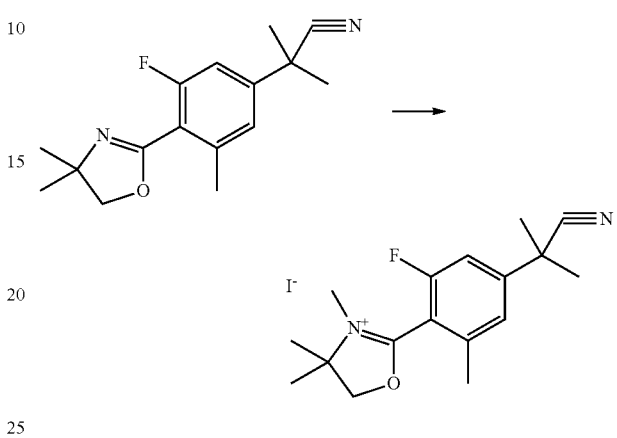

To a solution 2-[4-(4,4-dimethyl-4,5-dihydro-oxazol-2-yl)-3-fluoro-5-methyl-phenyl]-2-methyl-propionitrile (23.86 g, 60% purity, 52.2 mmol) in dry acetonitrile (237 ml) was added methyl iodide (37 g, 261 mmol) via drop-wise addition over 10 minutes. The mixture was transferred to an oil bath heated to 63° C. and stirred over night. The flask was cooled to ambient and then in an ice bath and a solid precipitated product was collected by decantation, providing the desired product as an off-white solid which turned light yellow on standing (21.9 g). Material was used "as is" in the next step.

Step 6. Preparation of 4-(cyano-dimethyl-methyl)-2-fluoro-6-methyl-benzoic acid

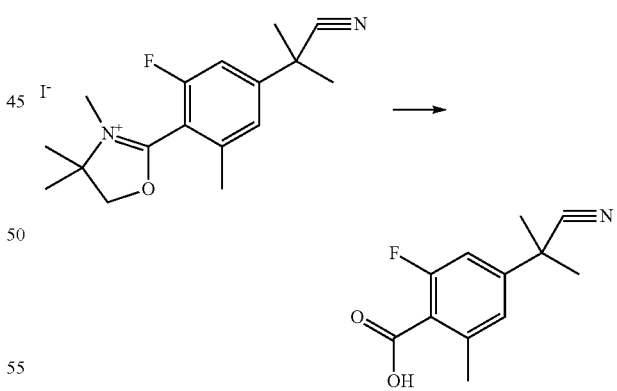

A flask was charged with 2-(4-(2-cyanopropyl-2-yl)-2-fluoro-6-methylphenyl)-3,4,4-trimethyl-4,5-dihydrooxazole-3-ium iodide (21.9 g, 52.7 mmol) and methanol (89 ml). To this slurry was added a solution of sodium hydroxide (10.5 g, 263 mmol) in water (178 ml) and the material was heated in an oil bath at 80° C. The mixture was vigorously stirred for 60 minutes and then toluene (120 ml) was added. The mixture was stirred and shaken for 5 minutes in the oil bath. While still hot the material was transferred to a separatory funnel and the aqueous phase was collected. This was acidified with aqueous 1.5 N hydrochloric acid (to pH=1). Ethyl acetate (25 ml) and water (5 ml) are added and the mixture was shaken in a separatory funnel. The organic phase was collected and the aqueous phase was back extracted with ethyl acetate (2×40 ml). The combined organic phases were dried with magnesium sulfate, filtered and concentrated in vacuo to provide semi-pure product as a light yellow solid (5.4 g). (M−H)−=220 m/e.

Step 7. Preparation of 4-(cyano-dimethyl-methyl)-2-fluoro-6-methyl-benzamide

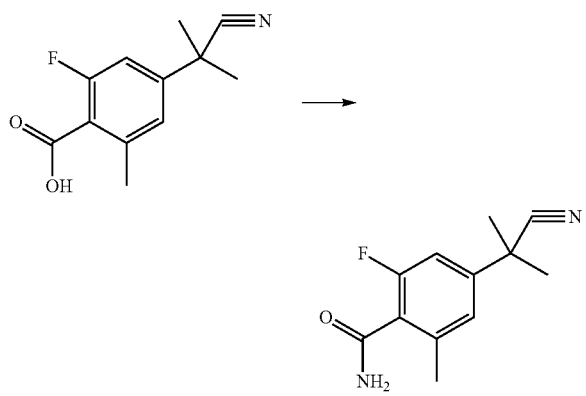

4-(2-cyanopropan-2-yl)-2-fluoro-6-methylbenzoic acid (14 g, 35 mmol, 75% pure) was taken up in dry tetrahydrofuran (100 ml). To this was added 1,1'-carbonyldiimidazole (11.2 g, 69.1 mmol) in four equal portions over 15 minutes. The mixture was stirred for 2.5 hours and then a 28% aqueous solution of ammonium hydroxide (20.4 ml) was added via drop-wise addition. The material was stirred for 4 hours and then concentrated under reduced pressure to remove 90% of the volatiles. The residue was taken up in water (80 ml) and dichloromethane (80 ml) and shaken in a reparatory funnel. The organic phase was collected and the aqueous phase was back extracted with dichloromethane (3×60 ml). The combined organic phase was dried (magnesium sulfate), filtered and concentrated in vacuo and the resultant semisolid was purified via trituration from hot dichloromethane/hexanes to provide the desired product as a slightly-impure off-white solid (10.71 g, 80% purity). (M+H)+=221 m/e.

Step 8. Preparation 4-(cyano-dimethyl-methyl)-N-[1-dimethylamino-meth-(E)-ylidene]-2-fluoro-6-methyl-benzamide

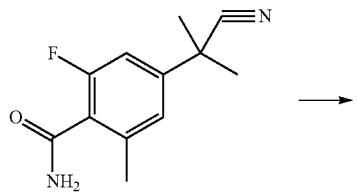

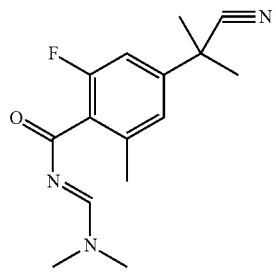

In a 250 ml round bottom flask was placed 4-(2-cyanopropan-2-yl)-2-fluoro-6-methylbenzamide (8.71 g, 31.6 mmol, 80% purity) and dimethylformamide dimethylacetal (7.26 ml, 51.4 mmol) in tetrahydrofuran (61 ml) to provide a non-homogeneous yellow suspension. The reaction mixture was heated to 63° C. (oil bath) and stirred for 3 hours. The mixture was concentrated on the rotary evaporator and then taken up in hexane (80 ml). This mixture was stirred vigorously for a few minutes until a white precipitate forms. The product was collected by filtration, rinsing well with hexane to provide product as a white solid (7.02 g). (M+H)+=276 m/e.

Step 9. Preparation of 2-(8-fluoro-1-oxo-1,2-dihydro-isoquinolin-6-yl)-2-methyl-propionitrile

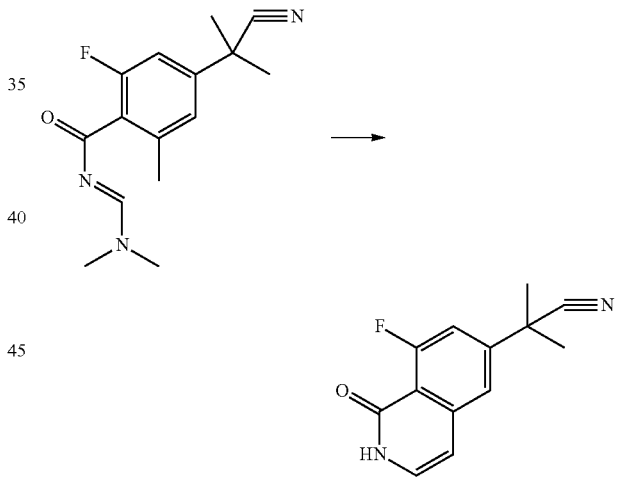

4-(Cyano-dimethyl-methyl)-N-[1-dimethylamino-meth-(E)-ylidene]-2-fluoro-6-methyl-benzamide. (10.66 g, 38.7 mmol) was taken up in dry tetrahydrofuran (100 ml) and placed in an oil bath heated to 55° C. A solution of potassium tert-butoxide (58.1 ml, 1M in tetrahydrofuran) was added drop-wise from an addition funnel over 15 minutes. The reaction mixture was heated to 62° C. and stirred for 2 hours. The resultant thick suspension was cooled to ambient and treated with concentrated hydrochloric acid (5.3 ml) via drop-wise addition. Water (30 ml) was added and the material was transferred to a separatory funnel. The organic phase was collected and washed with brine solution (25 ml). The aqueous phase was back extracted with ethyl acetate (25 ml) and the organics are combined, dried with magnesium sulfate, filtered and concentrated in vacuo. The residue was crystallized from hot dichloromethane/hexanes to provide the desired product as an off-white solid (5.91 g). (M+H)$^+$=231 m/e.

Step 10. Preparation of 2-[2-(3-bromo-2-formyl-phenyl)-8-fluoro-1-oxo-1,2-dihydro-isoquinolin-6-yl]-2-methyl-propionitrile

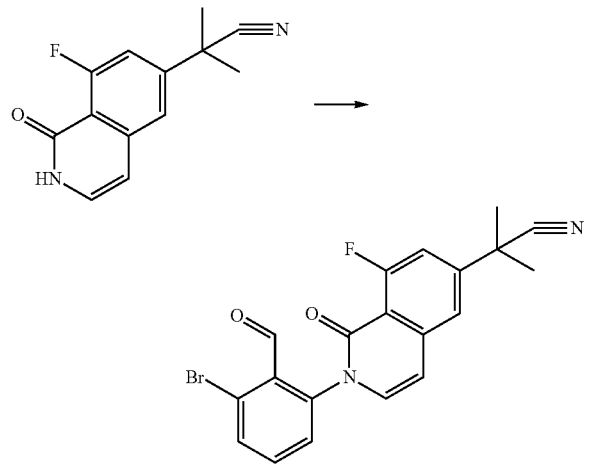

A solution of 2-(8-fluoro-1-oxo-1,2-dihydro-isoquinolin-6-yl)-2-methyl-propionitrile (250 mg, 1.09 mmol), 2,6-dibromobenzaldehyde (459 mg, 1.74 mmol) and sodium bicarbonate (182 mg, 2.17 mmol) in dry dimethylsulfoxide (8 ml) was placed under vacuum and back-filled with argon (repeat twice more). To this was added copper iodide (207 mg, 1.09 mmol) and the flask was evacuated and back-filled with argon (repeat twice more). The mixture was heated in an oil bath to 110° C. and stirred for 3.5 hours. The reaction mixture was cooled to ambient and taken up in ethyl acetate (40 ml) and water (40 ml). The biphasic material was filtered through a plug of celite, rinsing well with ethyl acetate. The filtrate and washes were transferred to a separatory funnel and the organic phase was collected. This was washed with an equal volume of 50% diluted brine solution and the ethyl acetate phase collected. The aqueous phases were back extracted with ethyl acetate (2×30 ml). The combined organic phase was dried with magnesium sulfate, filtered and concentrated in vacuo. The residue was purified by HPLC on silica gel, eluting with 1% methanol/dichloromethane to provide the desired product as a light yellow solid (285 mg). (M+H)$^+$=413/415 m/e.

Step 11. Preparation of 2-[8-fluoro-2-(2-formyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile

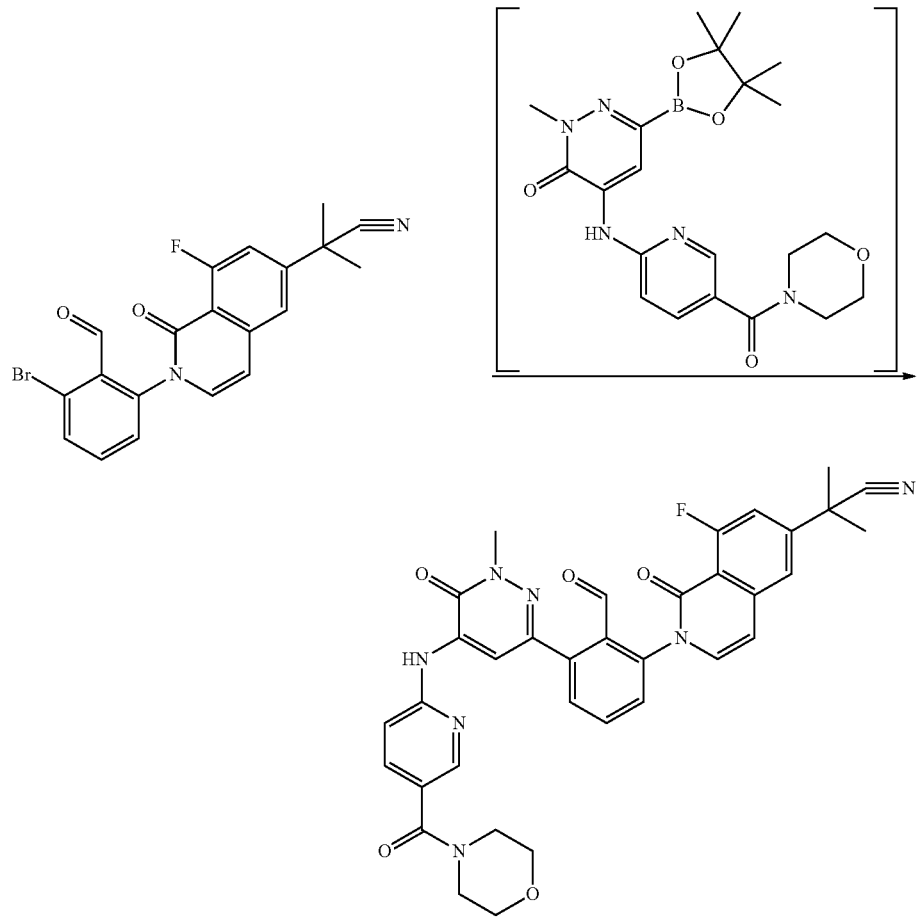

6-chloro-2-methyl-4-(5-morpholine-4-carbonyl)pyridine-2-ylamino)pyridazine-3(2H)-one (143 mg, 0.41 mmol), bis(pinacolato)diboron (135 mg, 0.53 mmol), 2-dicyclohexylphosphino-2',4',6'-triisopropylbiphenyl (x-phos, 29 mg, 0.061 mmol) and potassium acetate (120 mg, 1.23 mmol) were taken up in dry dioxane (6.4 ml) and placed under vacuum and back-filled with argon (repeat five times). To this was added palladium acetate (10 mg, 0.045 mmol) and the flask was evacuated and back-filled with argon (repeat five times). The mixture was heated in an oil bath to 100° C. and stirred for 16 minutes. The flask was cooled to ambient and the crude contents of this flask were filtered (through celite, rinse through with 3 ml dioxane) into a second flask (immersed in a 110° C. oil bath under argon balloon) which contained a vacuum de-gassed solution of the following reagents: 2-(2-(3-bromo-2-formylphenyl)-8-fluoro-1-oxo-1,2-dihydroisoquinolin-6-yl)-2-methylpropanenitrile (169 mg, 0.41 mmol), potassium carbonate (283 mg, 2.04 mmol), tricyclohexylphosphine (35.1 mg, 0.125 mmol) and bis(dibenzylideneacetone)palladium (35 mg, 0.061 mmol) in a mixture of n-butanol (0.5 ml), dioxane (2.1 ml) and water (2 ml). The flask was stirred and heated for 1 hour and then cooled to ambient. The crude reaction mixture was filtered through a short plug of celite, rinsing well with ethyl acetate. To the combined filtrate and washes was added water (30 ml) and the material was shaken in a separatory funnel. The organic phase was collected and the aqueous phase was back extracted with ethyl acetate (2×20 ml). The combined organic phase was dried with sodium sulfate, filtered and concentrated in vacuo. The residue was purified by HPLC on silica gel, eluting with 1% to 9% methanol/dichloromethane to provide the desired product as a light yellow solid (224 mg). (M−H)⁻=646 m/e.

Example 15

Step 12. Preparation of 2-[8-fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile

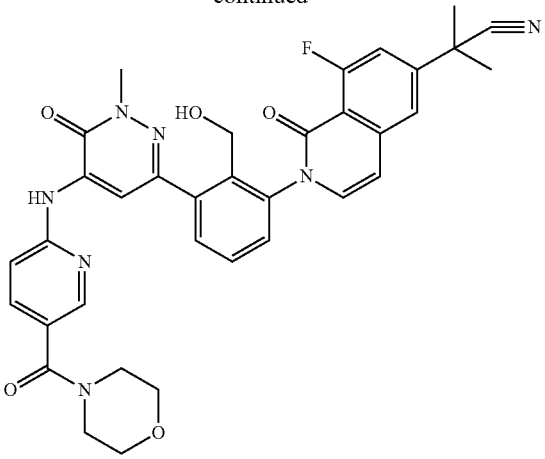

A solution of 2-[8-fluoro-2-(2-formyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile (224 mg, 0.35 mmol) in methanol (2.8 ml) and dichloromethane (4.3 ml) was cooled in an ice bath. To this was added a solution of sodium borohydride (65 mg, 1.7 mmol) in water (0.75 ml), via slow drop-wise addition. The mixture was stirred for 10 minutes and additional sodium borohydride (as describe above was added twice more over 20 minutes. The aqueous upper phase was carefully removed from the biphasic reaction solution. Methanol (1 ml) was added and with rapid stirring 3 more additions of aqueous sodium borohydride were made (as described above) over about 25 minutes. Water (60 ml) and dichloromethane (60 ml) were added and the material was transferred to a separatory funnel and the organic phase was collected. This was washed with an equal volume of 50% diluted brine solution and the dichloromethane phase collected. The aqueous phases were back extracted with dichloromethane (2×40 ml). The combined organic phase was dried with magnesium sulfate, filtered and concentrated in vacuo. The residue was purified by HPLC on silica gel, eluting with 1% to 8% methanol/dichloromethane to provide the desired product which was further purified by crystallization from hot dichloromethane/hexane to provide desired product as a white solid (120 mg). (M+H)⁺=650 m/e. ¹H NMR (300 MHz, CHLOROFORM-d) δ ppm 1.81 (s, 6H) 3.53-3.81 (m, 8H) 3.83-3.91 (m, 1H) 3.92 (s, 3H) 4.26-4.45 (m, 2H) 6.62 (dd, J=7.55, 1.89 Hz, 1H) 7.00 (d, J=8.31 Hz, 1H) 7.22 (dd, J=12.46, 1.89 Hz, 1H) 7.33 (d, J=7.18 Hz, 1H) 7.42 (dd, J=7.93, 1.51 Hz, 1H) 7.53 (d, J=1.89 Hz, 1H) 7.57 (t, J=7.93 Hz, 1H) 7.65-7.70 (m, 1H) 7.78 (dd, J=8.69, 2.27 Hz, 1H) 8.41-8.47 (m, 2H) 8.70 (s, 1H).

Preparation of I-16

Scheme E

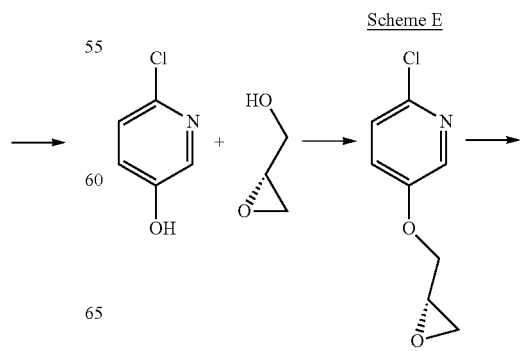

-continued

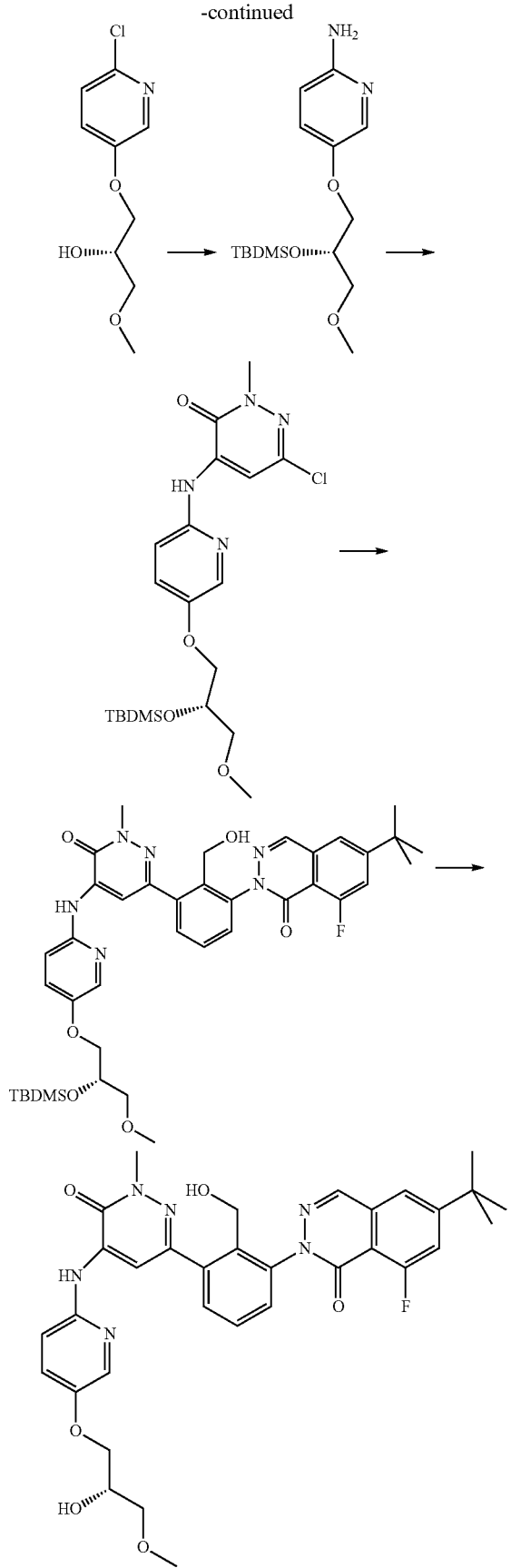

This example illustrates the synthesis of "6-tert-Butyl-8-fluoro-2-(3-{5-[5-((S)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one".

Step 1. Preparation of 2-Chloro-5-((S)-1-oxiranylmethoxy)-pyridine

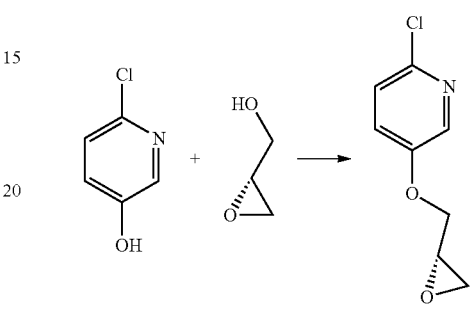

In a 250 mL round-bottomed flask, 6-chloropyridin-3-ol (2.116 g, 16.3 mmol), triphenylphosphine (5.14 g, 19.6 mmol) and (R)-oxiran-2-ylmethanol (1.21 g, 1.08 ml, 16.3 mmol) were combined with THF (75.0 ml) to give a colorless solution. Cooled to 0° C. DEAD (3.41 g, 3.1 ml, 19.6 mmol) was added. The reaction mixture was allowed to come to 25° C. and stirred for 30 h. The reaction mixture was concentrated in vacuo. The crude product was purified by flash chromatography (silica gel, 80 g, 5% to 25% EtOAc in hexanes) followed by flash chromatography (silica gel, 40 g, 0.5% to 1% MeOH in DCM) to afford the desired product (1.8 g, 59%) as a white solid. (M+H)$^+$=186 m/e.

Step 2. Preparation of (S)-1-(6-Chloro-pyridin-3-yloxy)-3-methoxy-propan-2-ol

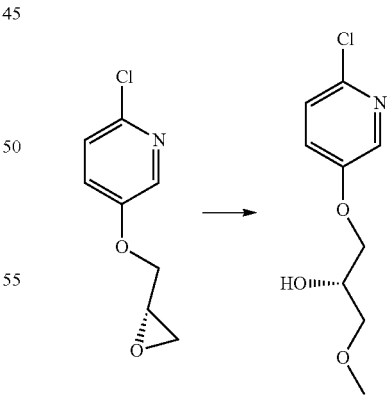

In a 125 mL round-bottomed flask, (S)-2-chloro-5-(oxiran-2-ylmethoxy)pyridine (1.8 g, 9.7 mmol) was combined with MeOH (5.88 ml) to give a colorless solution. Cooled to 0° C. Boron trifluoride etherate (138 mg, 123 µl, 970 µmol) was added. Allowed to warm to RT. The reaction mixture was stirred at room temperature for overnight. The crude reaction mixture was concentrated in vacuo. The crude material was purified by flash chromatography (silica gel, 80 g, 0% to 60% EtOAc in hexanes) to yield the desired product (1.37 g, 68%) as an oil. (M+H)⁺=218 m/e.

Step 3. Preparation of 5-[(S)-2-(tert-Butyl-dimethyl-silanyloxy)-3-methoxy-propoxy]-pyridin-2-ylamine

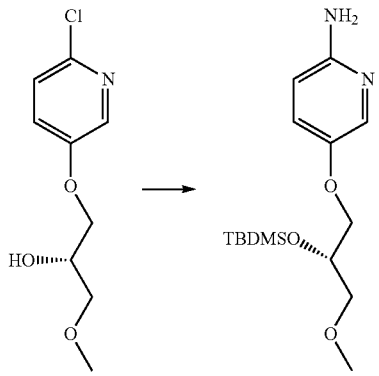 [SMILES: COC[C@H](O)COc1ccc(Cl)nc1 ; COC[C@@H](COc1ccc(N)nc1)O[Si](C)(C)C(C)(C)C]

(S)-1-(6-chloropyridin-3-yloxy)-3-methoxypropan-2-ol (1.37 g, 6.29 mmol) and imidazole (857 mg, 12.6 mmol) were combined in DMF (20 ml). DMAP (115 mg, 944 μmol) was added followed by TBDMS-Cl (1.23 g, 8.18 mmol). The reaction was stirred at 25° C. overnight. The reaction mixture was poured into 150 mL H₂O and extracted with diethyl ether (4×100 mL).

The organic extracts were washed with brine, dried over MgSO₄ and concentrated in vacuo. The crude material was purified by flash chromatography (silica gel, 40 g, 0% to 15% EtOAc in hexanes) to afford 1.81 g of (S)-5-(2-(tert-butyldimethylsilyloxy)-3-methoxypropoxy)-2-chloropyridine (5.4 mmol), which was dissolved in 14 mL of THF in a sealed tube. To that was added 2-(dicyclohexylphosphino)biphenyl (380 mg, 1.08 mmol) to give a light yellow solution. This solution was degassed with argon. Tris(dibenzylideneacetone)dipalladium(0) (497 mg, 542 μmol) was added followed by LiHMDS (16.3 ml of 1M solution in THF, 16.3 mmol). The reaction was placed under an argon atmosphere and was sealed. The reaction mixture was heated to 90° C. and stirred for 15 h. The reaction was complete by LCMS. The mixture was cooled and diluted with EtOAc. The reaction mixture was poured into 150 mL sat. NH₄Cl and extracted with EtOAc (4×75 mL). The organic layers were dried over MgSO₄ and concentrated in vacuo. The crude material was purified by flash chromatography with stepwise gradient (silica gel, 80 g, 20% to 70% EtOAc in hexanes) to afford the desired product (1.09 g). (M+H)⁺=313 m/e.

Step 4. Preparation of 4-{5-[(S)-2-(tert-Butyl-dimethyl-silanyloxy)-3-methoxy-propoxy]-pyridin-2-ylamino}-6-chloro-2-methyl-2H-pyridazin-3-one

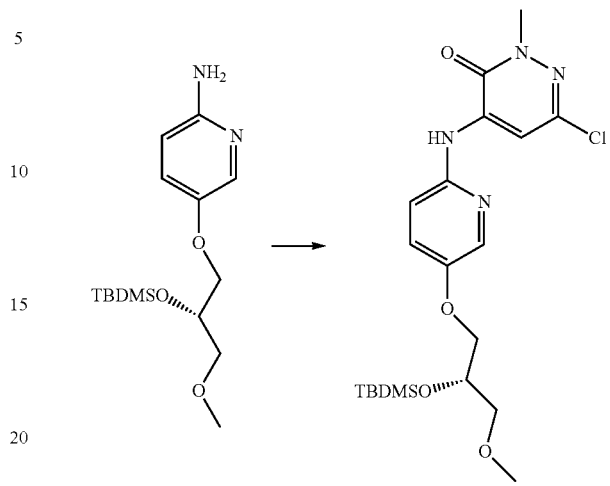

In a 50 mL round-bottomed flask, (S)-5-(2-(tert-butyldimethylsilyloxy)-3-methoxypropoxy)-pyridin-2-amine (340 mg, 1.09 mmol), 4-bromo-6-chloro-2-methylpyridazin-3 (2H)-one (292 mg, 1.31 mmol) and cesium carbonate (1.06 g, 3.26 mmol) were combined in dioxane (25 ml) to give an orange suspension. 4,5-bis(diphenylphosphino)-9,9-dimethylxanthene (94.4 mg, 163 μmol) was added followed by tris(dibenzylideneacetone)dipalladium(0) (49.8 mg, 54.4 μmol). The reaction solution was degassed with argon for 10 min. and warmed at 95-105° C. for 48 h.

The resultant reaction mixture was diluted with 200 ml DCM. MgSO₄ was added. The suspension was filtered and washed several times with DCM. The combined filtrate and washes were concentrated in vacuo. The crude material was purified by flash chromatography (silica gel, 40 g, 10% to 25% EtOAc in hexanes) to afford the desired product (451 mg, 91%) as a white solid. (M+H)⁺=455 m/e.

Step 5. Preparation of 6-tert-Butyl-2-[3-(5-{5-[(S)-2-(tert-butyl-dimethyl-silanyloxy)-3-methoxy-propoxy]-pyridin-2-ylamino}-1-methyl-6-oxo-1,6-dihydro-pyridazin-3-yl)-2-hydroxymethylphenyl]-8-fluoro-2H-phthalazin-1-one

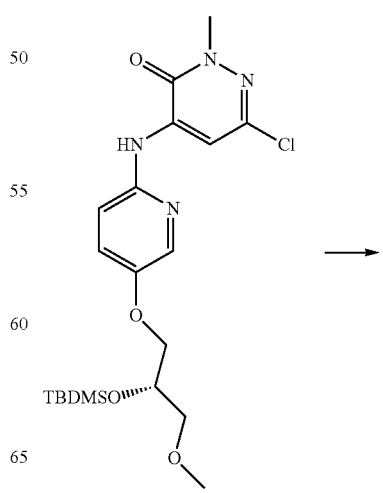

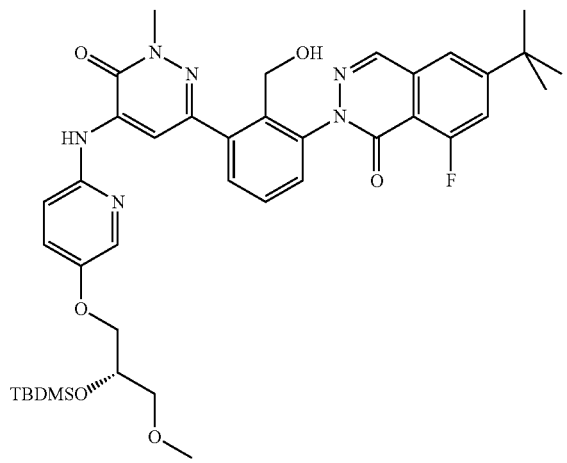

In a 50 mL test tube, (S)-4-(5-(2-(tert-butyldimethylsilyloxy)-3-methoxypropoxy)pyridin-2-ylamino)-6-chloro-2-methylpyridazin-3(2H)-one (178 mg, 391 μmol) and 2-(6-tert-butyl-8-fluoro-1-oxophthalazin-2(1H)-yl)-6-(4,4,5,5-tetramethyl-1,3,2-dioxaborolan-2-yl)benzyl acetate (332 mg, 469 μmol) were combined in n-butanol (4 ml) to give a orange solution. 1 mL of water was added and the reaction mixture was purged with argon. X-PHOS (18.6 mg, 39.1 μmol) and potassium phosphate tribasic (166 mg, 782 μmol) were added. After argon was bubbled through the reaction mixture for 5 min. bis(dibenzylideneacetone)-palladium (0) (11.2 mg, 19.6 μmol) was added. The resulting suspension was heated in a oil bath at 110° C. for 1.5 hours. No (S)-4-(5-(2-(tert-butyldimethylsilyloxy)-3-methoxypropoxy)-pyridin-2-ylamino)-6-chloro-2-methylpyridazin-3(2H)-one remained by LCMS. Two main products were observed by LCMS, acetylated and deacetylated product. The reaction mixture was allowed to cool to 25° C. overnight. The reaction mixture was concentrated to small volume, poured into 75 mL H$_2$O and extracted with EtOAc (3×75 mL). The organic layers were dried over Na$_2$SO4 and concentrated in vacuo. The crude material was purified by flash chromatography (silica gel, 24 g, 20% to 60% EtOAc in hexanes) to afford 2 product peaks. These were combined and conc. to give 290 mg of a 1:1 mixture of acetylated and deacetylated product. This mixture was taken up in 15 mL THF and treated with 2 mL of 1N NaOH. The reaction mixture was heated to 60° C. and stirred for 20 h. Mostly complete by tlc. The reaction mixture was poured into 100 mL H$_2$O and extracted with EtOAc (3×50 mL). The combined organic extracts were washed with brine, dried over MgSO$_4$ and concentrated in vacuo. The crude material was purified by flash chromatography (silica gel, 40 g, 20% to 70% EtOAc in hexanes) to afford 217 mg of the desired product (75% yield). (M+H)$^+$=745 m/e.

Example 16

Step 6. Preparation of 6-tert-Butyl-8-fluoro-2-(3-{5-[5-((S)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one

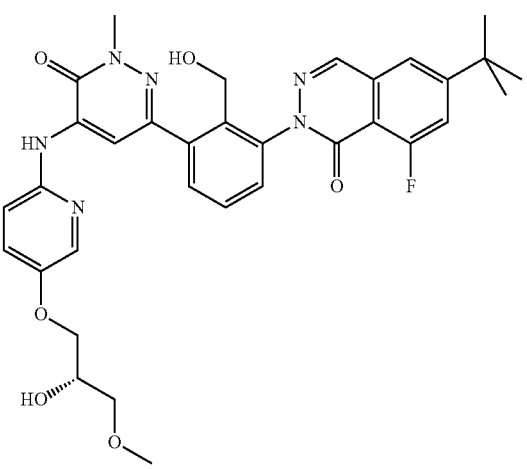 [SMILES: COC[C@H](O)COc1ccc(Nc2cc(-c3cccc(-n4ncc5cc(C(C)(C)C)cc(F)c5c4=O)c3CO)nn(C)c2=O)nc1]

In a 100 mL round-bottomed flask, (S)-6-tert-butyl-2-(3-(5-(5-(2-(tert-butyldimethylsilyloxy)-3-methoxypropoxy)pyridin-2-ylamino)-1-methyl-6-oxo-1,6-dihydropyridazin-3-yl)-2-(hydroxymethyl)phenyl)-8-fluorophthalazin-1(2H)-one (214 mg, 287 μmol, Eq: 1.00) was combined with THF (6.0 ml) to give a yellow solution. TBAF (500 μl of a 1M solution in THF, 500 μmol) was added and the resultant solution was stirred at 25° C. for 1 h. The reaction was complete by LCMS. The reaction mixture was poured into 75 mL H$_2$O and extracted with EtOAc (1×75 mL). An emulsion resulted. Saturated NaCl was added and the EtOAc layer was separated. Extracted 2 times with DCM. No product left in aqueous phase by LCMS. The organic layers were combined, dried over MgSO$_4$ and concentrated in vacuo. The crude material was purified by flash chromatography (silica gel, 24 g, 0.5% to 4% MeOH in DCM) to afford a glass. The glass was taken up in EtOAc/hexane and conc. to give a semisolid, which was triturated with ether. The resulting white solid was washed with ether/hexanes to give 112 mg of pure product as a white powder. (M+H)$^+$=631 m/e. $^1$H NMR (300 MHz, CHLOROFORM-d) δ ppm 1.44 (s, 9H) 3.44 (s, 3H) 3.53-3.64 (m, 2H) 3.91 (s, 3H) 4.03-4.11 (m, 2H) 4.13-4.22 (m, 1H) 4.42 (s, 2H) 6.98 (d, J=8.69 Hz, 1H) 7.28-7.35 (m, 1H) 7.43-7.62 (m, 4H) 7.64-7.69 (m, 1H) 8.06 (d, J=3.02 Hz, 1H) 8.27-8.32 (m, 2H) 8.48 (s, 1H)

Example 17

Preparation of 6-tert-Butyl-8-fluoro-2-(3-{5-[5-((R)-2-hydroxy-3-methoxy-propoxy)-pyridin-2-ylamino]-1-methyl-6-oxo-1,6-dihydro-pyridazin-3-yl}-2-hydroxymethyl-phenyl)-2H-phthalazin-1-one

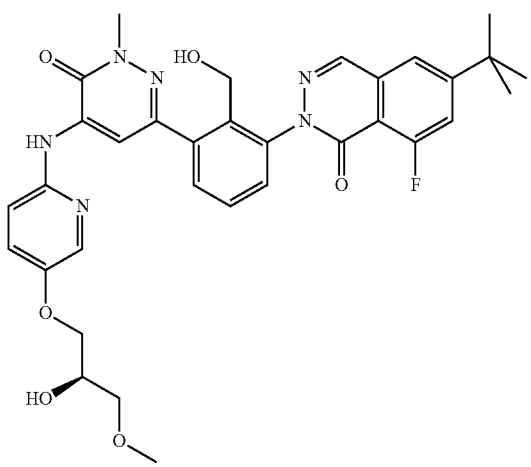 [SMILES: COC[C@@H](O)COc1ccc(Nc2cc(-c3cccc(-n4ncc5cc(C(C)(C)C)cc(F)c5c4=O)c3CO)nn(C)c2=O)nc1]

Preparation by a similar procedure to Example 16, except substituting (S)-oxiran-2-ylmethanol for (R)-oxiran-2-ylmethanol in step 1, afforded the desired product as a white powder (107 mg) (M+H)+=631 m/e. $^1$H NMR (400 MHz, CHLOROFORM-d) δ ppm 1.44 (s, 9H) 3.44 (s, 3H) 3.53-3.63 (m, 2H) 3.91 (s, 3H) 4.02-4.12 (m, 2H) 4.14-4.22 (m, 1H) 4.42 (s, 2H) 6.99 (d, J=8.78 Hz, 1H) 7.32 (dd, J=9.03, 3.01 Hz, 1H) 7.45-7.61 (m, 4H) 7.64-7.69 (m, 1H) 8.06 (d, J=2.76 Hz, 1H) 8.29 (d, J=2.51 Hz, 1H) 8.32 (s, 1H) 8.47 (s, 1H)

Preparation of I-18

Scheme F

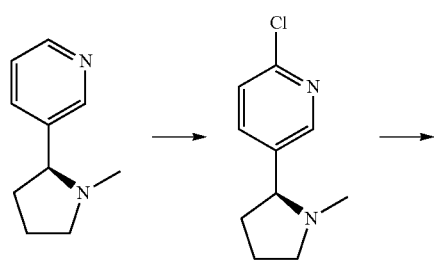

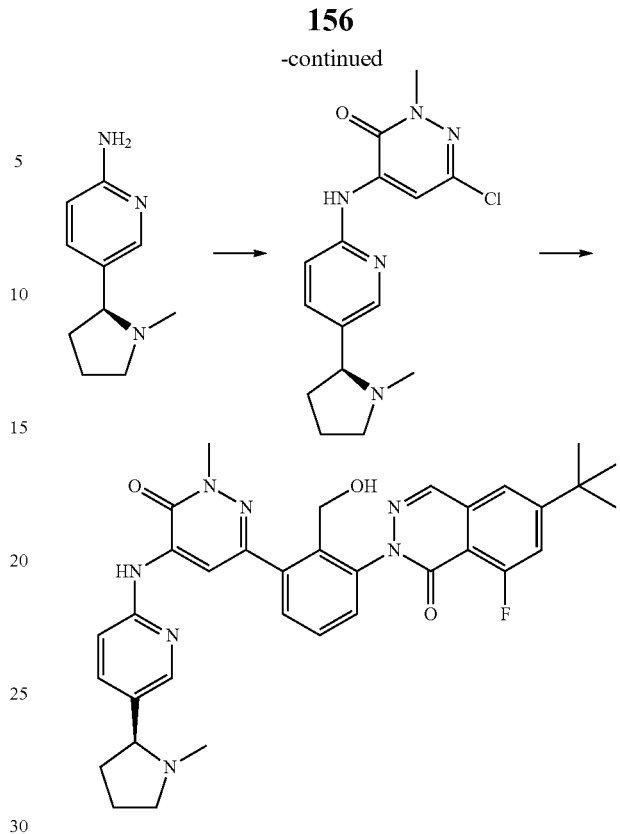

This example illustrates the synthesis of "6-tert-Butyl-8-fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one".

Step 1. Preparation of 2-Chloro-5-((S)-1-methyl-pyrrolidin-2-yl)-pyridine

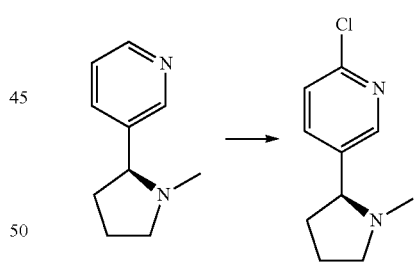

A 100 mL RB flask was placed under an argon atmosphere and degassed with argon by vacuum. The solvents (hexanes (4 ml) and toluene 12 ml)) were added to the flask. N,N-dimethylethanolamine (1.07 g, 1.21 ml, 12.0 mmol) was added. The reaction mixture was cooled to 0° C. N-butyl lithium (8.66 ml of 2.5M in hexanes, 21.6 mmol) was added. The reaction mixture was stirred at 0° C. for 30 min. The reaction mixture was cooled to −20° C. (S)-3-(1-methylpyrrolidin-2-yl)pyridine (650 mg, 0.64 ml, 4.01 mmol) was added. The reaction mixture was stirred −20° C. for 1 h. The reaction mixture was cooled to −78° C. and hexachloroethane (3.8 g, 16.0 mmol) was added in toluene (8 ml). The reaction mixture was stirred at −78° C. for 1 h. The reaction was quenched cold with satd. NaHCO₃ (4 mL). LCMS showed that the reaction gave the desired regioisomer in a 6:1 ratio over the undesired 6-chloro pyridine product. The reaction mixture was poured into 50 mL H₂O and extracted with DCM (3×125 mL). The organic layers were dried over Na₂SO₄ and concentrated in vacuo. The crude material was purified by flash chromatography (silica gel, 40 g, 0% to 55% EtOAc in hexanes) to afford the desired product (467 mg, 59%). ¹H NMR (300 MHz, CHLOROFORM-d) δ ppm 1.56-2.05 (m, 3H) 2.16-2.40 (m and overlapping s, 5H) 3.09 (t, J=8.31 Hz, 1H) 3.17-3.29 (m, 1H) 7.23-7.32 (m, 1H) 7.68 (dd, J=8.12, 2.45 Hz, 1H) 8.30 (d, J=2.27 Hz, 1H)

Step 2. Preparation of 5-((S)-1-Methyl-pyrrolidin-2-yl)-pyridin-2-ylamine

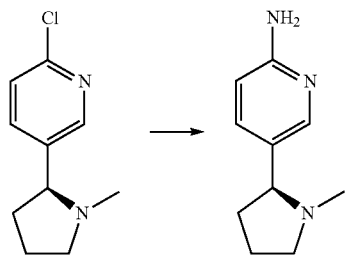

In a 75 mL sealed tube, (S)-2-chloro-5-(1-methylpyrrolidin-2-yl)pyridine (622 mg, 3.16 mmol) and 2-(dicyclohexylphosphino)biphenyl (222 mg, 633 µmol) were combined with THF (15 ml) to give a light yellow solution. The solution was degassed with argon. Tris(dibenzylideneacetone)dipalladium (0) (290 mg, 316 µmol) was added. LiHMDS (9.49 ml of 1M solution in THF, 9.49 mmol) was added. The reaction was placed under an argon atmosphere and sealed. The reaction mixture was heated to 90° C. and stirred for 15 h. Reaction was complete by tlc. The reaction mixture was cooled to room temperature and diluted with EtOAc. The reaction mixture was poured into 150 mL sat NH₄Cl and extracted with EtOAc (4×75 mL). The organic layers were dried over MgSO₄ and concentrated in vacuo. The crude material was purified by flash chromatography with stepwise gradient (silica gel, 40 g, 10% to 50% (60:10:1 CH₂Cl₂:methanol:NH₄OH)/CH₂Cl₂) gradient to afford the desired product (560 mg, 99%). ¹H NMR (300 MHz, CHLOROFORM-d) δ ppm 1.57-2.03 (m, 3H) 2.04-2.39 (m and overlapping s, 5H) 2.92 (t, J=8.12 Hz, 1H) 3.14-3.29 (m, 1H) 4.40 (br. s., 2H) 6.51 (d, J=8.69 Hz, 1H) 7.47 (dd, J=8.31, 2.27 Hz, 1H) 7.95 (d, J=2.27 Hz, 1H)

Step 3. Preparation of 6-Chloro-2-methyl-4-[5-((S)-1-methyl-pyrrolidin-2-yl)-pyridin-2-ylamino]-2H-pyridazin-3-one

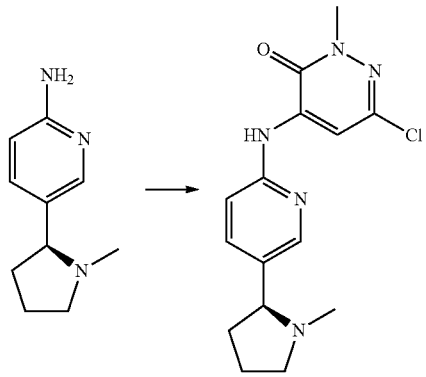 [SMILES: CN1CCC[C@H]1c1ccc(N)nc1 ; CN1CCC[C@H]1c1ccc(Nc2cc(Cl)nn(C)c2=O)nc1]

In a 50 mL round-bottomed flask, 5-((S)-1-methyl-pyrrolidin-2-yl)-pyridin-2-ylamine (560 mg, 3.16 mmol)], 4-bromo-6-chloro-2-methylpyridazin-3(2H)-one (847 mg, 3.79 mmol) and cesium carbonate (3.09 g, 9.48 mmol) were combined with dioxane (25 ml) to give a orange suspension. 4,5-bis(diphenylphosphino)-9,9-dimethylxanthene (274 mg, 474 µmol, Eq: 0.15) was added followed by tris(dibenzylideneacetone)dipalladium(0) (145 mg, 158 µmol, Eq: 0.05). The reaction was degassed with Ar for 10 min and heated at 95-105° C. for 4 h. No aniline starting material was left. The reaction mixture was diluted with 200 ml DCM. MgSO4 was added and stirred. The reaction was filtered and the filtercake was washed several times with DCM. The combined filtrate and washes were concentrated in vacuo. The crude material was purified by flash chromatography (silica gel, 40 g, 1% to 2% MeOH in DCM) to afford the desired product (522 mg, 52%). (M+H)⁺=320 m/e.

Example 18

Step 4. Preparation of 6-tert-Butyl-8-fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-2H-phthalazin-1-one

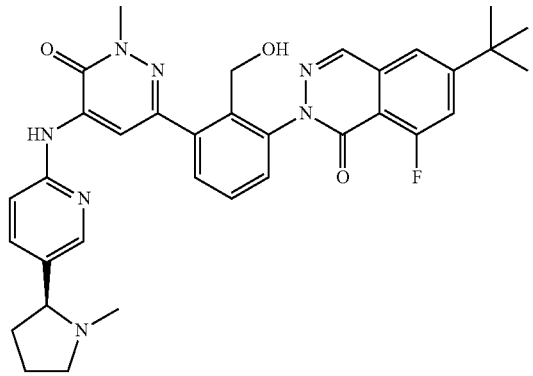 [SMILES: CN1CCC[C@H]1c1ccc(Nc2cc(-c3cccc(-n4ncc5cc(C(C)(C)C)cc(F)c5c4=O)c3CO)nn(C)c2=O)nc1]

In a 50 mL RB flask, (S)-6-chloro-2-methyl-4-(5-(1-methylpyrrolidin-2-yl)pyridin-2-ylamino)pyridazin-3(2H)-one (125 mg, 0.39 mmol) and 2-(6-tert-butyl-8-fluoro-1-oxophthalazin-2(1H)-yl)-6-(4,4,5,5-tetramethyl-1,3,2-dioxaborolan-2-yl)benzyl acetate (331 mg, 468 μmol) were combined with BuOH (4 ml) to give a orange solution. 1 mL of water was added. Purged with argon. X-PHOS (18.6 mg, 39.0 μmol) and potassium phosphate tribasic (166 mg, 780 μmol, were added. Argon was bubbled through for 10 min. Bis(dibenzylideneacetone)-palladium (0) (11.2 mg, 19.5 μmol) was added. The resultant reaction mixture was purged with argon and warmed in an oil bath at 110° C. for 1.5 hours. Two main products were observed by LCMS, acetylated and deacetylated product. The reaction was allowed to cool to RT overnight and then was concentrated to small volume. The reaction mixture was poured into 75 mL H₂O and extracted with EtOAc (3×75 mL). The organic layers were washed with brine and dried over MgSO4 and concentrated in vacuo. The crude material was purified by flash chromatography (silica gel, 24 g, 1% to 5% MeOH in DCM) to afford 2 peaks. The two peaks were combined and concentrated to give 238 mg of a 1:1 mixture of acetylated and deacetylated product. This mixture was taken up in 15 mL THF and treated with 2 mL of 1N NaOH. The reaction mixture was heated to 60° C. and stirred for 25 h. The reaction was almost complete by tlc. The reaction mixture was poured into 100 mL H₂O and extracted with EtOAc (2×50 mL) and DCM (1×). No product remained in the aqueous phase. The combined organic extracts were washed with brine, dried over MgSO4 and concentrated in vacuo. The crude material was purified by flash chromatography (silica gel, 24 g, 1% to 5% MeOH in DCM) two times, followed by trituration with ethyl acetate/hexanes to afford 57 mg pure product. (M+H)⁺=610 m/e.

Example 19

Preparation of 6-tert-Butyl-8-fluoro-2-(2-hydroxymethyl-3-{1-methyl-5-[5-((R)-1-methyl-pyrrolidin-2-yl)-pyridin-2-ylamino]-6-oxo-1,6-dihydro-pyridazin-3-yl}-phenyl)-2H-phthalazin-1-one

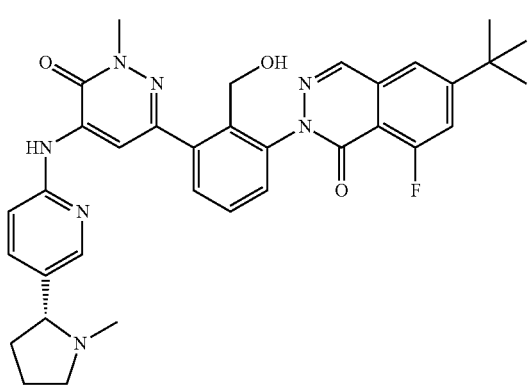 [SMILES: CN1CCC[C@@H]1c1ccc(Nc2cc(-c3cccc(-n4ncc5cc(C(C)(C)C)cc(F)c5c4=O)c3CO)nn(C)c2=O)nc1]

Preparation by a similar procedure to Example 18, except substituting (R)-3-(1-methylpyrrolidin-2-yl)pyridine for (S)-3-(1-methylpyrrolidin-2-yl)pyridine in step 1, afforded the desired product as a white powder (78 mg). (M+H)⁺=610 m/e.

Preparation of I-20

Step 1. Preparation of 6-Azido-N,N-dimethyl-nicotinamide

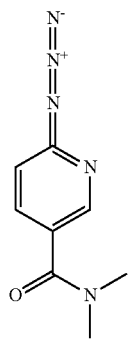

In a 500 mL round-bottomed flask, 6-chloro-N,N-dimethylnicotinamide (8.15 g, 44.1 mmol) was combined with DMF (50.0 ml) to give a brown solution. Sodium azide (3.44 g, 53.0 mmol) was added and the reaction mixture was heated to 120° C. and stirred for 60 h. The reaction mixture was diluted with 100 mL H₂O and extracted with EtOAc (2×200 mL). The organic layers were combined, washed with H₂O (1×50 mL), sat NaCl (1×100 mL), dried over Na₂SO₄ and concentrated in vacuo to a yellow oil. MeOH was added and the entire mixture solidified upon concentration. The crude product was dried under vacuum overnight. The pasty solid was recrystallized from EtOAc/Hex. The solid was filtered and washed with a minimal amount of hexane. The white powder was dried under vacuum at 45° C. for 3 hrs to give 2.23 g (26%) of the title compound. ¹H NMR (300 MHz, CHLOROFORM-d) δ: 8.95 (s, 1H), 8.09 (d, J=9.1 Hz, 1H), 7.75 (dd, J=9.1, 1.5 Hz, 1H), 3.15 (br. s., 6H).

Step 2. Preparation of 6-Amino-N,N-dimethyl-nicotinamide

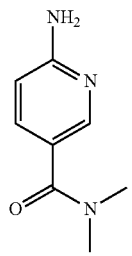

In a 250 mL round-bottomed flask, 6-azido-N,N-dimethylnicotinamide (2.26 g, 11.8 mmol) was combined with ethyl acetate (50 ml) and methanol (30 ml) to give a yellow solution. 10% Pd/C (200 mg, 1.88 mmol) was added and the reaction mixture was evacuated and filled with H₂ twice. The reaction mixture was stirred under balloon pressure of H₂ at 25° C. for 17 h. The reaction mixture was filtered through celite and the filter cake was washed with MeOH. The filtrate was concentrated in vacuo and the cream colored solid was dried under vacuum at 45° C. for 3 hrs to give the title compound in quantitative yield. (M+H)+=166 m/e. ¹H NMR (300 MHz, CHLOROFORM-d) δ: 8.21 (d, J=2.3 Hz, 1H), 7.59 (dd, J=8.3, 2.3 Hz, 1H), 6.50 (d, J=8.7 Hz, 1H), 4.69 (br. s., 2H), 3.08 (s, 6H).

Step 3. Preparation of acetic acid 2-(6-tert-butyl-8-fluoro-1-oxo-1H-phthalazin-2-yl)-6-[5-(5-dimethyl-carbamoyl-pyridin-2-ylamino)-1-methyl-6-oxo-1,6-dihydropyridazin-3-yl]-benzyl ester

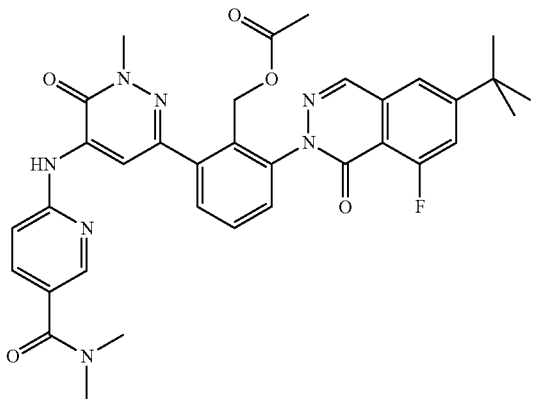 [SMILES: CC(=O)OCc1c(-c2cc(Nc3ccc(C(=O)N(C)C)cn3)c(=O)n(C)n2)cccc1-n1ncc2cc(C(C)(C)C)cc(F)c2c1=O]

In a 250 mL round-bottomed flask, 6-(6-chloro-2-methyl-3-oxo-2,3-dihydropyridazin-4-ylamino)-N,N-dimethylnicotinamide (1.053 g, 3.42 mmol), 2-(6-tert-butyl-8-fluoro-1-oxophthalazin-2(1H)-yl)-6-(4,4,5,5-tetramethyl-1,3,2-dioxaborolan-2-yl)benzyl acetate (2.2 g, 4.45 mmol) and Cs₂CO₃ (3.34 g, 10.3 mmol) were combined with dioxane (20 ml) and water (2.00 ml) to give a dark brown suspension. The suspension was purged with argon and PdCl₂(DPPF) (83.8 mg, 103 µmol) was added. The reaction mixture was heated to 85° C. and stirred for 3 h. Cooled to 25° C. and diluted with DCM. Na₂SO₄ was added and the mixture was filtered through celite. The filter cake was washed with DCM until clear and the brown filtrate was conc. in vacuo. The crude material was purified by flash chromatography (silica gel, 220 g, 0% to 5% MeOH in DCM). The product was isolated impure and repurified by flash chromatography (silica gel, 220 g, 100% EtOAc) to afford 1.1412 g (52%) of the title compound as a cream colored solid. (M+H)+=640 m/e.

Example 20

Step 4. Preparation of 6-{6-[3-(6-tert-butyl-8-fluoro-1-oxo-1H-phthalazin-2-yl)-2-hydroxymethyl-phenyl]-2-methyl-3-oxo-2,3-dihydropyridazin-4-ylamino}-N,N-dimethylnicotinamide

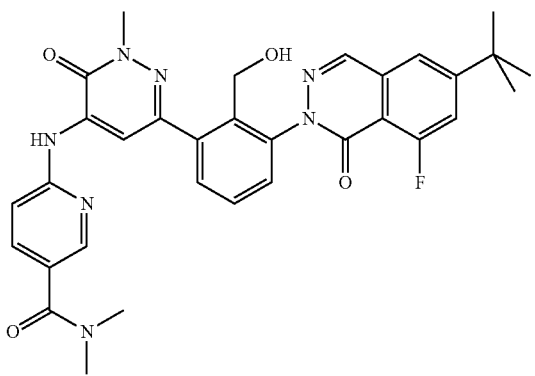 [SMILES: CN(C)C(=O)c1ccc(Nc2cc(-c3cccc(-n4ncc5cc(C(C)(C)C)cc(F)c5c4=O)c3CO)nn(C)c2=O)nc1]

In a 500 mL round-bottomed flask, 2-(6-tert-butyl-8-fluoro-1-oxophthalazin-2(1H)-yl)-6-(5-(5-(dimethylcarbamoyl)pyridin-2-ylamino)-1-methyl-6-oxo-1,6-dihydropyridazin-3-yl)benzyl acetate (1.142 g, 1.79 mmol) was combined with dioxane (25 ml) and 1M LiOH (10 ml) to give a light yellow suspension. The reaction mixture was stirred at 25° C. for 17 h. The crude reaction mixture was concentrated in vacuo. The residue was partitioned between DCM and water. An emulsion was obtained and the aqueous was extracted exhaustively with DCM. The organic layers were dried over Na₂SO₄ and concentrated in vacuo. The crude material was purified by flash chromatography (silica gel, 120 g, 0% to 4% MeOH in DCM) to afford 0.471 g (44%) of the title compound as a white solid. (M+H)+=598 m/e. ¹H NMR (300 MHz, CHLOROFORM-d) δ: 8.68 (s, 1H), 8.46 (d, J=2.6 Hz, 2H), 8.29 (d, J=2.6 Hz, 1H), 7.79 (dd, J=8.3, 2.3 Hz, 1H), 7.64-7.69 (m, 1H), 7.53-7.63 (m, 3H), 7.50 (t, J=2.1 Hz, 1H), 7.47 (d, J=1.5 Hz, 1H), 7.00 (d, J=8.7 Hz, 1H), 4.43 (s, 2H), 3.92 (s, 3H), 3.11 (s, 6H), 1.43 (s, 9H).

Preparation of I-21

Step 1. Preparation of 6-Chloro-4-[5-(4-hydroxy-4-methyl-piperidine-1-carbonyl)-pyridin-2-ylamino]-2-methyl-2H-pyridazin-3-one

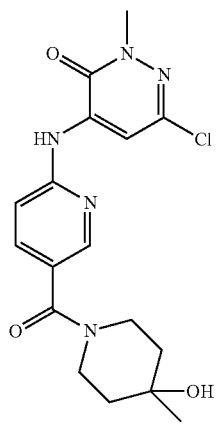 [SMILES: Cn1nc(Cl)cc(Nc2ccc(C(=O)N3CCC(C)(O)CC3)cn2)c1=O]

In a 250 mL round-bottomed flask, 6-(6-chloro-2-methyl-3-oxo-2,3-dihydropyridazin-4-ylamino)nicotinic acid (195 mg, 695 µmol), 4-methylpiperidin-4-ol (80.0 mg, 695 µmol), HOBT (138 mg, 903 µmol) and Hunig's base (269 mg, 364 µl, 2.08 mmol) were combined with DMF (13 ml) to give a light yellow suspension. EDC (173 mg, 903 µmol) was added and the reaction mixture was heated to 100° C. and stirred for 24 h. Additional 4-methylpiperidin-4-ol (80.0 mg, 695 µmol), HOBT (106 mg, 695 µmol) and EDC (133 mg, 695 µmol) were added with 2 ml DMF. The reaction mixture was heated to 100° C. and stirred for 24 h. The reaction was cooled to 25° C. and quenched with water. The aqueous layer was back-extracted with EtOAc (3×75 mL). The organic layers were combined, washed with sat NaCl (1×50 mL), dried over Na₂SO₄ and concentrated in vacuo. The residue was taken up in DCM/MeOH 9:1 and filtered. The filtrate was conc. in vacuo to give a light yellow solid. The crude material was purified by flash chromatography (silica gel, 12 g, 0% to 10% MeOH in DCM) to afford 0.033 g (13%) of the title compound as a yellow solid. (M+H)+=378/380 m/e.

Step 2. Preparation of acetic acid 2-(6-tert-butyl-8-fluoro-1-oxo-1H-phthalazin-2-yl)-6-{5-[5-(4-hydroxy-4-methyl-piperidine-1-carbonyl)-pyridin-2-ylamino]-1-methyl-6-oxo-1,6-dihydro-pyridazin-3-yl}-benzyl ester

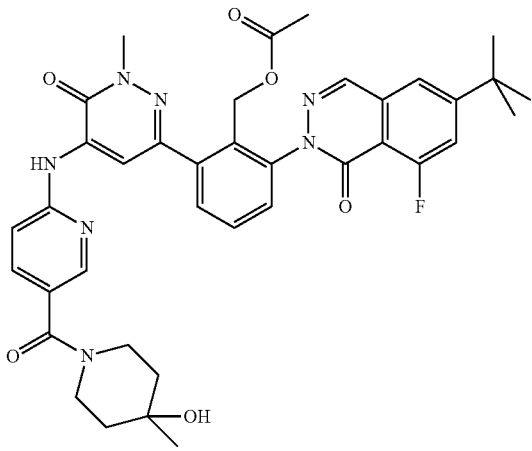 [SMILES: CC(=O)OCc1c(-c2cc(Nc3ccc(C(=O)N4CCC(C)(O)CC4)cn3)c(=O)n(C)n2)cccc1-n1ncc2cc(C(C)(C)C)cc(F)c2c1=O]

To a 10 mL microwave vial was added 6-chloro-4-(5-(4-hydroxy-4-methylpiperidine-1-carbonyl)pyridin-2-ylamino)-2-methylpyridazin-3(2H)-one (33 mg, 87.3 μmol), 2-(6-tert-butyl-8-fluoro-1-oxophthalazin-2(1H)-yl)-6-(4,4,5,5-tetramethyl-1,3,2-dioxaborolan-2-yl)benzyl acetate (56.1 mg, 114 μmol) and $Cs_2CO_3$ (99.6 mg, 306 μmol) in dioxane (5 ml) and water (0.5 ml). The yellow suspension was purged with argon and $PdCl_2$(DPPF) (7.13 mg, 8.73 μmol) was added. The vial was capped and heated in the microwave at 125° C. for 30 min. The reaction was cooled to 25° C. and diluted with DCM. $Na_2SO_4$ was added and the mixture was filtered through celite. The filter cake was washed with DCM until clear and the yellow filtrate was conc. in vacuo to afford the title compound as a brown solid in quantitative yield. $(M-H)^+$=708 m/e.

Example 21

Step 3. Preparation of 6-tert-butyl-8-fluoro-2-(2-hydroxymethyl-3-{5-[5-(4-hydroxy-4-methyl-piperidine-1-carbonyl)-pyridin-2-ylamino]-1-methyl-6-oxo-1,6-dihydro-pyridazin-3-yl}-phenyl)-2H-phthalazin-1-one

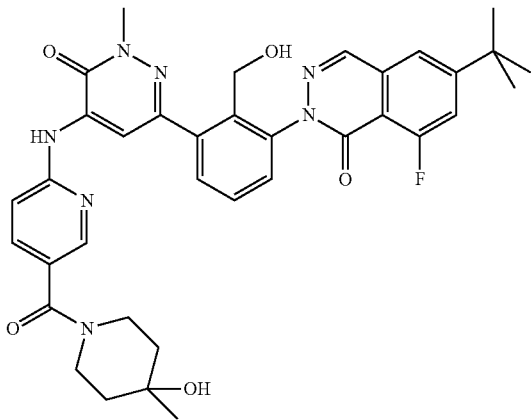 [SMILES: Cn1nc(-c2cccc(-n3ncc4cc(C(C)(C)C)cc(F)c4c3=O)c2CO)cc(Nc2ccc(C(=O)N3CCC(C)(O)CC3)cn2)c1=O]

In a 250 mL round-bottomed flask, 2-(6-tert-butyl-8-fluoro-1-oxophthalazin-2(1H)-yl)-6-(5-(5-(4-hydroxy-4-methylpiperidine-1-carbonyl)pyridin-2-ylamino)-1-methyl-6-oxo-1,6-dihydropyridazin-3-yl)benzyl acetate (62 mg, 87.4 μmol) was combined with dioxane (5 ml) and 1M LiOH (1 ml) to give a brown solution. The reaction mixture was stirred at 25° C. for 5 h. The crude reaction mixture was concentrated in vacuo and partitioned between DCM and water. The aqueous layer was back-extracted with DCM (2×25 mL). The organic layers were combined, washed with sat NaCl (1×10 mL), dried over $Na_2SO_4$ and concentrated in vacuo. The crude material was purified by flash chromatography (silica gel, 24 g, 0% to 8% MeOH in DCM), isolated as an off-white powder and dried under vacuum for 3 hrs at 25° C. The material was repurified by flash chromatography (silica gel, 24 g, 0% to 4% MeOH in DCM) to afford 0.008 g (14%) of the title compound as a white solid. $(M+H)^+$=668 m/e. $^1$H NMR (300 MHz, CHLOROFORM-d) δ: 8.69 (s, 1H), 8.39-8.47 (m, 2H), 8.29 (d, J=2.3 Hz, 1H), 7.75 (dd, J=8.5, 2.1 Hz, 1H), 7.43-7.70 (m, 5H), 6.99 (d, J=8.7 Hz, 1H), 4.43 (br. s., 2H), 3.91 (s, 3H), 3.20-3.87 (m, 4H), 1.65 (br. s., 6H) 1.43 (s, 9H).

Preparation of I-22

Step 1. Preparation of 6-(6-Nitro-pyridin-3-yl)-2,6-diaza-spiro[3.3]heptane-2-carboxylic acid tert-butyl ester

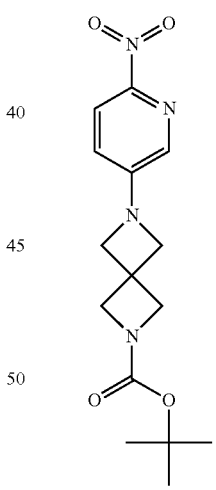

In a 25 mL pear-shaped flask, tert-butyl 2,6-diazaspiro[3.3]heptane-2-carboxylate (2.81 g, 14.2 mmol), 5-bromo-2-nitropyridine (2.88 g, 14.2 mmol), and TEA (1.58 g, 2.17 ml, 15.6 mmol) were combined with DMSO (12 ml) to give a light yellow solution. The reaction mixture was heated to 90° C. and stirred for 40 h. Cooled to 25° C. and the reaction mixture was diluted with 50 mL $H_2O$ and extracted with EtOAc (3×50 mL). The organic layers were combined, washed with sat NaCl (1×50 mL), dried over $Na_2SO_4$ and concentrated in vacuo. The purple oil was used crude in the subsequent reduction. $(M+H)^+$=321 m/e.

Step 2. Preparation of 6-(6-Amino-pyridin-3-yl)-2,6-diaza-spiro[3.3]heptane-2-carboxylic acid tert-butyl ester

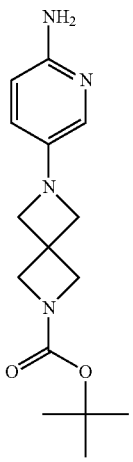

In a 500 mL pear-shaped flask, tert-butyl 6-(6-nitropyridin-3-yl)-2,6-diazaspiro[3.3]heptane-2-carboxylate (4.54 g, 14.2 mmol) and 10% Pd/C (662 mg, 6.22 mmol) were combined with ethyl acetate (150 ml) and methanol (50 ml) to give a black suspension. The mixture was evacuated and filled with $H_2$ twice, then stirred overnight at 25° C. under balloon pressure of $H_2$. The mixture was filtered over celite and the filter cake was washed with MeOH. The filtrate was concentrated in vacuo to give a purple oily solid. The crude material was purified by flash chromatography (silica gel, 12 g, 0% to 4% MeOH in DCM) to afford 1.29 g (31%) of the title compound as an impure dark red solid. $(M+H)^+=291$ m/e.

Step 3. Preparation of 6-[6-(6-Chloro-2-methyl-3-oxo-2,3-dihydro-pyridazin-4-ylamino)-pyridin-3-yl]-2,6-diaza-spiro[3.3]heptane-2-carboxylic acid tert-butyl ester

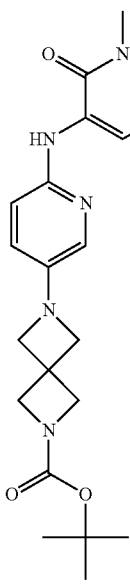

In a 250 mL round-bottomed flask, tert-butyl 6-(6-aminopyridin-3-yl)-2,6-diazaspiro[3.3]heptane-2-carboxylate (870 mg, 3.00 mmol), 4-bromo-6-chloro-2-methylpyridazin-3(2H)-one (670 mg, 3.00 mmol), xantphos (260 mg, 449 µmol), $Cs_2CO_3$ (2.93 g, 8.99 mmol) and $Pd_2(dba)_3$ (137 mg, 150 µmol) were combined with dioxane (25.0 ml) to give a dark brown solution. The reaction mixture was heated to 100° C. under argon and stirred for 20 h. The reaction was cooled to 25° C., diluted with DCM, and $Na_2SO_4$ was added. The mixture was filtered over celite, the filter cake was washed with DCM and the filtrate was conc. in vacuo to a dark brown semisolid. The crude material was purified by flash chromatography (silica gel, 220 g, 0% to 5% MeOH in DCM). The impure material was repurified by flash chromatography (silica gel, 220 g, 0% to 4% MeOH in DCM) to afford 0.320 g (25%) of the title compound as a light yellow powder. $(M+H)^+=433/435$ m/e. $^1H$ NMR (300 MHz, CHLOROFORM-d) δ: 8.12 (s, 1H), 8.08 (s, 1H), 7.65 (s, 1H), 6.82 (d, J=1.5 Hz, 2H), 4.12 (s, 4H), 4.01 (s, 3H), 3.80 (s, 4H), 1.45 (s, 9H).

Step 4. Preparation of 6-(6-{6-[2-Acetoxymethyl-3-(6-tert-butyl-8-fluoro-1-oxo-1H-phthalazin-2-yl)-phenyl]-2-methyl-3-oxo-2,3-dihydropyridazin-4-ylamino}-pyridin-3-yl)-2,6-diaza-spiro[3.3]heptane-2-carboxylic acid tert butyl ester

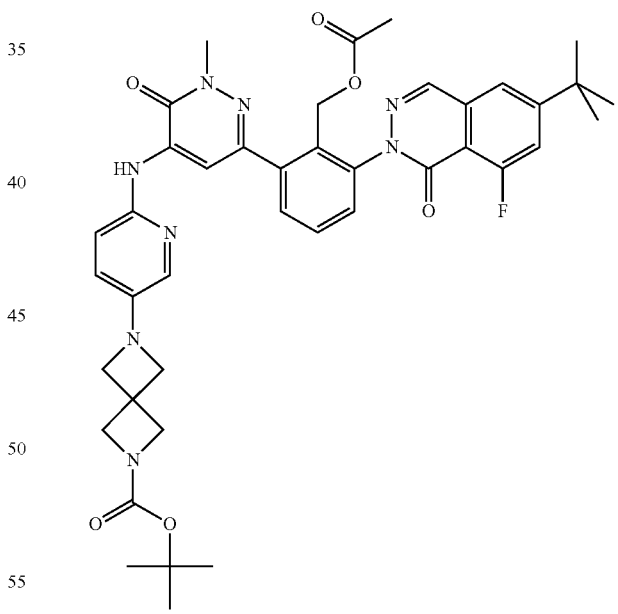

In a 250 mL round-bottomed flask, tert-butyl 6-(6-(6-chloro-2-methyl-3-oxo-2,3-dihydropyridazin-4-ylamino) pyridin-3-yl)-2,6-diazaspiro[3.3]heptane-2-carboxylate (300 mg, 693 µmol), 2-(6-tert-butyl-8-fluoro-1-oxophthalazin-2(1H)-yl)-6-(4,4,5,5-tetramethyl-1,3,2-dioxaborolan-2-yl)benzyl acetate (445 mg, 901 µmol) and $Cs_2CO_3$ (677 mg, 2.08 mmol) were combined with dioxane (20 ml) and water (2.00 ml) to give a yellow suspension. The flask was evacuated and filled with argon and $PdCl_2(DPPF)$ (17.0 mg, 20.8 µmol) was added. The reaction mixture was heated to 85° C. and stirred for 3 h under argon. Additional PdCl₂ (DPPF) (17 mg, 20.8 µmol) was added and the reaction mixture was heated to 85° C. and stirred for 60 h. Cooled to 25° C. and diluted with DCM. The reaction mixture was filtered through celite and the filtrate was dried over Na₂SO₄. The crude reaction mixture was concentrated in vacuo. The brown solid was used crude in the subsequent reaction. (M+H)⁺=765 m/e.

Step 5. Preparation of 6-(6-{6-[3-(6-tert-butyl-8-fluoro-1-oxo-1H-phthalazin-2-yl)-2-hydroxymethyl-phenyl]-2-methyl-3-oxo-2,3-dihydropyridazin-4-ylamino}-pyridin-3-yl)-2,6-diaza-spiro[3.3]heptane-2-carboxylic acid tert butyl ester

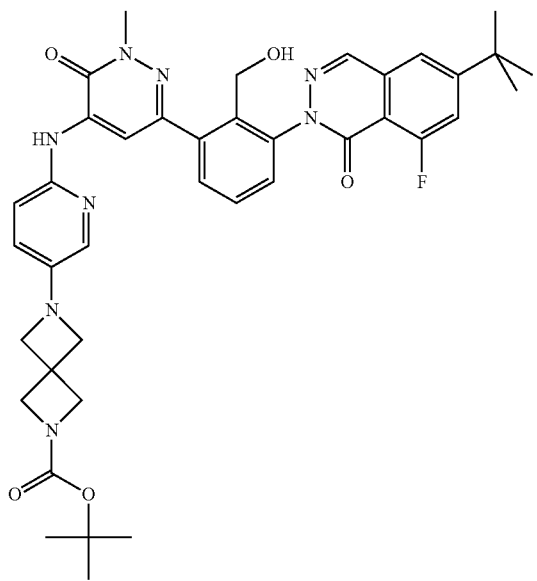 [SMILES: Cn1nc(-c2cccc(-n3ncc4cc(C(C)(C)C)cc(F)c4c3=O)c2CO)cc(Nc2ccc(N3CC4(CN(C(=O)OC(C)(C)C)C4)C3)cn2)c1=O]

In a 250 mL round-bottomed flask, tert-butyl 6-(6-(6-(2-(acetoxymethyl)-3-(6-tert-butyl-8-fluoro-1-oxophthalazin-2(1H)-yl)phenyl)-2-methyl-3-oxo-2,3-dihydropyridazin-4-ylamino)pyridin-3-yl)-2,6-diazaspiro[3.3]heptane-2-carboxylate (530 mg, 693 µmol) was combined with dioxane (15 ml) and 1M LiOH (3 ml) to give a dark brown solution. The reaction mixture was stirred at 25° C. for 4 h. The crude reaction mixture was concentrated in vacuo. The crude material was purified by flash chromatography (silica gel, 220 g, 0% to 4% MeOH in DCM) to afford 0.169 g (34%) of the title compound as a light yellow powder. (M+H)⁺=723 m/e. ¹H NMR (300 MHz, CHLOROFORM-d) δ: 8.36 (s, 1H), 8.26 (d, J=2.6 Hz, 1H), 8.19 (s, 1H), 7.37-7.69 (m, 6H), 6.84-6.94 (m, 1H), 6.80 (d, J=3.0 Hz, 1H), 4.39 (d, J=6.8 Hz, 2H), 4.08 (s, 4H), 3.96 (s, 4H), 3.85 (s, 3H), 1.42 (s, 9H), 1.39 (s, 9H).

Step 6. Preparation of 6-tert-butyl-2-(3-{5-[5-(2,6-diaza-spiro[3.3]hept-2-yl)-pyridin-2-ylamino]-1-methyl-6-oxo-1,6-dihydro-pyridazin-3-yl}-2-hydroxymethyl-phenyl)-8-fluoro-2H-phthalazin-1-one

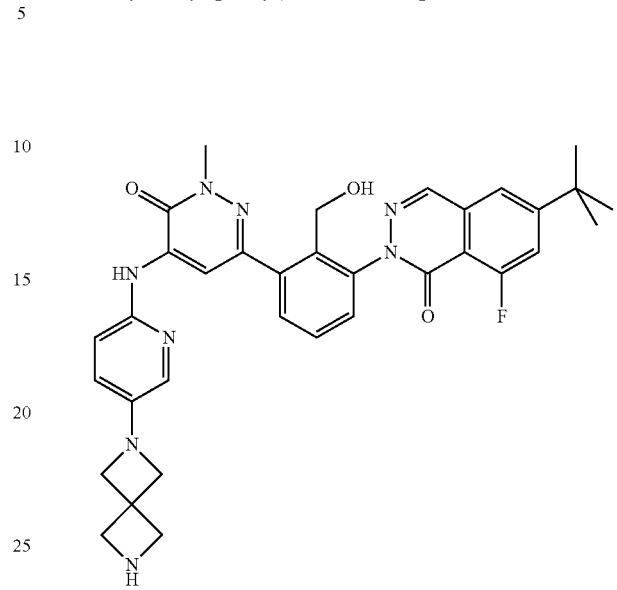

In a 250 mL round-bottomed flask, tert-butyl 6-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)-2,6-diazaspiro[3.3] heptane-2-carboxylate (169 mg, 234 µmol) was combined with DCM (10 ml) and TFA (2 ml) to give a yellow solution. The reaction mixture was stirred at 25° C. for 21 h. conc. in vacuo to afford the title compound as a yellow solid in quantitative yield. (M+H)⁺=623 m/e.

Example 22

Step 7. Preparation of 6-tert-butyl-8-fluoro-2-(2-hydroxymethyl-3-{1-methyl-5-[5-(6-methyl-2,6-diaza-spiro[3.3]hept-2-yl)-pyridin-2-ylamino]-6-oxo-1,6-dihydro-pyridazin-3-yl}-phenyl)-2H-phthalazin-1-one

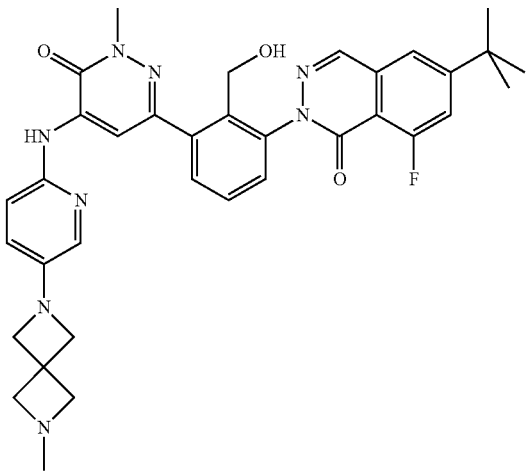 [SMILES: CN1CC2(C1)CN(c1ccc(Nc3cc(-c4cccc(-n5ncc6cc(C(C)(C)C)cc(F)c6c5=O)c4CO)nn(C)c3=O)nc1)C2]

In a 25 mL round-bottomed flask, 2-(3-(5-(5-(2,6-diaza-spiro[3.3]heptan-2-yl)pyridin-2-ylamino)-1-methyl-6-oxo-1,6-dihydropyridazin-3-yl)-2-(hydroxymethyl)phenyl)-6-tert-butyl-8-fluorophthalazin-1(2H)-one (146 mg, 234 μmol), 30% formaldehyde (42.2 mg, 38.8 μl, 1.41 mmol) and sodium cyanoborohydride (177 mg, 2.81 mmol) were combined with methanol (9 ml) to give an orange solution. The reaction mixture was stirred at 25° C. for 4 h. The crude reaction mixture was concentrated in vacuo, diluted with 10 mL 0.1 M NaOH and extracted with DCM (3×15 mL). The organic layers were dried over $Na_2SO_4$ and concentrated in vacuo. The crude material was purified by flash chromatography (silica gel, 40 g, 0% to 10% MeOH in DCM). The light yellow powder was dried under vacuum at 25° C. for 3 hrs to give 0.33 g (22%) of the title compound. $(M+H)^+=637$ m/e. $^1$H NMR (300 MHz, CHLOROFORM-d) δ: 8.37 (s, 1H), 8.28 (d, J=2.3 Hz, 1H), 8.13 (s, 1H), 7.38-7.71 (m, 6H), 6.75-6.93 (m, 2H), 4.40 (s, 2H), 3.96 (s, 4H), 3.88 (s, 3H), 3.47 (s, 4H), 2.37 (s, 3H), 1.42 (s, 9H).

Preparation of I-23

Step 1. Preparation of 5-Bromo-2-(2,2,5,5-tetramethyl-[1,2,5]azadisilolidin-1-yl)-pyridine

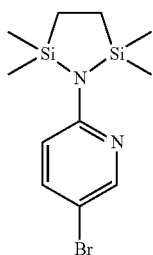

In a 500 mL three-necked flask, 5-bromopyridin-2-amine (5 g, 28.9 mmol) was combined with THF (80 ml) to give a light yellow solution. Cooled to −78° C. and n-butyllithium in hexane (18.2 ml, 29.2 mmol) was added via syringe. The reaction was stirred at −78° C. for 1 hr, then 1,2-bis(chlorodimethylsilyl)ethane (6.22 g, 28.9 mmol) was added dropwise over 15 min. After stirring for 90 min at −78° C., n-butyllithium in hexane (18.2 ml, 29.2 mmol) was added. The reaction was allowed to warm to 25° C. and stirred for 2 hr. The reaction mixture was diluted with 50 mL sat NaCl and extracted with diethyl ether (2×200 mL). The organic layers were combined, washed with $H_2O$ (1×25 mL), sat NaCl (1×25 mL), dried over $MgSO_4$ and concentrated in vacuo. The crude brown oil was purified by vacuum distillation (1 mm Hg, 170° C.). The product solidified upon cooling to give 4.89 g (54%) of the title compound as a white crystalline solid. $^1$H NMR (300 MHz, CHLOROFORM-d) δ: 8.15 (d, J=2.6 Hz, 1H), 7.47 (dd, J=8.9, 2.5 Hz, 1H), 6.47 (d, J=8.7 Hz, 1H), 0.83 (s, 4H), 0.24-0.38 (m, 12H).

Step 2. Preparation of 5-(ethylthio)pyridin-2-amine

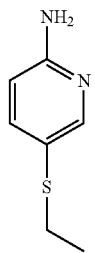

In a 100 mL round-bottomed flask, 5-bromo-2-(2,2,5,5-tetramethyl-1,2,5-azadisilolidin-1-yl)pyridine (519 mg, 1.65 mmol), ethanethiol (102 mg, 122 μl, 1.65 mmol), xantphos (47.6 mg, 82.3 μmol) and Hunig's base (425 mg, 575 μl, 3.29 mmol) were combined with dioxane (10.0 ml) to give a light yellow solution. $Pd_2(dba)_3$ (37.7 mg, 41.1 μmol) was added and the mixture was evacuated and filled with Argon. The reaction mixture was heated to 110° C. and stirred for 17 h under argon. The mixture was cooled to 25° C. and conc. in vacuo. The residue was partitioned between 1M HCl and ether. Separated and basified aqueous phase with 3M NaOH. The aqueous layer was extracted with EtOAc (2×125 mL). The organic layers were combined, washed with $H_2O$ (1×50 mL), sat NaCl (1×25 mL), dried over $Na_2SO_4$ and concentrated in vacuo to an orange oil. The oil was dried overnight at 25° C. under vacuum to give an orange gum that was used crude in the subsequent oxidation. $(M+H)^+=155$ m/e.

Step 3. Preparation of 5-(Ethanesulfonyl)-pyridin-2-amine

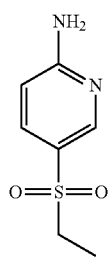

In a 250 mL round-bottomed flask, 5-(ethylthio)pyridin-2-amine (254 mg, 1.65 mmol), TFA (376 mg, 254 μL, 3.29 mmol) and m-CPBA (625 mg, 3.62 mmol) were combined with DCM (6 mL) to give a light yellow solution. The reaction mixture was stirred at 0° C. for 2 h. The heavy suspension was quenched with Aq $Na_2SO_3$ and diluted with DCM. The phases were separated and the aqueous layer was back-extracted with DCM (2×20 mL). The organic layers were combined, washed with sat $NaHCO_3$ (1×15 mL), sat NaCl (1×15 mL), dried over $Na_2SO_4$ and concentrated in vacuo. The crude material was purified by flash chromatography (silica gel, 24 g, 0% to 90% EtOAc in heptane) to afford 0.183 g (60%) of the title compound as a white powder. $(M+H)^+=187$ m/e. $^1$H NMR (300 MHz, CHLOROFORM-d) δ: 8.53 (d, J=2.6 Hz, 1H), 7.82 (dd, J=8.7, 2.3 Hz, 1H), 6.55 (d, J=8.7 Hz, 1H), 5.23 (br. s., 2H), 3.09 (q, J=7.6 Hz, 2H), 1.29 (t, 3H).

Step 4. Preparation of 6-Chloro-4-(5-ethanesulfonyl-pyridin-2-ylamino)-2-methyl-2H-pyridazin-3-one

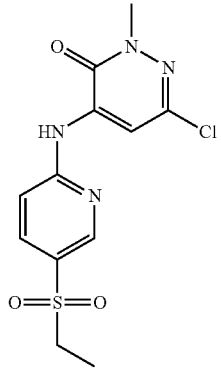 [SMILES: CCS(=O)(=O)c1ccc(Nc2cc(Cl)nn(C)c2=O)nc1]

In a 250 mL round-bottomed flask, 5-(ethylsulfonyl)pyridin-2-amine (183 mg, 983 μmol), 4-bromo-6-chloro-2-methylpyridazin-3(2H)-one (263 mg, 1.18 mmol), xantphos (85.3 mg, 147 μmol) and Cs$_2$CO$_3$ (960 mg, 2.95 mmol) were combined with dioxane (10 mL) to give a light brown suspension. The flask was evacuated and filled with argon. Pd$_2$(dba)$_3$ (45.0 mg, 49.1 μmol) was added and the reaction mixture was stirred at 100° C. for 20 h under argon. Cooled to 25° C. and diluted with DCM. The reaction mixture was filtered through celite and the filter cake was washed with DCM until clear. The filtrate was concentrated and purified by flash chromatography (silica gel, 40 g, 0% to 2% MeOH in DCM) to afford 0.323 g (25%) of the title compound as a tan powder. (M+H)$^+$=329/331 m/e. $^1$H NMR (300 MHz, DMSO-d$_6$) δ: 10.18 (s, 1H), 8.78 (d, J=2.3 Hz, 1H), 8.12 (dd, J=8.9, 2.5 Hz, 1H), 7.74 (d, J=9.1 Hz, 1H), 3.69 (s, 3H), 3.32 (q, J=7.4 Hz, 2H), 1.11 (t, J=7.4 Hz, 3H).

Step 5. Preparation of acetic acid 2-(6-tert-butyl-8-fluoro-1-oxo-1H-phthalazin-2-yl)-6-[5-(5-ethanesulfonyl-pyridin-2-ylamino)-1-methyl-6-oxo-1,6-dihydro-pyridazin-3-yl]-benzyl ester

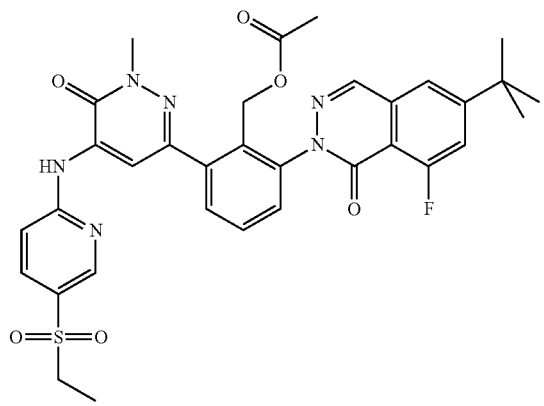 [SMILES: CCS(=O)(=O)c1ccc(Nc2cc(-c3cccc(-n4ncc5cc(C(C)(C)C)cc(F)c5c4=O)c3COC(C)=O)nn(C)c2=O)nc1]

In a 250 mL round-bottomed flask, 6-chloro-4-(5-(ethylsulfonyl)pyridin-2-ylamino)-2-methylpyridazin-3(2H)-one (79 mg, 240 μmol), 2-(6-tert-butyl-8-fluoro-1-oxophthalazin-2(1H)-yl)-6-(4,4,5,5-tetramethyl-1,3,2-dioxaborolan-2-yl)benzyl acetate (154 mg, 312 μmol) and Cs$_2$CO$_3$ (235 mg, 721 μmol) were combined with dioxane (10 ml) and water (1 ml) to give a light yellow suspension. The mixture was evacuated and filled with argon. PdCl$_2$(DPPF) (9.81 mg, 12.0 μmol) was added, the reaction mixture was purged with argon and heated to 85° C. for 60 h. The reaction mixture was diluted with DCM and filtered through celite. The filter cake was washed with DCM until clear. The filtrate was dried over Na$_2$SO$_4$ and concentrated in vacuo to give a dark brown oil. The brown oil was used crude in the subsequent reaction. (M−H)$^+$=659 m/e.

Example 23

Step 6. Preparation of 6-tert-Butyl-2-{3-[5-(5-ethanesulfonyl-pyridin-2-ylamino)-1-methyl-6-oxo-1,6-dihydro-pyridazin-3-yl]-2-hydroxymethyl-phenyl}-8-fluoro-2H-phthalazin-1-one

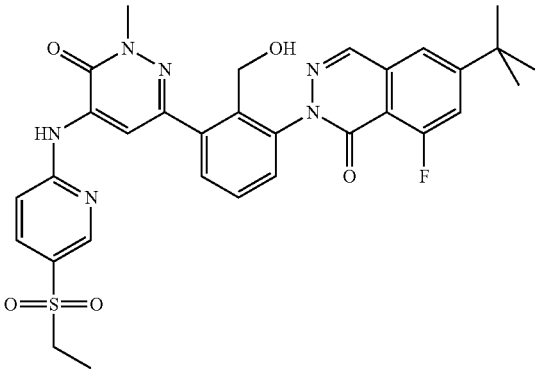 [SMILES: CCS(=O)(=O)c1ccc(Nc2cc(-c3cccc(-n4ncc5cc(C(C)(C)C)cc(F)c5c4=O)c3CO)nn(C)c2=O)nc1]

In a 250 mL round-bottomed flask, 2-(6-tert-butyl-8-fluoro-1-oxophthalazin-2(1H)-yl)-6-(5-(5-(ethylsulfonyl)pyridin-2-ylamino)-1-methyl-6-oxo-1,6-dihydropyridazin-3-yl)benzyl acetate (159 mg, 241 μmol) was combined with dioxane (5 ml) and 1M LiOH (1 ml) to give a brown solution. The reaction mixture was stirred at 25° C. for 18 h. The crude reaction mixture was concentrated in vacuo. The residue was partitioned between water and DCM. The organic layer was dried over MgSO$_4$ and concentrated in vacuo. The crude material was purified by flash chromatography (silica gel, 24 g, 0% to 4% MeOH in DCM) to afford 0.039 g (54%) of the title compound as a tan solid. (M−H)$^+$=617 m/e. $^1$H NMR (300 MHz, CHLOROFORM-d) δ: 8.85 (d, J=2.3 Hz, 1H), 8.79 (s, 1H), 8.63 (s, 1H), 8.30 (d, J=2.3 Hz, 1H), 8.06 (dd, J=8.7, 2.3 Hz, 1H), 7.43-7.73 (m, 5H), 7.07 (d, J=8.7 Hz, 1H), 4.45 (s, 2H), 3.94 (s, 3H), 3.15 (d, J=7.2 Hz, 2H), 1.44 (s, 9H), 1.33 (t, J=7.2 Hz, 3H).

Example 24

Preparation of 6-tert-Butyl-8-fluoro-2-(2-hydroxymethyl-3-{1-methyl-6-oxo-5-[5-(propane-2-sulfonyl)-pyridin-2-ylamino]-1,6-dihydro-pyridazin-3-yl}-phenyl)-2H-phthalazin-1-one

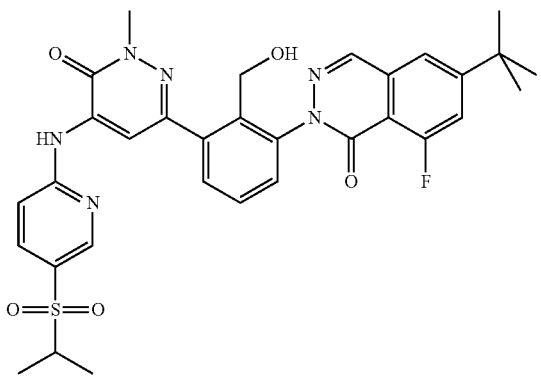 [SMILES: CC(C)S(=O)(=O)c1ccc(Nc2cc(-c3cccc(-n4ncc5cc(C(C)(C)C)cc(F)c5c4=O)c3CO)nn(C)c2=O)nc1]

Preparation by a similar procedure to Example 23, except substituting propane-2-thiol for ethanethiol in step 2 afforded 0.033 g (12%) of the title compound as a tan solid. $(M+H)^+=633$ m/e. $^1$H NMR (300 MHz, CHLOROFORM-d) δ: 8.81 (d, J=2.3 Hz, 1H), 8.73-8.79 (m, 1H), 8.62 (s, 1H), 8.29 (d, J=2.3 Hz, 1H), 8.04 (dd, J=8.7, 2.3 Hz, 1H), 7.43-7.70 (m, 5H), 7.07 (d, J=8.7 Hz, 1H), 4.45-4.59 (d, 2H), 3.94 (s, 3H), 3.21 (m, J=6.8 Hz, 1H), 1.44 (s, 9H), 1.34 (d, J=6.8 Hz, 6H).

Preparation of I-25

Step 1. Preparation of 2-(6-Aminopyridin-3-ylthio)-ethanol

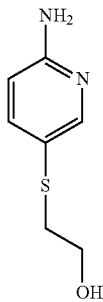

In a 100 mL round-bottomed flask, 5-bromo-2-(2,2,5,5-tetramethyl-1,2,5-azadisilolidin-1-yl)pyridine (502 mg, 1.59 mmol), 2-mercaptoethanol (124 mg, 112 µl, 1.59 mmol), xantphos (46.1 mg, 79.6 µmol) and Hunig's base (411 mg, 556 µl, 3.18 mmol) were combined with dioxane (10.0 ml) to give a light yellow solution. Pd$_2$(dba)$_3$ (36.4 mg, 39.8 µmol) was added and the mixture was evacuated and filled with argon. The reaction mixture was heated to 110° C. and stirred for 17 h under argon. The reaction mixture was cooled to 25° C., concentrated in vacuo and partitioned between 1M HCl and EtOAc. Separated and basified aqueous with 3M NaOH. The aqueous layer was extracted with EtOAc (3×125 mL). The organic layers were combined, washed with sat NaCl (1×25 mL), dried over Na$_2$SO$_4$ and concentrated in vacuo to a light yellow solid. The solid was dried under vacuum at 25° C. for 21 hrs to afford 0.259 g (96%) of the title compound. $^1$H NMR (300 MHz, DMSO-d$_6$) δ: 7.94 (d, J=2.3 Hz, 1H), 7.45 (dd, J=8.7, 2.3 Hz, 1H), 6.40 (d, J=8.7 Hz, 1H), 6.03-6.20 (m, 2H), 4.77 (t, J=5.7 Hz, 1H), 3.37-3.51 (m, 2H), 2.67-2.76 (m, 2H).

Example 25

Step 2. Preparation of 6-tert-Butyl-8-fluoro-2-(3-{5-[5-(2-hydroxyethylthio)-pyridin-2-ylamino]-1-methyl-6-oxo-1,6-dihydro-pyridazin-3-yl}-2-hydroxymethyl-phenyl)-2H-phthalazin-1-one

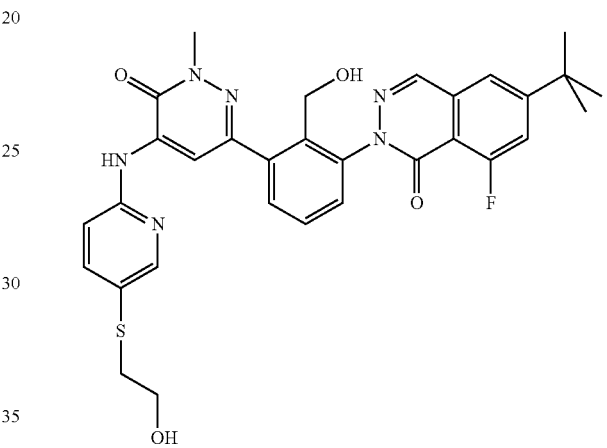

In a 250 mL round-bottomed flask, 2-(6-aminopyridin-3-ylthio)ethanol (247 mg, 1.45 mmol), 2-(5-bromo-1-methyl-6-oxo-1,6-dihydropyridazin-3-yl)-6-(6-tert-butyl-8-fluoro-1-oxophthalazin-2(1H)-yl)benzyl acetate (806 mg, 1.45 mmol), xantphos (126 mg, 218 µmol) and Cs$_2$CO$_3$ (1.42 g, 4.35 mmol) were combined with dioxane (20 ml) to give a brown suspension. The reaction was evacuated and filled with argon. Pd$_2$(dba)$_3$ (66.4 mg, 72.5 µmol) was added and the reaction mixture was heated to 100° C. and stirred for 17 h under argon. Cooled to 25° C. and diluted with DCM. The reaction mixture was filtered over celite and the filter cake was washed with DCM until clear. The filtrate was conc. in vacuo. The crude material was purified by flash chromatography (silica gel, 40 g, 0% to 3% MeOH in DCM). The material was repurified by flash chromatography (silica gel, 40 g, 0% to 50% Acetone in Heptane), concentrated in vacuo to a white powder and dried under vacuum at 25° C. overnight. The product was taken up in dioxane (15 ml) and 1M LiOH (3 ml) was added. The reaction was stirred at 25° C. for 17 hrs. The crude reaction mixture was concentrated in vacuo. The residue was diluted with 15 mL DCM and 15 mL H$_2$O. The aqueous layer was back-extracted with DCM (2×20 mL). The organic layers were dried over Na$_2$SO$_4$ and concentrated in vacuo. The crude material was purified by flash chromatography (silica gel, 40 g, 0% to 50% acetone in heptane) to afford 0.061 g (7%) of the title compound as a white powder. (M+H)$^+$=603 m/e. $^1$H NMR (300 MHz, CHLOROFORM-d) δ: 8.61 (s, 1H), 8.42 (d, J=2.3 Hz, 1H), 8.38 (s, 1H), 8.29 (d, J=2.6 Hz, 1H), 7.73 (dd, J=8.5, 2.5 Hz, 1H), 7.65 (d, J=1.5 Hz, 1H), 7.60 (d, J=7.6 Hz, 1H), 7.53-7.57 (m, 2H), 7.45-7.51 (m, 1H), 6.95 (d, J=8.3 Hz, 1H), 4.43 (s, 2H), 3.92 (s, 3H), 3.74 (t, J=5.9 Hz, 2H), 3.04 (t, J=5.9 Hz, 2H), 1.43 (s, 9H).

Example 26

Preparation of 6-tert-Butyl-8-fluoro-2-(3-{5-[5-(2-hydroxyethanesulfonyl)-pyridin-2-ylamino]-1-methyl-6-oxo-1,6-dihydro-pyridazin-3-yl}-2-hydroxymethyl-phenyl)-2H-phthalazin-1-one

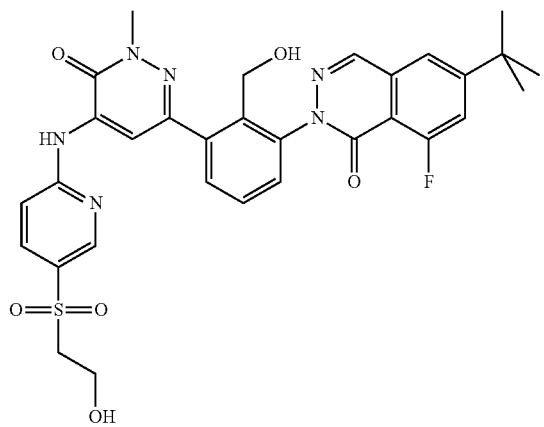 [SMILES: Cn1nc(-c2cccc(-n3ncc4cc(C(C)(C)C)cc(F)c4c3=O)c2CO)cc(Nc2ccc(S(=O)(=O)CCO)cn2)c1=O]

In a 100 mL round-bottomed flask, 6-tert-butyl-8-fluoro-2-(3-(5-(5-(2-hydroxyethylthio)pyridin-2-ylamino)-1-methyl-6-oxo-1,6-dihydropyridazin-3-yl)-2-(hydroxymethyl) phenyl)phthalazin-1(2H)-one (45 mg, 74.7 µmol) was combined with DCM (4 ml) to give a light yellow solution. The mixture was cooled to 0° C. and TFA (17.0 mg, 11.5 µl, 149 µmol) and m-CPBA (28.3 mg, 164 µmol) were added. The reaction was stirred at 0° C. for 3 hrs. The reaction was quenched with sat'd Na$_2$SO$_3$ and 1M NaOH. Diluted with DCM (emulsion) and separated. The aqueous layer was back-extracted with DCM (3×20 mL). The organic layers were combined, washed with sat NaCl (1×15 mL), dried over MgSO$_4$ and concentrated in vacuo. The crude material was purified by flash chromatography (silica gel, 12 g, 0% to 50% acetone in heptane) to afford 0.010 g (22%) of the title compound as a white powder. (M+H)$^+$=634 m/e. $^1$H NMR (300 MHz, CHLOROFORM-d) δ: 8.87 (d, J=2.3 Hz, 1H), 8.80 (s, 1H), 8.66 (s, 1H), 8.30 (d, J=2.3 Hz, 1H), 8.07 (dd, J=8.7, 2.6 Hz, 1H), 7.45-7.68 (m, 5H), 7.08 (d, J=8.7 Hz, 1H), 4.45 (s, 2H), 4.01-4.09 (m, 2H), 3.93 (s, 3H), 3.34-3.42 (m, 2H), 1.44 (s, 9H).

Preparation of I-27

Example 27

6-tert-Butyl-8-fluoro-2-(2-hydroxymethyl-3-{5-[5-(4-isopropyl-piperazin-1-yl)-pyridin-2-ylamino]-1-methyl-6-oxo-1,6-dihydro-pyridazin-3-yl}-phenyl)-2H-phthalazin-1-one HCl

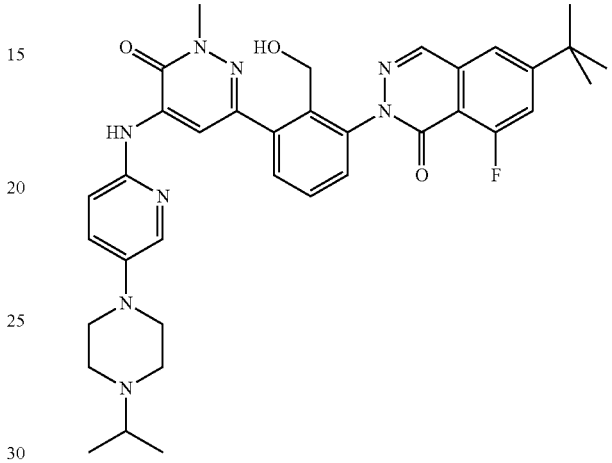

Step 1

To 5-bromo-2-nitropyridine (1.0 g, 4.93 mmol, Eq: 1.00) in DMSO (10.0 ml) was added 1-isopropylpiperazine (632 mg, 4.93 mmol, Eq: 1.00), and the resulting solution was heated at 70° C. for 18 hours. The solution was cooled to room temperature. The solution was diluted with 50 ml water. The resulting solid was filtered. The solid was washed with water and dried under vacuum. The crude material was purified by flash chromatography (silica gel, 80 g, 0% to 3% MeOH/DCM gradient) to give 1-isopropyl-4-(6-nitropyridin-3-yl) piperazine (788 mg, 64%). LC/MS-ESI observed [M+H]$^+$ 251.

Step 2

In a 250 mL round-bottomed flask, 1-isopropyl-4-(6-nitropyridin-3-yl)piperazine (788 mg, 3.15 mmol, Eq: 1.00) in EtOH (40 ml) was combined with palladium on carbon (DeGussa)(78.2 mg, 735 µmol, Eq: 0.233). The mixture was evacuated twice with hydrogen and then stirred under a hydrogen atmosphere for 18 h. The solution was filtered through celite, rinsing the celite with fresh ethanol. The solvent was evaporated under reduced pressure to give 5-(4-isopropylpiperazin-1-yl)pyridin-2-amine (425 mg, 61%). LC/MS-ESI observed [M+H]$^+$ 221.

Step 3

In a 50 mL round-bottomed flask, 5-(4-isopropylpiperazin-1-yl)pyridin-2-amine (200 mg, 908 µmol, Eq: 1.00), 4-bromo-6-chloro-2-methylpyridazin-3(2H)-one (243 mg, 1.09 mmol, Eq: 1.2) and cesium carbonate (887 mg, 2.72 mmol, Eq: 3) were combined with dioxane (20 ml) to give a orange suspension. 4,5-Bis(diphenylphosphino)-9,9-dimethylxanthene (78.8 mg, 136 µmol, eq: 0.15) was added. Tris (dibenzylideneacetone)dipalladium(0) (41.6 mg, 45.4 µmol, Eq: 0.05) was added. The solution was degassed with Ar for 10 min. The solution was heated at 95-105° C. for 48 h. The solution was diluted with 200 ml DCM. MgSO$_4$ was added and the suspension stirred for 10 min. The solid was filtered and washed several times with DCM. The organics were concentrated in vacuo. The crude material was purified by flash chromatography (silica gel, 40 g, 50% to 100% EtOAc/hexanes gradient) to give 6-chloro-4-(5-(4-isopropylpiperazin-1-yl)pyridin-2-ylamino)-2-methylpyridazin-3(2H)-one (273 mg, 83%). LC/MS-ESI observed [M+H]$^+$ 363.

Step 4

6-Chloro-4-(5-(4-isopropylpiperazin-1-yl)pyridin-2-ylamino)-2-methylpyridazin-3(2H)-one (123 mg, 340 µmol, Eq: 1.2), 2-(6-tert-butyl-8-fluoro-1-oxophthalazin-2(1H)-yl)-6-(4,4,5,5-tetramethyl-1,3,2-dioxaborolan-2-yl)benzyl acetate (140 mg, 283 µmol, Eq: 1.00), potassium phosphate tribasic (180 mg, 850 µmol, Eq: 3.00) and X-PHOS (13.5 mg, 28.3 µmol, Eq: 0.10) were dissolved in dioxane (10 ml) and water (1.0 mL). The reaction was degassed with Ar. Pd2(dba)3 (13.0 mg, 14.2 µmol, Eq: 0.05) was added and the reaction was heated to 125° C. for 30 min in the microwave. The solution was dried over MgSO$_4$ and filtered. Concentrated in vacuo. The crude material was purified by flash chromatography (silica gel, 12 g, 0% to 5% MeOH/DCM gradient) to give 2-(6-tert-butyl-8-fluoro-1-oxophthalazin-2(1H)-yl)-6-(5-(5-(4-isopropylpiperazin-1-yl)pyridin-2-ylamino)-1-methyl-6-oxo-1,6-dihydropyridazin-3-yl)benzyl acetate (153 mg, 78%). LC/MS-ESI observed [M+H]$^+$ 695.

Step 5

To 2-(6-tert-butyl-8-fluoro-1-oxophthalazin-2(1H)-yl)-6-(5-(5-(4-isopropylpiperazin-1-yl)pyridin-2-ylamino)-1-methyl-6-oxo-1,6-dihydropyridazin-3-yl)benzyl acetate (153 mg, 220 µmol, Eq: 1.00) in THF (2.0 ml) was added an aqueous solution of 1N NaOH (2.0 mL, 2.00 mmol, Eq: 9.08). The resulting solution heated at 60° C. for 2 h. The mixture was cooled to room temperature. The solution was diluted with saturated NaHCO$_3$ and DCM. The layers were separated. The aqueous layer was extracted three times with DCM. The combined organics were dried over MgSO$_4$. The solution was filtered. Concentrated in vacuo. The crude material was purified by flash chromatography (silica gel, 12 g, 0% to 50% (60:10:1 DCM:MeOH:NH$_4$OH)/DCM gradient) to give a cream solid. The solid was triturated with Et$_2$O. The solid was filtered, then dissolved in 2 ml DCM. A solution of 1.0 M HCl in Et$_2$O (2 ml) was added. A solid formed. The solid was filtered and dried under vacuum to give 6-tert-butyl-8-fluoro-2-(2-hydroxymethyl-3-{5-[5-(4-isopropyl-piperazin-1-yl)-pyridin-2-ylamino]-1-methyl-6-oxo-1,6-dihydro-pyridazin-3-yl}-phenyl)-2H-phthalazin-1-one HCl (57.5 mg, 38%). LC/MS-ESI observed [M+H]$^+$ 653. $^1$H NMR (300 MHz, DMSO-d$_6$) δ ppm 1.28 (d, J=6.80 Hz, 6H) 1.37 (s, 9H) 3.08 (d, J=11.33 Hz, 2H) 3.46 (d, J=10.20 Hz, 2H) 3.76 (s, 5H) 4.39 (d, J=6.04 Hz, 2H) 7.41-7.59 (m, 5H) 7.73 (d, J=13.97 Hz, 1H) 7.86 (s, 1H) 8.06 (d, J=2.27 Hz, 1H) 8.42 (s, 1H) 8.50 (d, J=2.27 Hz, 1H) 9.31 (s, 1H)

Preparation of I-28

Example 28

6-tert-Butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one

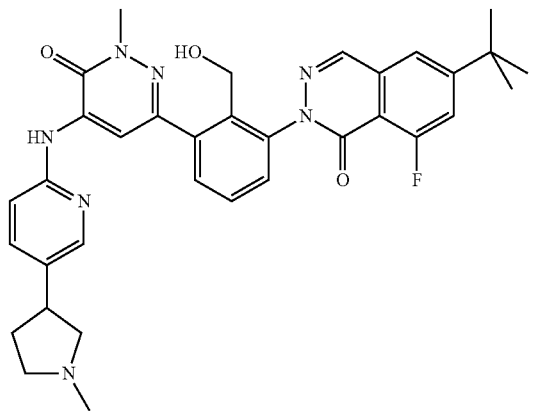 [SMILES: CN1CCC(c2ccc(Nc3cc(-c4cccc(-n5ncc6cc(C(C)(C)C)cc(F)c6c5=O)c4CO)nn(C)c3=O)nc2)C1]

Step 1

In a 100 mL three-necked flask, a solution of tert-butyl 3-oxopyrrolidine-1-carboxylate (1 g, 5.24 mmol, Eq: 1.00) in THF (30.0 ml) was treated with lithium bis(trimethylsilyl) amide 1M in THF (5.6 ml, 5.6 mmol, Eq: 1.07) at –78° C. After stirring for 15 min at –78° C., a solution of N-phenylbis (trifluoromethanesulfonimide) (2.27 g, 6.28 mmol, Eq: 1.20) in THF (10 ml) was added by drop. The reaction mixture was then warmed to room temperature. The reaction was quenched with the addition of saturated aqueous NaHCO$_3$, and then extracted with ethyl ether. The organic layer was washed with brine, dried over MgSO$_4$, filtered and concentrated in vacuo. The crude material was purified by flash chromatography (silica gel, 120 g, 0% to 30% EtOAc/Hex gradient) to give 3-trifluoromethanesulfonyloxy-2,5-dihydro-pyrrole-1-carboxylic acid tert-butyl ester (880 mg, 53%).

Step 2

In a 25 mL round-bottomed flask, 3-trifluoromethanesulfonyloxy-2,5-dihydro-pyrrole-1-carboxylic acid tert-butyl ester (780 mg, 2.46 mmol, Eq: 1.00) was combined with THF (20 ml) to give a colorless solution. The solution was purged with argon for 10 min. Potassium carbonate (1.72 g, 12.3 mmol, Eq: 5.0), 5-(4,4,5,5-tetramethyl-1,3,2-dioxaborolan-2-yl)pyridin-2-amine (649 mg, 2.95 mmol, Eq: 1.20), tetrakis(triphenylphosphine)palladium(0) (28.4 mg, 24.6 µmol, Eq: 0.01) and water (200 µl) were added. The reaction mixture was heated to 70° C. and stirred for 16 h. The reaction mixture was poured into saturated NaHCO₃ and extracted twice with Et₂O. The organic layer was washed with brine, dried over Na₂SO₄ and concentrated in vacuo. The crude material was purified by flash chromatography (silica gel, 40 g, 50% (60:10:1 DCM:MeOH:NH₄OH)/DCM) to give 3-(6-amino-pyridin-3-yl)-2,5-dihydro-pyrrole-1-carboxylic acid tert-butyl ester (538 mg, 84%). LC/MS-ESI observed [M+H]⁺ 262.

Step 3

3-(6-Amino-pyridin-3-yl)-2,5-dihydro-pyrrole-1-carboxylic acid tert-butyl ester (538 mg, 2.06 mmol, Eq: 1.00) was dissolved in methanol (20 ml). The solution was put under argon and then treated with palladium on activated carbon (43.8 mg, 20.6 µmol, Eq: 0.01). The suspension was purged with hydrogen and stirred under hydrogen for 18 h. The reaction mixture was filtered through silica gel. The filtrate was concentrated and the residue was dissolved in methanol (12 ml). The solution was purged with argon for 10 min and then treated with palladium on activated carbon (Degussa) (43.8 mg, 20.6 µmol, Eq: 0.01). The suspension was purged with hydrogen and stirred under hydrogen for 18 h. The reaction mixture was filtered through a 45 µm frit. The filtrate was concentrated in vacuo to give tert-butyl 3-(6-aminopyridin-3-yl)pyrrolidine-1-carboxylate (422 mg, 78%). LC/MS-ESI observed [M+H]⁺ 264.

Step 4

Tert-butyl 3-(6-aminopyridin-3-yl)pyrrolidine-1-carboxylate (422 mg, 1.6 mmol, Eq: 1.00), 4-bromo-6-chloro-2-methylpyridazin-3(2H)-one (430 mg, 1.92 mmol, Eq: 1.20), 4,5-bis(diphenylphosphino)-9,9-dimethylxanthene (139 mg, 240 µmol, Eq: 0.15), cesium carbonate (1.57 g, 4.81 mmol, Eq: 3) and tris(dibenzylideneacetone)dipalladium(0) (73.4 mg, 80.1 µmol, Eq: 0.05) were combined in dioxane (10 ml). The solution was degassed with Ar for 10 min. The mixture was heated at 100° C. for 18 h. The solution was cooled to room temperature then diluted with 100 ml DCM. The organics washed with water, then dried over MgSO₄. The solution was filtered. Concentrated in vacuo. The crude material was purified by flash chromatography (silica gel, 40 g, 50% to 100% EtOAC/Hex gradient) to give tert-butyl 3-(6-(6-chloro-2-methyl-3-oxo-2,3-dihydropyridazin-4-ylamino)pyridin-3-yl)pyrrolidine-1-carboxylate (325 mg, 50%) LC/MS-ESI observed [M+H]⁺ 406.

Step 5

Tert-butyl 3-(6-(6-chloro-2-methyl-3-oxo-2,3-dihydropyridazin-4-ylamino)pyridin-3-yl)pyrrolidine-1-carboxylate (160 mg, 394 µmol, Eq: 1.00) was dissolved in a solvent mixture of formic acid (6.0 ml) and formaldehyde, 37% (12.0 ml). The solution stirred at 70° C. for 18 h. The solution was cooled to room temperature. Water was added. The reaction mixture was extracted once with DCM. Solid K₂CO₃ was slowly added to the aqueous layer until the pH=14. A solid formed that was subsequently filtered. The solid was dried to give 6-chloro-2-methyl-4-(5-(1-methylpyrrolidin-3-yl)pyridin-2-ylamino)pyridazin-3(2H)-one (70 mg, 55%). LC/MS-ESI observed [M+H]⁺ 320.

Step 6

In a 50 mL test tube, 6-chloro-2-methyl-4-(5-(1-methylpyrrolidin-3-yl)pyridin-2-ylamino)pyridazin-3(2H)-one (69 mg, 216 µmol, Eq: 1.00) and 2-(6-tert-butyl-8-fluoro-1-oxophthalazin-2(1H)-yl)-6-(4,4,5,5-tetramethyl-1,3,2-dioxaborolan-2-yl)benzyl acetate (128 mg, 259 µmol, Eq: 1.20) were combined with BuOH (4 ml) to give an orange solution. Water (1.0 ml) was added, followed by X-PHOS (10.3 mg, 21.6 µmol, Eq: 0.1) and potassium phosphate tribasic (91.6 mg, 432 µmol, Eq: 2). Bis(dibenzylideneacetone)palladium (6.2 mg, 10.8 µmol, Eq: 0.05) was added. The solution was purged with argon. The reaction mixture was warmed in a oil bath at 110° C. for 1.5 hours. The solution was allowed to cool to room temperature. The reaction mixture was poured into 75 mL H₂O and extracted with EtOAc. The organic layer was concentrated in vacuo. The crude material was purified by flash chromatography (silica gel, 12 g, 50% to 100% (60:10:1 DCM:MeOH:NH₄OH)/DCM gradient) to give a mixture of products 2-(6-tert-butyl-8-fluoro-1-oxophthalazin-2(1H)-yl)-6-(1-methyl-5-(5-(1-methylpyrrolidin-3-yl)pyridin-2-ylamino)-6-oxo-1,6-dihydropyridazin-3-yl)benzyl acetate and 6-tert-butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one (1:7 ratio, 109 mg total, 75% overall). LC/MS-ESI observed [M+H]⁺ 652, 610.

Step 7

To a mixture of 2-(6-tert-butyl-8-fluoro-1-oxophthalazin-2(1H)-yl)-6-(1-methyl-5-(5-(1-methylpyrrolidin-3-yl)pyridin-2-ylamino)-6-oxo-1,6-dihydropyridazin-3-yl)benzyl acetate and 6-tert-butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one (106 mg, 163 µmol, Eq: 1.00) in THF (2.0 ml) was added aqueous 1N NaOH (1.95 ml, 1.95 mmol, Eq: 12.0). The solution was heated to 60° C. for 18 h. The solution was cooled to room temperature. The solution was diluted with saturated NaHCO₃ and DCM. The layers were separated. The aqueous layer was extracted three times with DCM, and then dried over Na₂SO₄. Concentrated in vacuo. The resulting solid was triturated with Et₂O. The solid was filtered. The mother liquor was evaporated to give a white solid. The solid was dried at 50° C. under reduced pressure for 18 h to give 6-tert-Butyl-8-fluoro-2-(2-hydroxymethyl-3-{1-methyl-5-[5-(1-methyl-pyrrolidin-3-yl)-pyridin-2-ylamino]-6-oxo-1,6-dihydro-pyridazin-3-yl}-phenyl)-2H-phthalazin-1-one (41 mg, 41%). LC/MS-ESI observed [M+H]⁺ 610. ¹H NMR (300 MHz, CHLOROFORM-d) δ ppm 1.45 (s, 9H) 1.86 (dd, J=13.03, 6.99 Hz, 1H) 2.23-2.60 (m, 5H) 2.76 (br. s., 2H) 3.00 (br. s., 1H) 3.24-3.42 (m, 1H) 3.91 (s, 4H) 4.43 (d, J=6.04 Hz, 2H) 6.92 (d, J=8.31 Hz, 1H) 7.40-7.78 (m, 6H) 8.26 (dd, J=12.65, 2.83 Hz, 3H) 8.62 (s, 1H).

Preparation of I-29

Example 29

6-tert-Butyl-8-fluoro-2-{2-hydroxymethyl-3-[5-(1'-isopropyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one

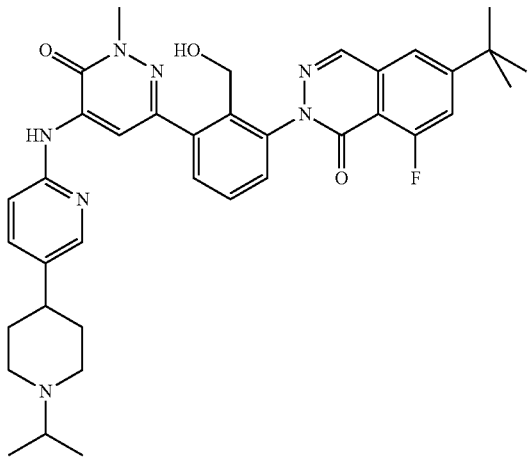 [SMILES: CC(C)N1CCC(c2ccc(Nc3cc(-c4cccc(-n5ncc6cc(C(C)(C)C)cc(F)c6c5=O)c4CO)nn(C)c3=O)nc2)CC1]

Step 1

In a 50 mL round-bottomed flask, 5-bromo-2-nitropyridine (3.28 g, 16.2 mmol, Eq: 1) and tert-butyl 4-(4,4,5,5-tetramethyl-1,3,2-dioxaborolan-2-yl)-5,6-dihydropyridine-1(2H)-carboxylate (5 g, 16.2 mmol, Eq: 1.00) were combined with dioxane (80.0 ml) to give a light yellow solution. $Cs_2CO_3$ (10.5 g, 32.3 mmol, Eq: 2) and 3 mL $H_2O$ were added. The solution was degassed with Ar before bis(triphenylphosphine)palladium(ii) dichloride (1.13 g, 1.62 mmol, Eq: 0.1) was added. The reaction mixture was heated to 80° C. and stirred for 15 h. The reaction mixture was poured into 300 mL $H_2O$ and extracted with EtOAc (3×100 mL). The combined organic extracts were washed with brine and dried over $MgSO_4$. The crude reaction mixture was concentrated in vacuo. The crude material was purified by flash chromatography (silica gel, 220 g, 10% to 100% EtOAc/Hex gradient) to give a dark brown impure solid. The solid was triturated with $Et_2O$ to afford tert-butyl 4-(6-nitropyridin-3-yl)-5,6-dihydropyridine-1(2H)-carboxylate (685 mg, 69%) as a tan solid. LC/MS-ESI observed $[M+H]^+$ 306.

Step 2

In a 250 mL round-bottomed flask, tert-butyl 4-(6-nitropyridin-3-yl)-5,6-dihydropyridine-1(2H)-carboxylate (632 mg, 2.07 mmol, Eq: 1.00) in EtOH (25.0 ml) and ethyl acetate (10 ml) was combined with palladium on carbon (66.1 mg, 62.1 µmol, Eq: 0.03). The mixture was evacuated twice with hydrogen and then stirred with a hydrogen-filled balloon for 22 h. The hydrogen was replaced with nitrogen. The solution was filtered through celite. The celite was washed several times with EtOAc. Concentrated in vacuo to give tert-butyl 4-(6-aminopyridin-3-yl)piperidine-1-carboxylate (635 mg, quantitative yield). LC/MS-ESI observed $[M+H]^+$ 278.

Step 3

4-Bromo-6-chloro-2-methylpyridazin-3(2H)-one (509 mg, 2.28 mmol, Eq: 1.00), tert-butyl 4-(6-aminopyridin-3-yl)piperidine-1-carboxylate (632 mg, 2.28 mmol, Eq: 1.00), 4,5-bis(diphenylphosphino)-9,9-dimethylxanthene (198 mg, 342 µmol, Eq: 0.15) and cesium carbonate (2.6 g, 7.98 mmol, Eq: 3.5) were suspended in dioxane (20 ml) under argon. Finally tris(dibenzylideneacetone)dipalladium(0) (156 mg, 171 µmol, Eq: 0.075) was added. The reaction mixture was heated to 90° C. for 18 h. The reaction mixture was filtered over celite; washed with dioxane, and concentrated in vacuo. The crude material was purified by flash chromatography (silica gel, 24 g, 20% to 50% EtOAc/Hex gradient) to give tert-butyl 4-(6-(6-chloro-2-methyl-3-oxo-2,3-dihydropyridazin-4-ylamino)pyridin-3-yl)piperidine-1-carboxylate (782 mg, 82%). LC/MS-ESI observed $[M+H]^+$ 420.

Step 4

To tert-butyl 4-(6-(6-chloro-2-methyl-3-oxo-2,3-dihydropyridazin-4-ylamino)pyridin-3-yl)piperidine-1-carboxylate (782 mg, 1.86 mmol, Eq: 1.00) in DCM (20 ml) was added TFA (2.12 g, 1.43 ml, 18.6 mmol, Eq: 10). The reaction mixture stirred under nitrogen for 18 h. Concentrated in vacuo to give 6-chloro-2-methyl-4-(5-(piperidin-4-yl)pyridin-2-ylamino)pyridazin-3(2H)-one (474 mg, 80%). LC/MS-ESI observed $[M+H]^+$ 320.

Step 5

To a solution of 6-chloro-2-methyl-4-(5-(piperidin-4-yl)pyridin-2-ylamino)pyridazin-3(2H)-one (200 mg, 625 µmol, Eq: 1.00) and acetone (799 mg, 1.01 ml, 13.8 mmol, Eq: 22) in MeOH (5 ml) was added sodium cyanoborohydride (39.3 mg, 625 µmol, Eq: 1.00) and acetic acid (656 mg, 625 µl, 10.9 mmol, Eq: 17.5). The reaction mixture stirred under $N_2$ for 18 h. Additional acetone (1 ml) was added, followed by THF (3 ml). The reaction mixture continued stirring under $N_2$ for 2 h. Additional sodium cyanoborohydride (19.7 mg, 313 µmol, Eq: 0.50) was added. The mixture stirred for 4 h. Concentrated in vacuo. The crude material was purified by flash chromatography (silica gel, 12 g, 50% to 100% (60:10:1 DCM:MeOH:$NH_4OH$)/DCM gradient) to give 6-chloro-4-(5-(1-isopropylpiperidin-4-yl)pyridin-2-ylamino)-2-methylpyridazin-3(2H)-one (220 mg, 97%). LC/MS-ESI observed $[M+H]^+$ 362.

Step 6

In a 50 mL test tube, 6-chloro-4-(5-(1-isopropylpiperidin-4-yl)pyridin-2-ylamino)-2-methylpyridazin-3(2H)-one (220 mg, 608 µmol, Eq: 1.00) and 1703-100 (288 mg, 608 µmol, Eq: 1.00) were combined with BuOH (12.9 ml). Water (3.24 ml) was added. X-PHOS (29.0 mg, 60.8 µmol, Eq: 0.1) and potassium phosphate tribasic (258 mg, 1.22 mmol, Eq: 2) were added. Bis(dibenzylideneacetone)palladium (17.5 mg, 30.4 µmol, Eq: 0.05) was added. The solution was purged with argon. The reaction warmed in an oil bath at 100° C. for 18 hours. The solution was cooled to room temperature. The reaction mixture was poured into 75 mL $H_2O$ and extracted twice with EtOAc. The organic layers were washed with brine, and then dried over $MgSO_4$. Concentrated in vacuo. The crude material was purified by flash chromatography (silica gel, 12 g, 50% to 100% (60:10:1 DCM:MeOH:NH$_4$OH)/DCM gradient) to give 2-(6-tert-butyl-8-fluoro-1-oxophthalazin-2(1H)-yl)-6-(5-(5-(1-isopropylpiperidin-4-yl)pyridin-2-ylamino)-1-methyl-6-oxo-1,6-dihydropyridazin-3-yl)benzyl acetate (248 mg, 59%). LC/MS-ESI observed [M+H]$^+$ 694.

Step 7

To a solution of 2-(6-tert-butyl-8-fluoro-1-oxophthalazin-2(1H)-yl)-6-(5-(5-(1-isopropylpiperidin-4-yl)pyridin-2-ylamino)-1-methyl-6-oxo-1,6-dihydropyridazin-3-yl)benzyl acetate (248 mg, 357 µmol, Eq: 1.00) in THF (5.0 ml) was added NaOH (4.29 ml, 4.29 mmol, Eq: 12.0). The reaction mixture heated at 60° C. for 18 h. The solution was cooled to room temperature, and then diluted with saturated NaHCO$_3$ and DCM. The layers were separated. The aqueous layer was extracted three times with DCM. The organic layers were combined, and then dried over Na$_2$SO$_4$. Concentrated in vacuo. The solid was triturated with Et$_2$O and dried under vacuum to give 6-tert-butyl-8-fluoro-2-{2-hydroxymethyl-3-[5-(1'-isopropyl-1',2',3',4',5',6'-hexahydro-[3,4']bipyridinyl-6-ylamino)-1-methyl-6-oxo-1,6-dihydro-pyridazin-3-yl]-phenyl}-2H-phthalazin-1-one (202 mg, 87%). LC/MS-ESI observed [M+H]$^+$ 652. $^1$H NMR (300 MHz, CHLOROFORM-d) δ ppm 1.10 (d, J=6.42 Hz, 6H) 1.43 (s, 9H) 1.84 (br. m., 5H) 2.28 (br. m., 2H) 2.50 (br. m., 1H) 2.79 (br. s., 1H) 3.03 (d, J=10.20 Hz, 2H) 3.90 (s, 4H) 4.42 (d, J=6.80 Hz, 2H) 6.92 (s, 1H) 7.40-7.73 (m, 6H) 8.17-8.32 (m, 4H) 8.60 (s, 2H)

Preparation of I-30

Preparation of Potassium (2-(acetoxymethyl)-3-(6-tert-butyl-8-fluoro-1-oxophthalazin-2(1H)-yl)phenyl)trifluoroborate

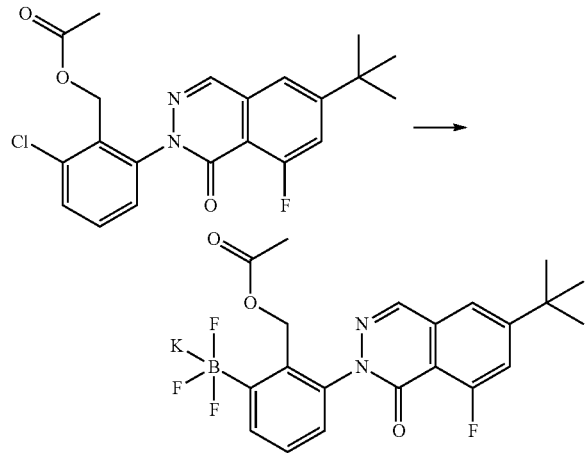

A round-bottomed flask equipped with a bubbler, a thermometer, and a magnetic stirrer was charged with 2-(6-tert-butyl-8-fluoro-1-oxophthalazin-2(1H)-yl)-6-chlorobenzyl acetate (10 g, 24.8 mmol, Eq: 1.00), 4,4,4',4',5,5,5',5'-octamethyl-2,2'-bi(1,3,2-dioxaborolane) (9.46 g, 37.2 mmol, Eq: 1.5), Pd(OAc)2 (69.7 mg, 310 µmol, Eq: 0.0125), X-PHOS (296 mg, 621 µmol, Eq: 0.025), and potassium acetate (5.29 g, 53.9 mmol, Eq: 2.17). Reaction mixture was degassed (3 times). Added MeTHF, then again degassed (3 times). Mixture was heated at 60° C. over night. Reaction was not finished. Reaction temperature was increased to 65° C. and stirred for 3 hours. HPLC showed that the reaction was completed. The reaction was cooled and 2 N HCl (31.0 ml, 62.1 mmol, Eq: 2.5) was added. The mixture was stirred for half an hour, then was passed through a celite plug to remove a black material. The layers were separated. The organic layer was washed with water (60.0 g, 60.0 ml) and then concentrated to a heavy oil. The oil was dissolved in MeOH (79.2 g, 100 ml) and treated with potassium hydrogen fluoride, 3M solution (20.7 ml, 62.1 mmol, Eq: 2.5). LC showed reaction was not finished over night. Another 0.5 equivalent of KHF2 was added. The resultant slurry was warmed at 45° C. for 3 hours. The mixture was stirred over night at room temperature. Product was isolated by filtration. Cake was washed with methanol.

After drying by vacuum, potassium (2-(acetoxymethyl)-3-(6-tert-butyl-8-fluoro-1-oxophthalazin-2(1H)-yl)phenyl)trifluoroborate (11.26 g, 23.7 mmol, 95.6% yield) was obtained.

Example 30

Preparation of 6-tert-Butyl-2-{3-[5-(1'-ethyl-1',2',3',4',5',6'-hexahydro-[3,4']bipyridinyl-6-ylamino)-1-methyl-6-oxo-1,6-dihydro-pyridazin-3-yl]-2-hydroxymethyl-phenyl}-8-fluoro-2H-phthalazin-1-one

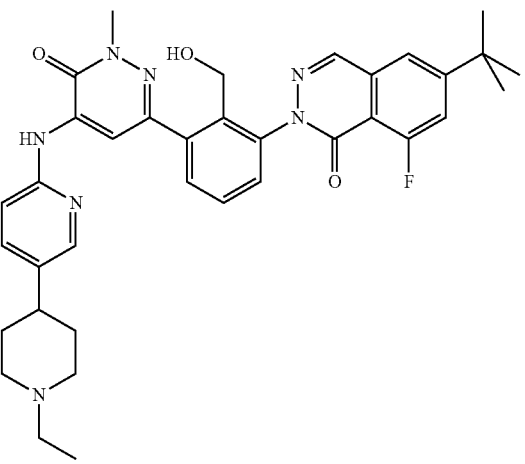 [SMILES: CCN1CCC(c2ccc(Nc3cc(-c4cccc(-n5ncc6cc(C(C)(C)C)cc(F)c6c5=O)c4CO)nn(C)c3=O)nc2)CC1]

Step 1

In a 100 mL round-bottomed flask, 6-chloro-2-methyl-4-(5-(piperidin-4-yl)pyridin-2-ylamino)pyridazin-3(2H)-one (179 mg, 560 µmol, Eq: 1.00) and acetaldehyde (247 mg, 316 µl, 5.6 mmol, Eq: 10.0) were combined with THF (5.0 ml) to give a light yellow solution. Acetic acid (33.6 mg, 32.0 µl, 560 µmol, Eq: 1.00) was added. The reaction mixture was cooled to 0° C. Sodium triacetoxyborohydride (178 mg, 840 µmol, Eq: 1.5) was added. The reaction mixture stirred at room temperature for 2 h. The reaction was poured into water, and then saturated NaHCO$_3$ was added to the solution until it was basic. The solution was extracted twice with EtOAc, and then the organic layers were washed with brine, dried over Na$_2$SO$_4$ and concentrated in vacuo to give a solid. The solid was triturated with ether to give 6-chloro-4-(5-(1-ethylpiperidin-4-yl)pyridin-2-ylamino)-2-methylpyridazin-3(2H)-one (121 mg, 62%). LC/MS-ESI observed [M+H]$^+$ 348.

Step 2

In a 50 mL test tube, 6-chloro-4-(5-(1-ethylpiperidin-4-yl)pyridin-2-ylamino)-2-methylpyridazin-3(2H)-one (121 mg, 348 µmol, Eq: 1.00) and potassium (2-(acetoxymethyl)-3-(6-tert-butyl-8-fluoro-1-oxophthalazin-2(1H)-yl)phenyl)trifluoroborate (165 mg, 348 µmol, Eq: 1.00) were combined with BuOH (4 ml) to give a orange solution. Water (1.00 ml) was added. X-PHOS (16.6 mg, 34.8 µmol, Eq: 0.1) and potassium phosphate tribasic (148 mg, 696 µmol, Eq: 2) were added. Bis(dibenzylideneacetone)palladium (10.0 mg, 17.4 µmol, Eq: 0.05) was added. The reaction mixture was purged with argon. The mixture was heated in an oil bath at 100° C. for 1.5 hours, then cooled to room temperature. The reaction mixture was poured into 75 mL $H_2O$ and extracted with twice with EtOAc. The organic layers were combined and dried over $Na_2SO_4$. Concentrated in vacuo. The crude material was purified by flash chromatography (silica gel, 12 g, 50% to 100% (60:10:1 DCM:MeOH:$NH_4OH$)/DCM gradient) to give a solid. The solid was triturated with $Et_2O$ to give 2-(6-tert-butyl-8-fluoro-1-oxophthalazin-2(1H)-yl)-6-(5-(5-(1-ethylpiperidin-4-yl)pyridin-2-ylamino)-1-methyl-6-oxo-1,6-dihydropyridazin-3-yl)benzyl acetate (147 mg, 62%). LC/MS-ESI observed $[M+H]^+$ 680.

Step 3

To 2-(6-tert-butyl-8-fluoro-1-oxophthalazin-2(1H)-yl)-6-(5-(5-(1-ethylpiperidin-4-yl)pyridin-2-ylamino)-1-methyl-6-oxo-1,6-dihydropyridazin-3-yl)benzyl acetate (147 mg, 216 µmol, Eq: 1.00) in MeOH (15 ml) was added potassium carbonate (59.8 mg, 432 µmol, Eq: 2.0). The reaction mixture stirred at 40° C. for 1 h. The solution was cooled to room temperature. Concentrated in vacuo. The residue was taken up in DCM/water and the layers were separated. The aqueous layer was extracted once with DCM. The organic layers were combined, and then dried over $Na_2SO_4$. Concentrated in vacuo. The crude material was purified by flash chromatography (silica gel, 12 g, 25% to 75% (60:10:1 DCM:MeOH:$NH_4OH$)/DCM gradient) to give 6-tert-butyl-2-{3-[5-(1'-ethyl-1',2',3',4',5',6'-hexahydro-[3,4']bipyridinyl-6-ylamino)-1-methyl-6-oxo-1,6-dihydropyridazin-3-yl]-2-hydroxymethyl-phenyl}-8-fluoro-2H-phthalazin-1-one (108 mg, 78%). LC/MS-ESI observed $[M+H]^+$ 638. $^1$H NMR (300 MHz, CHLOROFORM-d) δ ppm 1.16 (br. s., 2H) 1.43 (s, 9H) 1.84 (br. s., 4H) 2.06 (br. s., 2H) 2.51 (br. s., 3H) 3.11 (br. s., 2H) 3.69-4.09 (m and overlapping singlet, 4H) 4.42 (d, J=6.80 Hz, 2H) 6.91 (d, J=8.69 Hz, 1H) 7.37-7.77 (m, 6H) 8.11-8.36 (m, 3H) 8.60 (s, 1H)

Preparation of I-31

Example 31

6-tert-Butyl-2-{3-[5-(1,5-dimethyl-1H-pyrazol-3-ylamino)-1-methyl-6-oxo-1,6-dihydro-pyridazin-3-yl]-2-hydroxymethyl-phenyl}-8-fluoro-2H-phthalazin-1-one Step 1

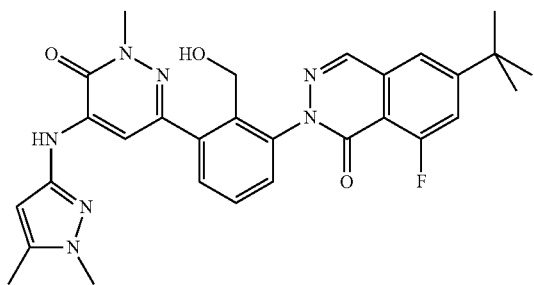 [SMILES: Cc1cc(Nc2cc(-c3cccc(-n4ncc5cc(C(C)(C)C)cc(F)c5c4=O)c3CO)nn(C)c2=O)nn1C]

1,5-Dimethyl-1H-pyrazol-3-amine (400 mg, 3.6 mmol, Eq: 1.00) and 4-bromo-6-chloro-2-methylpyridazin-3(2H)-one (965 mg, 4.32 mmol, Eq: 1.20) were combined with 4,5-bis(diphenylphosphino)-9,9-dimethylxanthene (312 mg, 540 µmol, Eq: 0.15), cesium carbonate (3.52 g, 10.8 mmol, Eq: 3) and tris(dibenzylideneacetone)dipalladium(0) (165 mg, 180 µmol, Eq: 0.05) in dioxane (10.0 ml). The solution was degassed with Ar. The reaction mixture heated at 100° C. for 18 h. The mixture was cooled to room temperature. The solution was diluted with 100 ml DCM. The organic layer was washed with water. The organic layer was dried over $MgSO_4$. Concentrated in vacuo. The crude material was purified by flash chromatography (silica gel, 40 g, 10% to 50% (60:10:1 DCM:MeOH:$NH_4OH$)/DCM gradient) to give 6-chloro-4-(1,5-dimethyl-1H-pyrazol-3-ylamino)-2-methylpyridazin-3(2H)-one (408 mg, 45%). LC/MS-ESI observed $[M+H]^+$ 235.

Step 2

In a 50 mL test tube, 6-chloro-4-(1,5-dimethyl-1H-pyrazol-3-ylamino)-2-methylpyridazin-3(2H)-one (100 mg, 394 µmol, Eq: 1.00) and potassium (2-(acetoxymethyl)-3-(6-tert-butyl-8-fluoro-1-oxophthalazin-2(1H)-yl)phenyl)trifluoroborate (224 mg, 473 µmol, Eq: 1.2) were combined with BuOH (4.00 ml) to give a orange solution. Water (1.00 ml) was added. X-PHOS (18.8 mg, 39.4 µmol, Eq: 0.1) and potassium phosphate tribasic (167 mg, 788 µmol, Eq: 2) were added. Bis(dibenzylideneacetone)palladium (11.3 mg, 19.7 µmol, Eq: 0.05) was added. The reaction mixture was purged with argon. The solution warmed in an oil bath at 100° C. for 1.5 hours. The solution was allowed to cool to room temperature. The reaction mixture was poured into 75 mL $H_2O$ and extracted with DCM. The organic layer was concentrated in vacuo. The crude material was purified by flash chromatography (silica gel, 25 g, 0% to 30% (60:10:1 DCM:MeOH:$NH_4OH$)/DCM gradient) to give a solid. The solid was triturated with $Et_2O$ to give 2-(6-tert-butyl-8-fluoro-1-oxophthalazin-2(1H)-yl)-6-(5-(1,5-dimethyl-1H-pyrazol-3-ylamino)-1-methyl-6-oxo-1,6-dihydropyridazin-3-yl)benzyl acetate (186 mg, 81%). LC/MS-ESI observed $[M+H]^+$ 586.

Step 3

To 2-(6-tert-butyl-8-fluoro-1-oxophthalazin-2(1H)-yl)-6-(5-(1,5-dimethyl-1H-pyrazol-3-ylamino)-1-methyl-6-oxo-1,6-dihydropyridazin-3-yl)benzyl acetate (186 mg, 318 µmol, Eq: 1.00) in MeOH (15.0 ml) was added potassium carbonate (87.8 mg, 635 µmol, Eq: 2.0). The reaction mixture stirred at 40° C. for 2 h. The solution was cooled to room temperature. Concentrated in vacuo. The residue was taken up in DCM/water. The layers were separated. The aqueous layer was extracted once with DCM. The organic layers were combined, and then dried over $Na_2SO_4$. Concentrated in vacuo. The crude material was purified by flash chromatography (silica gel, 12 g, 0% to 35% (60:10:1 DCM:MeOH:$NH_4OH$)/DCM gradient) to give 6-tert-butyl-2-{3-[5-(1,5-dimethyl-1H-pyrazol-3-ylamino)-1-methyl-6-oxo-1,6-dihydro-pyridazin-3-yl]-2-hydroxymethyl-phenyl}-8-fluoro-2H-phthalazin-1-one (75 mg, 44%). LC/MS-ESI observed $[M+H]^+$ 544. $^1$H NMR (300 MHz, CHLOROFORM-d) δ ppm 1.43 (s, 9H) 2.28 (s, 3H) 3.75 (s, 3H) 3.88 (s, 3H) 4.40 (s, 2H) 5.92 (s, 1H) 7.41-7.60 (m, 4H) 7.62-7.69 (m, 1H) 7.78 (s, 1H) 7.96 (s, 1H) 8.29 (d, J=2.64 Hz, 1H)

Preparation of I-32

Example 32

6-tert-Butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one

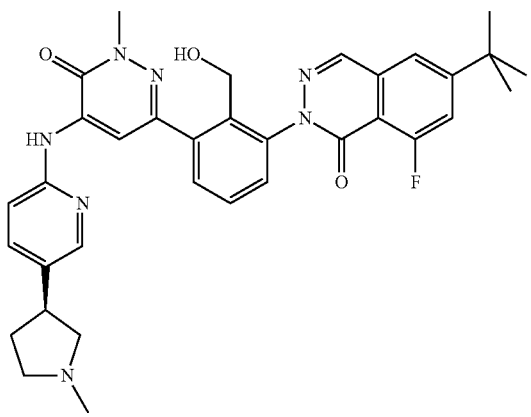 [SMILES: CN1CC[C@@H](c2ccc(Nc3cc(-c4cccc(-n5ncc6cc(C(C)(C)C)cc(F)c6c5=O)c4CO)nn(C)c3=O)nc2)C1]

Step 1

In a 500 mL three-necked flask, a solution of tert-butyl 3-oxopyrrolidine-1-carboxylate (4.5 g, 23.6 mmol, Eq: 1.00) in with THF (180 ml) was treated with lithium bis(trimethylsilyl)amide 1M in THF (25.2 ml, 25.2 mmol, Eq: 1.07) at −78° C. After stirring 15 min at −78° C., a solution of N-phenylbis(trifluoromethanesulfonimide) (10.2 g, 28.3 mmol, Eq: 1.20) in THF (60.0 ml) was added. The reaction mixture was then warmed to room temperature. The reaction was quenched with the addition of saturated aqueous NaHCO$_3$, and then extracted with ethyl ether. The organic layer was washed with brine, dried over MgSO$_4$, filtered and concentrated in vacuo. The crude material was purified by flash chromatography (silica gel, 300 g, 0% to 30% EtOAc in hexanes gradient) to give 3-trifluoromethanesulfonyloxy-2,5-dihydro-pyrrole-1-carboxylic acid tert-butyl ester (2.3 g, 31%).

Step 2

In a 250 mL round-bottomed flask, 3-trifluoromethanesulfonyloxy-2,5-dihydro-pyrrole-1-carboxylic acid tert-butyl ester (2.3 g, 7.25 mmol, Eq: 1.00) was combined with THF (60 ml) to give a colorless solution. The solution was purged with argon for 10 min. Potassium carbonate (5.06 g, 36.2 mmol, Eq: 5.0), 5-(4,4,5,5-tetramethyl-1,3,2-dioxaborolan-2-yl)pyridin-2-amine (1.91 g, 8.7 mmol, Eq: 1.20), tetrakis(triphenylphosphine)palladium(0) (83.8 mg, 72.5 µmol, Eq: 0.01) and water (1.2 ml) were added. The reaction mixture was heated to 70° C. and stirred for 16 h. The reaction mixture was poured into saturated NaHCO$_3$ and extracted twice with Et$_2$O. The organic layer was washed with brine, dried over Na$_2$SO$_4$ and concentrated in vacuo. The crude material was purified by flash chromatography (silica gel, 60 g, 50% (60:10:1 DCM:MeOH:NH$_4$OH)/DCM) to give tert-butyl 3-(6-aminopyridin-3-yl)-2,5-dihydro-1H-pyrrole-1-carboxylate (1.03 g, 54%). LC/MS-ESI observed [M+H]$^+$ 262.

Step 3 tert-Butyl 3-(6-aminopyridin-3-yl)-2,5-dihydro-1H-pyrrole-1-carboxylate (1.5 g, 5.74 mmol, Eq: 1.00) was dissolved in MeOH (60 ml). The solution was purged with argon and then treated with palladium on activated carbon (Degussa) (6.11 mg, 57.4 µmol, Eq: 0.01). The suspension was purged with hydrogen and stirred under a hydrogen atmosphere for 48 h. The reaction mixture was filtered through a 45 µm frit. The filtrate was concentrated in vacuo to give tert-butyl 3-(6-aminopyridin-3-yl)pyrrolidine-1-carboxylate (1.63 g) The enantiomers were separated using chiral SFC HPLC.

Prep Conditions
  Prep Column: DAICEL AD 2×25 Oven Temp: 40° C.
  Modifier: MeOH Modifier %: 15
  Flow rate: 70 mL Compound weight: 1610 mg
  Solubility: Good in MeOH Solubility: 40 mg/mL
  Amount of Injection: 10 mg Volume of Injection: 0.3 mL
  Wavelength: 220 nM Method of Collection: Forced Time Window
  Cycle Time: 6 min Number of Runs: 161

The (S)-3-(6-Amino-pyridin-3-yl)-pyrrolidine-1-carboxylic acid tert-butyl ester (307 mg, 20%) and (R)-3-(6-Amino-pyridin-3-yl)-pyrrolidine-1-carboxylic acid tert-butyl ester (399 mg, 26%) enantiomers were obtained. LC/MS-ESI observed [M+H]$^+$ 264 for both enantiomers.

Step 4

(S)-tert-Butyl 3-(6-aminopyridin-3-yl)pyrrolidine-1-carboxylate (307 mg, 1.17 mmol, Eq: 1.00) and 4-bromo-6-chloro-2-methylpyridazin-3(2H)-one (313 mg, 1.4 mmol, Eq: 1.20) were combined with 4,5-bis(diphenylphosphino)-9,9-dimethylxanthene (101 mg, 175 µmol, eq: 0.15), cesium carbonate (1.14 g, 3.5 mmol, eq: 3) and tris(dibenzylideneacetone)dipalladium(0) (53.4 mg, 58.3 µmol, Eq: 0.05) in dioxane (8.0 ml). The solution was degassed with Ar. The reaction mixture heated at 100° C. for 18 h. The solution was cooled to room temperature and diluted with 100 ml DCM. The organic layer was washed with water, and then dried over MgSO$_4$. Concentrated in vacuo. The crude material was purified by flash chromatography (silica gel, 24 g, 50% to 100% EtOAc/Hex gradient) to give (S)-tert-butyl 3-(6-(6-chloro-2-methyl-3-oxo-2,3-dihydropyridazin-4-ylamino)pyridin-3-yl)pyrrolidine-1-carboxylate (456 mg, 96%). LC/MS-ESI observed [M+H]$^+$ 405.

Step 5

(S)-tert-Butyl 3-(6-(6-chloro-2-methyl-3-oxo-2,3-dihydropyridazin-4-ylamino)pyridin-3-yl)pyrrolidine-1-carboxylate (456 mg, 1.12 mmol, Eq: 1.00) was dissolved in a mix of formic acid (20.0 ml) and formaldehyde, 37% (40 ml). The reaction mixture stirred at 70° C. for 18 h. The solution was cooled to room temperature and water was added. The aqueous solution was extracted once with DCM. The aqueous layer was Brought to pH=14 with solid $K_2CO_3$. A solid formed and was filtered to give (S)-6-chloro-2-methyl-4-(5-(1-methylpyrrolidin-3-yl)pyridin-2-ylamino)pyridazin-3(2H)-one (408 mg, quantitative yield). LC/MS-ESI observed [M+H]$^+$ 320.

Step 6

In a 50 mL test tube, (S)-6-chloro-2-methyl-4-(5-(1-methylpyrrolidin-3-yl)pyridin-2-ylamino)pyridazin-3(2H)-one (100 mg, 313 µmol, Eq: 1.00) and potassium (2-(acetoxymethyl)-3-(6-tert-butyl-8-fluoro-1-oxophthalazin-2(1H)-yl)phenyl)trifluoroborate (163 mg, 344 µmol, Eq: 1.1) were combined with BuOH (4.0 ml) to give a orange solution. Water (1.0 ml) was added. X-PHOS (14.9 mg, 31.3 µmol, Eq: 0.10) and potassium phosphate tribasic (133 mg, 625 µmol, eq: 2.0) were added. Bis(dibenzylideneacetone)palladium (8.99 mg, 15.6 µmol, eq: 0.05) was added. The reaction mixture was purged with argon, then heated in an oil bath at 100° C. for 18 hours. The reaction mixture was cooled to room temperature, then poured into 75 mL $H_2O$ and extracted with EtOAc. The organic layer was washed with brine and then dried over $MgSO_4$. Concentrated in vacuo. The crude material was purified by flash chromatography (silica gel, 12 g, 50% to 100% (60:10:1 DCM:MeOH:NH$_4$OH)/DCM) gradient) to give a mixture of (S)-2-(6-tert-butyl-8-fluoro-1-oxophthalazin-2(1H)-yl)-6-(1-methyl-5-(5-(1-methylpyrrolidin-3-yl)pyridin-2-ylamino)-6-oxo-1,6-dihydropyridazin-3-yl)benzyl acetate and 6-tert-butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one (105 mg total, 52% overall). LC/MS-ESI observed [M+H]$^+$ 652 and 610.

Step 7

To a mixture of (S)-2-(6-tert-butyl-8-fluoro-1-oxophthalazin-2(1H)-yl)-6-(1-methyl-5-(5-(1-methylpyrrolidin-3-yl)pyridin-2-ylamino)-6-oxo-1,6-dihydropyridazin-3-yl)benzyl acetate and 6-tert-butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one (105 mg, 161 µmol, Eq: 1.00) in MeOH (10 ml) was added potassium carbonate (44.5 mg, 322 µmol, Eq: 2.0). The reaction mixture stirred at 40° C. for 1.5 h. The mixture was cooled to room temperature and diluted with DCM/water. The layers were separated. The aqueous layer was extracted once with DCM. The organic layers were combined and dried over $Na_2SO_4$. Concentrated in vacuo. The resulting solid was triturated with $Et_2O$ to give 6-tert-butyl-8-fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-2H-phthalazin-1-one (80 mg, 81%). LC/MS-ESI observed [M+H]$^+$ 610. 1H NMR in CDCl$_3$ is consistent with desired product.

Preparation of I-33

Example 33

6-tert-Butyl-8-fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one

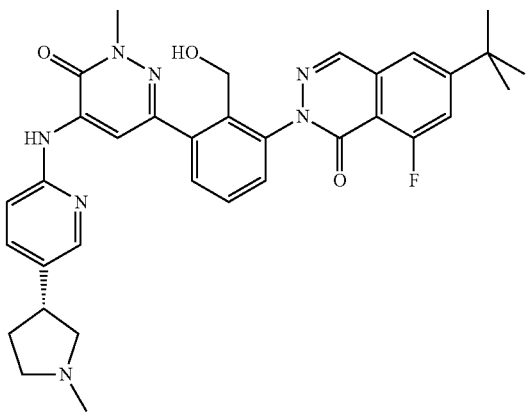 [SMILES: CN1CC[C@H](c2ccc(Nc3cc(-c4cccc(-n5ncc6cc(C(C)(C)C)cc(F)c6c5=O)c4CO)nn(C)c3=O)nc2)C1]

Step 1

This reaction was carried out under similar conditions to those described above in step 4 of the preparation of Example 32. (R)-tert-butyl 3-(6-(6-chloro-2-methyl-3-oxo-2,3-dihydropyridazin-4-ylamino)pyridin-3-yl)pyrrolidine-1-carboxylate (555 mg, 90%). LC/MS-ESI observed [M+H]$^+$ 405.

Step 2

This reaction was carried out under similar conditions to those described above in step 5 of the preparation of Example 32. (R)-6-chloro-2-methyl-4-(5-(1-methylpyrrolidin-3-yl)pyridin-2-ylamino)pyridazin-3(2H)-one (807 mg, quantitative). LC/MS-ESI observed [M+H]$^+$ 320.

Step 3

This reaction was carried out under similar conditions to those described above in step 6 of the preparation of Example 32 resulting in a mixture of (R)-2-(6-tert-butyl-8-fluoro-1-oxophthalazin-2(1H)-yl)-6-(1-methyl-5-(5-(1-methylpyrrolidin-3-yl)pyridin-2-ylamino)-6-oxo-1,6-dihydropyridazin-3-yl)benzyl acetate and 6-tert-butyl-8-fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-2H-phthalazin-1-one (135 mg total, 66% overall). LC/MS-ESI observed [M+H]$^+$ 652 and 610.

Step 4

This reaction was carried out under similar conditions to those described above in step 7 of the preparation of Example 32. 6-tert-Butyl-8-fluoro-2-(2-hydroxymethyl-3-{1-methyl-5-[5-((R)-1-methyl-pyrrolidin-3-yl)-pyridin-2-ylamino]-6- oxo-1,6-dihydro-pyridazin-3-yl}-phenyl)-2H-phthalazin-1-one (124 mg, 98%). LC/MS-ESI observed [M+H]+ 610. ¹H NMR in CDCl₃ is consistent with desired product.

Preparation of I-34

Step 1. Preparation of 4-Methyl-5'-nitro-3,4,5,6-tetrahydro-2H-[1,2']bipyrazinyl

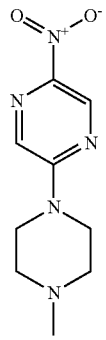

In a 15 mL argon dried microwave reaction vial, was added bromonitropyrazine (300 mg, 1.47 mmoL, Eq: 1.00) and K₂CO₃ (264 mg, 1.91 mmoL, Eq: 1.3) under argon to give a light yellow slurry. N-methylpiperazine (192 mg, 212 µl, 1.91 mmol, Eq: 1.3) was added dropwise and the reaction mixture became an orange yellow thick slurry. Heated to 70° C. in an oil bath for 1.5 hrs then stirred at room temperature overnight. The reaction mixture was diluted with dioxane (10 mL), filtered through a fitted funnel and washed with DCM (10 mL). The combined filtrate and washes were concentrated to dryness to give a yellow solid (328 mg, yield 89%) which was used directly in the next step.

Step 2. Preparation of 4-Methyl-3,4,5,6-tetrahydro-2H-[1,2]bipyrazinyl-5'-ylamine

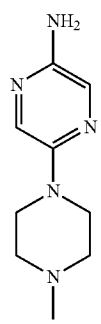

2-(4-methylpiperazin-1-yl)-5-nitropyrazine (328 mg, 1.47 mmol) was dissolved in MeOH (15 ml) at room temperature. Pd/C (10%) (50 mg) was added while the reaction mixture was stirred. The reaction mixture was placed under a H₂ balloon and stirred at rt for 1.5 hrs. The reaction mixture was filtered through celite and washed with MeOH (30 mL). The filtrate was stripped and dried under vacuum after azeotroping with toluene twice to give a light brown gummy material (280 mg, yield 89%).

Step 3. Preparation of 6-Chloro-2-methyl-4-(4-methyl-3,4,5,6-tetrahydro-2H-[1,2']bipyrazinyl-5'-ylamino)-2H-pyridazin-3-one

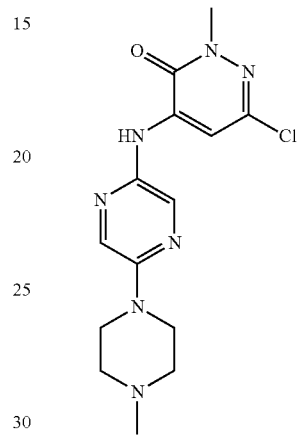

In a 15 mL microwave reaction vial (dried over heat and argon) was added a solution of aminopyrazine (280 mg, 1.45 mmol, Eq: 1.00 The reaction was sealed and heated in oil bath at 105° C. (bath temp) for 7 hrs then stirred at room temperature overnight. The reaction was filtered through a fritted funnel and washed with dioxane (20 mL). The combined filtrate and washes were concentrated to dryness. The residue was taken up in 10% MeOH in DCM and purified by prep TLC (9x) in 10% (10% NH₄OH in MeOH) in DCM. to afford 71 mg (15%) of a yellow solid.

Example 34

Step 4. Preparation of 6-tert-Butyl-8-fluoro-2-{2-hydroxymethyl-3-[1-methyl-5-(4-methyl-3,4,5,6-tetrahydro-2H-[1,2']bipyrazinyl-5'-ylamino)-6-oxo-1,6-dihydro-pyridazin-3-yl]-phenyl}-2H-phthalazin-1-one

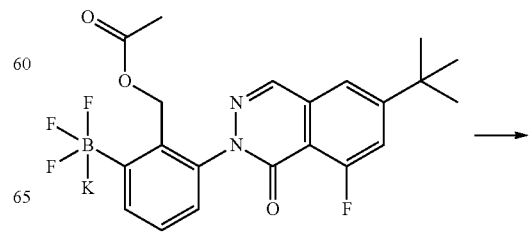

194

Preparation of I-35

Step 1. Preparation of (5-Cyclobutylaminomethyl-pyrazin-2-yl)-carbamic Acid Tert-butyl Ester

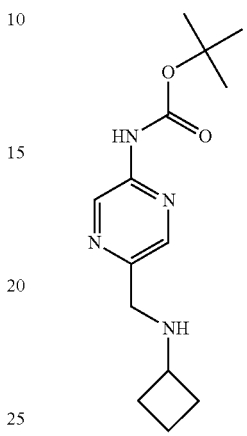

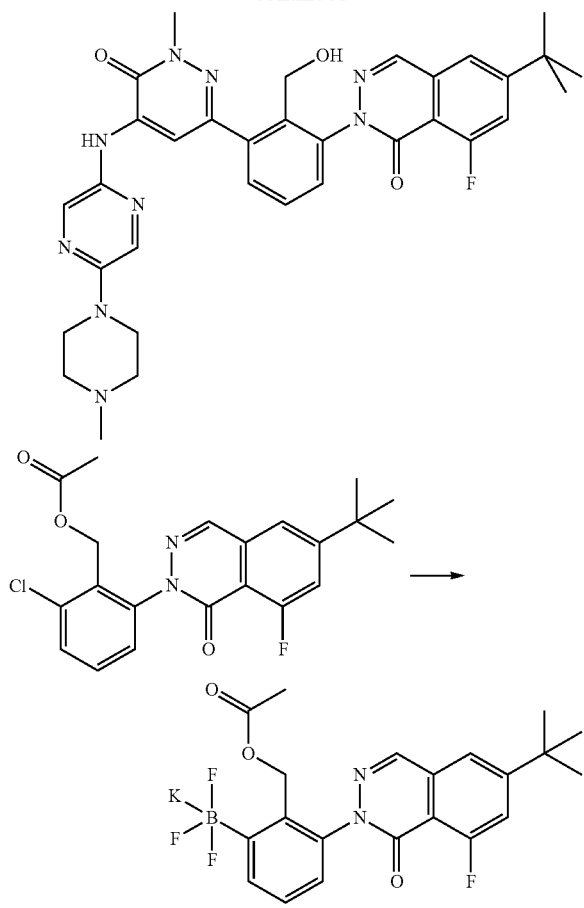

In a dried 100 mL round bottom flask was added cyclobutylamine (740 mg, 889 µl, 10.4 mmol, Eq: 3), K$_2$CO3 (480 mg, 3.47 mmol, Eq: 1.00) and THF at rt. under argon. To the mixture was added a solution of (5-Bromomethyl-pyrazin-2-yl)-carbamic acid tert-butyl ester (1 g, 3.47 mmol, Eq: 1.00) in THF dropwise. The resulting reaction mixture was stirred vigorously at room temperature under argon overnight. The reaction was concentrated, diluted with water/DCM and extracted with DCM (2×30 mL). Combined organic extracts were concentrated to give a solid. The crude product was purified by LC chromatography (50 g spherical silica column) eluting with 5 to 10% MeOH in 1/1 EtOAc/Hex to afford 348 mg (36%) of the title compound as a white solid.

Step 2. Preparation of 5-Cyclobutylaminomethyl-pyrazin-2-ylamine

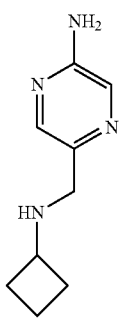 [SMILES: Nc1cnc(CNC2CCC2)cn1]

In a 15 mL microwave tube was dissolved tert-butyl 5-((cyclobutylamino)methyl)pyrazin-2-ylcarbamate (330 mg, 1.19 mmol, Eq: 1.00) in 2,2,2-trifluoroethanol (119 mg, 12 ml, 1.19 mmol, Eq: 1.00) and the resulting mixture was heated in seal tube at 150° C. for 3 hrs. The crude reaction mixture was concentrated in vacuo, treated with MeOH and re-concen-

193
-continued

To a 15 mL microwave reaction vial was added 6-chloro-2-methyl-4-(4-methyl-3,4,5,6-tetrahydro-2H-[1,2']bipyrazinyl-5'-ylamino)-2H-pyridazin-3-one (71 mg, 211 µmol, Eq: 1.00) in 7 mL n-butanol and 1.4 mL water. Argon was bubbled through the suspension. To the slurry was added potassium (2-(acetoxymethyl)-3-(6-tert-butyl-8-fluoro-1-oxophthalazin-2(1H)-yl)phenyl)trifluoroborate (149 mg, 211 µmol, Eq: 1.00), then X-PHOS (15.1 mg, 31.7 µmol, Eq: 0.15) with stirring. To this mixture was added bis(dibenzylideneacetone)palladium (9.12 mg, 15.9 µmol, Eq: 0.075). The tube was sealed and heated at 110° C. (bath temp) for 3 hrs then cooled to room temperature. A solution of NaOH (84 mg, 2.11 mmol, 10 eq) in water (1.5 mL) was added and the reaction was stirred for 3 days.

The layers were separated and the aqueous layer was extracted with EtOAc and combined with the previous organic layer. The combined extracts were concentrated to 4-5 mL. The crude material was purified by preparative TLC (11×) with 11% (10% NH$_4$OH in MeOH) in 1/1 (EtOAc/Heptane) to give 50 mg (36%) of a light yellow solid. Mp: 235-240° C. $^1$H NMR (300 MHz, CHLOROFORM-d) 1.43 (s, 9H), 2.36 (s, 3H), 2.51 (t, J=5.0 Hz, 4H), 3.50 (t, J=5.0 Hz, 4H), 3.90 (s, 3H), 3.95 (t, J=6.2 Hz, 1H), 4.40 (d, J=6.2 Hz, 2H), 7.43-7.65 (m, 5H), 7.88 (d, J=1.13 Hz, 1H), 8.03 (d, J=1.51 Hz, 1H), 8.15 (s, 1H), 8.25 (s, 1H), 8.30 (d, J=2.5, 1 H).

LCMS (ES): 626 (M+H), RT=1.94 min.

trated to remove residual trifluoroethanol. The material was azeotroped with toluene to afford 200 mg (95%) of the title compound.

Step 3. Preparation of 6-Chloro-4-(5-cyclobutylaminomethyl-pyrazin-2-ylamino)-2-methyl-2H-pyridazin-3-one

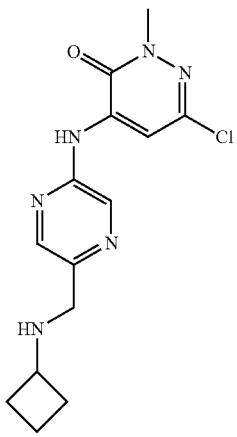 [SMILES: Cn1nc(Cl)cc(Nc2cnc(CNC3CCC3)cn2)c1=O]

In a 15 mL microwave reaction vial was added a solution of 5-((cyclobutylamino)methyl)pyrazin-2-amine (280 mg, 1.57 mmol, Eq: 1.00) in dioxane (7 ml) under argon bubbling. To the solution was added 4-bromo-6-chloro-2-methylpyridazin-3(2H)-one (456 mg, 2.04 mmol, Eq: 1.3), $Cs_2CO_3$ (1.3 g, 3.99 mmol, Eq: 2.54), xantphos (136 mg, 236 µmol, Eq: 0.15) and bis(dibenzylideneacetone)palladium (67.7 mg, 118 µmol, Eq: 0.075). The reaction tube was sealed and heated in oil bath at 105° C. (bath temp) for 7 hrs then stirred at room temperature overnight. The crude reaction mixture was filtered and the solid was washed with dioxane (20 mL) and DCM (5 mL). The combined filtrate and washes were concentrated and absorbed on silica gel. The mixture was purified by LC chromatography (silica gel, 60 g) and eluted with 0-10% (10% $NH_4OH$ in MeOH) in (1/1) EtOAc/Heptane to afford 197 mg (39%) of the title compound.

Example 35

Step 4. Preparation of 6-tert-Butyl-2-{3-[5-(5-cyclobutylaminomethyl-pyrazin-2-ylamino)-1-methyl-6-oxo-1,6-dihydro-pyridazin-3-yl]-2-hydroxymethyl-phenyl}-8-fluoro-2H-phthalazin-1-one

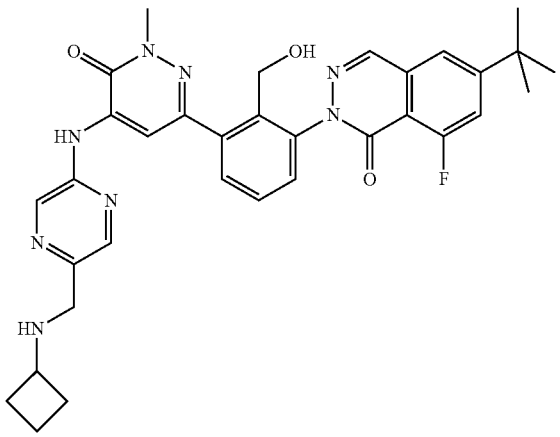 [SMILES: Cn1nc(-c2cccc(-n3ncc4cc(C(C)(C)C)cc(F)c4c3=O)c2CO)cc(Nc2cnc(CNC3CCC3)cn2)c1=O]

In a 15 mL microwave reaction vial was added 6-chloro-4-(5-cyclobutylaminomethyl-pyrazin-2-ylamino)-2-methyl-2H-pyridazin-3-one (71 mg, 221 µmol, Eq: 1.00) in 7 mL n-butanol and 1.4 mL water. Argon was bubbled through the reaction mixture. To the reaction was added acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (218 mg, 309 µmol, Eq: 1.39), potassium phosphate tribasic (103 mg, 487 µmol then X-PHOS (15.8 mg, 33.2 µmol, Eq: 0.15). The mixture was purged with argon and (dibenzylideneacetone)palladium (9.55 mg, 16.6 µmol, Eq: 0.075) was added. The tube was sealed and heated at 110° C. (bath temp) for 3 hrs. The reaction mixture was allowed to cool to room temperature, a solution of NaOH (189 mg) in water (1.5 mL) was added and the mixture was stirred in an oil bath at 37° C. for 3 hrs. The crude reaction mixture was diluted with water (10 mL) and extracted with dichloromethane (3×10 mL). The organic phase was concentrated and chromatographed on silica gel eluting with 5-10% (10% in $NH_4OH$ in MeOH) in (1/1) EtOAc/n-heptane to give a pure fraction (pale yellow) and mixed fractions (yellow). The pure fraction was concentrated and dissolved in DCM. Methanol was added to make a 10% solvent mixture of MeOH in DCM. Heptane was added which resulted in immediate precipitation of solid. The suspension was allowed to sit at room temperature overnight and the resultant solid was filtered, washed with n-heptane and dried to afford 35 mg (25%) of the title compound as an off-white solid. mp: 163-167° C.

$^1$H NMR (300 MHz, CHLOROFORM-d) 1.43 (s, 9H), 1.70-1.72 (m, 4H), 2.19-2.22 (m, 2H), 3.28-3.31 (m, 1H), 3.75 (t, J=6.2 Hz, 1H), 3.80 (s, 2H), 3.89 (s, 3H), 4.40 (d, J=6.2 Hz, 2H), 7.43-7.65 (m, 5H), 8.28 (d, J=1.13 Hz, 1H), 8.30 (d, J=2.5, 1 H), 8.36 (d, J=1.51 Hz, 1H), 8.40 (s, 1H), 8.60 (s, 1H). LCMS (ES): 611 (M+H), RT=2.511 min.

Preparation of I-36

Step 1. Preparation of Dimethyl-[2-(5-nitro-pyrazin-2-yloxy)-ethyl]-amine

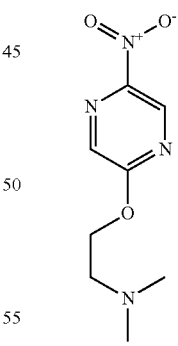

To a 100 ml dried round bottom flask was added bromonitropyrazine (300 mg, 1.47 mmol, Eq: 1.00) and $CH_3CN$ (10 ml). To the mixture was added $K_2CO_3$ (203 mg, 1.47 mmol, Eq: 1.00) under argon to afford a light yellow slurry. To the slurry was added NN-dimethylaminothanol (131 mg, 148 µl, 1.47 mmol, Eq: 1.00) dropwise. The reaction became an orange slurry and was stirred at room temperature overnight. The reaction mixture was filtered and the filter cake was washed with $CH_3CN$ (3×20 mL). The combined filtrate and washes were concentrated in vacuo and purified by column chromatography eluting with 5-10% (10% NH₄OH in MeOH) in 1/1 EtOAc/Hex eluent to afford 270 mg (87%) of the title compound.

Step 2. Preparation of
5-(2-Dimethylamino-ethoxy)-pyrazin-2-ylamine

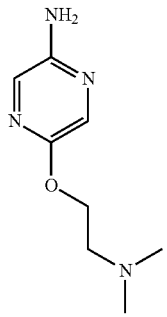

In a 500 mL round bottomed flask containing N,N-dimethyl-2-(5-nitropyrazin-2-yloxy)ethanamine (270 mg, 1.27 mmol, Eq: 1.00) was added MeOH (20 ml) and 10% Pd/C (60 mg). The reaction was stirred under a hydrogen atmosphere for 2 hrs then stored at 0° C. for 3 days. The reaction mixture was filtered through celite and washed with MeOH. The filtrate was concentrated in vacuo to afford 209 mg, (90%) of the title compound as a gummy solid.

Step 3. Preparation of 6-Chloro-4-[5-(2-dimethylamino-ethoxy)-pyrazin-2-ylamino]-2-methyl 2H-pyridazin-3-one

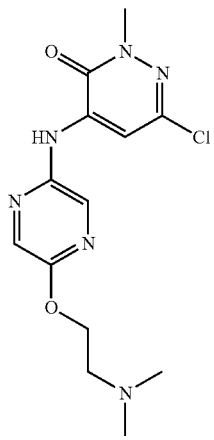 [SMILES: CN(C)CCOc1cnc(Nc2cc(Cl)nn(C)c2=O)cn1]

In a 15 mL microwave reaction vial was added a solution of 5-(2-(dimethylamino)ethoxy)pyrazin-2-amine (190 mg, 1.04 mmol, Eq: 1.00) in dioxane (7 ml) under argon. 4-bromo-6-chloro-2-methylpyridazin-3(2H)-one (303 mg, 1.36 mmol, Eq: 1.3), Cs₂CO₃ (1.02 g, 3.13 mmol, Eq: 3), xantphos (90.5 mg, 156 μmol, Eq: 0.15) and bis(dibenzylideneacetone)palladium (45.0 mg, 78.2 μmol, Eq: 0.075) were added and the reaction tube was heated in an oil bath at 105° C. (bath temp) for 7 hrs followed by stirring at room temperature overnight. The reaction mixture was filtered and the solid was washed with dioxane (20 mL) and DCM (5 mL). The combined filtrate and washes was concentrated. The residue was purified by LC chromatography eluting with 0-10% (10% NH₄OH in MeOH) in (1/1) EtOAc/heptane to afford 339 mg (67%) of the title compound.

Example 36

Step 4. Preparation of 6-tert-Butyl-2-(3-{5-[5-(2-dimethylamino-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one

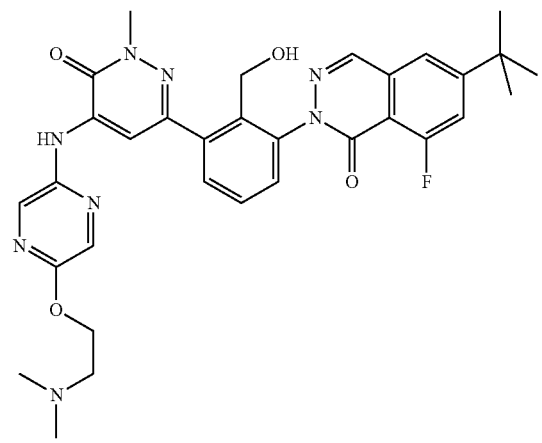 [SMILES: CN(C)CCOc1cnc(Nc2cc(-c3cccc(-n4ncc5cc(C(C)(C)C)cc(F)c5c4=O)c3CO)nn(C)c2=O)cn1]

In a 15 mL microwave reaction vial was added 6-chloro-4-[5-(2-dimethylamino-ethoxy)-pyrazin-2-ylamino]-2-methyl 2H-pyridazin-3-one (89 mg, 274 μmol, Eq: 1.00) in 7 mL n-butanol and 1.4 mL water. To the solution was added potassium phosphate tribasic (128 mg, 603 μmol), X-PHOS (19.6 mg, 41.1 μmol, Eq: 0.15) and acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester (279 mg, 395 μmol, Eq: 1.44) with stirring and bubbling of argon. To this mixture was added bis(dibenzylideneacetone)palladium (11.8 mg, 20.6 μmol, Eq: 0.075) and the reaction was heated at 110° C. for 3 hrs. The reaction was cooled to room temperature and treated with a solution of NaOH (220 mg) in water (1.5 mL). The resultant mixture was stirred at room temperature for 20 h. The reaction mixture was diluted with DCM (50 mL) and water (50 mL). The organic phase was separated, washed with water (30 mL) and concentrated. The residue was purified on silica gel with 0-10% (10% NH₄OH in MeOH) in (1/1) EtOAc/Hex. The pure fractions were concentrated and dissolved in DCM. Heptane was added to precipitate the product. The liquid was decanted off to afford 81 mg (46%) of the title compound as an off white solid. mp: 185-190° C.

¹H NMR (300 MHz, CHLOROFORM-d) 1.43 (s, 9H), 2.37 (s, 6H), 2.74 (t, J=5.5 Hz, 2H), 3.85 (t, J=6.2 Hz, 1H), 3.92 (s, 3H), 4.40 (m, 4H), 7.43-7.65 (m, 5H), 7.95 (d, J=1.13

Hz, 1H), 8.06 (d, J=1.51, 1 H), 8.26-8.35 (m, 3H). LCMS (ES): 615 (M+H), RT=1.925 min.

Example 37

Preparation of 6-tert-Butyl-8-fluoro-2-(2-hydroxymethyl-3-{1-methyl-5-[5-(4-methyl-piperazin-1-ylmethyl)-pyrazin-2-ylamino]-6-oxo-1,6-dihydro-pyridazin-3-yl}-phenyl)-2H-phthalazin-1-one

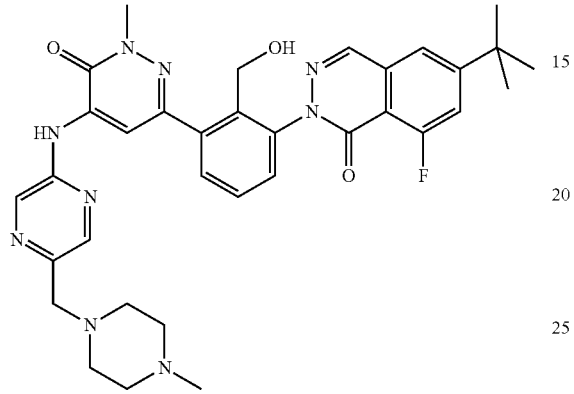

Preparation by a similar procedure to Example 35, except substituting methylpiperazine for cyclobutylamine in step 1, afforded 107 mg (53%) of the title compound as a white solid after LC chromatography and subsequent recrystallization from DCM/heptane. mp: 215-218° C. ¹H NMR (300 MHz, CHLOROFORM-d) 1.43 (s, 9H), 2.30 (s, 3H), 2.40-2.61 (m, 8H), 3.67 (s, 3H), 3.80 (t, J=6.2 Hz, 1H), 3.93 (s, 3H), 4.45 (d, J=6.2 Hz, 2H), 7.43-7.65 (m, 5H), 8.30 (d, J=2.5, 1 H), 8.33 (d, J=1.13 Hz, 1H), 8.36 (d, J=1.51 Hz, 1H), 8.43 (s, 1H), 8.65 (s, 1H). LCMS (ES): 640 (M+H), RT=2.104 min.

Example 38

Preparation of 6-tert-Butyl-2-(3-{5-[5-(2-dimethylamino-1,1-dimethyl-ethoxy)-pyrazin-2-ylamino]-1-methyl-6-oxo-1,6-dihydro-pyridazin-3-yl}-2-hydroxymethyl-phenyl)-8-fluoro-2H-phthalazin-1-one

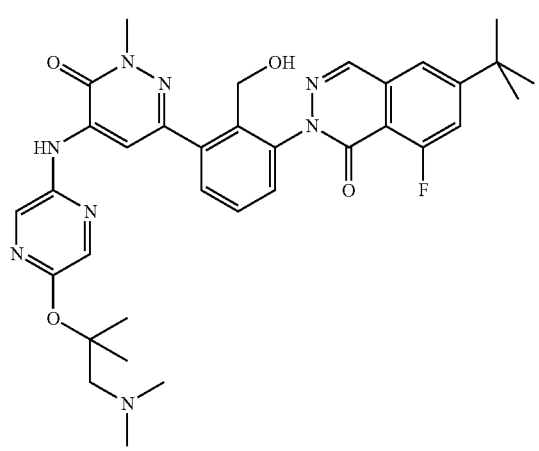 [SMILES: CN(C)CC(C)(C)Oc1cnc(Nc2cc(-c3cccc(-n4ncc5cc(C(C)(C)C)cc(F)c5c4=O)c3CO)nn(C)c2=O)cn1]

Preparation by a similar procedure to Example 36, except substituting 1-dimethylamino-2-methyl-propan-2-ol for NN-dimethylaminothanol in step 1, afforded 100 mg (50%) of the title compound. mp: 235-240° C. ¹H NMR (300 MHz, CHLOROFORM-d) 1.43 (s, 9H), 1.56 (s, 6H), 2.37 (s, 6H), 3.80 (t, J=6.2 Hz, 1H), 3.90 (s, 3H), 4.45 (d, J=6.2 Hz, 2H), 7.43-7.65 (m, 5H), 7.89 (d, J=1.13 Hz, 1H), 7.96 (d, J=1.51 Hz, 1H), 8.24 (s, 1H), 8.30 (d, J=2.5, 1 H), 8.35 (s, 1H). LCMS (ES): 643 (M+H), RT=2.516 min.

Preparation of I-39

Step 1. Preparation of [2-(6-Bromo-pyridazin-3-yloxy)-2-methyl-propyl]-dimethyl-amine

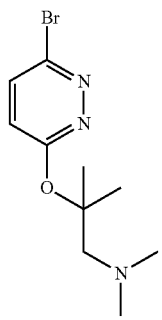

In a 100 mL round bottom flask was added 1-(dimethylamino)-2-methylpropan-2-ol (1.48 g, 12.6 mmol, Eq: 1.5), THF and 3,6-dibromopyridazine (2 g, 8.41 mmol, Eq: 1.00). The flask was cooled to 0° C. followed by addition of NaH (572 mg, 14.3 mmol, Eq: 1.7) in one portion. The turbid reaction mixture was allowed to warm to room temperature and was stirred at room temperature overnight. The resultant black reaction mixture was absorbed onto silica gel and purified by LC chromatography eluting with 0-5% MeOH in 1/1 EtOAc/Hex to afford 1.5 g (65%) of the title compound.

Step 2. Preparation of Benzhydrylidene-[6-(2-dimethylamino-1,1-dimethyl-ethoxy)-pyridazin-3-yl]-amine

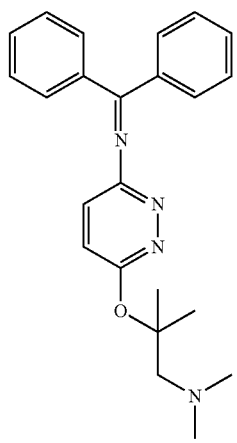 [SMILES: CN(C)CC(C)(C)Oc1ccc(N=C(c2ccccc2)c2ccccc2)nn1]

In a 15 ml microwave reaction vial was added 2-(6-bromopyridazin-3-yloxy)-N,N,2-trimethylpropan-1-amine (500 mg, 1.82 mmol, Eq: 1.00) and toluene (7 ml). Argon was bubbled through the mixture. To this mixture was added (R)-(+)-2,2'-bis(diphenylphosphino)-1,1'-binaphthyl (170 mg, 274 μmol, Eq: 0.15), Cs₂CO₃ (2.38 g, 7.3 mmol, Eq: 4) and Pd(OAc)₂ (30.7 mg, 137 μmol, Eq: 0.075). The reaction was heated at 120° C. in an oil bath for 7 hrs followed by stirring at room temperature overnight. The red solution was decanted away from the grey solid. The solid was washed with EtOAc and the combined organic phases were concentrated in vacuo. The residue was purified by LC chromatography eluting with 1/1 EtOAc/Hexane to afford 380 mg (56%) of the title compound as an orange oil.

Step 3. Preparation of 6-(2-Dimethylamino-1,1-dimethyl-ethoxy)-pyridazin-3-ylamine

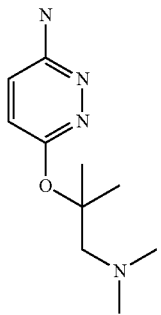

In a 10 mL pear shape flask was added 6-(1-(dimethylamino)-2-methylpropan-2-yloxy)-N-(diphenylmethylene)pyridazin-3-amine (200 mg, 534 μmol, Eq: 1.00) and MeOH (5.34 ml). To the mixture was added hydroxylamine hydrochloride (66.8 mg, 961 μmol, Eq: 1.8) and sodium acetate (105 mg, 1.28 mmol, Eq: 2.4). The mixture was stirred at room temperature for 25 min. The reaction mixture was absorbed on to silica and purified by LC chromatography eluting with 0-5% (10% NH₄OH in MeOH) in 1/1 EtOAc/Hexane to afford 110 mg (98%) of the title compound.

Step 4. Preparation of 6-Chloro-4-[6-(2-dimethylamino-1,1-dimethyl-ethoxy)-pyridazin-3-ylamino]-2-methyl-2H-pyridazin-3-one

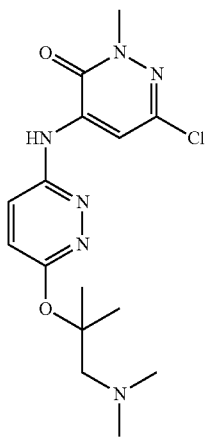 [SMILES: CN(C)CC(C)(C)Oc1ccc(Nc2cc(Cl)nn(C)c2=O)nn1]

In a 15 mL microwave reaction vial was added a solution of 6-(1-(dimethylamino)-2-methylpropan-2-yloxy)pyridazin-3-amine (110 mg, 523 μmol, Eq: 1.00) in dioxane (5 ml) under argon. To the solution was added 4-bromo-6-chloro-2-methylpyridazin-3(2H)-one (152 mg, 680 μmol, Eq: 1.3), Cs₂CO₃ (511 mg, 1.57 mmol, Eq: 3), xantphos (45.4 mg, 78.5 μmol, Eq: 0.15) and bis(dibenzylideneacetone)palladium (22.6 mg, 39.2 μmol, Eq: 0.075). The reaction tube was sealed and heated in oil bath at 110° C. (bath temp) for 7 hrs, then was cooled to room temperature and stirred overnight. The reaction mixture was filtered and the solid was washed with THF (20 mL). The combined filtrate and washes were concentrated in vacuo. The reaction mixture was absorbed on to silica and purified by LC chromatography eluting with 0-5% (MeOH) in 1/1 EtOAc/heptane to afford 130 mg (70%) of the title compound.

Example 39

Step 5. Preparation of 6-tert-Butyl-2-(3-{5-[6-(2-dimethylamino-1,1-dimethyl-ethoxy)-pyridazin-3-ylamino]-1-methyl-6-oxo-1,6-dihydro-pyridazin-3-yl}-2-hydroxymethyl-phenyl)-8-fluoro-2H-phthalazin-1-one

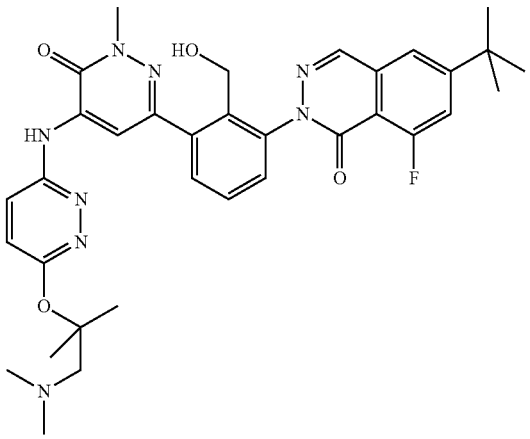 [SMILES: CN(C)CC(C)(C)Oc1ccc(Nc2cc(-c3cccc(-n4ncc5cc(C(C)(C)C)cc(F)c5c4=O)c3CO)nn(C)c2=O)nn1]

In a 15 mL microwave reaction vial was added 6-chloro-4-(6-(1-(dimethylamino)-2-methylpropan-2-yloxy)pyridazin-3-ylamino)-2-methylpyridazin-3(2H)-one (75 mg, 213 μmol, Eq: 1.00), n-BuOH (6 ml) and water (1.5 ml). To the mixture was added potassium (2-(acetoxymethyl)-3-(6-tert-butyl-8-fluoro-1-oxophthalazin-2(1H)-yl)phenyl)trifluoroborate (101 mg, 213 μmol, Eq: 1.00) under argon. X-PHOS (10.6 μl, 31.9 μmol, Eq: 0.15) and potassium phosphate tribasic (99.3 mg, 468 μmol, Eq: 2.2) was added followed by bis(dibenzylideneacetone)palladium (9.17 mg, 15.9 μmol, Eq: 0.075). The tube was sealed under argon and heated in an oil bath at 115° C. for 3 hrs then stirred at room temperature overnight. To this mixture was added 100 mg NaOH in 1 mL distilled water. The mixture was warmed in an oil bath at 50° C. for 3 hrs then stirred at room temperature overnight. The crude reaction mixture was diluted with water (20 mL) and extracted with DCM (2×30 mL). The combined organic extracts were concentrated and absorbed onto silica gel. The crude material was purified by LC chromatography eluting with 0-5% (10% NH₄OH in MeOH) in 1/1 EtOAc/heptane to afford 67 mg (47%) of the title compound as a pale yellow solid. Mp: 140-145° C. ¹H NMR (300 MHz, CHLO- ROFORM-d) 1.43 (s, 9H), 1.67 (s, 6H), 2.37 (s, 6H), 2.80 (s, 2H), 3.80 (t, J=6.2 Hz, 1H), 3.92 (s, 3H), 4.45 (d, J=6.2 Hz, 2H), 6.90 (d, J=9 Hz, 1H), 7.10 (d, J=9 Hz, 1H), 7.43-7.65 (m, 5H), 8.20 (s, 1H), 8.28 (d, J=2.5, 1 H), 8.55 (s, 1H). LCMS (ES): 643 (M+H), RT=1.942 min.

Preparation of I-40

Step 1. Preparation of 6-(1-Methyl-1,2,3,6-tetrahydro-pyridin-4-yl)-pyridazin-3-ylamine

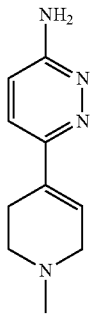

In a 15 mL microwave reaction vial was added potassium phosphate tribasic (1.43 g, 6.74 mmol), 6-bromopyridazin-3-amine (335 mg, 1.93 mmol), 1-methyl-4-(4,4,5,5-tetramethyl-1,3,2-dioxaborolan-2-yl)-1,2,3,6-tetrahydropyridinium chloride (500 mg, 1.93 mmol), X-PHOS (138 mg, 289 µmol) and bis(dibenzylideneacetone)palladium (83 mg, 144 µmol) in 7 mL n-butanol and 1.4 mL H₂O. The tube was sealed under argon and heated at 115° C. in oil bath for 3 hrs then stirred at room temperature overnight. The phases were separated and the aqueous was extracted with EtOAc. (10 ml). Water (20 mL) was added to the residual aqueous phase and was extracted with DCM (3×10 mL). The extracts were combined with the EtOAc organic phase. The resultant solution was absorbed onto silica gel and purified by LC chromatography eluting with 0-10% (10% NH₄OH in MeOH) in 1/1 EtOAc/hexane to afford 300 mg (82%) of the title compound.

Step 2. Preparation of 6-(1-Methyl-piperidin-4-yl)-pyridazin-3-ylamine

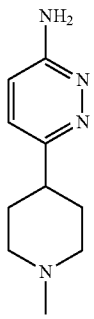

6-(1-methyl-1,2,3,6-tetrahydropyridin-4-yl)pyridazin-3-amine (300 mg, 1.58 mmol, Eq: 1.00) was dissolved in EtOH (30 ml). The reaction solution was hydrogenated in an H-Cube apparatus (60 psi) at room temperature with Pd/C by running mixture through the cycle twice until reaction was complete as determined by tlc. The solvent was removed in vacuo to afford 270 mg (89%) of the title compound.

Step 3. Preparation of 6-Chloro-2-methyl-4-[6-(1-methyl-piperidin-4-yl)-pyridazin-3-ylamino]-2H-pyridazin-3-one

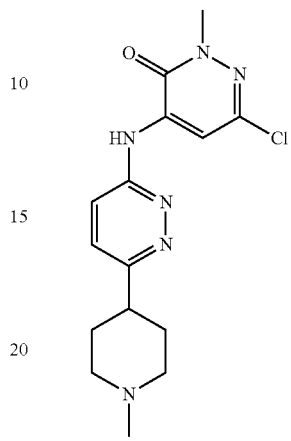

In a 15 mL reaction vial was added a solution of 6-(1-methylpiperidin-4-yl)pyridazin-3-amine (190 mg, 988 µmol, Eq: 1.00) in dioxane (7 ml). Argon was bubbled through the solution and 6-chloro-2-methyl-4-(6-(1-methylpiperidin-4-yl)pyridazin-3-ylamino)pyridazin-3(2H)-one (160 mg, 430 µmol, 43.5% yield) and Cs2CO3 (966 mg, 2.96 mmol, Eq: 3) were added. To this mixture was added xantphos (86 mg, 148 µmol, Eq: 0.15) and bis(dibenzylideneacetone)palladium (42.6 mg, 74.1 µmol, Eq: 0.075). The tube was sealed under argon and heated in an oil bath at 115° C. (bath temp) for 7 hrs then stirred at room temperature overnight. The reaction was diluted with THF (10 mL), filtered and the solid was washed with THF (3×10 mL). The combined washes were concentrated and purified by solid loading on 40 g silica gel column and eluting with 10% (10% NH₄OH in MeOH) in 1/1 EtOAc/hexane to afford 160 mg (44%) of the title compound as an orange solid.

Example 40

Step 3. Preparation of 6-tert-Butyl-8-fluoro-2-(2-hydroxymethyl-3-{1-methyl-5-[6-(1-methyl-piperidin-4-yl)-pyridazin-3-ylamino]-6-oxo-1,6-dihydro-pyridazin-3-yl}-phenyl)-2H-phthalazin-1-one

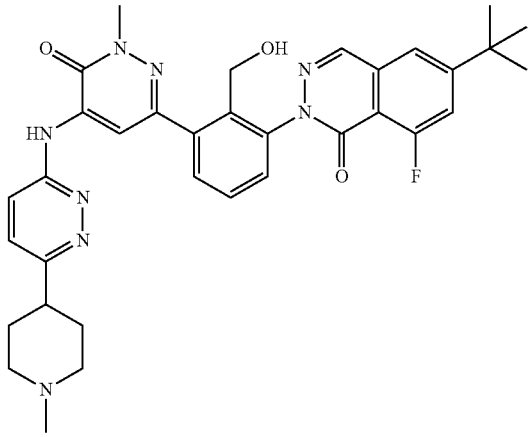 [SMILES: CN1CCC(c2ccc(Nc3cc(-c4cccc(-n5ncc6cc(C(C)(C)C)cc(F)c6c5=O)c4CO)nn(C)c3=O)nn2)CC1]

In a 15 mL microwave reaction vial was added 6-chloro-2-methyl-4-(6-(1-methylpiperidin-4-yl)pyridazin-3-ylamino)pyridazin-3(2H)-one (160 mg, 478 μmol, Eq: 1.00), potassium (2-(acetoxymethyl)-3-(6-tert-butyl-8-fluoro-1-oxophthalazin-2(1H)-yl)phenyl)trifluoroborate (272 mg, 573 μmol, Eq: 1.2) with n-BuOH (7.5 ml) and water (1.5 ml). Argon was bubbled through the solution for 5 min. To the mixture was added X-PHOS (34.2 mg, 71.7 μmol, Eq: 0.15) and potassium phosphate tribasic (304 mg, 1.43 mmol, Eq: 3). Argon was bubbled through the mixture for 5 min. To this mixture was added bis(dibenzylideneacetone)palladium (20.6 mg, 35.8 μmol, Eq: 0.075). The tube was sealed under argon and heated in oil bath at 110° C. for 3 hrs. The mixture was cooled to room temperature and treated with a solution of 220 mg NaOH in 1.5 mL water dropwise. The resultant mixture was heated in an oil bath at 50° C. for 3 hrs with strong stirring. The reaction mixture was diluted with water (20 mL) and extracted with DCM (3×30 mL). The combined extracts were concentrated and purified by solid loading on a 40 g silica gel column and eluting with 5-10% (10% NH₄OH in MeOH) in 1/1 EtOAc/hexane to afford 61 mg (20%) of the title compound as a yellow solid. mp: 260-265° C. ¹H NMR (300 MHz, CHLOROFORM-d) 1.43 (s, 9H), 1.80-2.20 (m, 6H), 2.37 (s, 3H), 2.90-3.07 (m, 3H), 3.85 (t, J=6.2 Hz, 1H), 3.92 (s, 3H), 4.45 (d, J=6.2 Hz, 2H), 7.15 (d, J=9 Hz, 1H), 7.35 (d, J=9 Hz, 1H), 7.43-7.65 (m, 5H), 8.28 (d, J=2.5, 1 H), 8.32 (s, 1H), 8.78 (s, 1H). LCMS (ES): 625 (M+H), RT=2.21 min.

Preparation of I-41

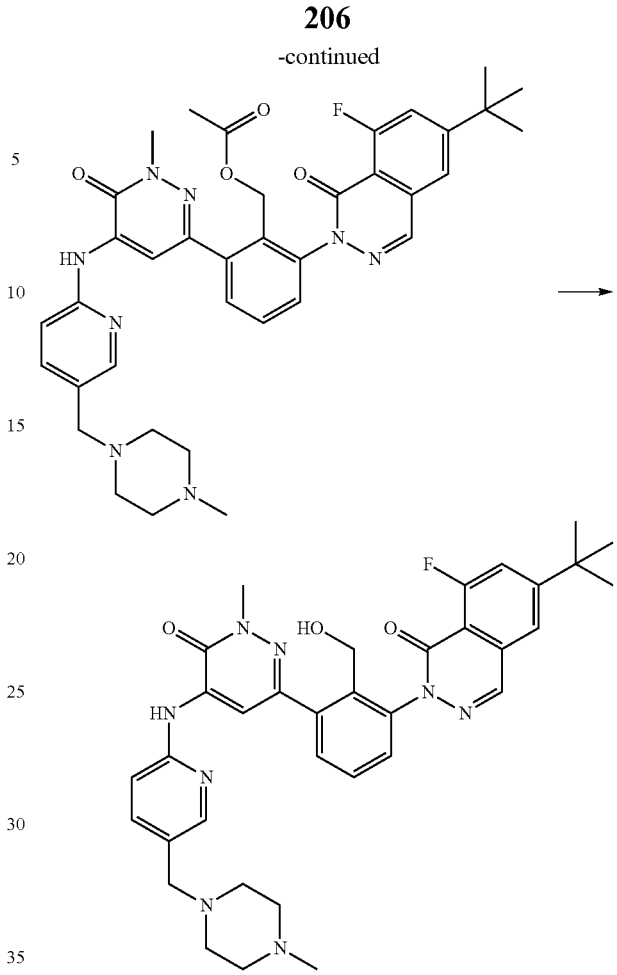

Scheme G

Step 1

1-(6-Chloro-pyridin-3-ylmethyl)-4-methyl-piperazine: 6-Chloronicotinaldehyde (10 g, 70.6 mmol, Eq: 1.00) was suspended in 700 ml DCM. 1-Methylpiperazine (8.84 g, 88.3 mmol, Eq: 1.25) and acetic acid (8.48 g, 8.09 ml, 141 mmol, Eq: 2.0) were added. Sodium triacetoxyborohydride (22.5 g, 106 mmol, Eq: 1.5) was added in portions over several minutes. The reaction mixture stirred at room temperature. After 3.5 hrs, there was no sign of starting material. LCMS showed product plus a little reduced starting material. Water was added, followed by DCM and the layers were separated. The DCM layer was washed with saturated ammonium chloride and the aqueous layer was combined with the initial aqueous layer. The aqueous extractions were bacidified with 1M NaOH. The resulting aqueous layer was extracted 3 times with DCM, and then dried, and concentrated to give 13.5 grams of a light yellow oil (84.7%) which was used without further purification.

Step 2

5-(4-Methyl-piperazin-1-ylmethyl)-pyridin-2-ylamine: To a sealed tube under nitrogen was added 1-((6-chloropyridin-3-ylmethyl)-4-methylpiperazine (13.5 g, 59.8 mmol, Eq: 1.00), 2-(dicyclohexylphosphino)biphenyl (4.19 g, 12.0 mmol, Eq: 0.20), tris(dibenzylideneacetone)-dipalladium (0) (5.48 g, 5.98 mmol, Eq: 0.10), and lithium bis(trimethylsilyl) amide, 150 ml of a 1.0M solution in THF. An additional 150 ml THF was added. The flask was degassed with argon. The flask was capped and the reaction heated at 100° C. overnight. 3M HCl was added along with DCM to the material and the layers were separated. The aqueous layer was bacidified with 3M NaOH. The aqueous layer was then extracted 3 times with DCM to provide 3.2 g (25.9%) of a yellow powder which was used without further purification.

Step 3

6-Chloro-2-methyl-4-[5-(4-methyl-piperazin-1-ylmethyl)-pyridin-2-ylamino]-2H-pyridazin-3-one: 5-((4-Methylpiperazin-1-yl)methyl)pyridin-2-amine (3.2 g, 15.5 mmol, Eq: 1.00), 4-bromo-6-chloro-2-methylpyridazin-3(2H)-one (3.64 g, 16.3 mmol, Eq: 1.05), xantphos (1.35 g, 2.33 mmol, Eq: 0.15) tris(dibenzylideneacetone)dipalladium (0) (1.07 g, 1.16 mmol, Eq: 0.075) and cesium carbonate (15.2 g, 46.5 mmol, Eq: 3.00) were added to a sealed tube under nitrogen. Dioxane (103 ml) was added and the solution was degassed with nitrogen. The tube was capped and heated at 110° C. overnight. The reaction mixture was filtered through celite and the cake was washed with DCM. 1M HCl was added to and the layers were separated. The aqueous layer was basified with 2M NaOH and extracted several times with DCM. Most of the solvent was evaporated and the residue was triturated with ether. The solid that formed was filtered and dried to give 2.75 g (50.8%) of product which was used without further purification.

Step 4

Acetic acid 2-(6-tert-butyl-8-fluoro-1-oxo-1H-phthalazin-2-yl)-6-{1-methyl-5-[5-(4-methyl-piperazin-1-ylmethyl)-pyridin-2-ylamino]-6-oxo-1,6-dihydro-pyridazin-3-yl}-benzyl ester: 6-Chloro-2-methyl-4-(5-((4-methylpiperazin-1-yl)methyl)pyridin-2-ylamino)pyridazin-3(2H)-one (3.1 g, 8.89 mmol, Eq: 1.00), 2-(6-tert-butyl-8-fluoro-1-oxophthalazin-2(1H)-yl)-6-(4,4,5,5-tetramethyl-1,3,2-dioxaborolan-2-yl) benzyl acetate (7.69 g, 15.6 mmol, Eq: 1.75), X-PHOS (424 mg, 0.89 mmol, Eq: 0.10), bis(dibenzylideneacetone)palladium (255 mg, 0.44 mmol, Eq: 0.05) and tripotassium phosphate (4.72 g, 22.2 mmol, Eq: 2.50) were added to a large microwave vial. The vial was capped and purged. N-butanol (35.5 ml) and water (9 ml) were added and the vial was purged again and backfilled with nitrogen. The reaction was heated in a sand bath at 115° C. for 2.5 hours. Water and DCM were added to the reaction and the layers were separated. The organic layer was filtered through celite, concentrated, and purified by chromatography using a gradient of 0% to 25% methanol in DCM. Fractions with and without the protecting group were combined to give a combined yield of 4.5 g (approximately 74%).

Example 41

Step 5

6-tert-Butyl-8-fluoro-2-(2-hydroxymethyl-3-{1-methyl-5-[5-(4-methyl-piperazin-1-ylmethyl)-pyridin-2-ylamino]-6-oxo-1,6-dihydro-pyridazin-3-yl}-phenyl)-2H-phthalazin-1-one Acetic acid 2-(6-tert-butyl-8-fluoro-1-oxo-1H-phthalazin-2-yl)-6-{1-methyl-5-[5-(4-methyl-piperazin-1-ylmethyl)-pyridin-2-ylamino]-6-oxo-1,6-dihydro-pyridazin-3-yl}-benzyl ester (4.5 g, 6.61 mmol, Eq: 1.00) and potassium carbonate (1.37 g, 9.92 mmol, Eq: 1.50) were dissolved in methanol and heated at 40° C. for 1 hour. The reaction was cooled to room temperature and water was added dropwise. The reaction was stirred at room temperature overnight. The solid that formed was filtered, washed with water, and dried in a vacuum oven over the weekend to give 3.64 g (86.2%) of an off-white crystalline solid. $^1$H NMR (300 MHz, DMSO-d6) δ ppm 9.39 (s, 1H) 8.53 (s, 1H) 8.50 (d, J=2.3 Hz, 1H) 8.15 (d, J=1.9 Hz, 1H) 7.86 (d, J=1.5 Hz, 1H) 7.74 (dd, J=13.4, 1.7 Hz, 1H) 7.57-7.62 (m, 1H) 7.50-7.57 (m, 2H) 7.43-7.49 (m, 2H) 4.52-4.61 (m, 1H) 4.40 (br. s., 2H) 3.77 (s, 3H) 3.36 (s, 2H) 2.30 (br. s., 8H) 2.11 (s, 3H) 1.37 (s, 9H). MS: (M+H)$^+$=639.

Preparation of I-42

Example 42

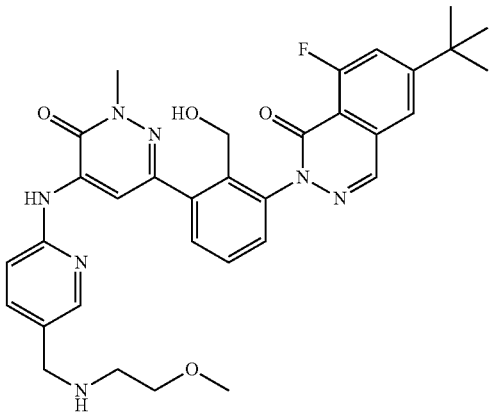 [SMILES: COCCNCc1ccc(Nc2cc(-c3cccc(-n4ncc5cc(C(C)(C)C)cc(F)c5c4=O)c3CO)nn(C)c2=O)nc1]

6-tert-Butyl-8-fluoro-2-[2-hydroxymethyl-3-(5-{5-[(2-methoxy-ethylamino)-methyl]-pyridin-2-ylamino}-1-methyl-6-oxo-1,6-dihydro-pyridazin-3-yl)-phenyl]-2H-phthalazin-1-one was prepared using the general procedure described in Example 41, substituting 2-methoxyethanamine for 1-methylpiperazine in step 1. The secondary amine was protected with a BOC group using a standard procedure prior to the second step of the synthesis. In the penultimate step of the synthesis for this compound, 1M NaOH was used to remove the acetate protecting group rather than potassium carbonate, using THF as the solvent and heating at 60° C. for two hours, then stirring at room temperature overnight. The BOC protecting group was removed at the end of the synthesis by heating the compound in 1,1,1,3,3,3-hexafluoro-2-propanol (used in large excess as the solvent) in a microwave at 140° C. for 30 minutes. After purification by chromatography using a gradient of 5% to 25% methanol in DCM, 75 mg of product was obtained as a yellow solid. $^1$H NMR (300 MHz, DMSO-d6) δ ppm 9.37 (s, 1H) 8.51-8.54 (m, 2H) 8.20 (d, J=2.3 Hz, 1H) 7.87 (s, 1H) 7.75 (d, J=14.4 Hz, 1H) 7.64-7.69 (m, 1H) 7.42-7.59 (m, 4H) 4.57 (t, J=5.3 Hz, 1H) 4.42 (br. s., 2H) 3.77 (s, 3H) 3.61 (s, 2H) 3.37 (t, J=5.7 Hz, 2H) 3.21 (s, 3H) 2.55-2.64 (m, 2H) 1.37 (s, 9H). MS: (M+H)$^+$=614. MP=108-110° C.

Preparation of I-43

(1S,4S)-5-(6-Chloro-pyridin-3-ylmethyl)-2,5-diaza-bicyclo[2.2.1]heptane-2-carboxylic acid tert-butyl ester was prepared as described in example 41 (step 1) except substituting (1S,4S)-2,5-diaza-bicyclo[2.2.1]heptane-2-carboxylic acid tert-butyl ester for 1-methylpiperazine.

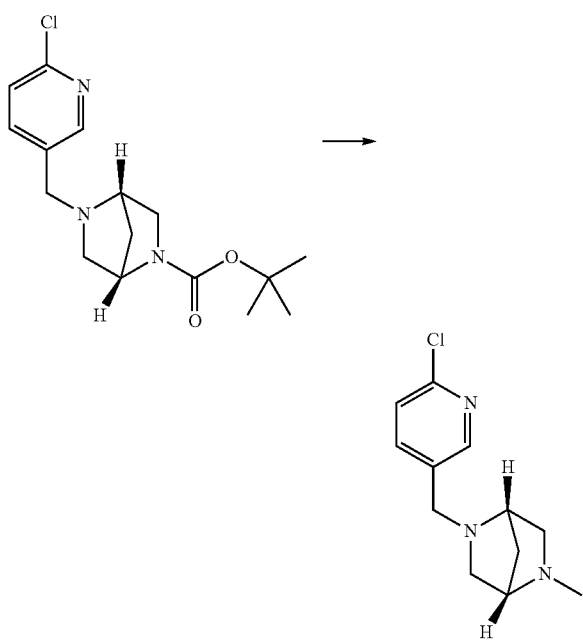

Preparation of (1S,4S)-2-(6-Chloro-pyridin-3-ylmethyl)-5-methyl-2,5-diazabicyclo[2.2.1]-heptane: (1S,4S)-5-(6-Chloro-pyridin-3-ylmethyl)-2,5-diaza-bicyclo[2.2.1]heptane-2-carboxylic acid tert-butyl ester (1.1 g, 3.4 mmol) was dissolved in a mixture of 11.3 ml of formic acid and 22.6 ml of formalin. The reaction was heated at 70° C. for 4 hours, and then cooled to room temperature. Water was added and the aqueous layer was extracted with DCM. The aqueous layer was carefully basified with solid potassium carbonate and extracted 3 times with DCM. The crude product was purified by chromatography using a gradient of 5% to 25% methanol in DCM. Ammonium hydroxide (approximately 2%) had been added to the methanol. 500 mg of a colorless liquid was obtained (61.9%).

Example 43

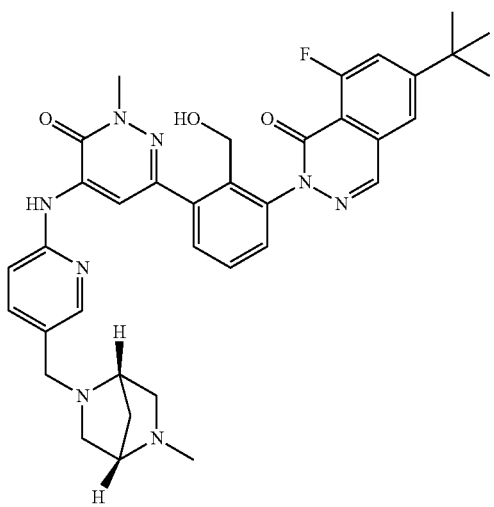 [SMILES: CN1C[C@@H]2C[C@H]1CN2Cc1ccc(Nc2cc(-c3cccc(-n4ncc5cc(C(C)(C)C)cc(F)c5c4=O)c3CO)nn(C)c2=O)nc1]

Preparation of 6-tert-Butyl-8-fluoro-2-(2-hydroxymethyl-3-{1-methyl-5-[5-((1S,4S)-5-methyl-2,5-diaza-bicyclo[2.2.1]hept-2-ylmethyl)-pyridin-2-ylamino]-6-oxo-1,6-dihydro-pyridazin-3-yl}-phenyl)-2H-phthalazin-1-one: 6-tert-Butyl-8-fluoro-2-(2-hydroxymethyl-3-{1-methyl-5-[5-((1S,4S)-5-methyl-2,5-diaza-bicyclo[2.2.1]hept-2-ylmethyl)-pyridin-2-ylamino]-6-oxo-1,6-dihydro-pyridazin-3-yl}-phenyl)-2H-phthalazin-1-one was prepared using the general procedure described in example 41 substituting (1S,4S)-2-(6-Chloro-pyridin-3-ylmethyl)-5-methyl-2,5-diazabicyclo[2.2.1]-heptane for 1-((6-chloropyridin-3-ylmethyl)-4-methylpiperazine in step 2 and using NaOH in THF to remove the acetate protecting group rather than potassium carbonate. 46 mg (98%) of an off-white powder was obtained. $^1$H NMR (300 MHz, DMSO-d6) δ ppm 9.38 (s, 1H) 8.54 (s, 1H) 8.52 (d, J=2.3 Hz, 1H) 8.20 (d, J=1.9 Hz, 1H) 7.87 (s, 1H) 7.72-7.76 (m, 1H) 7.64 (dd, J=8.5, 2.1 Hz, 1H) 7.43-7.59 (m, 4H) 4.58 (t, J=6.0 Hz, 1H) 4.41 (br. s., 2H) 3.79 (s, 3H) 3.49-3.61 (m, 2H) 3.18 (s, 1H) 3.09 (s, 1H) 3.49-3.61 (m, 2H) 2.54-2.66 (m, 2H) 2.24 (s, 3H) 1.57 (s, 2H) 1.38 (s, 9H). MS: (M+H)$^+$ =651. MP=183-186° C.

Preparation of I-44

6-Chloro-4-(5-{[(2-methoxy-ethyl)-methyl-amino]-methyl}-pyridin-2-ylamino)-2-methyl-2H-pyridazin-3-one was prepared using the general procedure described in Example 41 (step 1-2), substituting 2-methoxyethanamine for 1-methylpiperazine in step 1. The secondary amine was protected with a BOC group using a standard procedure.

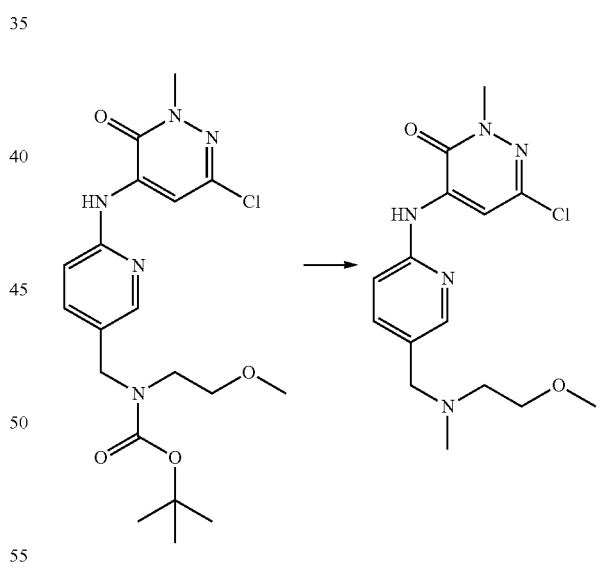

Preparation of 6-Chloro-4-(5-{[(2-methoxy-ethyl)-methyl-amino]-methyl}-pyridin-2-ylamino)-2-methyl-2H-pyridazin-3-one: tert-Butyl (6-(6-chloro-2-methyl-3-oxo-2,3-dihydropyridazin-4-ylamino)pyridin-3-yl)methyl(2-methoxyethyl)carbamate (95 mg, 0.22 mmol) was dissolved in 0.75 ml of formic acid and 1.4 ml of formalin. The reaction was heated at 70° C. for 4 hours. The reaction was cooled to room temperature, water was added and the aqueous layer was extracted with DCM. The aqueous layer was carefully basified with solid potassium carbonate and extracted 3 times with DCM. The crude product was purified by chromatogra-

Example 44

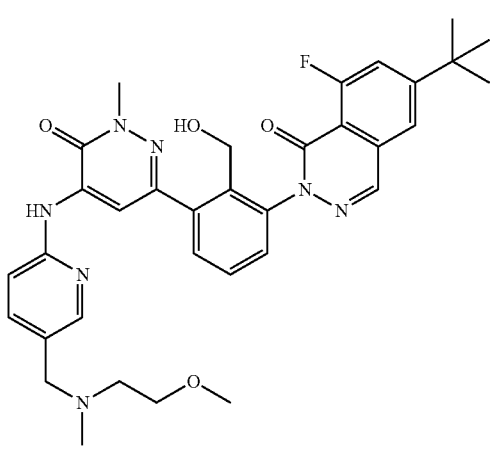 [SMILES: COCCN(C)Cc1ccc(Nc2cc(-c3cccc(-n4ncc5cc(C(C)(C)C)cc(F)c5c4=O)c3CO)nn(C)c2=O)nc1]

Preparation of 6-tert-Butyl-8-fluoro-2-{2-hydroxymethyl-3-[5-(5-{[(2-methoxy-ethyl)-methyl-amino]-methyl}-pyridin-2-ylamino)-1-methyl-6-oxo-1,6-dihydro-pyridazin-3-yl]-phenyl}-2H-phthalazin-1-one: 6-tert-Butyl-8-fluoro-2-{2-hydroxymethyl-3-[5-(5-{[(2-methoxy-ethyl)-methyl-amino]-methyl}-pyridin-2-ylamino)-1-methyl-6-oxo-1,6-dihydro-pyridazin-3-yl]-phenyl}-2H-phthalazin-1-one was prepared using the general procedure described in example 41 substituting 6-Chloro-4-(5-{[(2-methoxy-ethyl)-methyl-amino]-methyl}-pyridin-2-ylamino)-2-methyl-2H-pyridazin-3-one for 6-chloro-2-methyl-4-(5-((4-methylpiperazin-1-yl)methyl)pyridin-2-ylamino)pyridazin-3(2H)-one in step 3. For the Suzuki reaction, potassium (2-(acetoxymethyl)-3-(6-tert-butyl-8-fluoro-1-oxophthalazin-2(1H)-yl)phenyl)trifluoroborate (Eq: 1.2) was used in place of 2-(6-tert-butyl-8-fluoro-1-oxophthalazin-2(1H)-yl)-6-(4,4,5,5-tetramethyl-1,3,2-dioxaborolan-2-yl)benzyl acetate. After removal of the acetate protecting group using potassium carbonate in methanol, water was added dropwise and the reaction was stirred at room temperature overnight. The solid that formed was filtered, washed with water then ether and dried in a vacuum oven to give 52 mgs of a crystalline white solid. $^1$H NMR (300 MHz, DMSO-$d_6$) δ ppm 1.38 (s, 9H) 2.13 (s, 3H) 2.47 (s, 2H) 3.22 (s, 3H) 3.39-3.49 (m, 4H) 3.79 (s, 3H) 4.43 (br. s., 2H) 4.58 (br. s., 1H) 7.41-7.65 (m, 5H) 7.75 (d, J=13.22 Hz, 1H) 7.87 (s, 1H) 8.17 (s, 1H) 8.46-8.59 (m, 2H) 9.40 (s, 1H). MS: (M+H)$^+$=628.

Preparation of I-45

Example 45

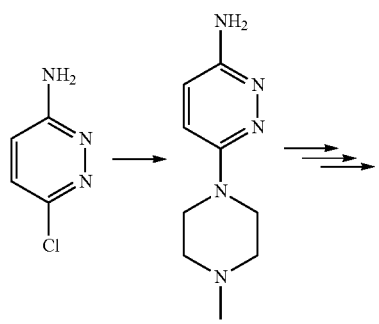

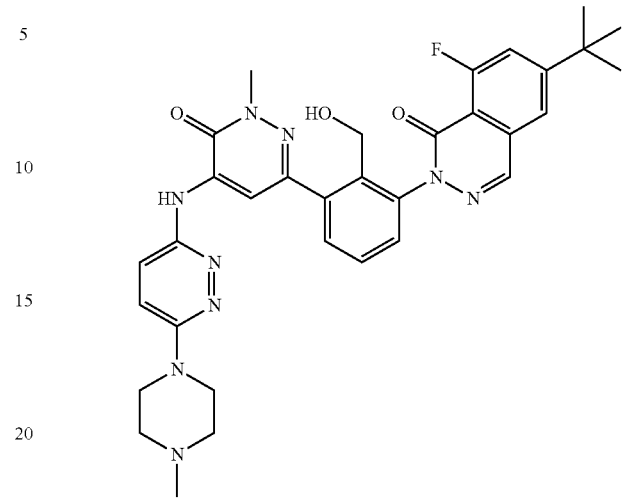

6-(4-Methyl-piperazin-1-yl)-pyridazin-3-ylamine: 6-Chloro-pyridazin-3-ylamine (2.0 g, 15.4 mmol, Eq: 1.00) was dissolved in 1-methylpiperazine (15.5 g, 154 mmol, Eq: 10.0) and heated in a sand bath at 165° C. for 4 hours. The reaction mixture was then heated at 200° C. for 2 hours in a microwave reactor. The crude product was purified by chromatography using 10% methanol (with approximately 2% ammonium hydroxide) in DCM. To the still impure product was added aqueous sodium bicarbonate and DCM and the layers were separated. The aqueous layer was back extracted twice with DCM. The combined organic layers were concentrated, triturated with isopropyl acetate, filtered and dried to give 730 mg (24.5%) of a yellow solid.

6-tert-Butyl-8-fluoro-2-(2-hydroxymethyl-3-{1-methyl-5-[6-(4-methyl-piperazin-1-yl)-pyridazin-3-ylamino]-6-oxo-1,6-dihydro-pyridazin-3-yl}-phenyl)-2H-phthalazin-1-one: 6-tert-Butyl-8-fluoro-2-(2-hydroxymethyl-3-{1-methyl-5-[6-(4-methyl-piperazin-1-yl)-pyridazin-3-ylamino]-6-oxo-1,6-dihydro-pyridazin-3-yl}-phenyl)-2H-phthalazin-1-one was prepared using the general procedure described in Example 41, substituting potassium (2-(acetoxymethyl)-3-(6-tert-butyl-8-fluoro-1-oxophthalazin-2(1H)-yl)phenyl)trifluoroborate (Eq: 1.2) for 2-(6-tert-butyl-8-fluoro-1-oxophthalazin-2(1H)-yl)-6-(4,4,5,5-tetramethyl-1,3,2-dioxaborolan-2-yl)benzyl acetate. After removal of the acetate protecting group with potassium carbonate in methanol, the product was purified by preparative TLC using 20% methanol in DCM to give 30 mgs of final product. $^1$H NMR (300 MHz, DMSO-$d_6$) δ ppm 1.38 (s, 9H) 2.21 (s, 3H) 2.34-2.44 (m, 4H) 3.44-3.53 (m, 4H) 3.79 (s, 3H) 4.41 (br. s., 1H) 4.50-4.61 (m, 1H) 7.39 (d, J=9.82 Hz, 1H) 7.44-7.60 (m, 3H) 7.66 (d, J=9.82 Hz, 1H) 7.75 (d, J=13.22 Hz, 1H) 7.87 (s, 1H) 8.45 (s, 1H) 8.51 (d, J=2.27 Hz, 1H) 9.38 (s, 1H). MS: (M+H)$^+$=626.

Preparation of I-46

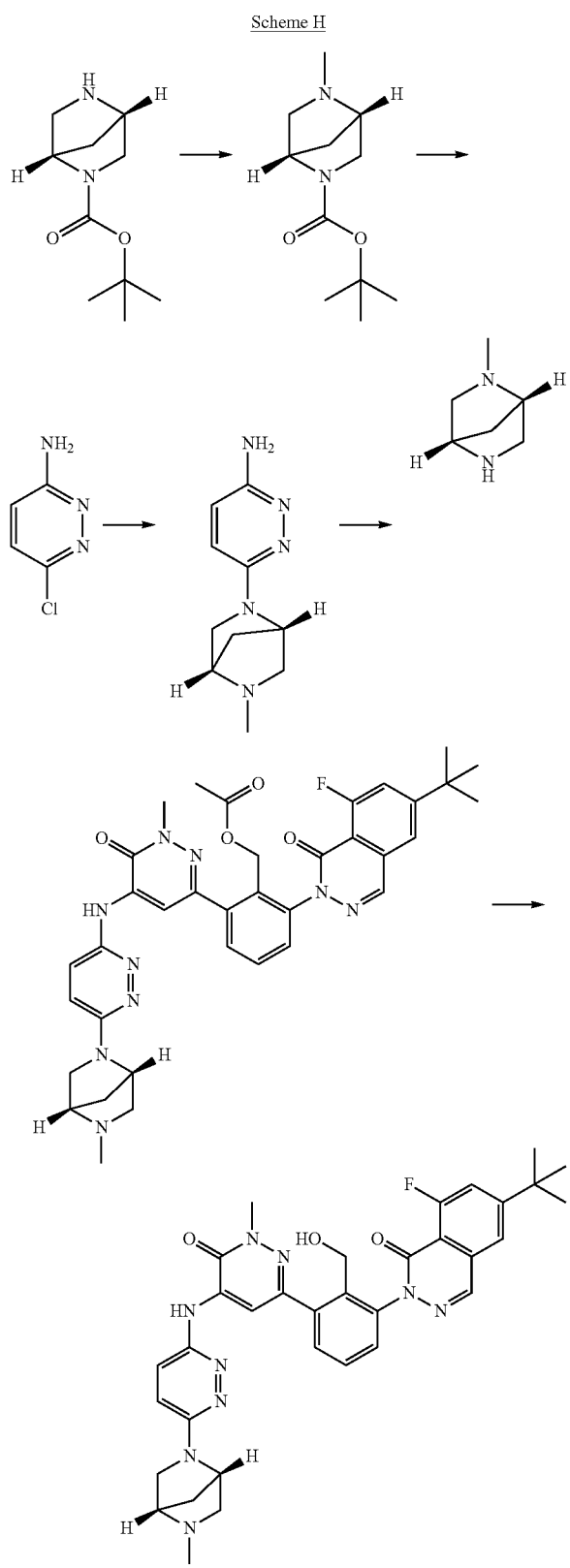

Scheme H

Step 1

(1S,4S)-tert-Butyl 5-methyl-2,5-diazabicyclo[2.2.1]heptane-2-carboxylate: (1S,4S)-tert-Butyl 2,5-diazabicyclo[2.2.1]heptane-2-carboxylate (2.5 g, 12.6 mmol, Eq: 1.00) was dissolved in 126 ml of methanol. Formaldehyde (23.5 ml of a 37% aqueous solution) and acetic acid (2.17 ml) were added. Sodium triacetoxyborohydride (4.01 g, 18.9 mmol, Eq: 1.50) was added in portions. The reaction was stirred at room temperature overnight. The reaction was concentrated on a rotary evaporator. DCM and sodium bicarbonate were added to the residue and the layers were separated. The organic layer was washed with dilute bicarbonate, concentrated, and used without further purification.

Step 2

(1S,4S)-2-methyl-2,5-diazabicyclo[2.2.1]heptane: (1S,4S)-tert-Butyl 5-methyl-2,5-diazabicyclo[2.2.1]heptane-2-carboxylate (2.5 g, 11.8 mmol) was dissolved a 50% mixture of DCM and TFA. The reaction was stirred at room temperature for 1 hour. The solvents were evaporated. DCM and aqueous sodium hydroxide were added to the residue and the layers were separated. The aqueous layer was back extracted two more times with DCM. The combined organic layers were concentrated and the crude product was used without purification.

Step 3

6-((1S,4S)-5-Methyl-2,5-diaza-bicyclo[2.2.1]hept-2-yl)-pyridazin-3-ylamine: 6-Chloropyridazin-3-amine (200 mg, 1.54 mmol, Eq: 1.00) and (1S,4S)-2-methyl-2,5-diazabicyclo[2.2.1]heptane (693 mg, 6.18 mmol, Eq: 4.00) were combined in a small round bottom flask and heated at 200° C. for 2 hours. The dark glassy residue was dissolved in DCM and purified by chromatography using a gradient of 0% to 25% methanol (with 2.5% ammonium hydroxide) in DCM to give about 100 mg (31.6%) of a brown, viscous oil.

Step 4

Acetic acid 2-(6-tert-butyl-8-fluoro-1-oxo-1H-phthalazin-2-yl)-6-{1-methyl-5-[6-((1S,4S)-5-methyl-2,5-diaza-bicyclo[2.2.1]hept-2-yl)-pyridazin-3-ylamino]-6-oxo-1,6-dihydro-pyridazin-3-yl}-benzyl ester: 6-((1S,4S)-5-Methyl-2,5-diaza-bicyclo[2.2.1]hept-2-yl)-pyridazin-3-ylamine (100 mg, 0.487 mmol, Eq: 1.00), acetic acid 2-(5-bromo-1-methyl-6-oxo-1,6-dihydro-pyridazin-3-yl)-6-(6-tert-butyl-8-fluoro-1-oxo-1H-phthalazin-2-yl)-benzyl ester (284 mg, 0.512 mmol, Eq: 1.05), xantphos (42.3 mg, 0.073 mmol, Eq: 0.15), tris(dibenzylideneacetone)-dipalladium (0) (33.5 mg, 0.036 mmol, Eq: 0.075) and cesium carbonate (476 mg, 1.46 mmol, Eq: 3.00) were added to a microwave vial. The vial was capped and purged. Degassed dioxane (about 5 ml) was added through a syringe and the vial was purged again and back filled with nitrogen. The reaction was heated at 100° C. overnight in a sand bath. The reaction was filtered through celite and concentrated. The crude product was purified by chromatography using a gradient of 0% to 25% methanol in DCM. LCMS and NMR showed major impurities. Took on to next step without further purification.

Example 46

Step 5

6-tert-Butyl-8-fluoro-2-(2-hydroxymethyl-3-{1-methyl-5-[6-((1S,4S)-5-methyl-2,5-diaza-bicyclo[2.2.1]hept-2-yl)- pyridazin-3-ylamino]-6-oxo-1,6-dihydro-pyridazin-3-yl}-phenyl)-2H-phthalazin-1-one: The impure mixture from the prior reaction was dissolved in methanol, potassium carbonate was added, and the reaction was heated at 40° C. for 1 hour. Water was added and the reaction was stirred at room temperature overnight. The solid that formed was filtered and dried. The crude product was purified by preparative TLC in 10% methanol in DCM. The plates were eluted twice to give 5 mg of a light yellow solid which was approximately 85% pure. $^1$H NMR (300 MHz, DMSO-d$_6$) δ ppm 1.40 (s, 9H) 1.70-1.79 (m, 1H) 1.83-1.92 (m, 1H) 2.26 (s, 3H) 2.42 (d, J=9.06 Hz, 1H) 2.70-2.85 (m, 1H) 3.37-3.55 (m, 4H) 3.79 (s, 3H) 4.33-4.66 (m, 3H) 7.06 (d, J=9.82 Hz, 1H) 7.44-7.57 (m, 3H) 7.64 (d, J=9.44 Hz, 1H) 7.75 (dd, J=13.41, 1.70 Hz, 1H) 7.88 (d, J=1.89 Hz, 1H) 8.42 (s, 1H) 8.52 (d, J=2.64 Hz, 1H) 9.32 (s, 1H). MS: (M+H)$^+$=638.

Preparation of I-47

Example 47

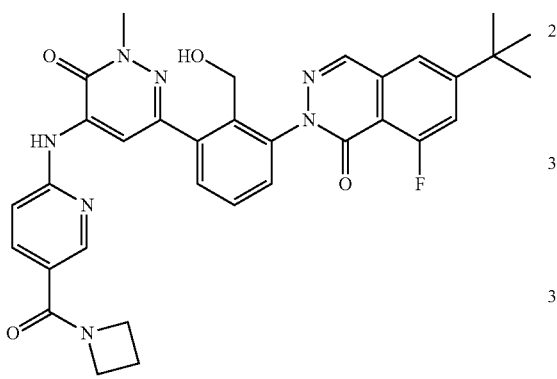

Step 1. Preparation of 6-(6-Chloro-2-methyl-3-oxo-2,3-dihydro-pyridazin-4-ylamino)-nicotinic acid methylester

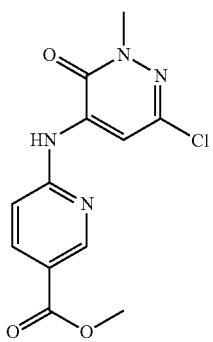 [SMILES: COC(=O)c1ccc(Nc2cc(Cl)nn(C)c2=O)nc1]

Methyl 6-aminonicotinate (2 g, 13.1 mmol, Eq: 1.00), 4-bromo-6-chloro-2-methylpyridazin-3(2H)-one (2.94 g, 13.1 mmol, Eq: 1), and (9,9-dimethyl-9H-xanthene-4,5-diyl)bis-(diphenylphosphine) (400 mg, 691 μmol, Eq: 0.0526) were dissolved in DMF (300 ml) under heating. Cesium carbonate (12.8 g, 39.4 mmol, Eq: 3) was added followed by Pd$_2$(dba)$_3$ (301 mg, 329 μmol, Eq: 0.025) under an argon atmosphere. The reaction mixture was heated to 105° C. overnight. The crude reaction mixture was poured into water (400 ml) and the resulting precipitate was filtered off and washed with water. The resultant filter cake was dissolved in dichloromethane. The organic phase was washed with brine, dried over sodium sulfate; filtered and concentrated to give the desired product as an off-white solid (1.523 g).
(M+H)$^+$=294.9 m/e Step 2. Preparation of 6-(6-Chloro-2-methyl-3-oxo-2,3-dihydro-pyridazin-4-ylamino)-nicotinic acid

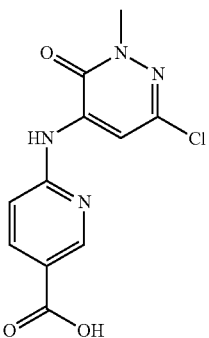 [SMILES: Cn1nc(Cl)cc(Nc2ccc(C(=O)O)cn2)c1=O]

Methyl 6-(6-chloro-2-methyl-3-oxo-2,3-dihydropyridazin-4-ylamino)nicotinate (1.523 g, 5.17 mmol, Eq: 1.00) was suspended in dioxane (90 ml). 1 M Lithium hydroxide (10.3 ml, 10.3 mmol, Eq: 2) was added dropwise. The light brown suspension was stirred overnight at room temperature. 1 M Lithium hydroxide (10.3 ml, 10.3 mmol, Eq: 2) was added again and stirred over the weekend. A mixture of ethyl acetate/ammonium chloride solution was added to the reaction mixture. The resulting precipitate was collected by filtration. The precipitate was triturated with water (200 ml), filtered, washed with ethyl acetate and dried in vacuo to give a light yellow solid (1.13 g). (M+H)$^+$=278.8 m/e Step 3. 4-[5-(azetidine-1-carbonyl)-pyridin-2-ylamino]-6-chloro-2-methyl-2H-pyridazin-3-one

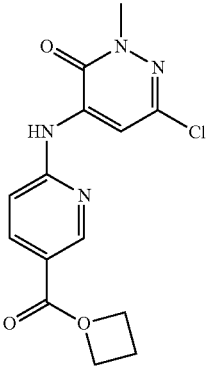

6-(6-chloro-2-methyl-3-oxo-2,3-dihydropyridazin-4-ylamino)nicotinic acid (100 mg, 356 μmol, Eq: 1.00) was suspended in dichloromethane. Oxalyl chloride (67.8 mg, 46.8 μl, 534 μmol, Eq: 1.5) was added followed by a drop of DMF (10 μl) and the reaction mixture was stirred for 2 hr at room temperature. The reaction mixture was concentrated. The acid chloride was used as is for the next step. It was dissolved in dichloromethane (10 ml). To that was added azetidine (20.3 mg, 24.0 µl, 356 µmol, Eq: 1.00) followed by DIEA (230 mg, 311 µl, 1.78 mmol, Eq: 5) and the reaction was stirred over night at room temperature. The reaction mixture was diluted with dichloromethane, washed with a saturated sodium carbonate solution, washed with brine, dried over sodium sulfate, filtered and concentrated to give a light brown solid (145 mg) which was triturated with DCM/Hex/EtOAc to give the desired product as a yellow solid (56 mg). $(M+H)^+=320.0$ m/e Step 4. Preparation of 2-(3-{5-[5-(Azetidine-1-carbonyl)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one 4-(5-(azetidine-1-carbonyl)pyridin-2-ylamino)-6-chloro-2-methylpyridazin-3(2H)-one (56 mg, 175 µmol, Eq: 1.00), potassium (2-(acetoxymethyl)-3-(6-tert-butyl-8-fluoro-1-oxophthalazin-2(1H)-yl)phenyl)trifluoroborate (83.1 mg, 175 µmol, Eq: 1), x-phos (13.0 mg, 27.3 µmol, Eq: 0.156) and potassium phosphate tribasic (81.8 mg, 385 µmol, Eq: 2.2) were dissolved in a 10% aq. methanol solution (10 ml). The reaction was degassed. Finally bis(dibenzylideneacetone)palladium (9.06 mg, 15.8 µmol, Eq: 0.09) was added and the reaction mixture was stirred at 100° C. for 100 min. The reaction mixture was filtered and the filtercake was washed with methanol. The combined filtrate and washes were concentrated and extracted with ethyl acetate and water. The organic phase was separated, washed with brine, dried over sodium sulfate, filtered and concentrated. The residue was dissolved in ethyl acetate. Hexane was added until precipitate was formed. The precipitate was filtered off to give crude product as a yellow solid. This crude product was purified by silica gel chromatography to give a yellow solid which was dissolved in dioxane. 1 M sodium hydroxide solution (263 µl, 263 µmol, Eq: 1.5) was added and the resulting reaction mixture was stirred over night at room temperature. The reaction mixture was treated again with 1 M sodium hydroxide solution (10 eq.) and heated to 40° C. for 4 hr. The reaction was diluted with dichlormethane and water and extracted with dichloromethane to give a crude solid after concentration. The crude product was purified by 12 g silica gel chromatography eluting with 0-10% methanol in ethyl acetate to afford 2-(3-{5-[5-(Azetidine-1-carbonyl)-pyridin-2-ylamino]-1-methyl-6-oxo-1,6-dihydro-pyridazin-3-yl}-2-hydroxymethyl-phenyl)-6-tert-butyl-8-fluoro-2H-phthalazin-1-one as a light yellow solid (16 mg). $(M+H)^+=610.1$ m/e $^1$H NMR (300 MHz, CHLOROFORM-d) δ ppm 1.42 (s, 9H) 2.38 (quin, J=7.70 Hz, 2H) 3.79 (br. s, 1H) 3.91 (s, 3H) 4.25 (br. s, 2H) 4.43 (br. s, 4H) 6.99 (d, J=8.69 Hz, 1H) 7.44-7.70 (m, 5H) 8.00 (dd, J=8.69, 2.27 Hz, 1H) 8.29 (d, J=2.64 Hz, 1H) 8.47 (s, 1H) 8.60 (d, J=2.27 Hz, 1H) 8.71 (s, 1H).

Preparation of I-48

Example 48

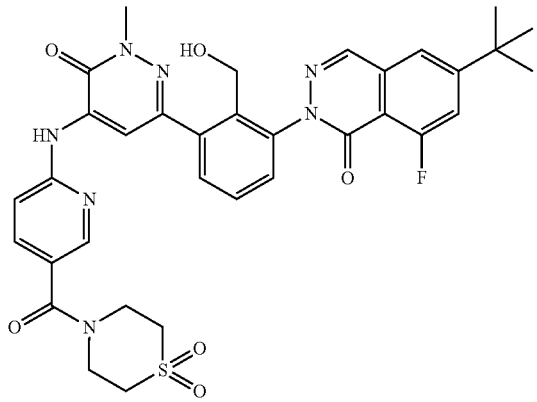 [SMILES: Cn1nc(-c2cccc(-n3ncc4cc(C(C)(C)C)cc(F)c4c3=O)c2CO)cc(Nc2ccc(C(=O)N3CCS(=O)(=O)CC3)cn2)c1=O]

Preparation by a similar procedure to Example 47, except substituting thiomorpholine 1,1-dioxide for azetidine in step 3, afforded 6-tert-Butyl-2-(3-{5-[5-(1,1-dioxo-1λ$^6$-thiomorpholine-4-carbonyl)-pyridin-2-ylamino]-1-methyl-6-oxo-1,6-dihydro-pyridazin-3-yl}-2-hydroxymethyl-phenyl)-8-fluoro-2H-phthalazin-1-one $(M+H)^+=687.9$ m/e $^1$H NMR (300 MHz, CHLOROFORM-d) δ ppm 1.43 (s, 9H) 3.12 (br. s., 4H) 3.76 (br. s, 1H) 3.91 (s, 3H) 4.13 (br. s., 4H) 4.44 (s, 2H) 7.04 (d, J=8.31 Hz, 1H) 7.44-7.67 (m, 5H) 7.78 (dd, J=8.69, 2.27 Hz, 1H) 8.29 (d, J=2.64 Hz, 1H) 8.46 (d, J=2.27 Hz, 1H) 8.54 (s, 1H) 8.71 (s, 1H)

Preparation of I-49

Example 49

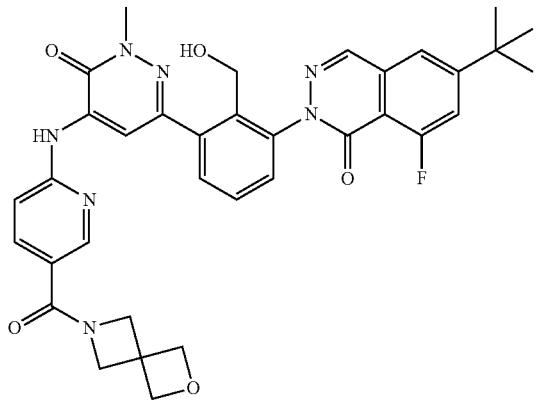 [SMILES: Cn1nc(-c2cccc(-n3ncc4cc(C(C)(C)C)cc(F)c4c3=O)c2CO)cc(Nc2ccc(C(=O)N3CC4(COC4)C3)cn2)c1=O]

Preparation by a similar procedure to Example 47, except substituting 2-oxa-6-aza-spiro[3.3]heptane for azetidine in step 3, afforded 2-(3-(5-(5-(2-oxa-6-azaspiro[3.3]heptane-6-carbonyl)pyridin-2-ylamino)-1-methyl-6-oxo-1,6-dihydro-pyridazin-3-yl)-2-(hydroxymethyl)phenyl)-6-tert-butyl-8-fluorophthalazin-1(2H)-one (M+H)⁺=652.1 m/e
¹H NMR (300 MHz, CHLOROFORM-d) δ: ppm 1.43 (s, 9H) 3.92 (s, 3H) 4.29-4.61 (m, 6H) 4.83 (s, 4H) 7.00 (d, J=8.69 Hz, 1H) 7.45-7.68 (m, 5H) 7.98 (dd, J=8.69, 2.27 Hz, 1H) 8.29 (d, J=2.64 Hz, 1H) 8.50 (s, 1H) 8.58 (d, J=2.27 Hz, 1H) 8.72 (s, 1H)

Preparation of I-50

Example 50

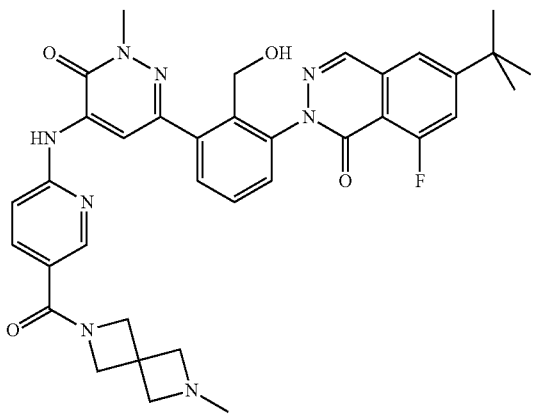 [SMILES: CN1CC2(C1)CN(C(=O)c1ccc(Nc3cc(-c4cccc(-n5ncc6cc(C(C)(C)C)cc(F)c6c5=O)c4CO)nn(C)c3=O)nc1)C2]

Preparation by a similar procedure to Example 1, except substituting 2-methyl-2,6-diaza-spiro[3.3]heptane for azetidine in step 3, afforded 6-tert-butyl-8-fluoro-2-(2-(hydroxymethyl)-3-(1-methyl-5-(5-(6-methyl-2,6-diazaspiro[3.3]heptane-2-carbonyl)pyridin-2-ylamino)-6-oxo-1,6-dihydropyridazin-3-yl)phenyl)phthalazin-1(2H)-one
(M+H)⁺=665.1 m/e
¹H NMR (300 MHz, CHLOROFORM-d) δ: ppm 1.38-1.47 (m, 9H) 2.38 (s, 3H) 3.52 (br. s., 4H) 3.91 (s, 3H) 4.26 (br. s., 2H) 4.44 (s, 4H) 6.96 (d, J=8.69 Hz, 1H) 7.41-7.78 (m, 5H) 7.95 (dd, J=8.50, 2.08 Hz, 1H) 8.30 (d, J=2.27 Hz, 1H) 8.48 (s, 1H) 8.57 (d, J=1.89 Hz, 1H) 8.68-8.71 (m, 1H)

Preparation of I-51

Example 51

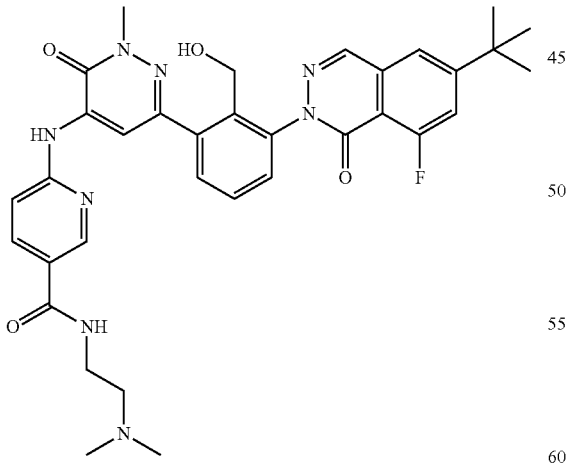

Preparation by a similar procedure to Example 47, except substituting N,N-dimethyl-ethane-1,2-diamine for azetidine in step 3, afforded 6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)-N-(2-(dimethylamino)ethyl)nicotinamide (M+H)⁺=641.1 m/e
¹H NMR (300 MHz, CHLOROFORM-d) δ: ppm 1.41 (s, 9H) 2.35 (s, 6H) 2.62 (br. t, J=1.00, 1.00 Hz, 2H) 3.56 (t, J=4.90 Hz, 2H) 3.84 (m, J=7.20 Hz, 1H) 3.92 (s, 3H) 4.44 (br. s., 2H) 6.98 (d, J=8.69 Hz, 1H) 7.46-7.71 (m, 5H) 8.14 (d, J=9.44 Hz, 1H) 8.29 (s, 1H) 8.46 (s, 1H) 8.72-8.82 (m, 2H)

Preparation of I-52

Example 52

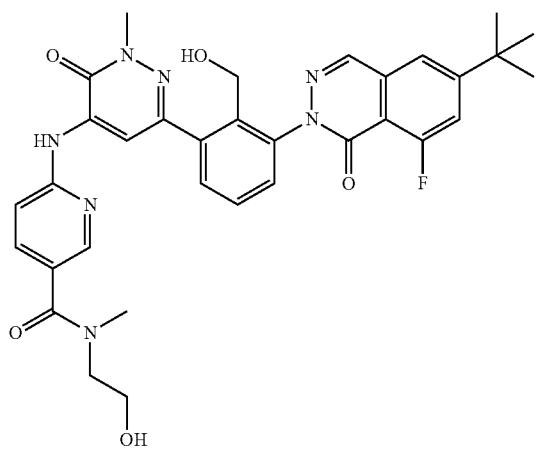 [SMILES: CN(CCO)C(=O)c1ccc(Nc2cc(-c3cccc(-n4ncc5cc(C(C)(C)C)cc(F)c5c4=O)c3CO)nn(C)c2=O)nc1]

Preparation by a similar procedure to Example 47, except substituting 2-methylamino-ethanol for azetidine in step 3, afforded 6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)-N-(2-hydroxyethyl)-N-methylnicotinamide
(M+H)⁺=628.1 m/e
¹H NMR (300 MHz, CHLOROFORM-d) δ: ppm 1.39-1.47 (m, 9H) 3.15 (s, 3H) 3.59-3.90 (m, 4H) 3.91 (s, 3H) 4.43 (d, J=5.67 Hz, 2H) 6.99 (d, J=8.31 Hz, 1H) 7.45-7.69 (m, 5H) 7.81 (dd, J=8.69, 2.27 Hz, 1H) 8.29 (d, J=2.64 Hz, 1H) 8.46 (s, 1H) 8.50 (d, J=2.27 Hz, 1H) 8.70 (s, 1H)

Preparation of I-53

Example 53

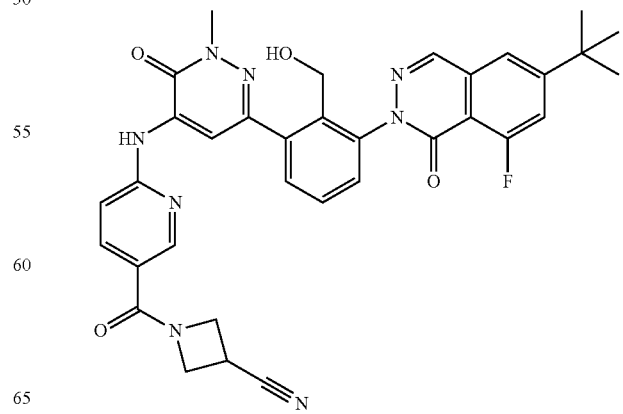

221

Preparation by a similar procedure to Example 47, except substituting azetidine-3-carbonitrile for azetidine in step 3, afforded 1-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)nicotinoyl)azetidine-3-carbonitrile MS (m−1)=633.2

$^1$H NMR (300 MHz, CHLOROFORM-d) δ: ppm 1.44 (s, 9H) 3.54-3.68 (m, 2H) 3.93 (s, 3H) 4.44 (s, 2H) 4.49-4.71 (m, 2H) 7.01 (d, J=8.69 Hz, 1H) 7.45-7.70 (m, 5H) 7.98 (dd, J=1.00 Hz, 1H) 8.30 (d, J=2.27 Hz, 1H) 8.50 (s, 1H) 8.56 (s, 1H) 8.73 (s, 1H)

Preparation of I-54

Example 54

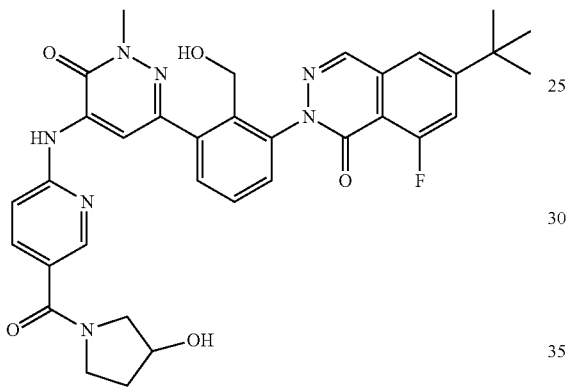

Preparation by a similar procedure to Example 47, except substituting pyrrolidin-3-ol for azetidine in step 3, afforded 6-tert-butyl-8-fluoro-2-(2-(hydroxymethyl)-3-(5-(5-(3-hydroxypyrrolidine-1-carbonyl)pyridin-2-ylamino)-1-methyl-6-oxo-1,6-dihydropyridazin-3-yl)phenyl)phthalazin-1(2H)-one (M−H)=640.1 m/e

222

$^1$H NMR (300 MHz, CHLOROFORM-d) δ: ppm 1.41 (s, 9H) 1.99 (br. s., 2H) 3.38-4.00 (m, 9H) 4.42 (br. s., 2H) 4.48-4.60 (m, 1H) 6.93-7.07 (m, 1H) 7.39-7.72 (m, 5H) 7.80-7.89 (m, 1H) 8.29 (d, J=2.27 Hz, 1H) 8.43-8.61 (m, 2H) 8.70 (s, 1H)

Preparation of I-55

Example 55

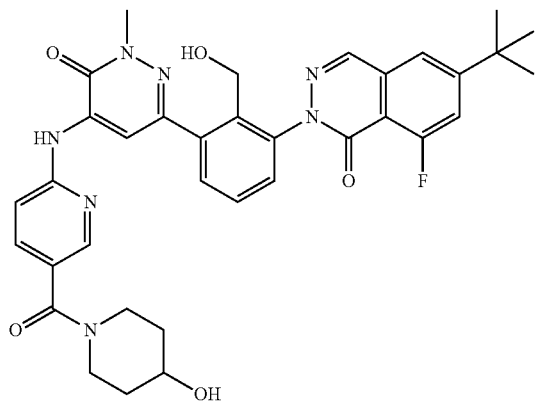 [SMILES: Cn1nc(-c2cccc(-n3ncc4cc(C(C)(C)C)cc(F)c4c3=O)c2CO)cc(Nc2ccc(C(=O)N3CCC(O)CC3)cn2)c1=O]

Preparation by a similar procedure to Example 47, except substituting 1-methylamino-pentan-3-ol for azetidine in step 3, afforded 6-tert-butyl-8-fluoro-2-(2-(hydroxymethyl)-3-(5-(5-(4-hydroxypiperidine-1-carbonyl)pyridin-2-ylamino)-1-methyl-6-oxo-1,6-dihydropyridazin-3-yl)phenyl)phthalazin-1(2H)-one. (M+H)$^+$=654.0 m/e. $^1$H NMR (300 MHz, CHLOROFORM-d) δ: ppm 1.42 (s, 9H) 1.58 (br. s., 3H) 1.87-2.02 (m, 2H) 3.29-3.45 (m, 2H) 3.65 (s, 1H) 3.81 (t, J=1.00 Hz, 1H) 3.93 (s, 3H) 3.97-4.07 (m, 2H) 4.43 (d, J=6.42 Hz, 2H) 6.99 (d, J=8.31 Hz, 1H) 7.45-7.69 (m, 5H) 7.76 (dd, J=8.31, 2.27 Hz, 1H) 8.29 (d, J=2.64 Hz, 1H) 8.41-8.45 (m, 2H) 8.69 (s, 1H)

Preparation of I-56

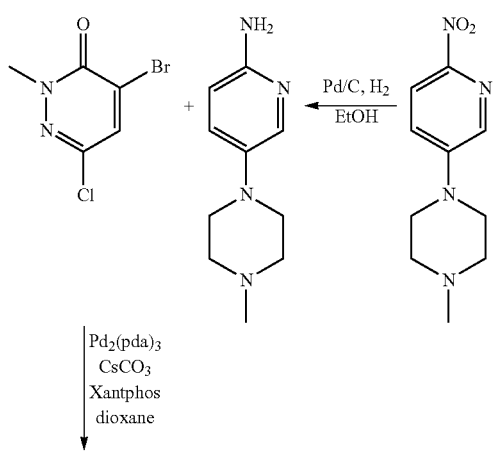

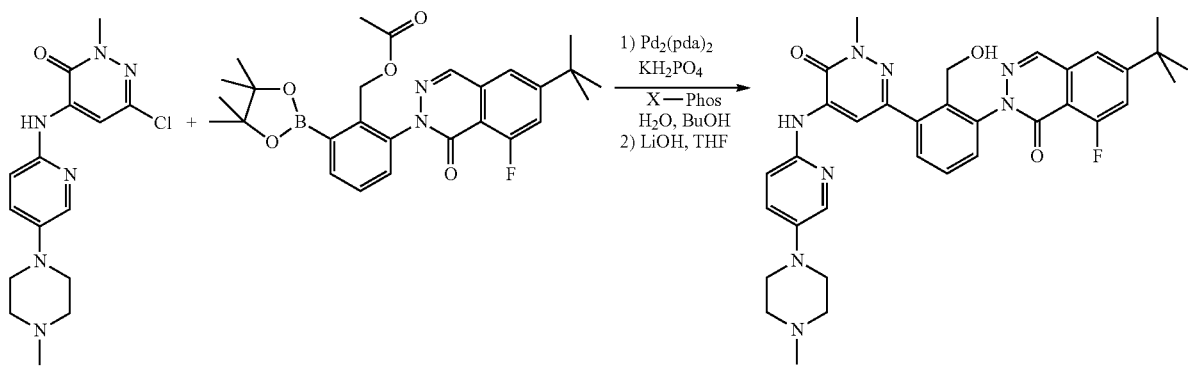

Example 56

6-tert-Butyl-8-fluoro-2-(2-hydroxymethyl-3-{1-methyl-5-[5-(4-methyl-piperazin-1-yl)-pyridin-2-ylamino]-6-oxo-1,6-dihydro-pyridazin-3-yl}-phenyl)-2H-phthalazin-1-one

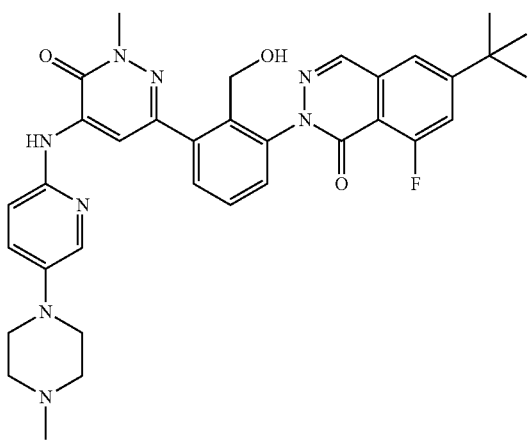 [SMILES: CN1CCN(c2ccc(Nc3cc(-c4cccc(-n5ncc6cc(C(C)(C)C)cc(F)c6c5=O)c4CO)nn(C)c3=O)nc2)CC1]

To a solution of 1-methyl-4-(6-nitropyridin-3-yl)piperazine (500 mg, 2.25 mmol) in ethanol (20 mL) was added 10% Pd/C (80 mg, 0.75 mmol) and the resulting mixture was stirred under a hydrogen atmosphere for 18 h. The reaction mixture was filtered through celite, washed with ethanol and concentrated to give 5-(4-methylpiperazin-1-yl)pyridin-2-amine.

A solution of 5-(4-methylpiperazin-1-yl)pyridin-2-amine (172 mg, 0.90 mmol), 4-bromo-6-chloro-2-methylpyridazin-3(2H)-one (200 mg, 0.90 mmol) cesium carbonate (1.02 g, 3.13 mmol) and 4,5-bis(diphenylphosphino)-9,9-dimethylxanthene (77.7 mg, 0.13 mmol) in dioxane (10 ml) was flushed with argon before tris(dibenzylideneacetone)dipalladium(0) (61.5 mg, 0.07 mmol) was added and the resulting solution was heated at 90° C. for 18 h. The mixture was cooled to room temperature and diluted with dichloromethane and water. The layers were separated and the aqueous layer was extracted with dichloromethane (2×25 mL). The organic layers were combined, dried over magnesium sulfate. The resulting mixture was filtered and concentrated in vacuo. The residue was triturated with methanol and dichloromethane and filtered, washed with ether and dried to give 6-chloro-4-[5-(4-methyl-piperazin-1-yl)-pyridin-2-ylamino]-2-methyl-2H-pyridazin-3-one (223 mg, 74%) as a yellow solid.

A solution of 2-(6-tert-butyl-8-fluoro-1-oxophthalazin-2(1H)-yl)-6-(4,4,5,5-tetramethyl-1,3,2-dioxaborolan-2-yl) benzyl acetate (221 mg, 0.45 mmol), 6-chloro-4-(5-(4-methylpiperazin-1-yl)pyridin-2-ylamino)-2-methylpyridazin-3(2H)-one (100 mg, 0.30 mmol), potassium phosphate (159 mg, 0.75 mmol) and dicyclohexyl(2',4',6'-triisopropylbiphenyl-2-yl)phosphine (14.2 mg, 0.03 mmol) in butanol (4 ml) and water (1 mL) was flushed with argon before (bis[dibenzylideneacetone]dipalladium) (8.59 mg, 0.01 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×50 mL). The layers were separated and the organic phase dried over magnesium sulfate. The mixture was filtered and concentrated in vacuo. The residue was purified by flash chromatography (silica gel, 24 g, 1% to 14% methanol in dichloromethane) and recrystallized from dichloromethane and isopropyl acetate to give 6-tert-butyl-2-(3-{5-[5-(4-methyl-piperazin-1-yl)-pyridin-2-ylamino]-1-methyl-6-oxo-1,6-dihydro-pyridazin-3-yl}-2-hydroxymethyl-phenyl)-8-fluoro-2H-phthalazin-1-one (45 mg, 24%) as a light yellow solid: mp 260-264° C.; $^1$H NMR (300 MHz, DMSO-$d_6$) δ: ppm 1.38 (s, 9H) 2.20 (s, 3H) 2.33-2.46 (m, 4H) 2.98-3.19 (m, 4H) 3.77 (s, 3H) 4.27-4.69 (m, 3H) 7.24-8.07 (m, 8H) 8.32-8.74 (m, 2H) 9.23 (s, 1H).

Preparation of I-57
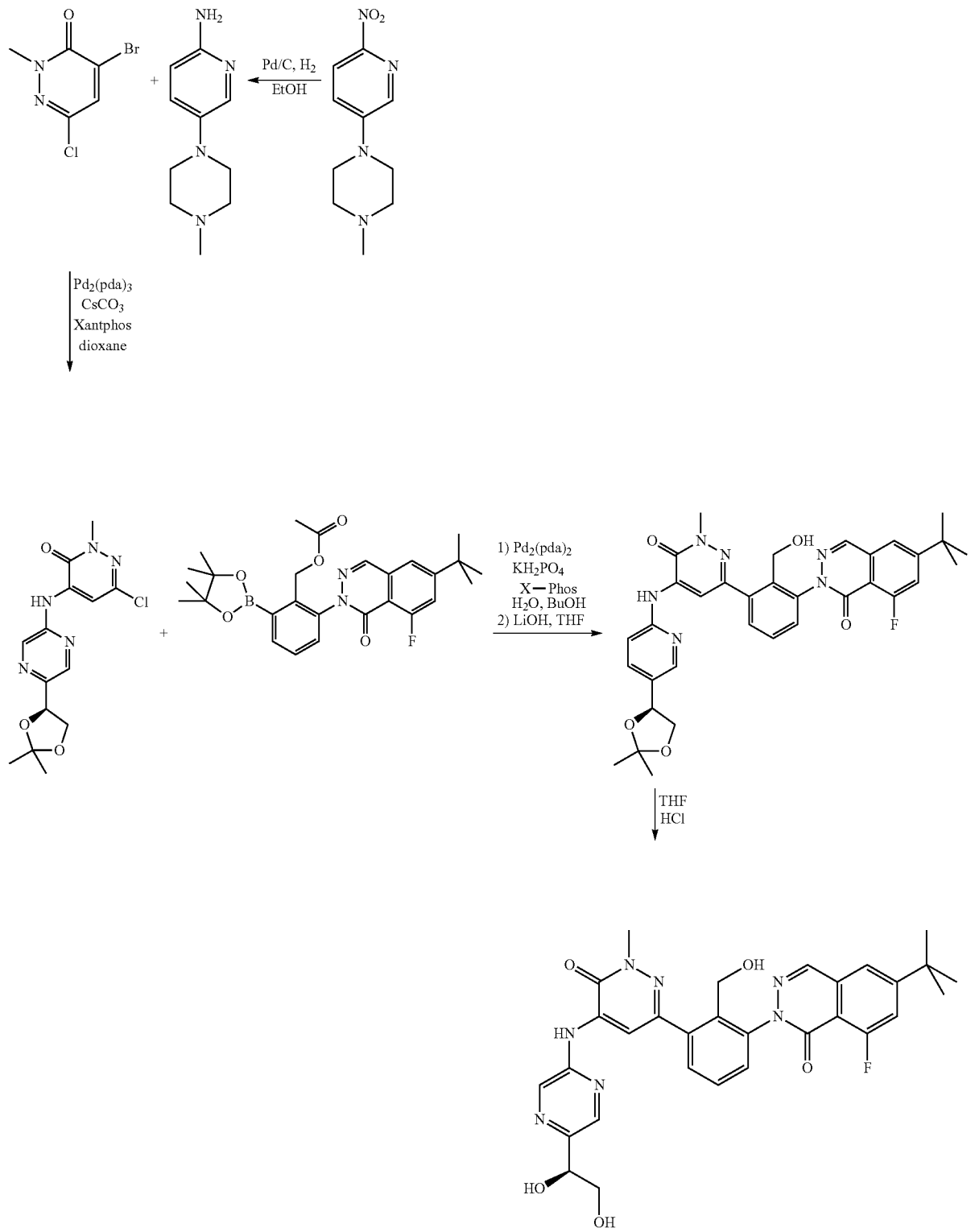

Example 57

6-tert-Butyl-2-(3-{5-[5-((S)-1,2-dihydroxy-ethyl)-pyrazin-2-ylamino]-1-methyl-6-oxo-1,6-dihydro-pyridazin-3-yl}-2-hydroxymethyl-phenyl)-8-fluoro-2H-phthalazin-1-one

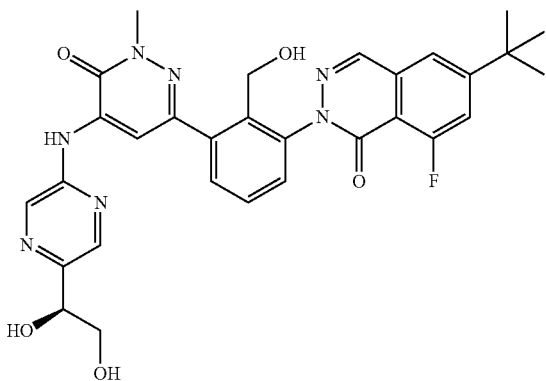 [SMILES: Cn1nc(-c2cccc(-n3ncc4cc(C(C)(C)C)cc(F)c4c3=O)c2CO)cc(Nc2cnc([C@H](O)CO)cn2)c1=O]

A solution of (S)-5-(2,2-dimethyl-1,3-dioxolan-4-yl)pyrazin-2-amine (prepared as in WO2004052869, Example 54, 175 mg, 0.90 mmol), 4-bromo-6-chloro-2-methylpyridazin-3(2H)-one (200 mg, 0.90 mmol), cesium carbonate (1.02 g, 3.13 mmol) and 4,5-bis(diphenylphosphino)-9,9-dimethylxanthene (77.7 mg, 0.13 mmol) in dioxane (10 ml) was flushed with argon before tris(dibenzylideneacetone)dipalladium(0) (61.5 mg, 0.07 mmol) was added and the resulting solution was heated at 90° C. for 18 h. The mixture was cooled to room temperature and diluted with dichloromethane (50 mL) and water. The layers were separated and the aqueous layer was extracted with dichloromethane (2×25 mL). The organic layers were combined, dried over magnesium sulfate. The resulting mixture was filtered and concentrated in vacuo. The precipitate formed was isolated by filtration, washed with ether and dried under vacuum to give 6-chloro-4-[5-((S)-2,2-dimethyl-[1,3]dioxolan-4-yl)-pyrazin-2-ylamino]-2-methyl-2H-pyridazin-3-one (150 mg, 50%) as a yellow solid.

A solution of 2-(6-tert-butyl-8-fluoro-1-oxophthalazin-2(1H)-yl)-6-(4,4,5,5-tetramethyl-1,3,2-dioxaborolan-2-yl)benzyl acetate (307 mg, 0.62 mmol), (S)-6-chloro-4-(5-(2,2-dimethyl-1,3-dioxolan-4-yl)pyrazin-2-ylamino)-2-methylpyridazin-3(2H)-one (150 mg, 0.44 mmol), potassium phosphate (236 mg, 0.01 mmol) and dicyclohexyl(2',4',6'-triisopropylbiphenyl-2-yl)phosphine (21.2 mg, 0.04 mmol) in butanol (4 ml) and water (1 mL) was flushed with argon before (bis[dibenzylideneacetone]dipalladium) (12.8 mg, 0.02 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×150 mL). The layers were separated and the organic phase dried over magnesium sulfate. The mixture was filtered and concentrated in vacuo. The residue was purified by flash chromatography (silica gel, 24 g, 1% to 7% methanol in dichloromethane) to give (S)-6-tert-butyl-2-(3-(5-(5-(2,2-dimethyl-1,3-dioxolan-4-yl)pyrazin-2-ylamino)-1-methyl-6-oxo-1,6-dihydropyridazin-3-yl)-2-(hydroxymethyl)phenyl)-8-fluorophthalazin-1(2H)-one (99 mg, 36%) as a light yellow solid.

To a solution of (S)-6-tert-butyl-2-(3-(5-(5-(2,2-dimethyl-1,3-dioxolan-4-yl)pyrazin-2-ylamino)-1-methyl-6-oxo-1,6-dihydropyridazin-3-yl)-2-(hydroxymethyl)phenyl)-8-fluorophthalazin-1(2H)-one (99 mg, 0.16 mmol) in tetrahydrofuran (4 mL) was added hydrochloric acid (1.0 N, 4 mL) and the resulting mixture stirred at room temperature overnight. The reaction mixture was poured into a saturated ammonium chloride solution and extracted with dichloromethane (2×50 mL). The combined organic layers were dried over magnesium sulfate. The mixture was filtered and evaporated and the residue recrystallized from dichloromethane and isopropyl acetate to give 6-tert-butyl-2-(3-{5-[5-((S)-1,2-dihydroxy-ethyl)-pyrazin-2-ylamino]-1-methyl-6-oxo-1,6-dihydro-pyridazin-3-yl}-2-hydroxymethyl-phenyl)-8-fluoro-2H-phthalazin-1-one (15.4 mg, 17%) as an off white solid: Mp. 218-224° C.; $^1$H NMR (300 MHz, DMSO-$d_6$) δ ppm 1.37 (s, 10H) 3.44-3.95 (m, 5H) 4.32-4.82 (m, 4H) 5.40 (d, J=4.91 Hz, 1H) 7.22-7.99 (m, 5H) 8.16-8.65 (m, 3H) 8.78 (s, 1H) 9.81 (s, 1H).

Preparation of I-58

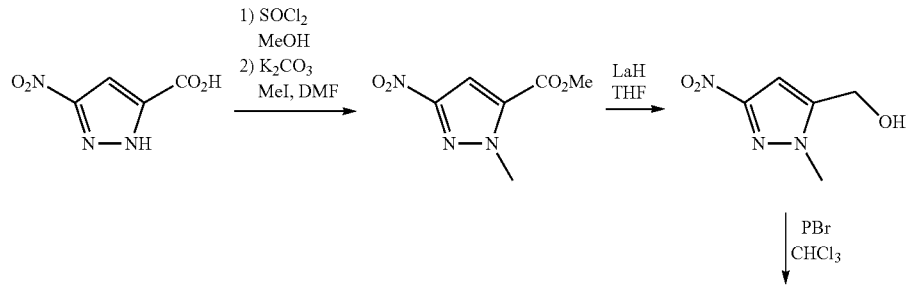

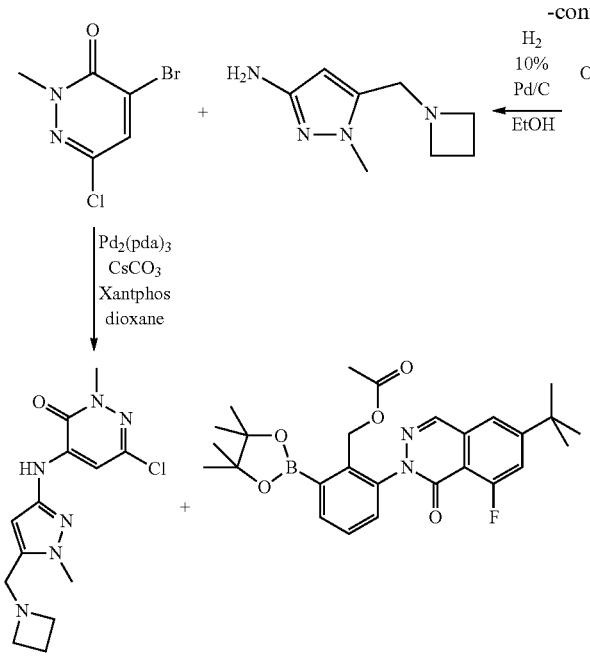
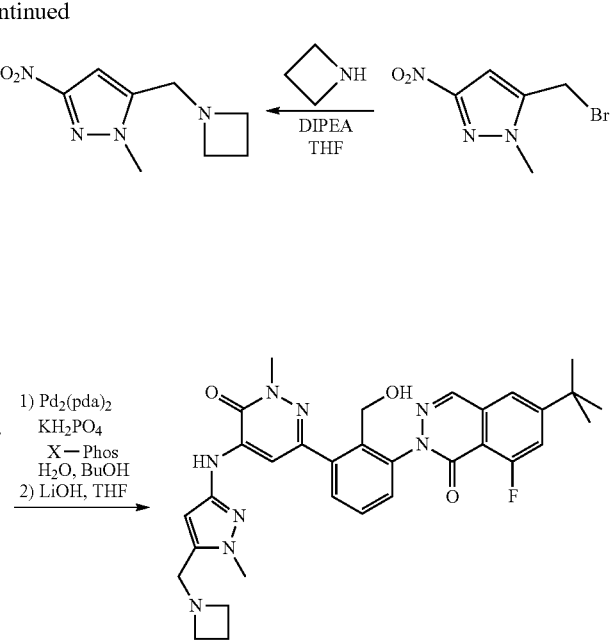

Example 58

Acetic acid 2-[5-(5-azetidin-1-ylmethyl-1-methyl-4H-pyrazol-3-ylamino)-1-methyl-6-oxo-1,6-dihydro-pyridazin-3-yl]-6-(6-tert-butyl-8-fluoro-1-oxo-1H-phthalazin-2-yl)-benzyl ester

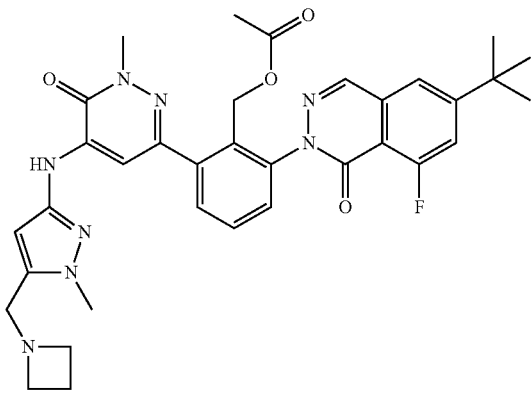 [SMILES: CC(=O)OCc1c(-c2cc(Nc3cc(CN4CCC4)n(C)n3)c(=O)n(C)n2)cccc1-n1ncc2cc(C(C)(C)C)cc(F)c2c1=O]

To a solution of 5-nitro-1H-pyrazole-3-carboxylic acid (1.13 g, 7.19 mmol) in anhydrous methanol (20 ml) at to 0° C. was added thionyl chloride (2.23 g, 1.37 ml, 18.7 mmol) dropwise. The resulting solution was heated to reflux for 2 h. The cooled solution was evaporated to dryness to give 5-nitro-2H-pyrazole-3-carboxylic acid methyl ester (1.17 g, 95%) as a white solid.

To a solution of methyl 5-nitro-1H-pyrazole-3-carboxylate (1.87 g, 10.9 mmol) in anhydrous dimethyl formamide (20 mL) was added potassium carbonate (3.02 g, 21.9 mmol) and methyl iodide (2.02 g, 0.89 mL, 14.2 mmol) and the resulting solution stirred at room temperature for 18 h. The resulting mixture was diluted with water (1×150 mL) and extracted with dichloromethane (3×75 mL). The combined organic layers were dried over magnesium sulfate. The mixture was filtered and evaporated and the residue purified by flash chromatography (silica gel, 25 g, 20% to 60% dichloromethane in hexanes) to give a mixture of 2-methyl-5-nitro-2H-pyrazole-3-carboxylic acid methyl ester and 1-methyl-5-nitro-1H-pyrazole-3-carboxylic acid methyl ester (1.64 g, 81%) as a white solid.

To a solution of 2-methyl-5-nitro-2H-pyrazole-3-carboxylic acid methyl ester and 1-methyl-5-nitro-1H-pyrazole-3-carboxylic acid methyl ester (1.18 g, 6.37 mmol) in tetrahydrofuran (20 mL) at 0° C. was added a lithium aluminum hydride solution (1.0M in tetrahydrofuran, 7.65 mL, 7.65 mmol) drop wise. The resulting mixture was stirred at 0° C. for 20 min. To this solution was added ethyl acetate (1 mL) followed by few crystals of sodium sulphate decahydrate. The resulting mixture was stirred for 30 min then filtered, the filter cake washed with ethyl acetate and the filtrate evaporated. The residue was purified by flash chromatography (silica gel, 80 g, 50% to 70% ethyl acetate in hexanes) to give 1-methyl-3-nitro-1H-pyrazol-5-yl)methanol (496 mg, 50%) as a white solid.

To a solution of (1-methyl-3-nitro-1H-pyrazol-5-yl) methanol (496 mg, 3.16 mmol) in chloroform (10 mL) at 0° C. was added phosphorus tribromide (854 mg, 0.30 mL, 3.16 mmol) drop wise via syringe. The resulting solution was warmed to room temperature and stirred for 1 h. The resulting solution was cooled to 0° C. and diluted with dichloromethane (50 ml). The resulting solution was made basic (pH 8.5) with saturated aqueous sodium bicarbonate (20 mL). The layers were separated, and the aqueous layer was extracted with dichloromethane (3×20 mL). The combined organic layers were dried over magnesium sulfate. The resulting mixture was filtered and concentrated in vacuo and the residue purified by flash chromatography (silica gel, 40 g, 20% to 40% ethyl acetate in hexanes) to give 5-(bromomethyl)-1-methyl-3-nitro-1H-pyrazole (436 mg, 63%) as a white solid.

To a solution of 5-(bromomethyl)-1-methyl-3-nitro-1H-pyrazole (436 mg, 1.98 mmol) in tetrahydrofuran (10 mL)

was added azetidine (141 mg, 0.17 mL, 2.48 mmol) and diisopropylethyl amine (307 mg, 0.42 mL, 2.38 mmol) drop wise and the resulting mixture was stirred at room temperature for 24 h. The solution was concentrated and the residue dissolved in dichloromethane (50 mL), washed with water (50 mL). The aqueous layer was extracted with methylene chloride (2×50 mL) and the organic phases combined and dried over magnesium sulfate. The resulting mixture was filtered and evaporated and the residue purified by flash chromatography (40 g, 1% to 5% methanol in dichloromethane) to give 5-(azetidin-1-ylmethyl)-1-methyl-3-nitro-1H-pyrazole (349 mg, 90%) as a colorless oil.

To a solution of 5-(azetidin-1-ylmethyl)-1-methyl-3-nitro-1H-pyrazole (349 mg, 1.78 mmol) in ethanol (20 mL) was treated with palladium on carbon (10%, 50 mg). The resulting mixture was stirred under a hydrogen (1 atm) for 48 h. The reaction mixture was filtered through a celite pad, and the pad washed with ethanol. The filtrate was concentrated in vacuo to give 5-(azetidin-1-ylmethyl)-1-methyl-1H-pyrazol-3-amine (292 mg, 99%) as a light yellow oil.

A solution of 5-(azetidin-1-ylmethyl)-1-methyl-1H-pyrazol-3-amine (292 mg, 1.76 mmol), 4-bromo-6-chloro-2-methylpyridazin-3(2H)-one (393 mg, 1.76 mmol) cesium carbonate (2.00 g, 6.15 mmol) and 4,5-bis(diphenylphosphino)-9,9-dimethylxanthene (152 mg, 0.26 mmol) in dioxane (10 ml) was flushed with argon before tris(dibenzylideneacetone) dipalladium(0) (121 mg, 0.13 mmol) was added and the resulting solution was heated at 90° C. for 18 h. The mixture was cooled to room temperature and diluted with dichloromethane (50 mL) and water. The layers were separated and the aqueous layer was extracted with dichloromethane (2×25 mL). The organic layers were combined, dried over magnesium sulfate. The resulting mixture was filtered and concentrated in vacuo. The precipitate formed was isolated by filtration, washed with ether and dried under vacuum to give 4-(5-(azetidin-1-ylmethyl)-1-methyl-1H-pyrazol-3-ylamino)-6-chloro-2-methylpyridazin-3(2H)-one (272 mg, 50%) as a light yellow solid.

A solution of 2-(6-tert-butyl-8-fluoro-1-oxophthalazin-2 (1H)-yl)-6-(4,4,5,5-tetramethyl-1,3,2-dioxaborolan-2-yl) benzyl acetate (498 mg, 1.01 mmol), 4-(5-(azetidin-1-ylmethyl)-1-methyl-1H-pyrazol-3-ylamino)-6-chloro-2-methylpyridazin-3(2H)-one (183 mg, 0.59 mmol), potassium phosphate (315 mg, 1.48 mmol) and dicyclohexyl(2',4',6'-triisopropylbiphenyl-2-yl)phosphine (28.3 mg, 0.06 mmol) in butanol (4 ml) and water (1 mL) was flushed with argon before (bis[dibenzylideneacetone]dipalladium) (17.0 mg, 0.03 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×150 mL). The layers were separated and the organic phase dried over magnesium sulfate. The mixture was filtered and concentrated in vacuo. The residue was purified by flash chromatography (silica gel, 24 g, 1% to 10% methanol in dichloromethane) to give acetic acid 2-[5-(5-azetidin-1-ylmethyl-1-methyl-1H-pyrazol-3-ylamino)-1-methyl-6-oxo-1,6-dihydro-pyridazin-3-yl]-6-(6-tert-butyl-8-fluoro-1-oxo-1H-phthalazin-2-yl)-benzyl ester (112 mg, 32%) as an off white solid: mp. 214-217° C.; $^1$H NMR (300 MHz, DMSO-$d_6$) δ ppm 1.01-1.55 (m, 10H) 1.72-2.08 (m, 2H) 2.90-3.67 (m, 11H) 4.28-4.62 (m, 3H) 6.08 (s, 1H) 7.22-8.08 (m, 6H) 8.50 (d, J=1.89 Hz, 1H) 9.15 (s, 1H).

Preparation of I-59

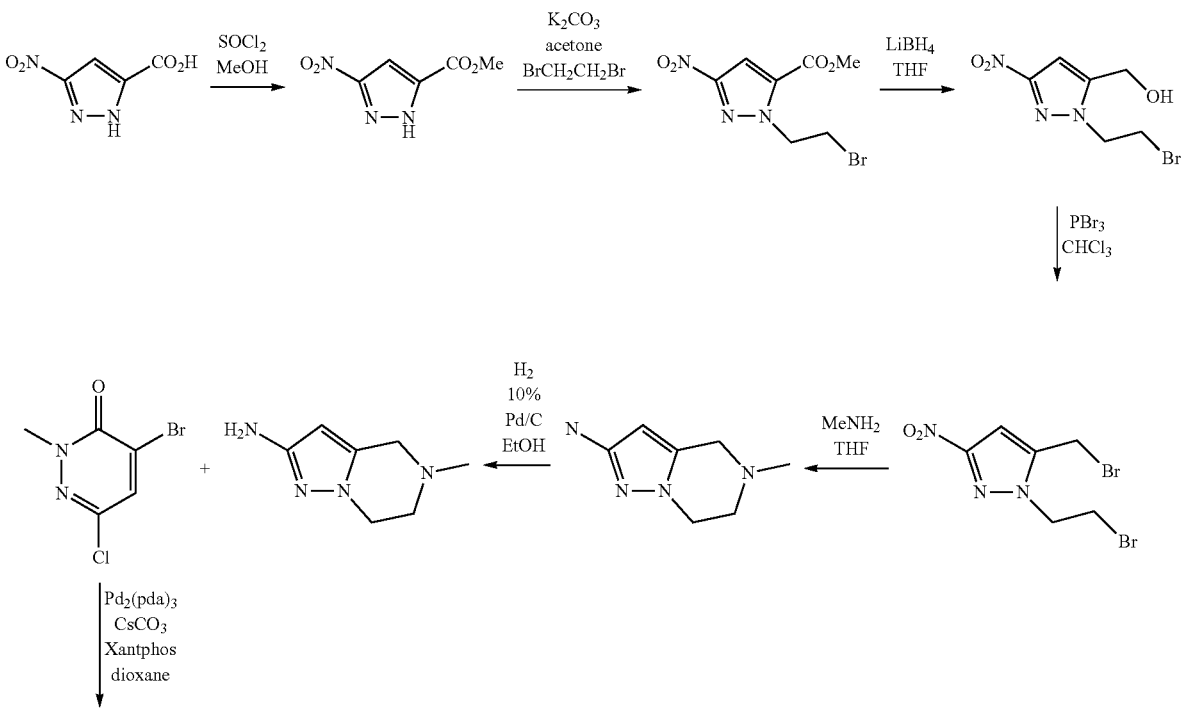

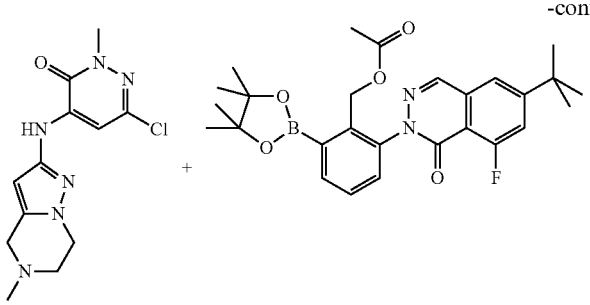 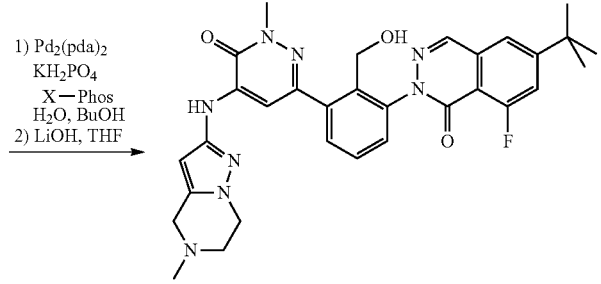

1) Pd$_2$(pda)$_2$
KH$_2$PO$_4$
X—Phos
H$_2$O, BuOH
2) LiOH, THF

Example 59

Acetic acid 2-(6-tert-butyl-8-fluoro-1-oxo-1H-phthalazin-2-yl)-6-[1-methyl-5-(5-methyl-4,5,6,7-tetrahydro-pyrazolo[1,5-a]pyrazin-2-ylamino)-6-oxo-1,6-dihydro-pyridazin-3-yl]-benzyl ester

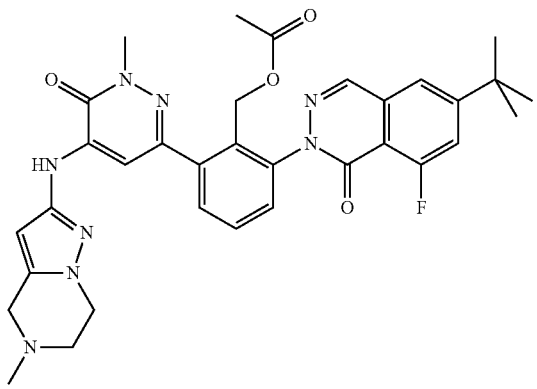 [SMILES: CC(=O)OCc1c(-c2cc(Nc3cc4n(n3)CCN(C)C4)c(=O)n(C)n2)cccc1-n1ncc2cc(C(C)(C)C)cc(F)c2c1=O]

To a solution of 5-nitro-1H-pyrazole-3-carboxylic acid (2.0 g, 12.7 mmol) in anhydrous methanol (20 ml) at to 0° C. was added thionyl chloride (3.94 g, 2.42 ml, 33.1 mmol) drop wise. The resulting solution was heated to reflux for 2 h. The cooled solution was evaporated to dryness and the residue was treated with methanol (20 ml). The resulting solution was evaporated to dryness to give 5-nitro-2H-pyrazole-3-carboxylic acid methyl ester (1.97 g, 90%) as a white solid.

To a solution of methyl 5-nitro-1H-pyrazole-3-carboxylate (1 g, 5.84 mmol) in acetone (30 mL) was added potassium carbonate (4.04 g, 29.2 mmol) and 1,2-dibromoethane (3.29 g, 1.51 mL, 17.5 mmol) and the resulting solution heated to reflux for 2 h. The resulting mixture was cooled to 0° C. filtered and concentrated and the residue purified by flash chromatography (silica gel, 60 g, 20% to 40% ethyl acetate in hexanes) to give methyl 1-(2-bromoethyl)-3-nitro-1H-pyrazole-5-carboxylate (1.03 g, 63%) as a white solid.

To a solution of methyl 1-(2-bromoethyl)-3-nitro-1H-pyrazole-5-carboxylate (500 mg, 1.8 mmol) in tetrahydrofuran (20 mL) was cooled to 0° C. and lithium borohydride (78.3 mg, 3.6 mmol) was added in portions. The resulting mixture was allowed to warm to room temperature overnight. To the resulting mixture was added ethyl acetate (20 ml) and water (50 ml). The biphasic mixture was separated and aqueous layer extracted with ethyl acetate (3×20 mL). The combined organic layers were dried over magnesium sulfate and the resulting mixture was filtered and concentrated in vacuo. The residue was purified by flash chromatography (silica gel, AnaLogix system SF25-40 g column, 20% to 60% ethyl acetate in hexanes) to give (1-(2-bromoethyl)-3-nitro-1H-pyrazol-5-yl)methanol (158 mg, 35%) as a light yellow oil.

To as solution of (1-(2-bromoethyl)-3-nitro-1H-pyrazol-5-yl)methanol (482 mg, 1.93 mmol) in chloroform (20 mL) was cooled to 0° C. was added phosphorus tribromide (522 mg, 0.18 mL, 1.93 mmol) drop wise via syringe. The resulting solution was warmed to room temperature and stirred for 1 h. The resulting solution was cooled to 0° C. and diluted with dichloromethane (50 ml). The resulting solution was made basic (pH 8.5) with saturated aqueous sodium bicarbonate was (20 mL). The layers were separated, and the aqueous layer was extracted with dichloromethane (3×20 mL). The combined organic layers were washed with brine (30 mL), dried over magnesium sulfate. The resulting mixture was filtered and concentrated in vacuo to give 1-(2-bromoethyl)-5-(bromomethyl)-3-nitro-1H-pyrazole (469 mg, 78%) as a yellow solid.

To a solution of 1-(2-bromoethyl)-5-(bromomethyl)-3-nitro-1H-pyrazole (469 mg, 1.5 mmol) in tetrahydrofuran (20 mL) was added methylamine (2.0M in tetrahydrofuran, 5.25 mL, 10.5 mmol) drop wise and the resulting mixture was stirred at room temperature for 76 h. The solution was concentrated and the resulting solid was stirred with a mixture of ethyl acetate (10 mL) and 10% aqueous potassium carbonate (10 mL). The layers were separated and the aqueous phase was extracted with ethyl acetate (2×30 mL). The organic layers were combined and dried over magnesium sulfate. The resulting mixture was filtered and reduced in volume in vacuo and the precipitate removed by filtration. The filtrate was concentrated and the residue purified by flash chromatography (silica gel, 12 g, 2% to 10% methanol in dichloromethane) to give 5-methyl-2-nitro-4,5,6,7-tetrahydropyrazolo[1,5-a]pyrazine (67 mg, 24%) as a light yellow solid.

To a solution of 5-methyl-2-nitro-4,5,6,7-tetrahydro-pyrazolo[1,5-a]pyrazine (67 mg, 0.37 mmol) in ethanol (15 mL) was treated with palladium on carbon (10%, 20 mg) and flushed with argon. The resulting mixture was stirred under a hydrogen (1 atm) overnight. The reaction mixture was filtered through a celite pad, and the pad washed with ethanol. The filtrate was concentrated in vacuo to give 5-methyl-4,5,6,7-tetrahydropyrazolo[1,5-a]pyrazin-2-amine (72 mg, quantitative) as a light yellow oil.

A solution of 5-methyl-4,5,6,7-tetrahydropyrazolo[1,5-a]pyrazin-2-amine (55.7 mg, 0.37 mmol), 4-bromo-6-chloro-2-methylpyridazin-3(2H)-one (81.8 mg, 0.37 mmol) cesium carbonate (417 mg, 1.28 mmol) and 4,5-bis(diphenylphosphino)-9,9-dimethylxanthene (31.8 mg, 0.05 mmol) in dioxane (6 ml) was flushed with argon before tris(dibenzylideneacetone)dipalladium(0) (25.1 mg, 0.03 mmol) was added and the resulting solution was heated at 90° C. for 18 h. The mixture was cooled to room temperature and diluted with dichloromethane (50 mL) and water. The layers were separated and the aqueous layer was extracted with dichloromethane (2×25 mL). The organic layers were combined, dried over magnesium sulfate. The resulting mixture was filtered and concentrated in vacuo. The residue was purified by flash chromatography (silica gel, 24 g, 2% to 7% methanol in dichloromethane) to give 6-chloro-2-methyl-4-(5-methyl-4,5,6,7-tetrahydropyrazolo[1,5-a]pyrazin-2-ylamino)pyridazin-3(2H)-one (61 mg, 57%) as a light yellow solid.

A solution of 2-(6-tert-butyl-8-fluoro-1-oxophthalazin-2 (1H)-yl)-6-(4,4,5,5-tetramethyl-1,3,2-dioxaborolan-2-yl) benzyl acetate (153 mg, 0.31 mmol), 6-chloro-2-methyl-4-(5-methyl-4,5,6,7-tetrahydropyrazolo[1,5-a]pyrazin-2-ylamino)pyridazin-3(2H)-one (61 mg, 0.21 mmol), potassium phosphate (110 mg, 0.52 mmol) and dicyclohexyl (2',4',6'-triisopropylbiphenyl-2-yl)phosphine (9.87 mg, 0.02 mmol) in butanol (4 ml) and water (1 mL) was flushed with argon before (bis[dibenzylideneacetone]dipalladium) (5.95 mg, 0.01 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×150 mL). The layers were separated and the organic phase dried over magnesium sulfate. The mixture was filtered and concentrated in vacuo. The residue was purified by flash chromatography (silica gel, 24 g, 1% to 10% methanol in dichloromethane) to give acetic acid 2-(6-tert-butyl-8-fluoro-1-oxo-1H-phthalazin-2-yl)-6-[1-methyl-5-(5-methyl-4,5,6,7-tetrahydro-pyrazolo[1,5-a]pyrazin-2-ylamino)-6-oxo-1,6-dihydro-pyridazin-3-yl]-benzyl ester (56 mg, 46%) as a light yellow solid: mp. 188-193° C.; $^1$H NMR (300 MHz, DMSO-$d_6$) δ ppm 1.37 (s, 9H) 2.34 (s, 3H) 2.77 (t, J=5.29 Hz, 2H) 3.50 (s, 2H) 3.63-4.06 (m, 5H) 4.17-4.67 (m, 3H) 5.98 (s, 1H) 7.33-8.05 (m, 6H) 8.50 (d, J=2.64 Hz, 1H) 9.24 (s, 1H).

Preparation of I-60

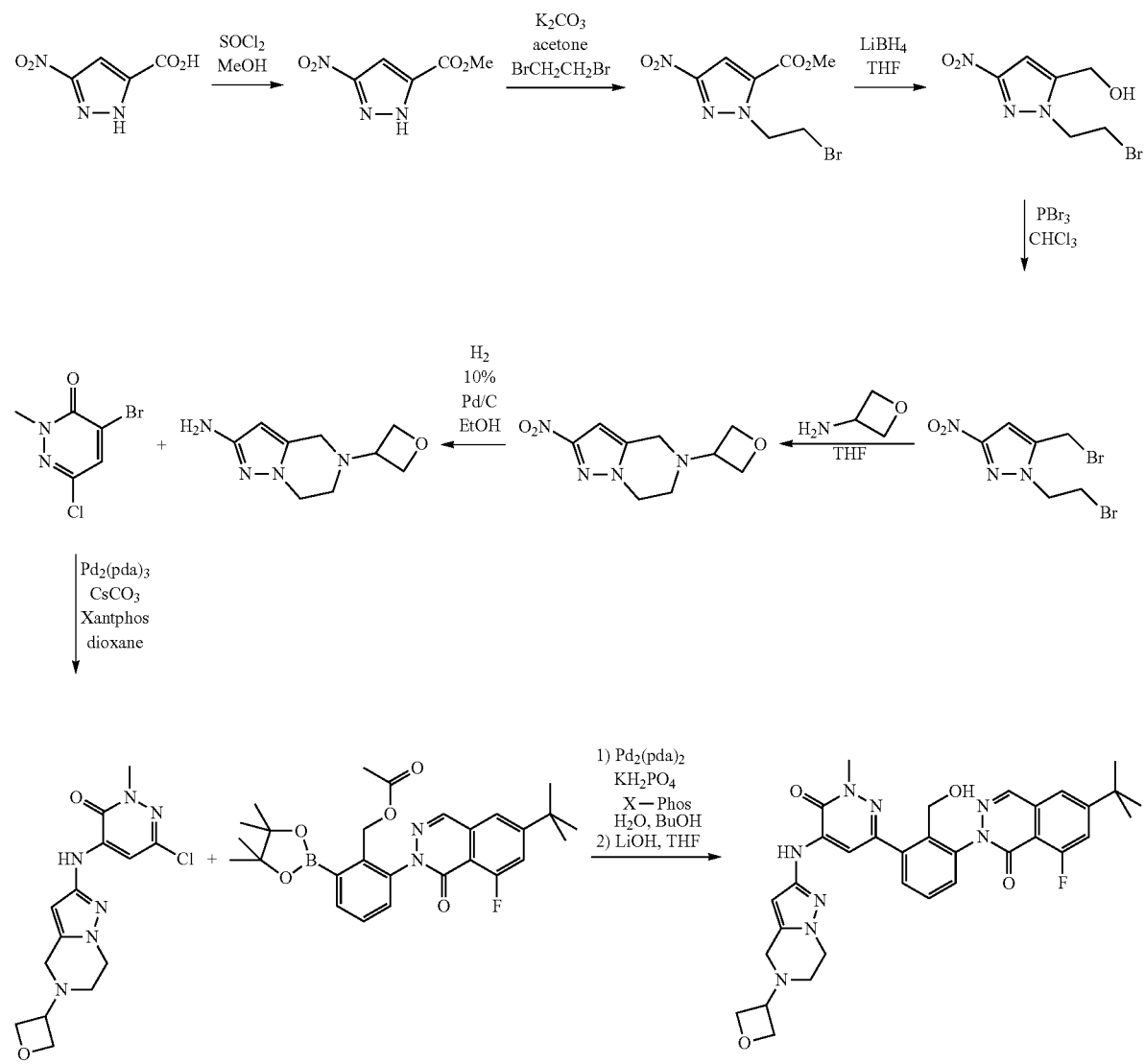

Example 60

Acetic acid 2-(6-tert-butyl-8-fluoro-1-oxo-1H-phthalazin-2-yl)-6-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-benzyl ester

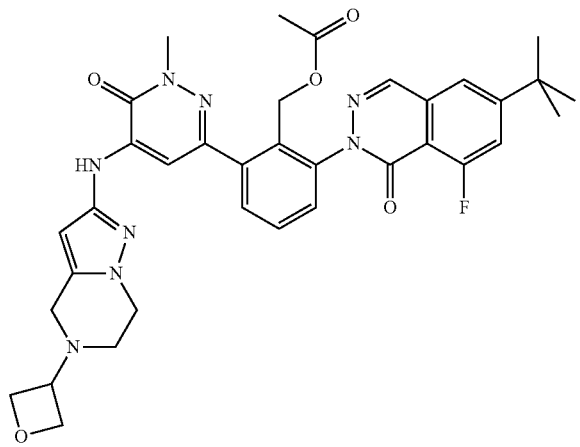 [SMILES: CC(=O)OCc1c(-c2cc(Nc3cc4n(n3)CCN(C3COC3)C4)c(=O)n(C)n2)cccc1-n1ncc2cc(C(C)(C)C)cc(F)c2c1=O]

To a solution of 5-nitro-1H-pyrazole-3-carboxylic acid (4.88 g, 31.1 mmol) in anhydrous methanol (50 ml) at to 0° C. was added thionyl chloride (9.61 g, 5.9 ml, 80.8 mmol) drop wise. The resulting solution was heated to reflux for 2 h. The cooled solution was evaporated to dryness to give 5-nitro-2H-pyrazole-3-carboxylic acid methyl ester (4.58 g, 86%) as a off-white solid.

To a solution of methyl 5-nitro-1H-pyrazole-3-carboxylate (5.97 g, 34.9 mmol) in acetone (100 mL) was added potassium carbonate (24.1 g, 174 mmol) and 1,2-dibromoethane (19.7 g, 9.02 ml, 105 mmol) and the resulting solution heated to reflux for 2 h and then stirred at room temperature overnight. The resulting mixture was filtered and concentrated and the residue purified by flash chromatography (silica gel, SF65-400 g, 20% to 70% ethyl acetate in hexanes) to give methyl 1-(2-bromoethyl)-3-nitro-1H-pyrazole-5-carboxylate (4.86 g, 50%) as a light yellow solid.

To a suspension of lithium borohydride (755 mg, 34.7 mmol) in tetrahydrofuran (100 mL) at 0° C. was added a solution of methyl 1-(2-bromoethyl)-3-nitro-1H-pyrazole-5-carboxylate (4.82 g, 17.3 mmol) in tetrahydrofuran (10 mL) drop wise maintain a temperature below 0° C. The resulting solution was allowed to stir at room temperature for 2 h. To the resulting mixture was slowly added ethyl acetate (20 ml) and water (20 ml). The biphasic mixture was separated and aqueous layer extracted with ethyl acetate (3×20 mL). The combined organic layers were dried over magnesium sulfate and the resulting mixture was filtered and concentrated in vacuo to give (1-(2-bromoethyl)-3-nitro-1H-pyrazol-5-yl)methanol (4.24 g, 98%) as a light yellow oil.

To a solution of (1-(2-bromoethyl)-3-nitro-1H-pyrazol-5-yl)methanol (4.24 g, 17.0 mmol) in chloroform (100 mL) was cooled to 0° C. was added phosphorus tribromide (4.59 g, 1.6 ml, 17.0 mmol) drop wise via syringe. The resulting solution was warmed to room temperature and stirred for 2 h. The resulting solution was cooled to 0° C. and diluted with dichloromethane (50 ml). The resulting solution was made basic (pH 8.5) with saturated aqueous sodium bicarbonate was (20 mL). The layers were separated, and the aqueous layer was extracted with dichloromethane (3×50 mL). The combined organic layers were washed with brine (30 mL), dried over magnesium sulfate. The resulting mixture was filtered and concentrated in vacuo and the residue purified by flash chromatography (silica gel, SF40-240 g, 15% to 40% ethyl acetate in hexanes) to give 1-(2-bromoethyl)-5-(bromomethyl)-3-nitro-1H-pyrazole (3.56 g, 67%) as a white solid.

To a solution of 1-(2-bromoethyl)-5-(bromomethyl)-3-nitro-1H-pyrazole (500 mg, 1.6 mmol) in acetonitrile (20 mL) was added oxetan-3-amine (140 mg, 1.92 mmol) and diisopropylethyl amine (372 mg, 0.50 ml, 2.88 mmol) drop wise and the resulting mixture was stirred at room temperature for 24 h. The solution was concentrated and the residue dissolved in ethyl acetate (50 mL), washed with water (50 mL) and dried over magnesium sulfate. The resulting mixture was filtered and evaporated and the residue purified by flash chromatography (SF25-40 g, 50% to 100% ethyl acetate in hexanes) to give 2-nitro-5-oxetan-3-yl-4,5,6,7-tetrahydro-pyrazolo[1,5-a]pyrazine (255 mg, 71%) as a light yellow solid.

To a solution of 2-nitro-5-oxetan-3-yl-4,5,6,7-tetrahydro-pyrazolo[1,5-a]pyrazine (255 mg, 1.13 mmol) in ethanol (20 mL) was treated with palladium on carbon (10%, 60 mg) and flushed with argon. The resulting mixture was stirred under a hydrogen (1 atm) overnight. The reaction mixture was filtered through a celite pad, and the pad washed with ethanol. The filtrate was concentrated in vacuo to give 5-oxetan-3-yl-4,5,6,7-tetrahydro-pyrazolo[1,5-a]pyrazin-2-ylamine (217 mg, 99%) as a off-white solid.

A solution of 5-oxetan-3-yl-4,5,6,7-tetrahydro-pyrazolo[1,5-a]pyrazin-2-ylamine (110 mg, 0.57 mmol), 4-bromo-6-chloro-2-methylpyridazin-3(2H)-one (127 mg, 0.57 mmol) cesium carbonate (646 mg, 1.98 mmol) and 4,5-bis(diphenylphosphino)-9,9-dimethylxanthene (49.2 mg, 0.08 mmol) in dioxane (8 ml) was flushed with argon before tris(dibenzylideneacetone)dipalladium(0) (38.9 mg, 0.04 mmol) was added and the resulting solution was heated at 90° C. for 18 h. The mixture was cooled to room temperature and diluted with dichloromethane (50 mL) and water. The layers were separated and the aqueous layer was extracted with dichloromethane (2×25 mL). The organic layers were combined, dried over magnesium sulfate. The resulting mixture was filtered and concentrated in vacuo. The precipitate formed was isolated by filtration, washed with ether and dried under vacuum to 6-chloro-2-methyl-4-(5-oxetan-3-yl-4,5,6,7-tetrahydro-pyrazolo[1,5-a]pyrazin-2-ylamino)-2H-pyridazin-3-one (113 mg, 59%) as a light yellow solid.

A solution of 2-(6-tert-butyl-8-fluoro-1-oxophthalazin-2 (1H)-yl)-6-(4,4,5,5-tetramethyl-1,3,2-dioxaborolan-2-yl) benzyl acetate (249 mg, 0.50 mmol), 6-chloro-2-methyl-4-(5-oxetan-3-yl-4,5,6,7-tetrahydro-pyrazolo[1,5-a]pyrazin-2-ylamino)-2H-pyridazin-3-one (113 mg, 0.34 mmol), potassium phosphate (178 mg, 0.84 mmol) and dicyclohexyl (2',4',6'-triisopropylbiphenyl-2-yl)phosphine (16.0 mg, 0.03 mmol) in butanol (8 ml) and water (2 mL) was flushed with argon before (bis[dibenzylideneacetone]dipalladium) (9.65 mg, 0.02 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×100 mL). The layers were separated and the organic phase dried over magnesium sulfate. The mixture was filtered and concentrated in vacuo. The residue was purified by flash chromatography (silica gel, 24 g, 1% to 10% methanol in dichloromethane) to give acetic acid 2-(6-tert-butyl-8-fluoro-1-oxo-1H-phthalazin-2-yl)-6-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-benzyl ester (113 mg, 54%) as a light yellow solid: mp. 180-185° C.; $^1$H NMR (300 MHz, DMSO-$d_6$) δ ppm 1.37 (s, 9H) 2.66-2.92 (m, 2H) 3.40-3.83 (m, 6H) 3.98 (t, J=5.48 Hz, 2H) 4.26-4.82 (m, 7H) 6.01 (s, 1H) 7.36-8.00 (m, 6H) 8.50 (d, J=2.64 Hz, 1H) 9.25 (s, 1H).

Preparation of I-61

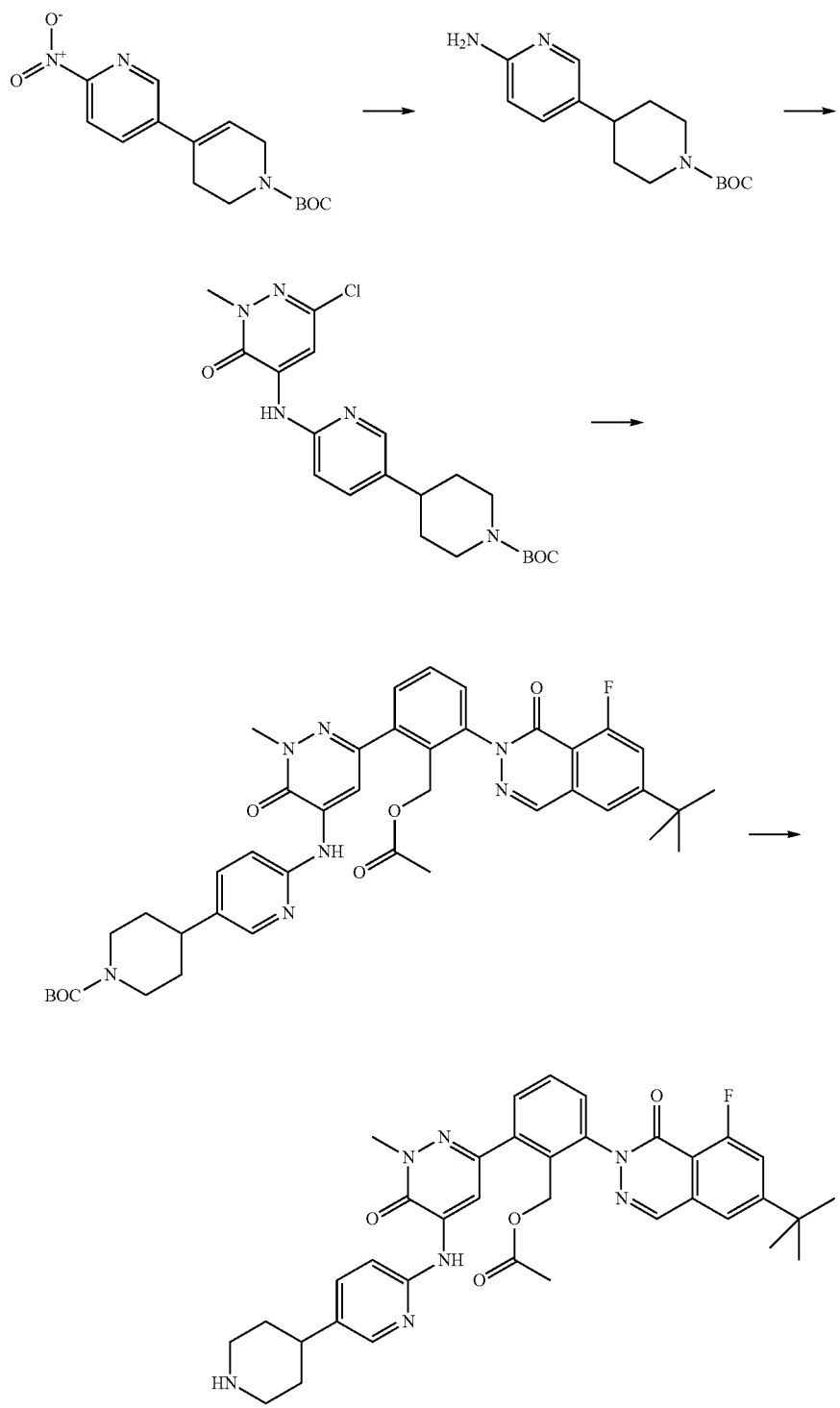

Scheme I

Step 1. Preparation of tert-butyl 4-(6-aminopyridin-3-yl)piperidine-1-carboxylate

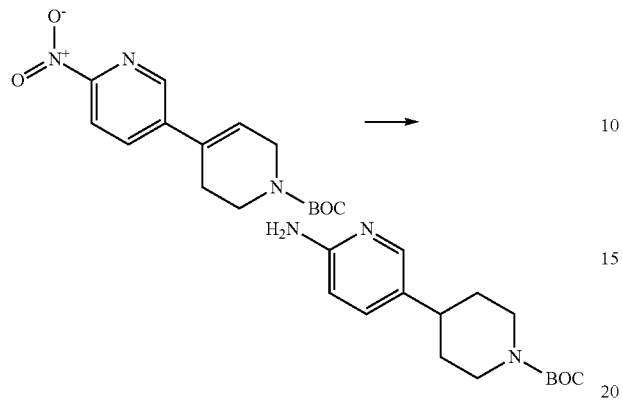

tert-Butyl 4-(6-aminopyridin-3-yl)piperidine-1-carboxylate (3 g, 9.83 mmol) in methanol (50 ml) was hydrogenated under 50 psi with 10% Pd/C (314 mg, 295 μmol) overnight. The catalyst was filtered off and the filtrate was concentrated in vacuo to afford a colorless oil 2.73 g. (M+H)+=278 m/e.

Step 2. Preparation of tert-butyl 4-(6-(6-chloro-2-methyl-3-oxo-2,3-dihydropyridazin-4-ylamino)pyridin-3-yl)piperidine-1-carboxylate

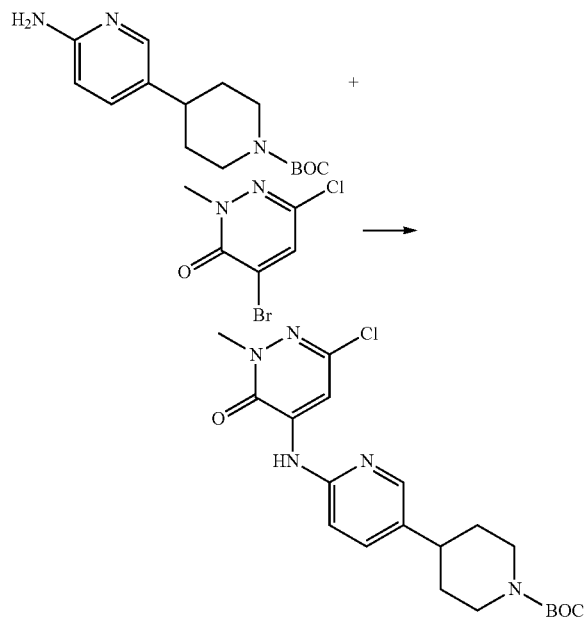

This reaction was carried out under similar conditions to those described in step 6 of the preparation of I-6.

A solution of 4-bromo-6-chloro-2-methylpyridazin-3(2H)-one (2.42 g, 10.8 mmol), tert-butyl 4-(6-aminopyridin-3-yl)piperidine-1-carboxylate (2.73 mg, 9.83 mmol), Xantphos (853 mg, 1.47 mmol) and cesium carbonate (9.61 g, 29.5 mmol) in dry dioxane (80 ml) was vacuum de-gassed and place under an argon atmosphere. To this mixture was added tris(dibenzylideneacetone)dipalladium (0) (203 mg, 197 μmol) and the vacuum de-gas cycle was repeated. The material was heated at 90° C. (oil bath) with vigorous stirring overnight. The flask was cooled to ambient temperature and the contents were filtered through a plug of celite, rinsing well with dioxane, the filtrate concentrated and the resulting residue triturated with 1;1 ratio of ether/ethyl acetate. This provided the desired product as an off-white powder (2.73 g, 71.2%). (M+H)+=420.2 m/e.

Step 3. Preparation of tert-butyl 4-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)piperidine-1-carboxylate

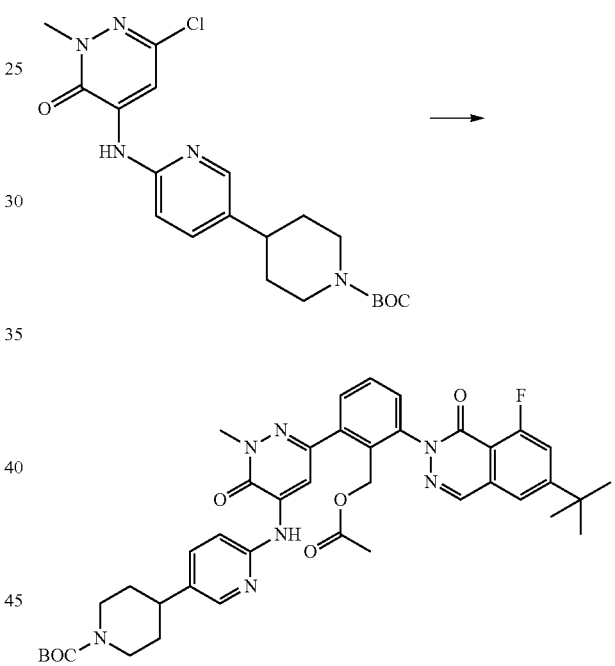

This reaction was carried out under similar conditions to those described above in step 7 of the preparation of Example 6. A solution of tert-butyl 4-(6-(6-chloro-2-methyl-3-oxo-2,3-dihydropyridazin-4-ylamino)pyridin-3-yl)piperidine-1-carboxylate (150 mg, 357 μmol), 2-(6-tert-butyl-8-fluoro-1-oxophthalazin-2(1H)-yl)-6-(4,4,5,5-tetramethyl-1,3,2-dioxaborolan-2-yl)benzyl acetate (177 mg, 357 μmol), xPhos (17 mg, 35.7 μmol) and potassium phosphate (190 mg, 893 mol) in 10 ml of dioxane/water (9:1) was degassed with nitrogen for 10 minutes and bis(dibenzylideneacetone)palladium (0) (10.3, 17.9 μmol) was added.

The reaction mixture was heated to 100° C. for 2 hr. After work up, the product was purified by preparative HPLC on silica gel, using a gradient of 5% to 70% ethylacetate/hexane to afford the desired product as a light yellow solid (220 mg, 81.9%).

Step 4. Preparation of tert-butyl 4-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)piperidine-1-carboxylate

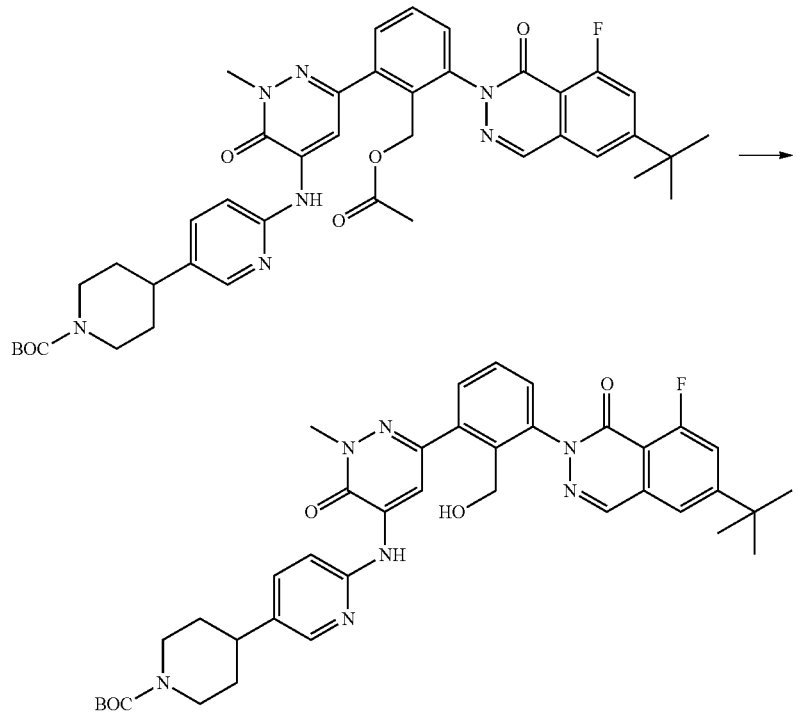

This reaction was carried out under similar conditions to those described above in step 8 of the preparation for I-6. After work up, the desired product was afforded (85 mg, 40.9%). (M+H)+=710.5 m/e.

Example 61

Step 5. Preparation of 6-tert-butyl-8-fluoro-2-(2-(hydroxymethyl)-3-(1-methyl-6-oxo-5-(5-(piperidin-4-yl)pyridin-2-ylamino)-1,6-dihydropyridazin-3-yl)phenyl)phthalazin-1(2H)-one

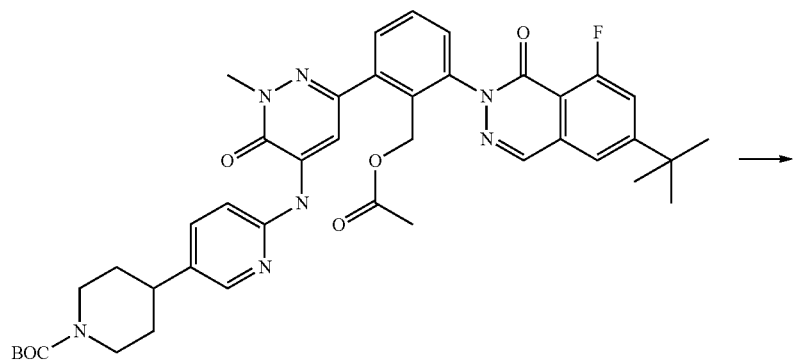

-continued

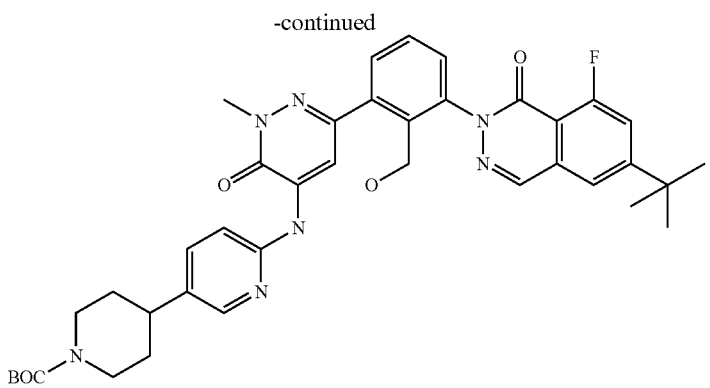

tert-butyl 4-(6-(6-(3-(6-tert-butyl-8-fluoro-1-oxophthalazin-2(1H)-yl)-2-(hydroxymethyl)phenyl)-2-methyl-3-oxo-2,3-dihydropyridazin-4-ylamino)pyridin-3-yl)piperidine-1-carboxylate (85 mg, 120 µmol) was deprotected by treatment with 50% trifluoro acid in dichloromethane (10 mL) for 2 hr. The reaction mixture was concentrated to dryness, then partitioned between ethyl acetate and saturated sodium bicarbonate. The organic phase was dried over sodium sulfate, filtered and concentrated. The resulting crude product was further purified by crystallization from hot isopropylacetate/hexanes. A crystalline product was collected by filtration, providing the desired product as a white solid (48 mg, 65.7%). (M+H)+=610 m/e. $^1$H NMR (300 MHz, CHLOROFORM-d) δ: 8.63 (s, 1H), 8.27-8.33 (m, 2H), 8.21 (d, J=2.0 Hz, 1H), 7.44-7.72 (m, 6H), 6.94 (d, J=8.5 Hz, 1H), 4.46 (s, 2H), 3.88-3.96 (m, 3H), 3.35-3.44 (m, 2H), 2.85-2.99 (m, 2H), 2.65-2.78 (m, 1H), 1.83-1.97 (m, 4H), 1.43 (s, 9H).

Preparation of I-62

Example 62

Preparation of 6-tert-butyl-8-fluoro-2-(2-(hydroxymethyl)-3-(1-methyl-5-(5-(1-(methylsulfonyl)-piperidin-4-yl)pyridin-2-ylamino)-6-oxo-1,6-dihydropyridazin-3-yl)phenyl)phthalazin-1(2H)-one In a 10 mL round-bottomed flask, 6-tert-butyl-8-fluoro-2-(2-(hydroxymethyl)-3-(1-methyl-6-oxo-5-(5-(piperidin-4-yl)pyridin-2-ylamino)-1,6-dihydropyridazin-3-yl)phenyl)phthalazin-1(2H)-one (35.03 mg, 57.5 µmol, Eq: 1.00) was combined with DCM (3 ml) and cooled to 0° C. DIPEA (8.91 mg, 12.0 µl, 68.9 µmol, Eq: 1.2) was added, followed by addition of methanesulfonyl chloride (6.58 mg, 4.48 µl, 57.5 µmol, Eq: 1). The reaction mixture was stirred at 0° C. to room temperature for 1 hr. The crude material was purified by flash chromatography (silica gel, 4 g, 0% to 5% of MeOH in 50% EtOAc/Hexane) to afford white solid (16 mg, 45%). (M+H)+=688.4 m/e. $^1$H NMR (300 MHz, CHLOROFORM-d) δ: 8.56 (s, 1H), 8.48 (br. s., 1H), 8.29 (br. s., 1H), 8.20 (br. s., 1H), 7.42-7.70 (m, 6H), 7.04 (d, J=8.2 Hz, 1H), 4.42 (br. s., 2H), 4.11 (q, J=7.0 Hz, 2H), 3.95 (d, J=11.3 Hz, 2H), 2.82 (s, 3H), 2.74-2.81 (m, 2H), 2.62 (t, J=11.5 Hz, 1H), 2.04 (s, 3H), 1.77-1.99 (m, 4H), 1.42 (s, 9H).

Preparation of I-63

Step 1. Preparation of 4-(5-(1-acetylpiperidin-4-yl)pyridin-2-ylamino)-6-chloro-2-methylpyridazin-3(2H)-one

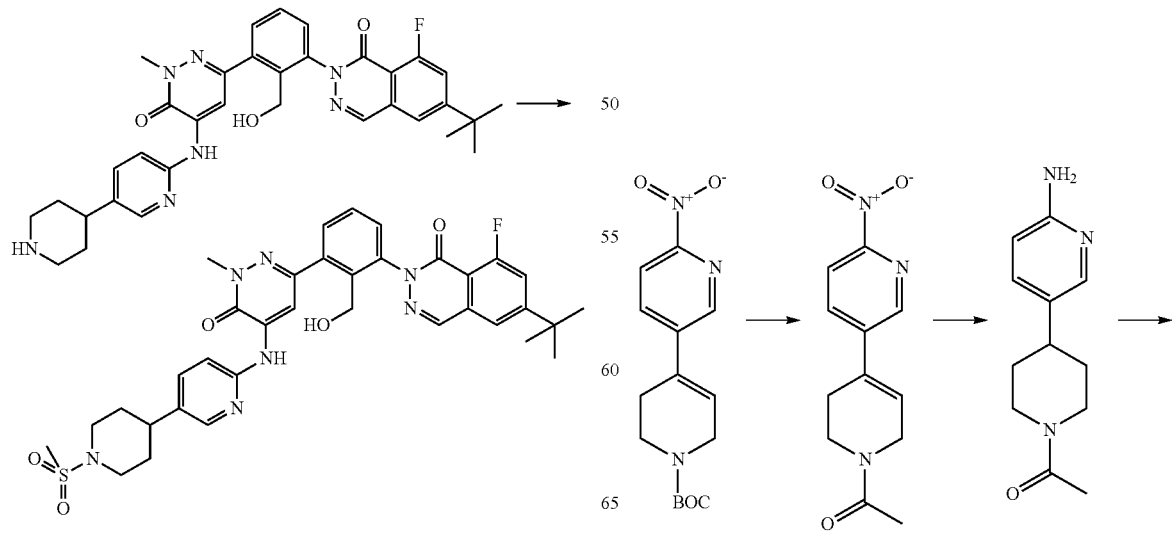

247
-continued

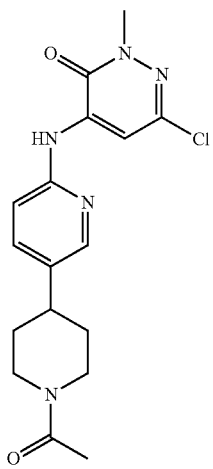

In a 50 mL round-bottomed flask, tert-butyl 4-(6-nitropyridin-3-yl)-5,6-dihydropyridine-1(2H)-carboxylate (250 mg, 819 µmol, Eq: 1.00) was combined with DCM (2.5 ml) to give a light yellow solution. TFA (5 mL) was added and the resulting reaction mixture was stirred at room temperature for 1 hr. until the reaction was complete as determined by LCMS. The crude reaction mixture was concentrated in vacuo, and the resultant residue was dissolved in DCM and cooled to 0° C. TEA (228 µl, 1.64 mmol, Eq: 2.00) was added followed by acetyl chloride (58 µl, 819 µmol, Eq: 1.00) dropwise. The reaction was allowed to warm up to room temperature. The reaction was worked up after half hour by extraction into ethyl acetate. The organic layer was washed with water and sat. NH4Cl, dried over Na2SO4 and concentrated to dryness to afford crude product (187 mg) as off white solid. (M+H)+=247.9 m/e This product was dissolved in methanol (15 ml) and subjected to hydrogenation at 50 psi with 10% Pd/C (87.2 mg, 819 µmol) over night. The catalyst was filtered off and the resulting filtrate was concentrated in vacuo and carried onto the next reaction without further purification.

A solution of 4-bromo-6-chloro-2-methylpyridazin-3(2H)-one (201 mg, 901 µmol), 1-(4-(6-aminopyridin-3-yl)piperidin-1-yl)ethanone (180 mg, 819 µmol), Xantphos (35.5 mg, 61.4 µmol) and cesium carbonate (801 mg, 2.46 mmol) in dry dioxane (6 ml) was vacuum de-gassed and place under argon atmosphere. To this mixture was added tris(dibenzylideneacetone)dipalladium (0) (8.48 mg, 8.19 µmol) and the vacuum de-gas cycle was repeated. The material was heated at 90° C. (oil bath) with vigorous stirring overnight. The flask was cooled to ambient and the contents were filtered through a plug of celite, rinsing well with dioxane. The combined filtrate and washes were concentrated and the resulting residue was triturated with 1:1 ratio of ether/ethyl acetate. This provided the desired product as a off-white powder (66 mg, 22%). (M+H)+=362, 364 m/e 248
Example 63

Step 2. Preparation of 2-(3-(5-(5-(1-acetylpiperidin-4-yl)pyridin-2-ylamino)-1-methyl-6-oxo-1,6-dihydropyridazin-3-yl)-2-(hydroxymethyl)phenyl)-6-tert-butyl-8-fluorophthalazin-1(2H)-one

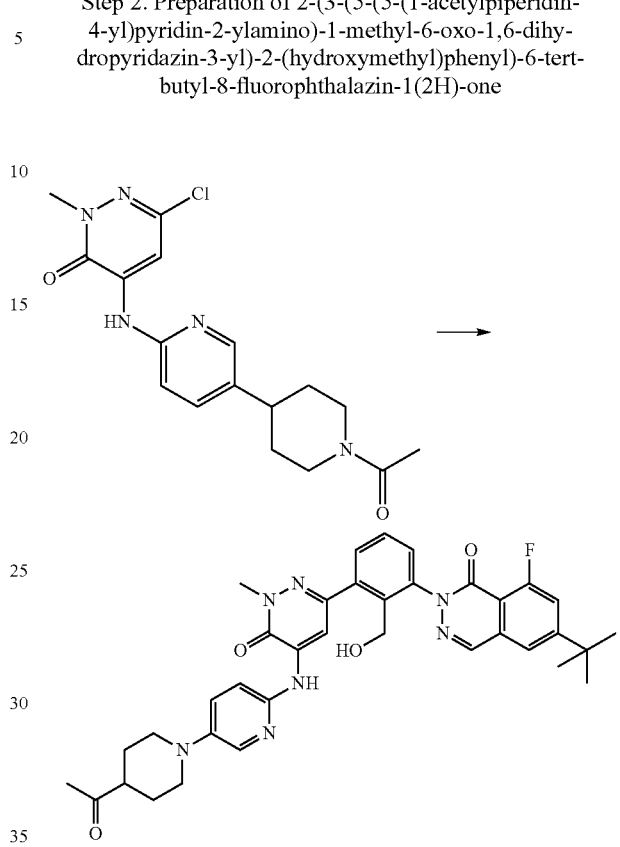

This reaction was carried out under similar conditions to those described above in step 7 of preparation of Example 6. A solution of 4-(5-(1-acetylpiperidin-4-yl)pyridin-2-ylamino)-6-chloro-2-methylpyridazin-3(2H)-one (66 mg, 182 µmol), 2-(6-tert-butyl-8-fluoro-1-oxophthalazin-2(1H)-yl)-6-(4,4,5,5-tetramethyl-1,3,2-dioxaborolan-2-yl)benzyl acetate (90.2 mg, 182 µmol), xPhos (8.7 mg, 18.2 µmol) and potassium phosphate (96.8 mg, 456 µmol) in 10 ml of dioxane/water (9:1) was degassed with nitrogen for 10 minutes and bis(dibenzylideneacetone)palladium (0) (5.24 mg, 9.12 µmol) was added. The reaction mixture was heated to 100° C. for 2 hr. After work up, the product was purified by preparative HPLC on silica gel, using a gradient of 0% to 5% methanol/ethyl acetate. This provided 1:1 ratio of desired compound and 2-(5-(5-(1-acetylpiperidin-4-yl)pyridin-2-ylamino)-1-methyl-6-oxo-1,6-dihydropyridazin-3-yl)-6-(6-tert-butyl-8-fluoro-1-oxophthalazin-2(1H)-yl)benzyl acetate. The resultant mixture was dissolved in methanol (4 ml) and to this was added 2 N NaOH (468 µl). The reaction was stirred at room temperature for 56 h. The methanol was removed by evaporation and the resultant solution was acidified with 1N HCl and extracted with EtOAc. The organic extract was washed with water, dried over NaSO4, filtered and concentrated in vacuo. The crude residue was purified by flash chromatography (silica gel, 4 g, 0% to 50% of MeOH in 50% EtOAc/Hexane) to afford the desired product as a white solid (61 mg, 26.2%). (M+H)+=652.5, 653.7 m/e. $^1$H NMR (300 MHz, CHLOROFORM-d) δ: 8.57 (s, 1H), 8.41 (br. s., 1H), 8.28 (br. s., 1H), 8.19 (br. s., 1H), 7.40-7.71 (m, 6H), 6.99

(d, J=8.2 Hz, 1H), 4.80 (d, J=12.9 Hz, 1H), 4.41 (br. s., 2H), 4.11 (q, J=7.0 Hz, 2H), 3.85-3.99 (m, 3H), 3.18 (t, J=12.7 Hz, 1H), 2.52-2.83 (m, 2H), 2.13 (s, 3H), 1.89 (t, J=12.7 Hz, 2H), 1.60 (br. s., 2H), 1.38-1.46 (m, 9H).

Preparation of I-64

Step 1. Preparation of 4-methyl-1-(6-nitropyridin-3-yl)piperidin-4-ol

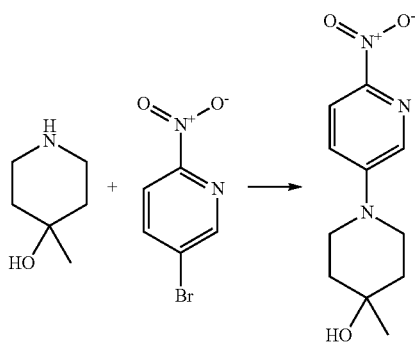

4-Methylpiperidin-4-ol (2.72 g, 23.6 mmol), 5-bromo-2-nitropyridine (3.2 g, 15.8 mmol), and tetrabutylammonium iodide (72 mg, 195 umol) in DMSO (20 ml) was heated to 120° C. for 18 hr. After cooling to room temperature, the reaction mixture was then diluted with EtOAc and washed with water (3×20 mL). The organic phase was then concentrated and triturated with ether to give 4-methyl-1-(6-nitropyridin-3-yl)piperidin-4-ol as a yellow solid (2.55 g, 68.2%). (M+H)+=327.9 m/e.

Step 2. Preparation of 6-chloro-4-(5-(4-hydroxy-4-methylpiperidin-1-yl)pyridin-2-ylamino)-2-methylpyridazin-3(2H)-one

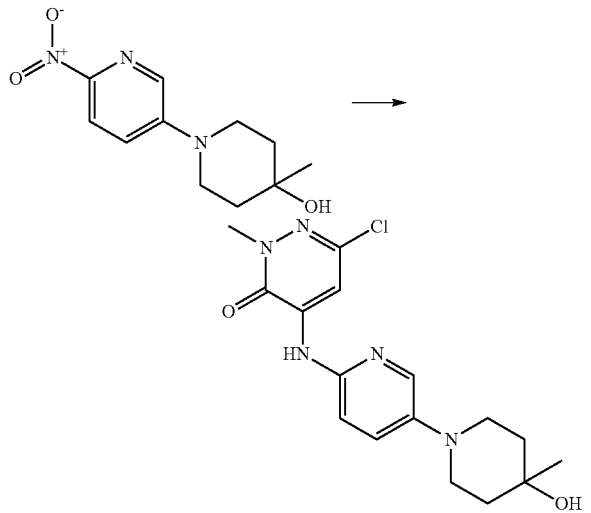

A solution of 4-methyl-1-(6-nitropyridin-3-yl)piperidin-4-ol (807 mg, 3.67 mmol) in methanol (15 ml) was hydrogenated at 50 psi with 10% Pd/C (117 mg, 110 umol) overnight. The catalyst was filtered off and the resultant filtrate was concentrated in vacuo to afford 1-(6-aminopyridin-3-yl)-4-methylpiperidin-4-ol. The product was carried to next reaction without further purification.

A solution of 4-bromo-6-chloro-2-methylpyridazin-3 (2H)-one (902 mg, 4.04 mmol), 1-(6-aminopyridin-3-yl)-4-methylpiperidin-4-ol (761 mg, 3.67 mmol), Xantphos (159 mg, 275 μmol) and cesium carbonate (3.59 g, 11 mmol) in dry dioxane (10 ml) was vacuum de-gassed and placed under an argon atmosphere. To this mixture was added tris(dibenzylideneacetone)dipalladium (0) (38 mg, 36.7 μmol) and the vacuum de-gas cycle was repeated. The material was heated at 90° C. (oil bath) with vigorous stirring overnight. The flask was cooled to ambient and the contents were filtered through a plug of celite, rinsing well with dioxane, and concentrating. The product was purified by preparative HPLC on silica gel, using a gradient of 5% to 70% ethylacetate/hexane. This provided the desired product as a light yellow solid (807 mg 62.9%). (M+H)+=350, 352 m/e.

Example 64

Step 3. Preparation of 6-tert-butyl-8-fluoro-2-(3-(5-(5-(4-hydroxy-4-methylpiperidin-1-yl)pyridin-2-ylamino)-1-methyl-6-oxo-1,6-dihydropyridazin-3-yl)-2-(hydroxymethyl)-phenyl)phthalazin-1(2H)-one

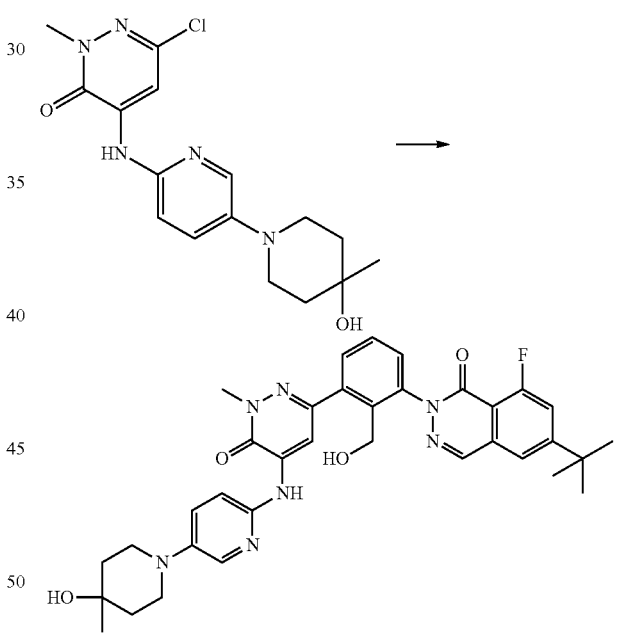

This reaction was carried out under similar conditions to those described above in step 7 of preparation of Example 6. A solution of 6-chloro-4-(5-(4-hydroxy-4-methylpiperidin-1-yl)pyridin-2-ylamino)-2-methylpyridazin-3(2H)-one (150 mg, 429 μmol), 2-(6-tert-butyl-8-fluoro-1-oxophthalazin-2 (1H)-yl)-6-(4,4,5,5-tetramethyl-1,3,2-dioxaborolan-2-yl) benzyl acetate (212 mg, 429 μmol), xPhos (20.4 mg, 42.9 μmol) and potassium phosphate (228 mg, 1.07 mmol) in 10 ml of dioxane/water (9:1) was degassed with nitrogen for 10 minutes and bis(dibenzylideneacetone)palladium (0) (12.3 mg, 21.4 μmol) was added. The reaction mixture was heated to 100° C. for 2 hr. After work up, the product was purified by preparative HPLC on silica gel, using a gradient of 0% to 5% methanol/ethyl acetate. This provided 1:1 ratio of desire compound and 2-(6-tert-butyl-8-fluoro-1-oxophthalazin-2(1H)-yl)-6-(5-(5-(4-hydroxy-4-methylpiperidin-1-yl)pyridin-2-ylamino)-1-methyl-6-oxo-1,6-dihydropyridazin-3-yl)benzyl acetate. The reaction mixture was dissolved in methanol (4 ml) and to this was added 2 N NaOH (600 µl). The reaction was stirred at room temperature for 2 h. The methanol was removed by evaporation and the resultant solution was acidified with 1N HCl and extracted with DCM. The resultant organic extract was dried over NaSO$_4$, filtered and concentrated in vacuo. The resultant yellow solid was triturated with ether to afford the desired product as a yellow solid (40 mg, 45.8%). (M+H)+=640.4 m/e. 1H NMR (400 MHz, DMSO-d6) δ ppm 1.14-1.24 (m, 3H) 1.31-1.48 (m, 12H) 1.64 (br. s., 2H) 2.35-2.68 (m, 2H) 3.31 (br. s., 2H) 3.52-3.62 (m, 1H) 4.41 (d, J=11.29 Hz, 2H) 7.33-7.60 (m, 7H) 7.75 (d, J=13.30 Hz, 1H) 7.87 (s, 1H) 8.44 (br. s., 1H) 8.52 (br. s., 1H).

Preparation of I-65

Example 65

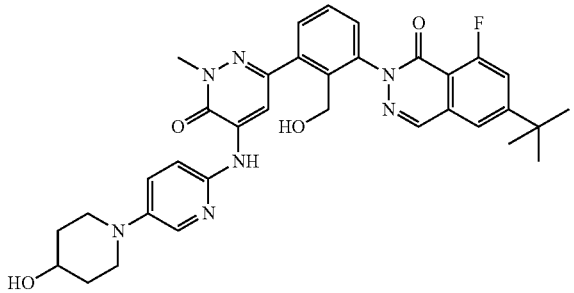 [SMILES: Cn1nc(-c2cccc(-n3ncc4cc(C(C)(C)C)cc(F)c4c3=O)c2CO)cc(Nc2ccc(N3CCC(O)CC3)cn2)c1=O]

Preparation by a similar procedure to Example 64, except substituting piperidin-4-ol for 4-methylpiperidin-4-ol in step 1 afforded 6-tert-butyl-8-fluoro-2-(2-(hydroxymethyl)-3-(5-(5-(4-hydroxypiperidin-1-yl)pyridin-2-ylamino)-1-methyl-6-oxo-1,6-dihydropyridazin-3-yl)phenyl)phthalazin-1(2H)-one as a yellow solid (65 mg, 38.7%). (M+H)+=626.4 m/e. 1H NMR (400 MHz, CHLOROFORM-d) δ ppm 1.41 (s, 9H) 1.64-1.77 (m, 2H) 1.96-2.07 (m, 2H) 2.91 (t, J=9.77 Hz, 2H) 3.39-3.53 (m, 2H) 3.80-3.91 (m, 3H) 3.97-4.04 (m, 1H) 4.40 (d, J=6.64 Hz, 2H) 6.89 (d, J=8.98 Hz, 1H) 7.28 (br. s., 1H) 7.42-7.59 (m, 3H) 7.62-7.67 (m, 1H) 8.03 (br. s., 1H) 8.17 (s, 1H) 8.27 (d, J=2.34 Hz, 1H) 8.45 (s, 1H).

Preparation of I-66

Step 1. Preparation of (1R,5S)-3-methyl-8-(6-nitro-pyridin-3-yl)-3,8-diazabicyclo[3.2.1]octane

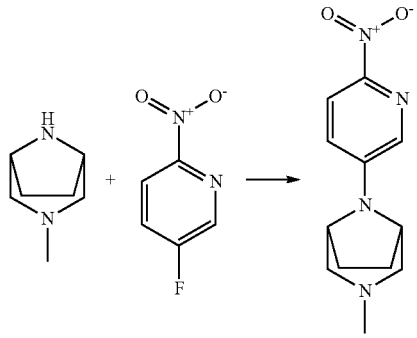

A solution of (1R,5S)-3-Methyl-3,8-diazabicyclo[3.2.1]octane dihydrochloride (981 mg, 4.93 mmol), 5-fluoro-2-nitropyridine (100 mg, 4.93 mmol), and triethylamine (4.99 g, 49.3 mmol) in DMSO (8 ml) was heated to 80° C. for 2 hr. After cooling to room temperature, the reaction mixture was diluted with EtOAc and washed with saturated ammonium chloride, and water. The organic phase was then concentrated and triturated with ether to give desire product as a yellow solid (1 g, 81.8%).

Step 2. Preparation of 6-chloro-2-methyl-4-(5-((1R,5S)-3-methyl-3,8-diazabicyclo[3.2.1]octan-8-yl)pyridin-2-ylamino)pyridazin-3(2H)-one

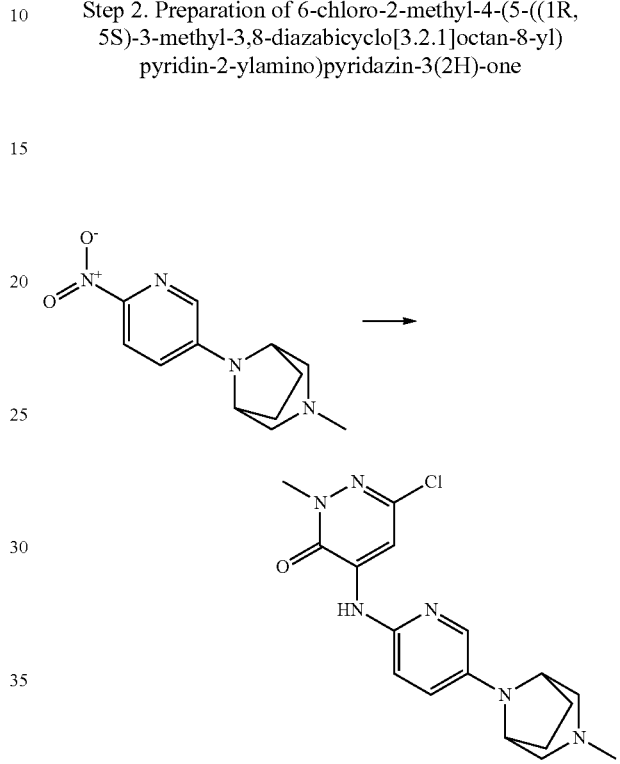

This reaction was carried out under similar conditions to those described above in preparation of 6-chloro-4-(5-(4-hydroxy-4-methylpiperidin-1-yl)pyridin-2-ylamino)-2-methyl-pyridazin-3(2H)-one. (1R,5S)-3-methyl-8-(6-nitropyridin-3-yl)-3,8-diazabicyclo[3.2.1]octane (500 mg, 2.01 mmol) in methanol (15 ml) was hydrogenated at 50 psi with 10% Pd/C (42.9 mg, 40.3 umol) overnight. The catalyst was filtered off and the resultant filtrate was concentrated in vacuo to afford 5-(3-methyl-3,8-diazabicyclo[3.2.1]octan-8-yl)pyridin-2-amine. The product was carried to next reaction without further purification.

A solution of 4-bromo-6-chloro-2-methylpyridazin-3(2H)-one (492 mg, 2.20 mmol), 5-(3-methyl-3,8-diazabicyclo[3.2.1]octan-8-yl)pyridin-2-amine (437 mg, 2.0 mmol), Xantphos (86.8 mg, 150 µmol) and cesium carbonate (1.95 g, 6.00 mmol) in dry dioxane (10 ml) was vacuum de-gassed and place under argon atmosphere. To this mixture was added tris(dibenzylideneacetone)dipalladium (0) (31.1 mg, 30 µmol) and the vacuum de-gas cycle was repeated. The reaction was heated at 90° C. (oil bath) with vigorous stirring overnight. The flask was cooled to ambient and the contents were filtered through a plug of celite, rinsing well with dioxane. The combined filtrate and washes were concentrated. The resultant crude residue was triturated with ether to provide the desired product as a light yellow solid (345 mg, 47.8%). (M+H)+=361.0, 363 m/e.

Example 66

Step 3. Preparation of 6-tert-Butyl-8-fluoro-2-(2-hydroxymethyl-3-{1-methyl-5-[5-((1R,5S)-3-methyl-3,8-diaza-bicyclo[3.2.1]oct-8-yl)-pyridin-2-ylamino]-6-oxo-1,6-dihydro-pyridazin-3-yl}-phenyl)-2H-phthalazin-1-one

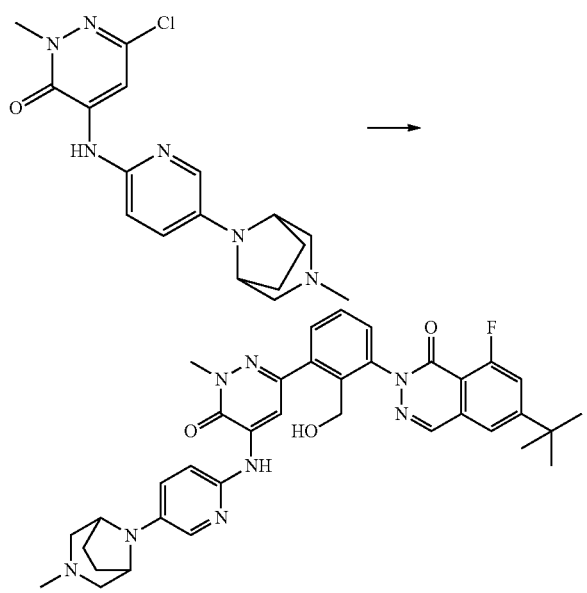

This reaction was carried out under similar conditions to those described above in step 7 of preparation of Example 6. A solution of 6-chloro-2-methyl-4-(5-((1R,5S)-3-methyl-3,8-diazabicyclo[3.2.1]-octan-8-yl)pyridin-2-ylamino)pyridazin-3(2H)-one (150 mg, 416 μmol), 2-(6-tert-butyl-8-fluoro-1-oxophthalazin-2(1H)-yl)-6-(4,4,5,5-tetramethyl-1,3,2-dioxaborolan-2-yl)benzyl acetate (206 mg, 416 μmol), xPhos (19.8 mg, 41.6 μmol) and potassium phosphate (221 mg, 1.04 mmol) in 10 ml of dioxane/water (9:1) was degassed with nitrogen for 10 minutes and bis(dibenzylideneacetone) palladium (0) (12.0 mg, 20.8 μmol) was added. The reaction mixture was heated to 100° C. for 2 hr. After work up, the product was purified by preparative HPLC on silica gel, using a gradient of 10% to 20% methanol/dichloromethane to afford 2-(6-tert-butyl-8-fluoro-1-oxophthalazin-2(1H)-yl)-6-(1-methyl-5-(5-(3-methyl-3,8-diazabicyclo[3.2.1]octan-8-yl)pyridin-2-ylamino)-6-oxo-1,6-dihydropyridazin-3-yl) benzyl acetate as light yellow solid (69 mg, 24%). %). (M+H)+=693, 694 m/e.

The 2-(6-tert-butyl-8-fluoro-1-oxophthalazin-2(1H)-yl)-6-(1-methyl-5-(5-(3-methyl-3,8-diazabi-cyclo[3.2.1]octan-8-yl)pyridin-2-ylamino)-6-oxo-1,6-dihydropyridazin-3-yl) benzyl acetate (55 mg, 79 μmol) was dissolved in MeOH (3 ml) and to this was added 2 N NaOH (794 μl). The reaction was stirred at room temperature for 18 h. The crude reaction was extracted with DCM. The resultant organic extract was dried over NaSO₄, filtered and concentrated in vacuo and triturated with ether to afford desired product as an yellow solid (10.3 mg, 20%). (M+H)+=651.5, 652.6 m/e. 1H NMR (400 MHz, CHLOROFORM-d) δ ppm 1.41 (s, 9H) 1.59 (d, J=11.72 Hz, 1H) 1.93-2.07 (m, 2H) 2.16-2.35 (m, 2H) 3.88 (s, 3H) 3.95-4.04 (m, 1H) 4.09-4.20 (m, 2H) 4.40 (d, J=7.03 Hz, 2H) 5.17-5.40 (m, 3H) 6.90 (d, J=8.98 Hz, 1H) 7.12 (dd, J=8.98, 2.73 Hz, 2H) 7.41-7.59 (m, 10H) 7.65 (d, J=7.81 Hz, 2H) 7.91 (d, J=2.73 Hz, 2H) 8.12 (s, 2H) 8.25-8.31 (m, 2H) 8.40 (s, 2H).

Preparation of I-67

Step 1. Preparation of 6-Chloro-4-(1',2',3',4',5',6'-hexahydro-[3,4']bipyridinyl-6-ylamino)-2-methyl-2H-pyridazin-3-one

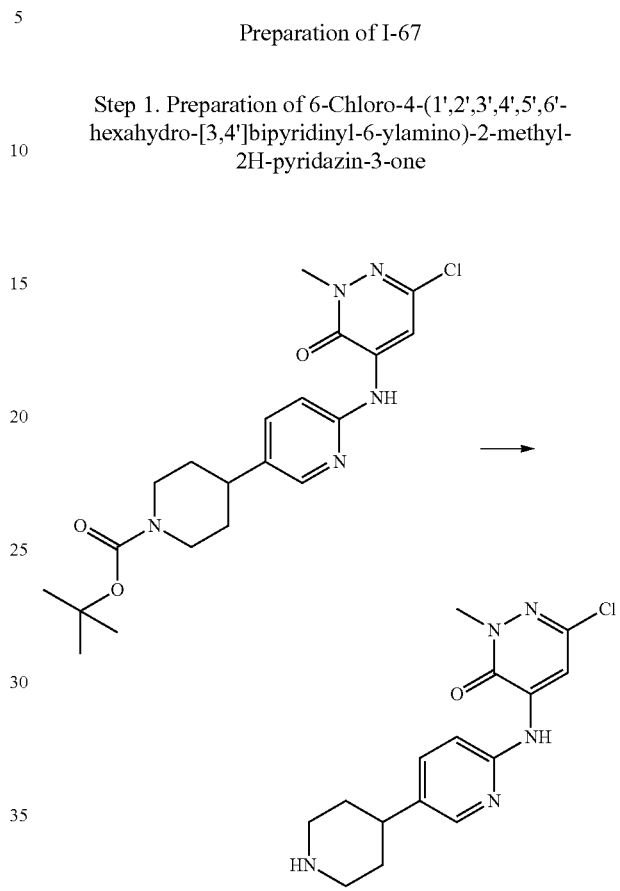

tert-Butyl 4-(6-(6-chloro-2-methyl-3-oxo-2,3-dihydropyridazin-4-ylamino)pyridin-3-yl)piperidine-1-carboxylate, which was prepared as described in example 29, steps 1-3 (1.8 g, 4.3 mmol) was dissolved in 15 mL DCM and treated with 7.5 mL TFA. The reaction mixture was stirred at room temperature for 1 h. The crude reaction mixture was concentrated in vacuo. The resulting residue was diluted with DCM and sat. NaHCO₃ and extracted with DCM. The extracts were dried over Na₂SO₄ and concentrated in vacuo to afford 620 mg of the desired product which was carried on as is to the next step.

Step 2. Preparation of 6-Chloro-2-methyl-4-(1'-methyl-1',2',3',4',5',6'-hexahydro-[3,4']bipyridinyl-6-ylamino)-2H-pyridazin-3-one

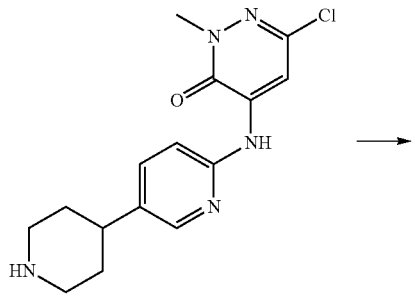

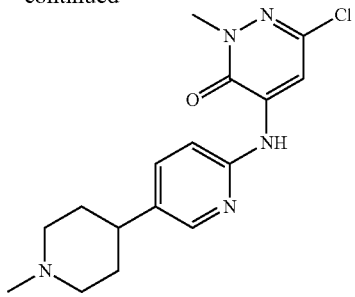

In a 25 mL round-bottomed flask, 6-chloro-2-methyl-4-(5-(piperidin-4-yl)pyridin-2-ylamino)pyridazin-3(2H)-one (620 mg, 1.94 mmol, Eq: 1.00) and formaldehyde (1.57 g, 1.44 ml, 19.4 mmol, Eq: 10) were combined with THF to give a light yellow solution. Acetic acid (116 mg, 111 μl, 1.94 mmol, Eq: 1.00) was added. The reaction mixture was cooled to 0° C. Sodium triacetoxyborohydride (616 mg, 2.91 mmol, Eq: 1.5) was added. The reaction mixture was stirred at room temperature 2 hr. LC/MS showed reaction was complete. The reaction mixture was poured into water. Saturated NaHCO$_3$ was added to make it basic and the resultant mixture was extracted with EtOAc. The combined extracts were washed with water, dried over Na$_2$SO$_4$ and concentrated in vacuo. The resultant solid was triturated with ether to afford the desired product as an off-white solid (580 mg). (M+H)+=334 m/e. This was combined with previous batches to give 1.06 g 6-chloro-2-methyl-4-(1'-methyl-1',2',3',4',5',6'-hexahydro-[3,4']bipyridinyl-6-ylamino)-2H-pyridazin-3-one, which was carried on as is into the next reaction.

Example 67

Step 3. Preparation of 6-tert-Butyl-8-fluoro-2-{2-hydroxymethyl-3-[1-methyl-5-(1'-methyl-1',2',3',4',5',6'-hexahydro-[3,4']bipyridinyl-6-ylamino)-6-oxo-1,6-dihydro-pyridazin-3-yl]-phenyl}-2H-phthalazin-1-one

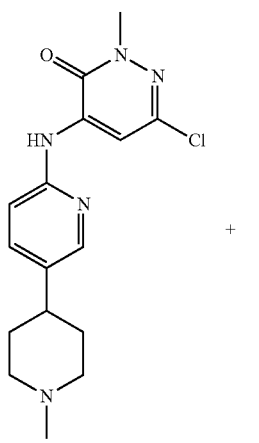

+

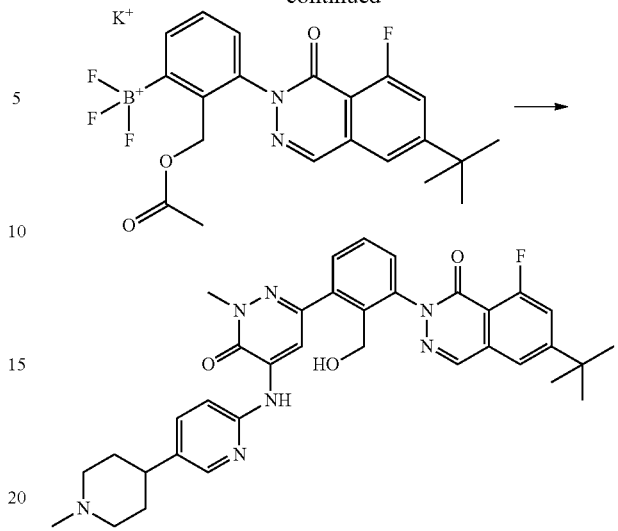

A mixture of 6-chloro-2-methyl-4-(5-(1-methylpiperidin-4-yl)pyridin-2-ylamino)pyridazin-3(2H)-one (1.06 g, 3.18 mmol), potassium (2-(acetoxymethyl)-3-(6-tert-butyl-8-fluoro-1-oxophthalazin-2(1H)-yl)phenyl)trifluoroborate (1.51 g, 3.18 mmol), xPhos (227 mg, 476 μmol) and potassium phosphate (1.48 g, 6.99 mmol) in 60 ml of butanol/water (5:1) was degassed with nitrogen for 10 minutes and bis(dibenzylideneacetone)palladium (0) (137 mg, 238 μmol) was added. The reaction mixture was heated to 110° C. for 3 hr. The crude reaction mixture was extracted with DCM, washed with water, dried over Na$_2$SO$_4$, filtered and concentrated to form a solid during concentration. This solid was triturated with ether to afford 1.67 g of crude product. Combined with 300 mg of crude material from a previous batch and purified by silica chromatography to afford 2-(6-tert-butyl-8-fluoro-1-oxophthalazin-2(1H)-yl)-6-(1-methyl-5-(5-(1-methylpiperidin-4-yl)pyridin-2-ylamino)-6-oxo-1,6-dihydropyridazin-3-yl)benzyl acetate (1.6 g) as a white solid.

2-(6-tert-butyl-8-fluoro-1-oxophthalazin-2(1H)-yl)-6-(1-methyl-5-(5-(1-methylpiperidin-4-yl)pyridin-2-ylamino)-6-oxo-1,6-dihydropyridazin-3-yl)benzyl acetate (1.6 g) was dissolved in 20 mL THF. To the reaction solution was added 12 mL of 2 N NaOH. The reaction mixture was stirred at room temperature overnight. Reaction was not complete. An additional 10 equiv. of 2 N NaOH was added and the reaction mixture was stirred at room temperature for an additional 2 hours. THF was added until the reaction mixture was homogeneous and the reaction was heated to 40° C. for 30 min. The reaction was allowed to cool to room temperature and stirred overnight. The reaction had gone to completion as indicated by LC/MS. The reaction was concentrated to a reduced volume to remove most of the THF. A solid formed which was collected by filtration. The solid was redissolved in DCM, filtered through pack of celite, washed with water, dried over Na$_2$SO$_4$, filtered and conc in vacuo. to afford the desired product as a white solid (1.27 g). (M+H)+=624 m/e. $^1$H NMR (400 MHz, CHLOROFORM-d) δ ppm 1.45 (s, 9H) 1.80-1.92 (m, 5H) 2.31-2.58 (m, 3H) 3.03 (d, J=8.28 Hz, 1H) 3.92 (s and overlapping multiplet, 4H) 4.45 (d, J=6.53 Hz, 2H) 6.93 (d, J=8.28 Hz, 1H) 7.45-7.63 (m, 5H) 7.65-7.71 (m, 1H) 8.22-8.32 (m, 3H) 8.61 (s, 1H).

Preparation of I-68
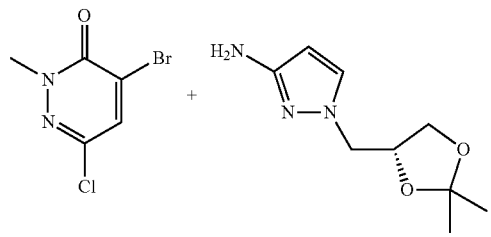
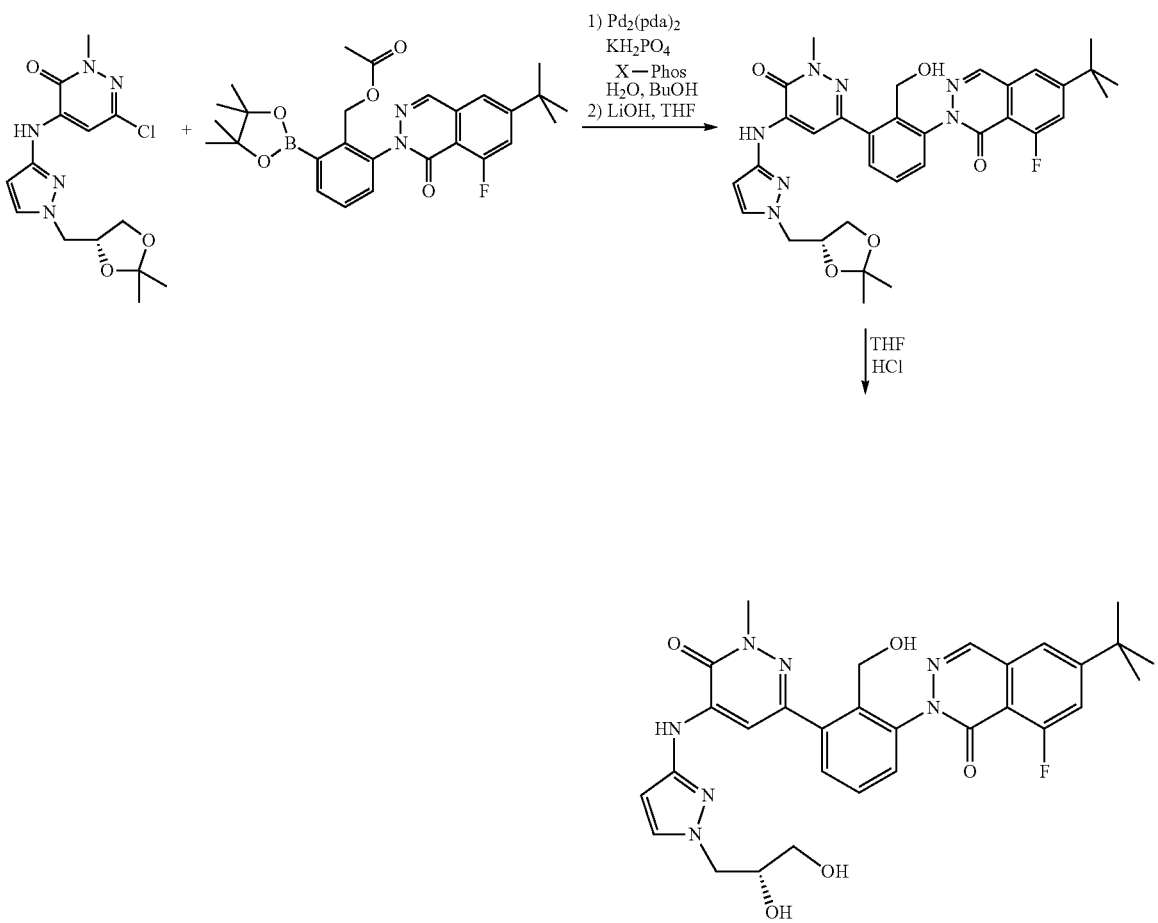

Example 68

Preparation of 6-tert-Butyl-2-(3-{5-[1-((R)-2,3-dihydroxy-propyl)-1H-pyrazol-3-ylamino]-1-methyl-6-oxo-1,6-dihydro-pyridazin-3-yl}-2-hydroxymethyl-phenyl)-8-fluoro-2H-phthalazin-1-one

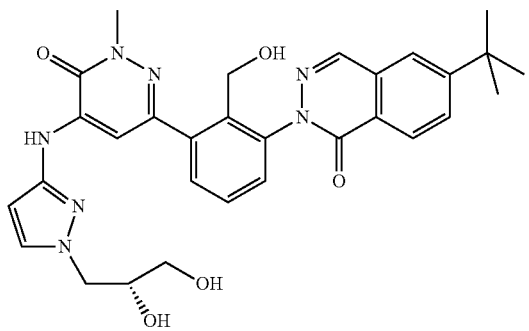 [SMILES: Cn1nc(-c2cccc(-n3ncc4cc(C(C)(C)C)ccc4c3=O)c2CO)cc(Nc2ccn(C[C@@H](O)CO)n2)c1=O]

A solution of (R)-1-((2,2-dimethyl-1,3-dioxolan-4-yl)methyl)-1H-pyrazol-3-amine (prepared as in WO2009127546 (A1), Example 49, 177 mg, 0.90 mmol), 4-bromo-6-chloro-2-methylpyridazin-3(2H)-one (200 mg, 0.90 mmol) cesium carbonate (1.02 g, 3.13 mmol) and 4,5-bis(diphenylphosphino)-9,9-dimethylxanthene (77.7 mg, 0.134 mmol) in dioxane (10 ml) was flushed with argon before tris(dibenzylideneacetone)dipalladium(0) (61.5 mg, 0.07 mmol) was added and the resulting solution was heated at 90° C. for 18 h. The mixture was cooled to room temperature and diluted with dichloromethane and water. The layers were separated and the aqueous layer was extracted with dichloromethane. The organic layers were combined, dried over magnesium sulfate. The resulting mixture was filtered and concentrated in vacuo. The residue was purified by flash chromatography (silica gel, 24 g, 0% to 10% methanol/dichloromethane) to give (R)-6-chloro-4-(1-((2,2-dimethyl-1,3-dioxolan-4-yl)methyl)-1H-pyrazol-3-ylamino)-2-methylpyridazin-3(2H)-one (249 mg, 82%) as a yellow solid.

A solution of 2-(6-tert-butyl-8-fluoro-1-oxophthalazin-2(1H)-yl)-6-(4,4,5,5-tetramethyl-1,3,2-dioxaborolan-2-yl)benzyl acetate (247 mg, 0.50 mmol), 6-chloro-2-methyl-4-(5-oxetan-3-yl-4,5,6,7-tetrahydro-pyrazolo[1,5-a]pyrazin-2-ylamino)-2H-pyridazin-3-one (100 mg, 0.29 mmol), potassium phosphate (156 mg, 0.74 mmol) and dicyclohexyl (2',4',6'-triisopropylbiphenyl-2-yl)phosphine (14.0 mg, 0.03 mmol) in butanol (4 ml) and water (1 mL) was flushed with argon before (bis[dibenzylideneacetone]dipalladium) (8.46 mg, 0.01 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (1 mL, 2.0 M), and the resulting mixture was stirred at room temperature overnight. The resulting mixture was poured into a saturated ammonium chloride solution and extracted with methylene chloride (2×150 mL). The layers were separated and the organic phase dried over magnesium sulfate. The mixture was filtered and concentrated in vacuo. The residue was purified by flash chromatography (silica gel, 40 g, 2% to 10% methanol in dichloromethane) to give acetic acid 2-(6-tert-butyl-8-fluoro-1-oxo-1H-phthalazin-2-yl)-6-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-benzyl ester (138 mg, 72%) as a light yellow solid.

To a solution of (R)-6-tert-butyl-2-(3-(5-(1-((2,2-dimethyl-1,3-dioxolan-4-yl)methyl)-1H-pyrazol-3-ylamino)-1-methyl-6-oxo-1,6-dihydropyridazin-3-yl)-2-(hydroxymethyl)phenyl)-8-fluorophthalazin-1(2H)-one (135 mg, 0.21 mmol) in tetrahydrofuran (4 ml) was added a solution of hydrochloric acid (1.0 N, 4 ml) and the resulting solution was stirred at room temperature overnight. The resulting mixture was poured into a saturated aqueous ammonium chloride solution and extracted with dichloromethane (2×50 mL). The organic layers were combined and dried over magnesium sulfate. The mixture was filtered and evaporated and the residue crystallized from dichloromethane and isopropyl acetate. The crystals were washed with ether and dried to give 6-tert-butyl-2-(3-{5-[1-((R)-2,3-dihydroxy-propyl)-1H-pyrazol-3-ylamino]-1-methyl-6-oxo-1,6-dihydro-pyridazin-3-yl}-2-hydroxymethyl-phenyl)-8-fluoro-2H-phthalazin-1-one (52 mg, 41%) as a light yellow solid: mp. 245-250° C.; $^1$H NMR (300 MHz, DMSO-$d_6$) δ ppm 1.38 (s, 9H) 3.67-4.24 (m, 6H) 4.27-5.06 (m, 5H) 6.19 (d, J=2.27 Hz, 1H) 7.18-7.96 (m, 7H) 8.51 (d, J=2.27 Hz, 1H) 9.23 (s, 1H).

Preparation of I-69

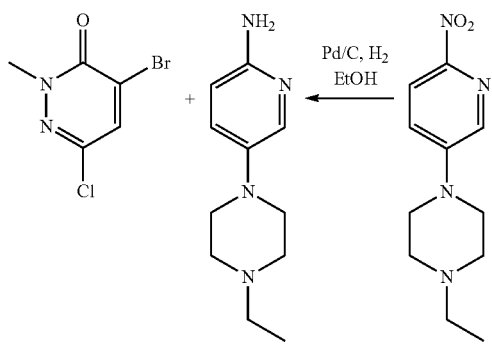

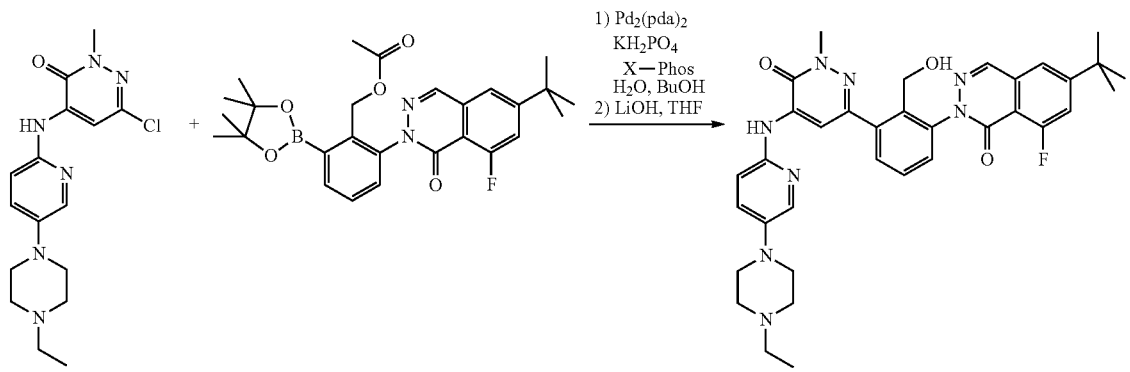

Example 69

Preparation of 6-tert-Butyl-2-(3-{5-[5-(4-ethyl-piperazin-1-yl)-pyridin-2-ylamino]-1-methyl-6-oxo-1,6-dihydro-pyridazin-3-yl}-2-hydroxymethyl-phenyl)-8-fluoro-2H-phthalazin-1-one

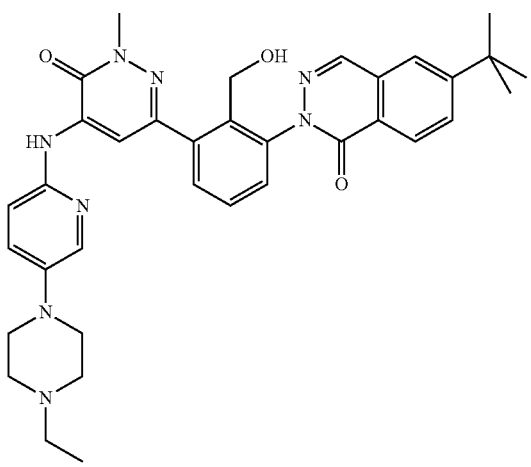 [SMILES: CCN1CCN(c2ccc(Nc3cc(-c4cccc(-n5ncc6cc(C(C)(C)C)ccc6c5=O)c4CO)nn(C)c3=O)nc2)CC1]

To a solution of 1-ethyl-4-(6-nitropyridin-3-yl)piperazine (500 mg, 2.12 mmol) in ethanol (20 mL) was added 10% Pd/C (113 mg, 0.11 mmol) and the resulting mixture was stirred under a hydrogen atmosphere for 18 h. The reaction mixture was filtered through celite, washed with ethanol and concentrated to give N-[(E)-2-(4-ethyl-piperazin-1-yl)-penta-2,4-dien-(Z)-ylidene]-methanediamine (377 mg, 86%) as a grey solid.

A solution of 5-(4-ethylpiperazin-1-yl)pyridin-2-amine (185 mg, 0.90 mmol), 4-bromo-6-chloro-2-methylpyridazin-3(2H)-one (200 mg, 0.90 mmol) cesium carbonate (1.02 g, 3.13 mmol) and 4,5-bis(diphenylphosphino)-9,9-dimethylxanthene (77.7 mg, 0.13 mmol) in dioxane (10 ml) was flushed with argon before tris(dibenzylideneacetone)dipalladium(0) (61.5 mg, 0.07 mmol) was added and the resulting solution was heated at 90° C. for 18 h. The mixture was cooled to room temperature and diluted with dichloromethane and water. The layers were separated and the aqueous layer was extracted with dichloromethane (2×25 mL). The organic layers were combined, dried over magnesium sulfate. The resulting mixture was filtered and concentrated in vacuo. The residue was triturated with methanol and dichloromethane and filtered, washed with ether and dried to give 6-chloro-4-[5-(4-ethyl-piperazin-1-yl)-pyridin-2-ylamino]-2-methyl-2H-pyridazin-3-one (138 mg, 44%) as a yellow solid.

A solution of 2-(6-tert-butyl-8-fluoro-1-oxophthalazin-2(1H)-yl)-6-(4,4,5,5-tetramethyl-1,3,2-dioxaborolan-2-yl)benzyl acetate (241 mg, 0.49 mmol), 6-chloro-4-(5-(4-ethylpiperazin-1-yl)pyridin-2-ylamino)-2-methylpyridazin-3(2H)-one (100 mg, 0.29 mmol), potassium phosphate (152 mg, 0.72 mmol) and dicyclohexyl(2',4',6'-triisopropylbiphenyl-2-yl)phosphine (13.7 mg, 0.03 mmol) in butanol (4 ml) and water (1 mL) was flushed with argon before (bis[dibenzylideneacetone]dipalladium) (8.24 mg, 0.01 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×50 mL). The layers were separated and the organic phase dried over magnesium sulfate. The mixture was filtered and concentrated in vacuo. The residue was purified by flash chromatography (silica gel, 24 g, 1% to 14% methanol in dichloromethane) and recrystallized from dichloromethane and isopropyl acetate to give 6-tert-Butyl-2-(3-{5-[5-(4-ethyl-piperazin-1-yl)-pyridin-2-ylamino]-1-methyl-6-oxo-1,6-dihydro-pyridazin-3-yl}-2-hydroxymethyl-phenyl)-8-fluoro-2H-phthalazin-1-one (47 mg, 26%) as a light yellow solid: mp 245-247° C.; $^1$H NMR (300 MHz, DMSO-$d_6$) δ ppm 1.02 (t, J=7.18 Hz, 4H) 1.38 (s, 10H) 2.13-2.42 (m, 2H) 3.09 (br. s., 5H) 3.77 (s, 3H) 4.16-4.72 (m, 3H) 7.20-8.10 (m, 9H) 8.28-8.64 (m, 2H) 9.23 (s, 1H).

263

Preparation of I-70

Example 70

Preparation of 6-tert-Butyl-8-fluoro-2-(2-hydroxymethyl-3-{5-[1-(2-hydroxy-2-methyl-propyl)-1H-pyrazol-3-ylamino]-1-methyl-6-oxo-1,6-dihydro-pyridazin-3-yl}-phenyl)-2H-phthalazin-1-one

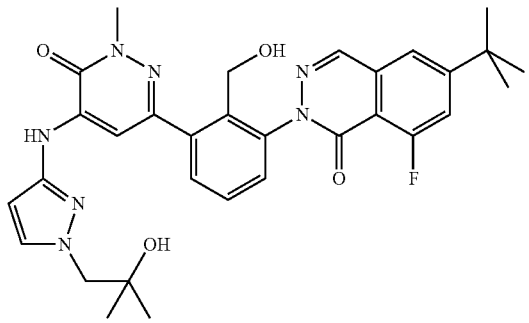 [SMILES: Cn1nc(-c2cccc(-n3ncc4cc(C(C)(C)C)cc(F)c4c3=O)c2CO)cc(Nc2ccn(CC(C)(C)O)n2)c1=O]

A solution of 1-(3-amino-1H-pyrazol-1-yl)-2-methylpropan-2-ol (prepared as in U.S. Pat. No. 7,935,699 B2, Example 74, 139 mg, 0.90 mmol), 4-bromo-6-chloro-2-methylpyridazin-3(2H)-one (200 mg, 0.90 mmol) cesium carbonate (1.02 g, 3.13 mmol) and 4,5-bis(diphenylphosphino)-9,9-dimethylxanthene (77.7 mg, 0.13 mmol) in dioxane (10 ml) was flushed with argon before tris(dibenzylideneacetone)dipalladium(0) (61.5 mg, 0.07 mmol) was added and the resulting solution was heated at 90° C. for 18 h. The mixture was cooled to room temperature and diluted with dichloromethane and water. The layers were separated and the aqueous layer was extracted with dichloromethane. The organic layers were combined, dried over magnesium sulfate. The resulting mixture was filtered and concentrated in vacuo. The residue was purified by flash chromatography (silica gel, 24 g, 0% to 10% methanol in dichloromethane) to give 6-chloro-4-[1-(2-hydroxy-2-methyl-propyl)-1H-pyrazol-3-ylamino]-2-methyl-2H-pyridazin-3-one (156 mg, 59%) as a light yellow solid.

A solution of 2-(6-tert-butyl-8-fluoro-1-oxophthalazin-2(1H)-yl)-6-(4,4,5,5-tetramethyl-1,3,2-dioxaborolan-2-yl)benzyl acetate (282 mg, 0.57 mmol), 6-chloro-4-(1-(2-hydroxy-2-methylpropyl)-1H-pyrazol-3-ylamino)-2-methylpyridazin-3(2H)-one (100 mg, 0.34 mmol), potassium phosphate (178 mg, 0.84 mmol) and dicyclohexyl(2',4',6'-triisopropylbiphenyl-2-yl)phosphine (16.0 mg, 0.03 mmol) in butanol (4 ml) and water (1 mL) was flushed with argon before (bis[dibenzylideneacetone]dipalladium) (9.66 mg, 0.02 mmol) was added and the resulting solution heated at 100° C. in for 2 h. The resulting mixture was cooled, poured into a saturated solution of ammonium chloride and extracted with methylene chloride (2×100 mL). The layers were separated and the organic phase dried over magnesium sulfate. The mixture was filtered and concentrated in vacuo. The residue was dissolved in dioxane (10 mL) and treated with a lithium hydroxide solution (0.5 mL, 2.0 M), and the resulting mixture was stirred at room temperature overnight. The resulting mixture was poured into a saturated ammonium chloride solution and extracted with methylene chloride (2×150 mL). The layers were separated and the organic phase dried over magnesium sulfate. The mixture was filtered and concentrated in vacuo. The residue was purified by flash chromatography (silica gel, 24 g, 1% to 10% methanol in dichloromethane) to give 6-tert-butyl-8-fluoro-2-(2-hydroxymethyl-3-{5-[1-(2-hydroxy-2-methyl-propyl)-1H-pyrazol-3-ylamino]-1-methyl-6-oxo-1,6-dihydro-pyridazin-3-yl}-phenyl)-2H-phthalazin-1-one (119 mg, 60%) as a white solid: MP. 165-170° C.; $^1$H NMR (300 MHz, DMSO-$d_6$) δ ppm 0.91-1.13 (m, 6H) 1.38 (s, 8H) 3.16-3.36 (m, 2H) 3.91 (s, 2H) 4.35-4.65 (m, 4H) 6.20 (d, J=2.27 Hz, 1H) 7.28-7.64 (m, 4H) 7.75 (d, J=13.22 Hz, 1H) 7.82-7.99 (m, 2H) 8.51 (d, J=2.27 Hz, 1H) 9.24 (s, 1H).

Preparation of I-71

Example 71

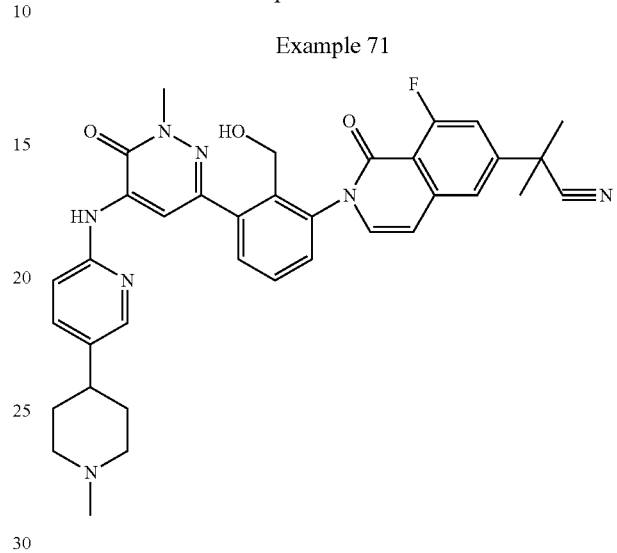

2-(8-Fluoro-2-{2-hydroxymethyl-3-[1-methyl-5-(1'-methyl-1',2',3',4',5',6'-hexahydro-[3,4']pyridinyl-6-ylamino)-6-oxo-1,6-dihydro-pyridazin-3-yl]-phenyl}-1-oxo-1,2-dihydro-isoquinolin-6-yl)-2-methyl-propionitrile was prepared using the general procedure described for compound I-15, but substituting 6-Chloro-2-methyl-4-(1'-methyl-1',2',3',4',5',6'-hexahydro-[3,4']bipyridinyl-6-ylamino)-2H-pyridazin-3-one for 6-chloro-2-methyl-4-(5-morpholine-4-carbonyl)pyridine-2-ylamino)pyridazin-3(2H)-one in step 11 to provide 106 mg of final product as a light yellow powder. (M+H)$^+$=634 m/e, $^1$H NMR (300 MHz, CHLOROFORM-d) δ ppm 1.81 (s, 6H) 1.82-1.90 (m, 4H) 2.02-2.22 (m, 2H) 2.36 (s, 3H) 2.41-2.60 (m, 1H) 2.91-3.12 (m, 2H) 3.91 (s, 3H) 3.96-4.09 (m, 1H) 4.23-4.49 (m, 2H) 6.61 (dd, J=7.55, 1.89 Hz, 1H) 6.91 (d, J=8.31 Hz, 1H) 7.21 (dd, J=12.09, 1.89 Hz, 1H) 7.35 (d, J=7.55 Hz, 1H) 7.42 (dd, J=7.74, 1.32 Hz, 1H) 7.50-7.55 (m, 2H) 7.59 (t, J=7.74 Hz, 1H) 7.67 (dd, J=7.93, 1.51 Hz, 1H) 8.23 (d, J=2.27 Hz, 1H) 8.28 (s, 1H) 8.62 (s, 1H).

Preparation of I-72

Example 72

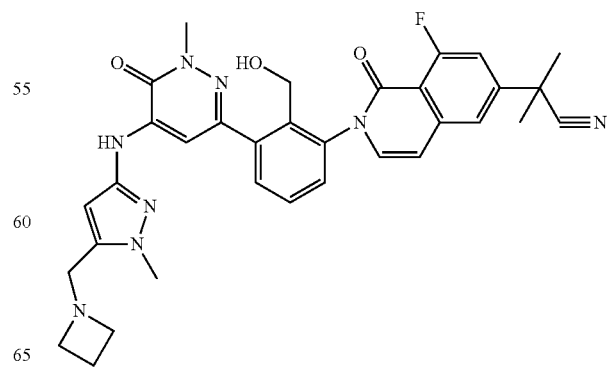

2-(2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile was prepared using the general procedure described for compound I-15, but substituting 4-(5-azetidin-1-ylmethyl-1-methyl-1H-pyrazol-3-ylamino)-6-chloro-2-methyl-2H-pyridazin-3-one for 6-chloro-2-methyl-4-(5-morpholine-4-carbonyl)pyridine-2-ylamino)pyridazin-3(2H)-one in step 11 to provide 471 mg of final product as an off-white powder. (M+H)$^+$=609 m/e, $^1$H NMR (300 MHz, CHLOROFORM-d) δ ppm 1.81 (s, 6H) 2.12 (quin, J=7.20 Hz, 2H) 3.27 (t, J=7.0 Hz, 4H) 3.55 (s, 2H) 3.81 (s, 3H) 3.88 (s, 3H) 4.03-4.19 (m, 1H) 4.22-4.44 (m, 2H) 5.94 (s, 1H) 6.61 (dd, J=7.36, 2.08 Hz, 1H) 7.21 (dd, J=12.09, 1.89 Hz, 1H) 7.35 (d, J=7.55 Hz, 1H) 7.41 (dd, J=7.74, 1.32 Hz, 1H) 7.52 (d, J=1.51 Hz, 1H) 7.56 (t, J=7.74 Hz, 1H) 7.65 (dd, J=7.55, 1.51 Hz, 1H) 7.82 (s, 1H) 7.91 (s, 1H).

Preparation of I-73

Example 73

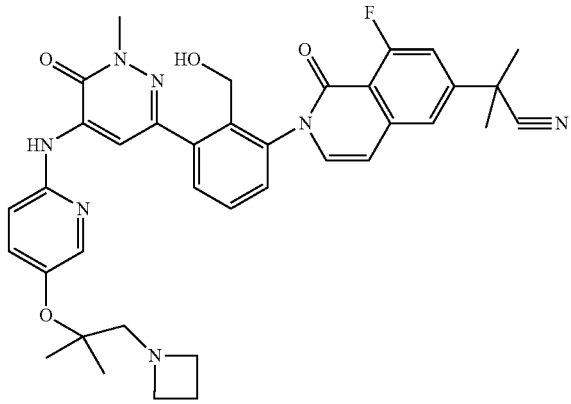 [SMILES: Cn1nc(-c2cccc(-n3ccc4cc(C(C)(C)C#N)cc(F)c4c3=O)c2CO)cc(Nc2ccc(OC(C)(C)CN3CCC3)cn2)c1=O]

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2-dihydro-isoquinolin-6-yl]-2-methyl-propionitrile was prepared using the general procedure described for compound I-15, but substituting 4-[5-(2-azetidin-1-yl-1,1-dimethyl-ethoxy)-pyridin-2-ylamino]-6-chloro-2-methyl-2H-pyridazin-3-one for 6-chloro-2-methyl-4-(5-morpholine-4-carbonyl)pyridine-2-ylamino)pyridazin-3(2H)-one in step 11. The resultant Suzuki product was carried through the remaining step 12 of the synthesis to provide 143 mg of final product as a light yellow powder.

(M+H)$^+$=664 m/e, $^1$H NMR (300 MHz, CHLOROFORM-d) δ ppm 1.24 (s, 6H) 1.81 (s, 6H) 2.12 (quin, J=6.80 Hz, 2H) 2.59 (s, 2H) 3.35 (t, J=6.99 Hz, 4H) 3.91 (s, 3H) 3.95-4.06 (m, 1H) 4.25-4.44 (m, 2H) 6.61 (dd, J=7.37, 2.08 Hz, 1H) 6.89 (d, J=8.69 Hz, 1H) 7.21 (dd, J=12.28, 1.70 Hz, 1H) 7.33 (dd, J=8.69, 2.64 Hz, 2H) 7.34 (d, J=7.18 Hz, 1H) 7.42 (dd, J=7.74, 1.32 Hz, 1H) 7.53 (d, J=1.89 Hz, 1H) 7.59 (t, J=7.74 Hz, 1H) 7.68 (dd, J=7.93, 1.51 Hz, 1H) 8.08 (d, J=2.64 Hz, 1H) 8.27 (s, 1H) 8.55 (s, 1H)

Preparation of I-74

Example 74

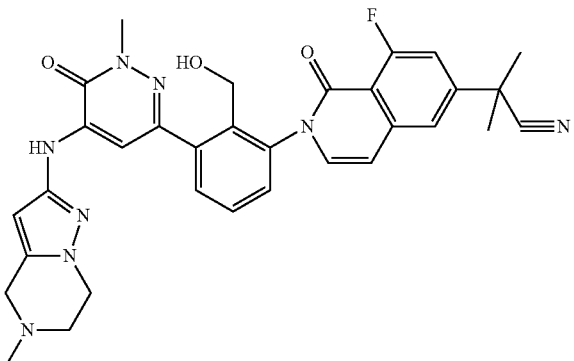

2-(8-Fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile was prepared using the general procedure described for compound I-15, but substituting 6-chloro-2-methyl-4-(5-methyl-4,5,6,7-tetrahydro-pyrazolo[1,5-a]pyrazin-2-ylamino)-2H-pyridazin-3-one for 6-chloro-2-methyl-4-(5-morpholine-4-carbonyl)pyridine-2-ylamino)pyridazin-3(2H)-one in step 11 to provide 29 mg of final product as a light yellow powder.

(M+H)$^+$=595 m/e, $^1$H NMR (300 MHz, CHLOROFORM-d) δ ppm 1.80 (s, 6H) 2.49 (s, 3H) 2.90 (t, J=5.70 Hz, 2H) 3.61 (s, 2H) 3.88 (s, 3H) 4.04-4.11 (m, 1H) 4.10 (t, J=5.70 Hz, 2H) 4.24-4.42 (m, 2H) 5.78 (s, 1H) 6.61 (dd, J=7.37, 2.08 Hz, 1H) 7.21 (dd, J=12.09, 1.89 Hz, 1H) 7.34 (d, J=7.55 Hz, 1H) 7.40 (dd, J=7.74, 1.32 Hz, 1H) 7.52 (d, J=1.89 Hz, 1H) 7.55 (t, J=7.93 Hz, 1H) 7.65 (dd, J=7.93, 1.51 Hz, 1H) 7.84 (s, 1H) 7.98 (s, 1H).

Preparation of I-75

Example 75

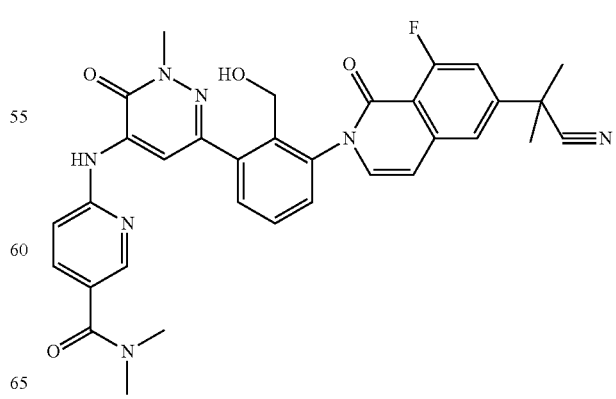

6-(6-{3-[6-(Cyano-dimethyl-methyl)-8-fluoro-1-oxo-1H-isoquinolin-2-yl]-2-hydroxymethyl-phenyl}-2-methyl-3-oxo-2,3-dihydro-pyridazin-4-ylamino)-N,N-dimethyl-nicotinamide was prepared using the general procedure described for compound I-15, but substituting 6-(6-chloro-2-methyl-3-oxo-2,3-dihydro-pyridazin-4-ylamino)-N,N-dimethyl-nicotinamide for 6-chloro-2-methyl-4-(5-morpholine-4-carbonyl)pyridine-2-ylamino)pyridazin-3(2H)-one in step 11 to provide 246 mg of final product as a white powder. (M+H)$^+$=608 m/e, $^1$H NMR (300 MHz, CHLOROFORM-d) δ ppm 1.80 (s, 6H) 3.11 (s, 6H) 3.85-3.91 (m, 1H) 3.92 (s, 3H) 4.26-4.46 (m, 2H) 6.62 (dd, J=7.55, 1.89 Hz, 1H) 6.98 (d, J=8.69 Hz, 1H) 7.21 (dd, J=12.28, 1.70 Hz, 1H) 7.34 (d, J=7.55 Hz, 1H) 7.42 (m, 1H) 7.53 (d, J=1.51 Hz, 1H) 7.60 (t, J=7.74 Hz, 1H) 7.65-7.72 (m, 1H) 7.79 (dd, J=8.69, 2.27 Hz, 1H) 8.44 (s, 1H) 8.47 (d, J=2.27 Hz, 1H) 8.71 (s, 1H).

Preparation of I-76

Example 76

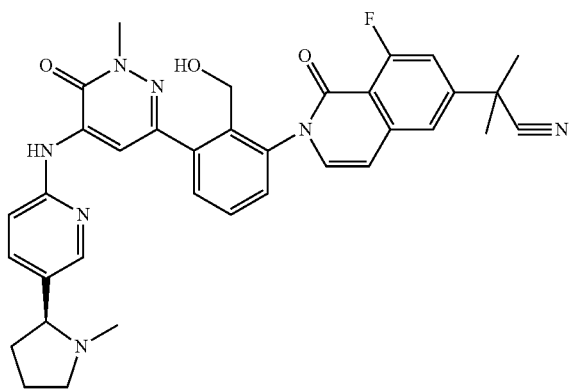 [SMILES: CN1CCC[C@H]1c1ccc(Nc2cc(-c3cccc(-n4ccc5cc(C(C)(C)C#N)cc(F)c5c4=O)c3CO)nn(C)c2=O)nc1]

2-[8-Fluoro-2-(2-hydroxymethyl-3-{1-methyl-5-[5-((S)-1-methyl-pyrrolidin-2-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile was prepared using the general procedure described for compound I-15, but substituting 6-chloro-2-methyl-4-[5-((S)-1-methyl-pyrrolidin-2-yl)-pyridin-2-ylamino]-2H-pyridazin-3-one for 6-chloro-2-methyl-4-(5-morpholine-4-carbonyl)pyridine-2-ylamino)pyridazin-3(2H)-one in step 11 to provide 107 mg of final product as a white powder. (M+H)$^+$=620 m/e, $^1$H NMR (300 MHz, CHLOROFORM-d) δ ppm 1.65-1.79 (m, 1H), 1.80 (s 3H) 1.81-2.06 (m, 3H) 2.17 (d, J=1.89 Hz, 3H) 2.23-2.37 (m, 2H) 2.99-3.11 (m, 1H) 3.18-3.31 (m, 1H) 3.91 (s, 3H) 3.96-4.09 (m, 1H) 4.26-4.44 (m, 2H) 6.61 (dd, J=7.37, 2.08 Hz, 1H) 6.95 (d, J=8.31 Hz, 1H) 7.21 (dd, J=12.46, 1.89 Hz, 1H) 7.35 (d, J=7.55 Hz, 1H) 7.42 (dd, J=7.93, 1.13 Hz, 1H) 7.52 (d, J=1.89 Hz, 1H) 7.58 (t, J=7.74 Hz, 1H) 7.65-7.73 (m, 2H) 8.24-8.28 (m, 1H) 8.30 (s, 1H) 8.67 (s, 1H).

Preparation of I-77

Example 77

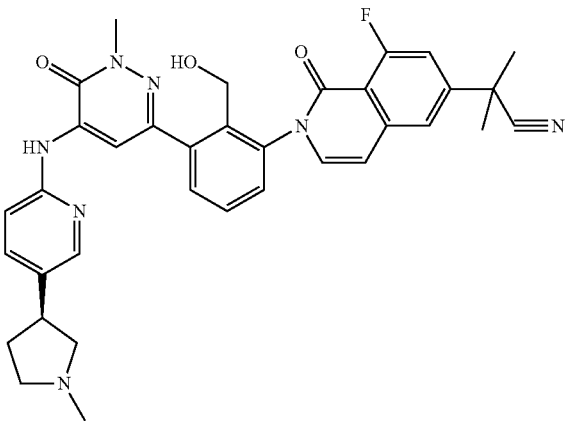 [SMILES: CN1CC[C@@H](c2ccc(Nc3cc(-c4cccc(-n5ccc6cc(C(C)(C)C#N)cc(F)c6c5=O)c4CO)nn(C)c3=O)nc2)C1]

2-[8-Fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile was prepared using the general procedure described for compound I-15, but substituting 6-chloro-2-methyl-4-[5-((S)-1-methyl-pyrrolidin-3-yl)-pyridin-2-ylamino]-2H-pyridazin-3-one for 6-chloro-2-methyl-4-(5-morpholine-4-carbonyl)pyridine-2-ylamino)pyrid-azin-3(2H)-one in step 11 to provide 18 mg of final product as a light yellow powder.

(M+H)$^+$=620 m/e, $^1$H NMR (300 MHz, CHLOROFORM-d) δ ppm 1.81 (s, 6H) 1.82-1.91 (m, 1H) 2.29-2.40 (m, 1H) 2.42 (s, 3H) 2.47-2.52 (m, 1H) 2.63-2.82 (m, 2H) 2.91-3.02 (m, 1H) 3.31-3.40 (m, 1H) 3.90 (s, 3H) 4.23-4.47 (m, 2H) 6.61 (dd, J=7.55, 1.89 Hz, 1H) 6.92 (d, J=8.31 Hz, 1H) 7.21 (dd, J=12.09, 1.89 Hz, 1H) 7.35 (d, J=7.18 Hz, 1H) 7.42 (dd, J=7.74, 1.32 Hz, 1H) 7.52 (d, J=1.51 Hz, 1H) 7.54-7.65 (m, 2H) 7.65-7.71 (m, 1H) 8.25 (d, J=2.64 Hz, 1H) 8.28 (s, 1H) 8.63 (s, 1H)

Scheme E

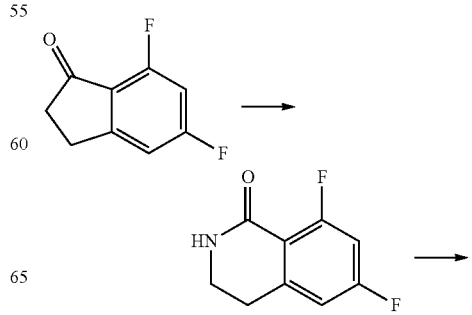

269

-continued

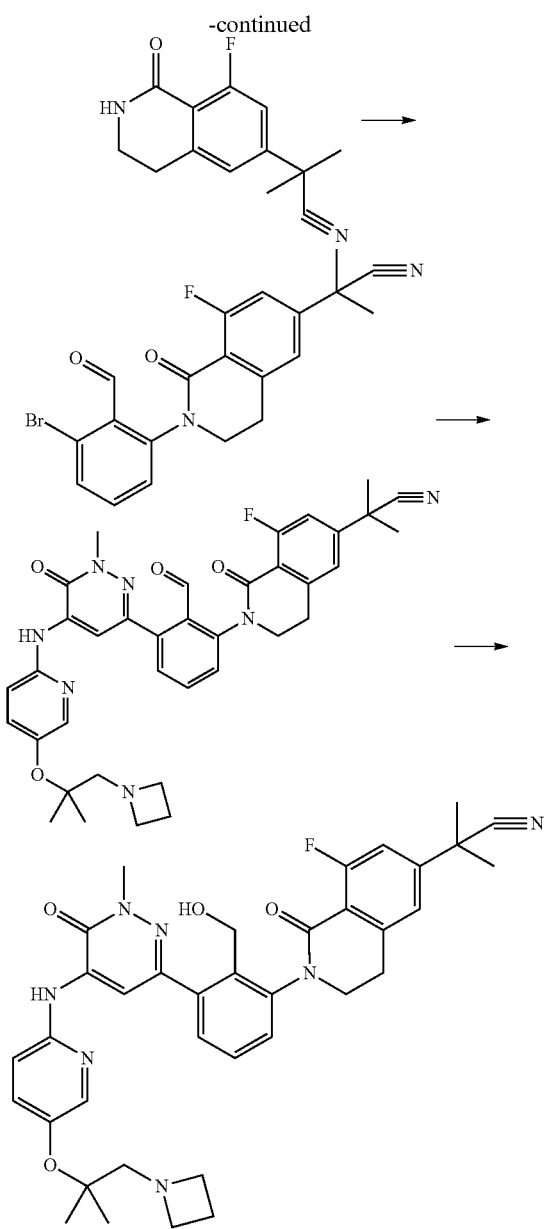

This example illustrates the synthesis of "2-[2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile.

Step 1. Preparation of 6,8-difluoro-3,4-dihydro-2H-isoquinolin-1-one

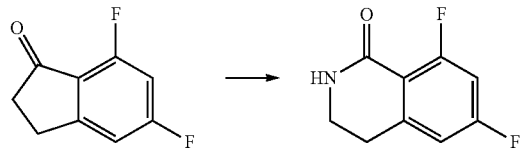 [SMILES: O=C1CCc2cc(F)cc(F)c21 ; O=C1NCCc2cc(F)cc(F)c21]

A 1000 ml 3-neck round bottom flask, fitted with an overhead stirrer, was charged with 5,7-difluoro-2,3-dihydro-1H-indene-1-one (10 g, 59.4 mmol) followed by dry dichloromethane (100 ml) and methanesulfonic acid (71.3 ml, 1.1 mol). The reaction was cooled to 0° C. (ice bath) and to this was added sodium azide (5.41 g; 83.2 mmol) in 4 equal portions over 20 minutes. The reaction was stirred at 0° C. for 2 hours and then a 20% aqueous solution of sodium hydroxide (175 ml) was added over 30 minutes with vigorous stirring. After complete addition the mixture was transferred to a separatory funnel and the methylene chloride phase was isolated. This was shaken with an equal volume of 50% diluted brine solution. The organic phase was collected and the aqueous phases were back extracted with dichloromethane (2×80 ml). The organic phases were combined, dried (magnesium sulfate), filtered and concentrated in vacuo. The crude residue was purified via HPLC on silica gel, eluting with 40% to 95% ethyl acetate/hexanes to provide the desired product as a white solid (8.364 g). (M+H)$^+$=184 m/e.

Step 2. Preparation of 2-(8-fluoro-1-oxo-1,2,3,4-tetrahydro-isoquinolin-6-yl)-2-methyl-propionitrile

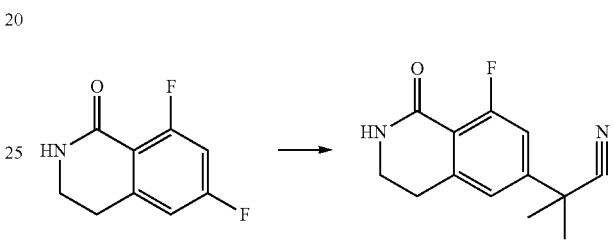

To a flask containing a solution of 6,8-difluoro-3,4-dihydro-2H-isoquinolin-1-one (4 g, 21.8 mmol) and isobutyronitrile (6.04 g, 87.4 mmol) in dry tetrahydrofuran (45 ml) was added a solution of potassium bis(trimethylsilyl)amide (50.4 ml, 0.91M in tetrahydrofuran) and the mixture was placed in an oil bath and heated to 70° C. On heating a red-brown homogeneous solution was obtained within 5 minutes. After 1 hour at 70° C., additional potassium bis(trimethylsilyl)amide (5 ml of 0.91 M) was added and was stirring continued for another 30 minutes. The flask was cooled to ambient temperature and the reaction was quenched with water (125 ml). Ethyl acetate (100 ml) was added and the material was transferred to a separatory funnel. The organic phase was collected and the aqueous phase was back extracted with ethyl acetate (2×70 ml). The combined organic phases were dried over magnesium sulfate, filtered and concentrated in vacuo. The residue was purified by chromatography on silica gel eluting with 100% dichloromethane to 3% methanol/dichloromethane to provide a semi-pure component (710 mg, 33% purity) as well as pure product as a white powder (316 mg). (M+H)$^+$=233 m/e.

Step 3. Preparation of 2-[2-(3-bromo-2-formyl-phenyl)-8-fluoro-1-oxo-1,2,3,4-tetrahydro-isoquinolin-6-yl]-2-methyl-propionitrile

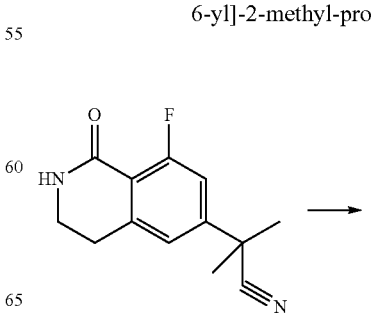

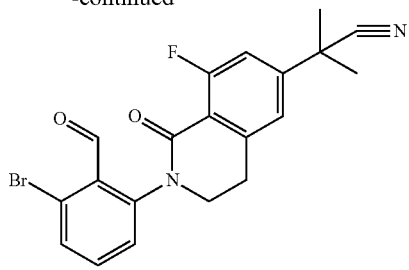

This reaction was carried out under similar conditions to those described in step 10, example I-15 (Scheme D). After workup the product was purified by HPLC on silica gel, eluting with a gradient of 100% methylene chloride to 1% methanol/methylene chloride. This provided the desired product as a light yellow solid (278 mg). (M+H)$^+$=415/417 m/e.

Step 4. Preparation of 2-[2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile

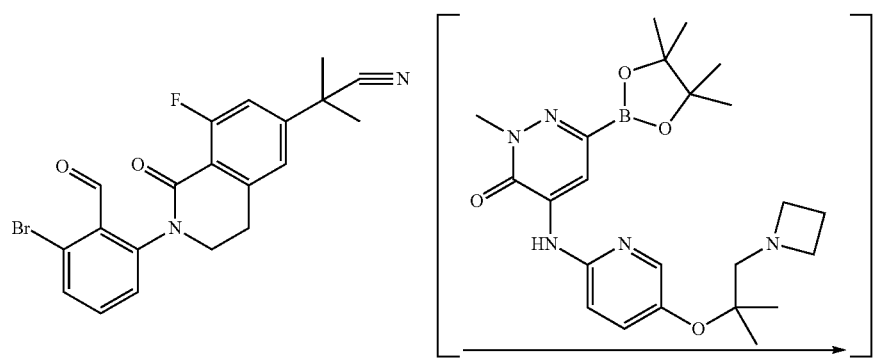

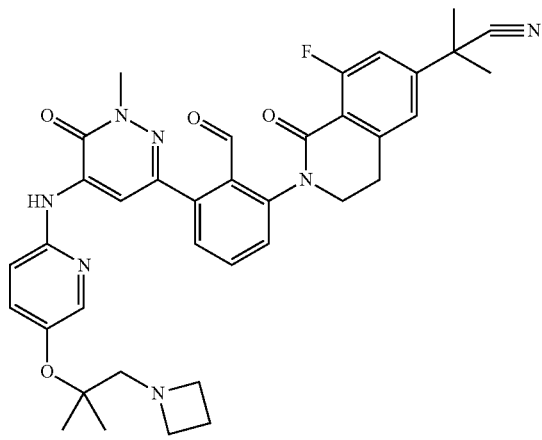

This reaction was carried out under similar conditions to those described in step 11, example 1-15 (Scheme D), but substituting 4-[5-(2-azetidin-1-yl-1,1-dimethyl-ethoxy)-pyridin-2-ylamino]-6-chloro-2-methyl-2H-pyridazin-3-one for 6-Chloro-2-methyl-4-[5-(morpholine-4-carbonyl)-pyridin-2-ylamino]-2H-pyridazin-3-one. After work-up the product was purified by HPLC on silica gel, eluting with a gradient of 100% methylenechloride to 1% methanol/methylenechloride. This provided the desired product as a light brown solid (172 mg). (M+H)$^+$=664 m/e.

Preparation of I-78

Example 78

Step 5. Preparation of 2-[2-(3-{5-[5-(2-azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile

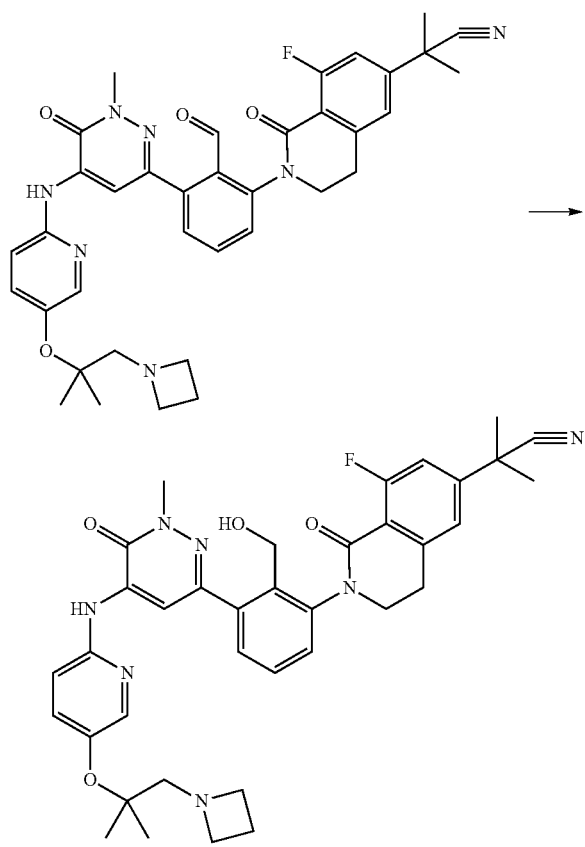

This reaction was carried out under similar conditions to those described in step 12, example 1-15 (Scheme D). After work-up the product was purified by HPLC on silica gel, eluting with a gradient of 3% to 14% methanol/methylene chloride. This material was then crystallized from hot methylene chloride/hexanes to provide the desired product as a white solid (108 mg). (M+H)$^+$=666 m/e. $^1$H NMR (300 MHz, CHLOROFORM-d) δ ppm 1.23 (s, 6H) 1.76 (s, 6H) 2.11 (quin, J=6.99 Hz, 2H) 2.58 (s, 2H) 3.12 (dt, J=16.15, 4.77 Hz, 1H) 3.27 (t, J=7.0 Hz, 4H) 3.36-3.45 (m, 3H) 3.90 (s, 3H) 3.93-4.16 (m, 3H) 4.34-4.69 (m, 2H) 6.89 (d, J=8.69 Hz, 1H) 7.14 (dd, J=11.71, 1.51 Hz, 1H) 7.25 (s, 1H) 7.32 (dd, J=8.69, 2.64 Hz, 1H) 7.37-7.44 (m, 1H) 7.47-7.64 (m, 2H) 8.07 (d, J=2.64 Hz, 1H) 8.26 (s, 1H) 8.52 (s, 1H).

Preparation of I-79

Example 79

Preparation of 2-(8-Fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydroisoquinolin-6-yl)-2-methyl-propionitrile

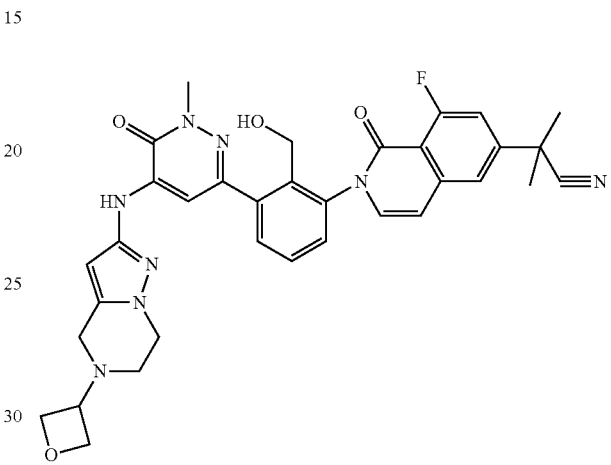

6-chloro-2-methyl-4-(5-(oxetan-3-yl)-4,5,6,7-tetrahydropyrazolo[1,5-a]pyrazin-2-ylamino)-pyridazin-3(2H)-one (prepared as described in example 60, 65 mg, 194 μmol) bis(pinacolato)diboron (54.1 mg, 213 μmol) and potassium acetate (57.0 mg, 581 μmol) were suspended in dioxane (9 ml). The reaction mixture was degassed under argon. X-PHOS (13.8 mg, 29.0 μmol) and palladium(II) acetate (2.17 mg, 9.68 μmol) were added and the reaction mixture was stirred at 100° C. (external temperature) for 45 min under an argon atmosphere. LCMS (taken in methanol) showed some conversion to boronic acid (M+1=347) and some of the undesired 2-methyl-4-(5-oxetan-3-yl-4,5,6,7-tetrahydropyrazolo[1,5-a]pyrazin-2-ylamino)-2H-pyridazin-3-one. Heating was turned down to 80° C. The flask was raised out of the heating bath, but continued stirring. 2-(2-(3-bromo-2-formylphenyl)-8-fluoro-1-oxo-1,2-dihydroisoquinolin-6-yl)-2-methylpropanenitrile (prepared as describe in example 15, 80 mg, 194 μmol) in 2 mL dioxanes and potassium carbonate (80.3 mg, 581 μmol) were added, followed by 1 mL H$_2$O. Tricyclohexylphosphine (5.43 mg, 19.4 μmol) and bis(dibenzylideneacetone)-palladium (0) (5.57 mg, 9.68 μmol) were added. The reaction mixture was heated with vigorous stirring at 80° C. for 1.5 h. The crude reaction was poured onto H$_2$O and EtOAc and extracted 3 times with EtOAc and 1 time with DCM. The combined organic extracts were washed with brine and dried over MgSO$_4$. The crude material was purified by flash chromatography (silica gel, 24 g, 1% to 5% MeOH in DCM) to afford approx. 90 mg the intermediate 2-(8-fluoro-2-(2-formyl-3-(1-methyl-5-(5-(oxetan-3-yl)-4,5,6,7-tetrahydropyrazolo[1,5-a]pyrazin-2-ylamino)-6-oxo-1,6-dihydropyridazin-3-yl)phenyl)-1-oxo-1,2-dihydroisoquinolin-6-yl)-2-methylpropanenitrile. In a 25 mL round-bottomed flask, 2-(8-fluoro-2-(2-formyl-3-(1-methyl-5-(5-(oxetan-3-yl)-4, 5,6,7-tetrahydropyrazolo[1,5-a]pyrazin-2-ylamino)-6-oxo- 1,6-dihydropyridazin-3-yl)phenyl)-1-oxo-1,2-dihydroisoquinolin-6-yl)-2-methylpropanenitrile (90 mg, 142 µmol) was combined with dry CH₂Cl₂ (2 ml) and dry MeOH (0.5 mL) to give a light yellow solution. The solution was cooled to 0° C. Sodium borohydride (9.66 mg, 255 µmol) was added. The reaction mixture was stirred at 0° C. for 40 min. Complete by LCMS. Quenched with sat'd NH₄Cl. The reaction mixture was poured into 25 mL H₂O and extracted with DCM (2×50 mL). The organic layers were dried over Na₂SO₄ and concentrated in vacuo. The crude material was purified by flash chromatography (silica gel, 24 g, 0% to 3% MeOH). Pure fractions were concentrated to give a glass, which was dissolved in 1 mL DCM and precipitated with 20 mL ether to afford the desired product (18 mg) as a white solid. (M+H)⁺=637 m/e. ¹H NMR (300 MHz, CHLOROFORM-d) δ ppm 1.81 (s, 6H) 2.90 (t, J=5.48 Hz, 2H) 3.55-3.71 (m, 2H) 3.77-3.86 (m, 1H) 3.89 (s, 3H) 4.17 (t, J=5.48 Hz, 2H) 4.26-4.42 (m, 2H) 4.66-4.87 (m, 4H) 5.83 (s, 1H) 6.62 (dd, J=7.55, 1.89 Hz, 1H) 7.22 (dd, J=12.28, 1.70 Hz, 1H) 7.34 (d, J=7.18 Hz, 1H) 7.41 (dd, J=7.74, 1.32 Hz, 1H) 7.50-7.61 (m, 2H) 7.63-7.72 (m, 1H) 7.85 (s, 1H) 7.95 (s, 1H).

Preparation of I-80

Example 80

Preparation of 6-tert-Butyl-8-fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one

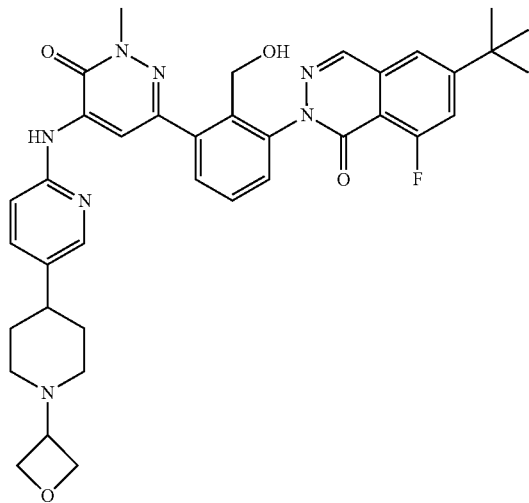 [SMILES: Cn1nc(-c2cccc(-n3ncc4cc(C(C)(C)C)cc(F)c4c3=O)c2CO)cc(Nc2ccc(C3CCN(C4COC4)CC3)cn2)c1=O]

Step 1. To a solution of 6-chloro-2-methyl-4-(5-(piperidin-4-yl)pyridin-2-ylamino)pyridazin-3(2H)-one (639 mg, 2.00 mmol, Eq: 1.00) and oxetan-3-one (288 mg, 4.00 mmol, Eq: 2.0) in THF (10 ml) was added acetic acid (360 mg, 343 µl, 5.99 mmol, Eq: 3.0). The reaction mixture stirred under N₂, at 55° C. for 1 h. Then sodium triacetoxyborohydride (847 mg, 4.00 mmol, Eq: 2.0) was added and the mixture was stirred at 65° C. for 2 h. The reaction mixture was cooled to room temperature and concentrated in vacuo. The residue was partitioned between DCM and saturated NaHCO₃. The layers were separated and the organic layer was washed with water. The organic layer was then dried over Na₂SO₄ and concentrated in vacuo. The crude material was purified by flash chromatography (silica gel, 24 g, 0% to 40% (60:10:1 DCM:MeOH:NH₄OH)/DCM) gradient) to give 6-chloro-2-methyl-4-(1'-oxetan-3-yl-1',2',3',4',5',6'-hexahydro-[3,4']bipyridinyl-6-ylamino)-2H-pyridazin-3-one (453 mg, 60%). LC/MS-ESI observed [M+H]⁺ 376. 1H NMR in CDCl₃ is consistent with desired product.

Step 2. In a 50 mL test tube, 6-chloro-2-methyl-4-(5-(1-(oxetan-3-yl)piperidin-4-yl)pyridin-2-ylamino)pyridazin-3(2H)-one (120 mg, 319 µmol) and 2-(6-tert-butyl-8-fluoro-1-oxophthalazin-2(1H)-yl)-6-(4,4,5,5-tetramethyl-1,3,2-dioxaborolan-2-yl)benzyl acetate (271 mg, 383 µmol) were combined with BuOH (4 ml) to give a orange solution. 1 mL of water was added. Purged with argon. X-PHOS (15.2 mg, 31.9 µmol) and potassium phosphate tribasic (136 mg, 639 µmol) were added. Argon was bubbled through for 5 min. bis(Dibenzylideneacetone)-palladium (0) (9.18 mg, 16.0 µmol) was added and the reaction mixture was placed under an argon atmosphere and was warmed in a oil bath at 110° C. for 1.5 hours. No 6-chloro-2-methyl-4-(5-(1-(oxetan-3-yl)piperidin-4-yl)pyridin-2-ylamino)pyridazin-3(2H)-one remained by LCMS. Two main products were observed by LCMS, acetylated and deacetylated product. The reaction mixture was allowed to cool to RT overnight and the concentrated to a small volume. The reaction mixture was poured into 75 mL H₂O and extracted with EtOAc (3×75 mL). The organic layers were dried over Na₂SO₄ and concentrated in vacuo. The crude material was purified by flash chromatography (silica gel, 24 g, 1% to 6% MeOH in DCM). Pure acetylated and deacetylated products and mixed fractions were combined and conc. to afford 162 mg of the mixture. This mixture of 2-(6-tert-butyl-8-fluoro-1-oxophthalazin-2(1H)-yl)-6-(1-methyl-5-(5-(1-(oxetan-3-yl)piperidin-4-yl)pyridin-2-ylamino)-6-oxo-1,6-dihydropyridazin-3-yl)benzyl acetate (162 mg, 229 µmol, Eq: 1.00) and 6-tert-butyl-8-fluoro-2-(2-(hydroxymethyl)-3-(1-methyl-5-(5-(1-(oxetan-3-yl)piperidin-4-yl)pyridin-2-ylamino)-6-oxo-1,6-dihydropyridazin-3-yl)phenyl)phthalazin-1(2H)-one (152 mg, 229 µmol) was dissolved in 8 mL THF. 2 mL of 1N NaOH was added. The reaction was warmed at 50° C. for 6 hrs and then at 60° C. for 18 h. The reaction mixture was poured into 100 mL H₂O and extracted with EtOAc (2×75 mL) and DCM (1×75 ml). The combined organic extracts were washed with brine, dried over MgSO₄ and concentrated in vacuo. The crude material was purified by flash chromatography (silica gel, 24 g, 0% to 4% MeOH in DCM) and then by preparative tlc (3% MeOH in DCM eluent) to afford the desired product (78 mg) as a white solid. (M+H)⁺=666 m/e. ¹H NMR (300 MHz, CHLOROFORM-d) δ ppm 1.43 (s, 9H) 1.58 (br. s., 1H) 1.72-2.06 (m, 3H) 2.89 (br. s., 1H) 3.75-4.09 (m, 4H) 4.43 (d, J=6.80 Hz, 2H) 4.69 (d, J=6.42 Hz, 3H) 6.92 (d, J=8.31 Hz, 1H) 7.42-7.62 (m, 5H) 7.63-7.71 (m, 1H) 8.17-8.35 (m, 3H) 8.61 (s, 1H)

277

Preparation of I-81

Example 81

Preparation of 6-tert-Butyl-8-fluoro-2-{2-hydroxymethyl-3-[1-methyl-5-(1'-oxetan-3-yl-1',2',3',4',5',6'-hexahydro-[3,4']bipyridinyl-6-ylamino)-6-oxo-1,6-dihydro-pyridazin-3-yl]-phenyl}-2H-phthalazin-1-one

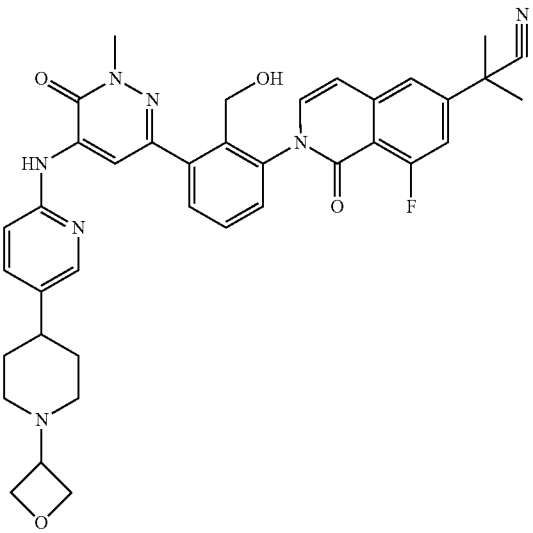 [SMILES: Cn1nc(-c2cccc(-n3ccc4cc(C(C)(C)C#N)cc(F)c4c3=O)c2CO)cc(Nc2ccc(C3CCN(C4COC4)CC3)cn2)c1=O]

Preparation by a similar procedure to Example 79, except substituting 6-chloro-2-methyl-4-(1'-oxetan-3-yl-1',2',3',4',5',6'-hexahydro-[3,4']bipyridinyl-6-ylamino)-2H-pyridazin-3-one for 6-chloro-2-methyl-4-(5-(oxetan-3-yl)-4,5,6,7-tetrahydropyrazolo[1,5-a]pyrazin-2-ylamino)-pyridazin-3(2H)-one, afforded the desired product as a white powder (173 mg). (M+H)$^+$=676 m/e. $^1$H NMR (300 MHz, CHLOROFORM-d) δ ppm 1.43-2.10 (m and overlapping singlet, 14H) 2.54 (d, J=7.18 Hz, 1H) 2.91 (d, J=9.44 Hz, 2H) 3.55 (br. s., 1H) 3.91 (s, 3H) 4.01 (dd, J=10.20, 4.15 Hz, 1H) 4.20-4.50 (m, 2H) 4.69 (d and m, J=6.42 Hz, 3H) 6.62 (dd, J=7.36, 2.08 Hz, 1H) 6.92 (d, J=8.69 Hz, 1H) 7.22 (dd, J=12.46, 1.89 Hz, 1H) 7.35 (d, J=7.55 Hz, 1H) 7.42 (dd, J=7.74, 1.32 Hz, 1H) 7.49-7.64 (m, 3H) 7.65-7.74 (m, 1H) 8.17-8.33 (m, 2H) 8.63 (s, 1H).

Preparation of I-82

Example 82

Preparation of 6-tert-Butyl-2-{3-[5-(5-ethyl-4,5,6,7-tetrahydro-pyrazolo[1,5-a]pyrazin-2-ylamino)-1-methyl-6-oxo-1,6-dihydro-pyridazin-3-yl]-2-hydroxymethyl-phenyl}-8-fluoro-2H-phthalazin-1-one

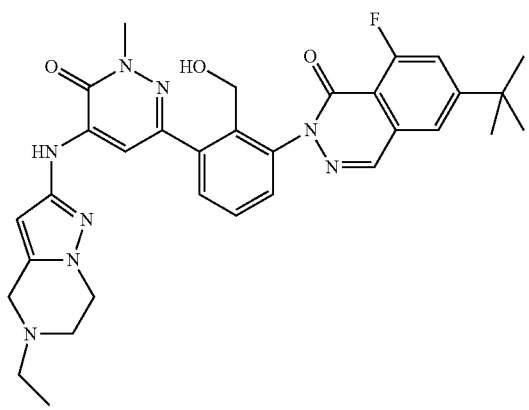 [SMILES: CCN1CCn2nc(Nc3cc(-c4cccc(-n5ncc6cc(C(C)(C)C)cc(F)c6c5=O)c4CO)nn(C)c3=O)cc2C1]

278

Preparation by a similar procedure to Example 59, except substituting ethylamine for methyl amine in step 5 afforded the desired product as a white powder (196 mg). (M+H)$^+$=599 m/e. $^1$H NMR (300 MHz, CHLOROFORM-d) δ ppm 1.21 (t, J=7.18 Hz, 3H) 1.43 (s, 9H) 2.67 (d, J=6.42 Hz, 2H) 2.99 (br. s., 2H) 3.70 (br. s., 2H) 3.88 (s, 3H) 4.02 (t, J=6.99 Hz, 1H) 4.15 (br. s., 2H) 4.40 (d, J=6.80 Hz, 2H) 5.83 (s, 1H) 7.41-7.59 (m, 4H) 7.61-7.67 (m, 1H) 7.81 (s, 1H) 7.92 (s, 1H) 8.28 (d, J=2.64 Hz, 1H)

Preparation of I-83

Example 83

Preparation of 2-(2-{3-[5-(5-Ethyl-4,5,6,7-tetrahydro-pyrazolo[1,5-a]pyrazin-2-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile

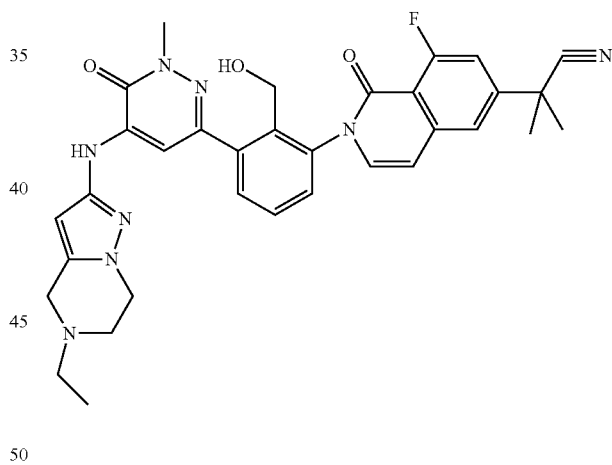

Preparation by a similar procedure to Example 80, except substituting 6-Chloro-4-(5-ethyl-4,5,6,7-tetrahydro-pyrazolo[1,5-a]pyrazin-2-ylamino)-2-methyl-2H-pyridazin-3-one for 6-chloro-2-methyl-4-(5-(oxetan-3-yl)-4,5,6,7-tetrahydropyrazolo[1,5-a]pyrazin-2-ylamino)-pyridazin-3(2H)-one, afforded the desired product as a white powder (70 mg). (M+H)$^+$=609 m/e. $^1$H NMR (300 MHz, CHLOROFORM-d) δ ppm 1.13-1.29 (m, 3H) 1.57 (br. s., 2H) 1.81 (s, 7H) 2.67 (br. s., 1H) 2.99 (br. s., 1H) 3.70 (br. s., 1H) 3.89 (s, 3H) 4.02-4.21 (m, 3H) 4.22-4.47 (m, 2H) 5.81 (s, 1H) 6.61 (dd, J=7.36, 2.08 Hz, 1H) 7.21 (dd, J=12.09, 1.89 Hz, 1H) 7.35 (d, J=7.18 Hz, 1H) 7.38-7.44 (m, 1H) 7.49-7.60 (m, 2H) 7.63-7.69 (m, 1H) 7.83 (s, 1H) 7.94 (s, 1H).

Preparation of I-84

Example 84

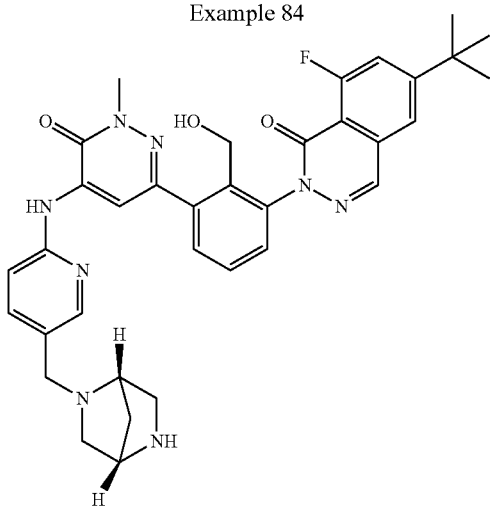

6-tert-Butyl-2-[3-(5-{5-[(1S,4S)-1-(2,5-diaza-bicyclo[2.2.1]hept-2-yl)methyl]-pyridin-2-ylamino}-1-methyl-6-oxo-1,6-dihydro-pyridazin-3-yl)-2-hydroxymethyl-phenyl]-8-fluoro-2H-phthalazin-1-one was prepared using the general procedure described in Example 41, substituting (1S,4S)-tert-butyl 2,5-diazabicyclo[2.2.1]heptane-2-carboxylate for 1-methylpiperazine. In the penultimate step of the synthesis for this compound, 1M NaOH was used to remove the acetate protecting group rather than potassium carbonate, using THF as the solvent and heating at 60° C. for two hours, then stirring at room temperature overnight. The BOC protecting group was removed with 1,1,1,3,3,3-hexafluoro-2-propanol using the alcohol as the solvent and heating at 140° C. for 30 minutes in a microwave reactor, then another 45 minutes at 150° C. After purification by chromatography using a gradient of 5% to 25% methanol in DCM, 50 mg of product was obtained as an off-white powder. $^1$H NMR (300 MHz, DMSO-d6) δ ppm 9.39 (s, 1H) 8.49-8.56 (m, 2H) 8.19-8.50 (m, 1H) 7.88 (s, 1H) 7.71-7.76 (m, 1H) 7.54-7.61 (m, 1H) 7.44-7.51 (m, 4H) 4.56 (t, J=5.7 Hz, 1H) 4.42 (br. s., 2H) 3.91 (s, 1H) 3.77 (s, 3H) 3.52-3.64 (m, 4H) 3.06 (d, J=10.2 Hz, 1H) 2.71 (d, J=9.4 Hz, 2H) 2.38 (d, J=9.1 Hz, 1H) 1.72 (d, J=10.2 Hz, 1H) 1.44 (d, J=7.6 Hz, 1H) 1.38 (s, 9H). MS: (M+H)$^+$=637. MP>250° C.

Preparation of I-85

Example 85

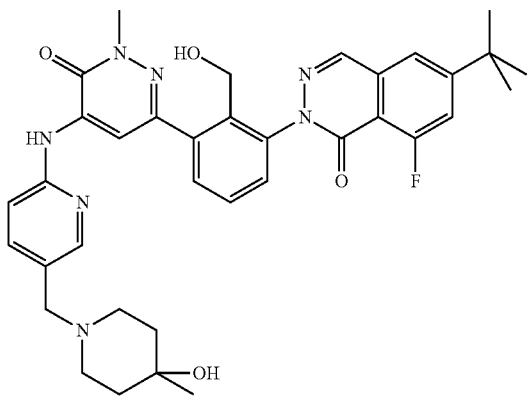 [SMILES: Cn1nc(-c2cccc(-n3ncc4cc(C(C)(C)C)cc(F)c4c3=O)c2CO)cc(Nc2ccc(CN3CCC(C)(O)CC3)cn2)c1=O]

Preparation by a similar procedure to Example 41, except substituting 4-methyl-piperidin-4-ol for 1-methylpiperazine in step 1, afforded 6-tert-Butyl-8-fluoro-2-(2-hydroxymethyl-3-{5-[5-(4-hydroxy-4-methyl-piperidin-1-ylmethyl)-pyridin-2-ylamino]-1-methyl-6-oxo-1,6-dihydro-pyridazin-3-yl}-phenyl)-2H-phthalazin-1-one (83 mg) as a white solid. (M+H)$^+$=654 m/e. $^1$H NMR (300 MHz, CHLOROFORM-d) δ ppm 1.26 (s, 3H) 1.43 (s, 9H) 1.60 (d, J=13.97 Hz, 4H) 3.91 (s and overlapping multiplet, 4H) 4.43 (d, J=7.18 Hz, 2H) 6.94 (d, J=8.31 Hz, 1H) 7.42-7.71 (m, 5H) 8.23-8.34 (m, 3H) 8.65 (s, 1H)

Preparation of I-86

Example 86

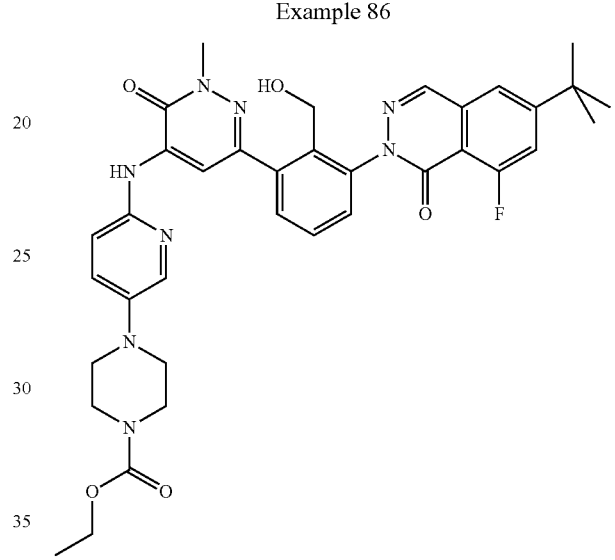

Preparation by a similar procedure to Example 56, except substituting 4-(6-nitro-pyridin-3-yl)-piperazine-1-carboxylic acid ethyl ester for 1-methyl-4-(6-nitropyridin-3-yl)piperazine in step 1, afforded 4-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridin-3-yl)-piperazine-1-carboxylic acid ethyl ester (43 mg) as a yellow solid. (M+H)$^+$=654 m/e. $^1$H NMR (400 MHz, CHLOROFORM-d) δ ppm 1.22 (t, J=7.15 Hz, 3H) 1.36 (s, 9H) 3.10 (br. s., 4H) 3.66 (br. s., 3H) 3.83 (s, 3H) 4.11 (q, J=7.11 Hz, 2H) 4.29-4.30 (m, 1H) 4.35 (s, 2H) 7.03 (d, J=8.28 Hz, 1H) 7.34-7.64 (m, 6H) 8.00 (br. s., 1H) 8.22 (d, J=2.51 Hz, 1H) 8.36 (s, 1H).

Preparation of I-87

Scheme F

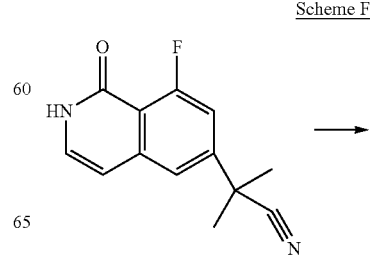

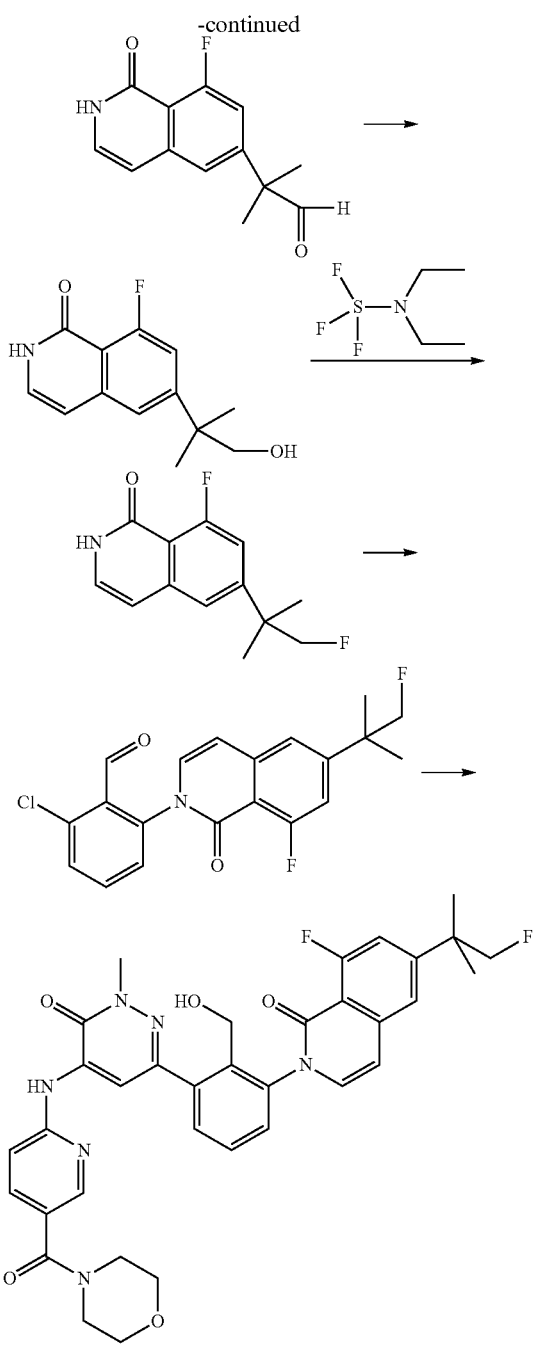

Preparation of 8-Fluoro-6-(2-fluoro-1,1-dimethylethyl)-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one Step 1. Preparation of 2-(8-fluoro-1-oxo-1,2-dihydroisoquinolin-6-yl)-2-methylpropanal A solution of 2-(8-fluoro-1-oxo-1,2-dihydroisoquinolin-6-yl)-2-methylpropanenitrile (1.77 g, 3.34 mmol) was prepared in THF/Toluene in an oven dried flask. The flask was cooled to −78° C. under a N₂ atmosphere. To this was added a DiBAL-H (14 mL of 1M in hexanes, 14 mmol) via syringe over about 10 minutes. The reaction mixture was stirred for 60 min at −78° C. and then warmed to 0° C. and stirred for 1 hour. To this resultant solution was added 50 ml of 3 N HCl (aq) and 50 ml of EtOAc. The mixture was shaken and the EtOAc phase was collected and washed with 25 ml of brine. The aqueous phase was back extracted (2×40 ml EtOAc). The organic layer was dried (MgSO4), filtered and conc. in vacuo. Only 344 mg of crude product was obtained. Product was crystallized from hot DCM/Hexane. Product was collected by filtration to afford 280 mg of a white crystalline product. (M+H)$^+$=234 m/e.

Step 2. Preparation of 8-fluoro-6-(1-hydroxy-2-methylpropan-2-yl)isoquinolin-1(2H)-one 2-(8-Fluoro-1-oxo-1,2-dihydroisoquinolin-6-yl)-2-methylpropanal (137 mg, 587 μmol) was dissolved in MeOH and cooled in an ice bath. To the resulting solution was added NaBH₄ (33 mg, 881 μmol) in one portion. The reaction mixture was stirred vigorously for 5 minutes before removing the cooling bath and stirring for 30 minutes. To the reaction mixture was added about 40 ml of 10% HCl and 40 ml EtOAc. The mixture was shaken and the EtOAc phase collected. The organic phase was washed with an equal volume of water. The aqueous phase was back extracted with 2×30 ml EtOAc. The combined organic phase was dried (MgSO₄), filtered and concentrated in vacuo to afford 109 mg of a off-white powder. (M+H)$^+$=236 m/e.

Step 3. Preparation of 8-fluoro-6-(1-fluoro-2-methylpropan-2-yl)isoquinolin-1(2H)-one 8-fluoro-6-(1-hydroxy-2-methylpropan-2-yl)isoquinolin-1(2H)-one (114 mg, 485 μmol) was dissolved in DCM (dry) and cooled to −78° C. under argon. To this solution was added the diethylaminosulfur trifluoride (90 μl, 678 μmol) and the reaction was stirred for about 10 min before removal of the cooling bath. The reaction was warmed to ambient and stirred at this temperature for 2 hrs. To the reaction mixture was added 25 ml water and 20 ml DCM. The mixture was shaken and the organics collected. The organics were washed with 25 ml brine. The aqueous phase was extracted (2×20 ml DCM). The combined organics were dried (MgSO₄), filtered and concentrated in vacuo. The crude product was purified by preparative tlc (2 plates, eluted with 4.5% MeOH/DCM) to afford 92 mg of the desired product as an off-white powder. (M+H)$^+$=238 m/e.

Step 4. Preparation of 2-Chloro-6-[8-fluoro-6-(2-fluoro-1,1-dimethyl-ethyl)-1-oxo-1H-isoquinolin-2-yl]-benzaldehyde6,8-difluoro-3,4-dihydro-2H-isoquinolin-1-one In a 250 mL round-bottomed flask, 8-fluoro-6-(1-fluoro-2-methylpropan-2-yl)isoquinolin-1(2H)-one (92 mg, 388 μmol), 2-bromo-6-chlorobenzaldehyde (136 mg, 620 μmol) and potassium carbonate (107 mg, 776 μmol) were combined with DMSO (1.23 ml) to give a yellow suspension. The mixture was degassed with argon for 5 min. Copper(I) iodide (73.9 mg, 13.1 μl, 388 μmol) was added and the resulting mixture was placed in a oil bath at 110° C. The reaction mixture was heated to 110° C. and stirred for 1.5 h. Reaction was not complete by LCMS. More 2-bromo-6-chlorobenzaldehyde (70 mg) was added. The reaction mixture was heated to 110° C. and stirred for 3 h, then allowed to cool to ambient. The crude reaction mixture was filtered through a plug of celite and washed through with EtOAc. The combined filtrate and washes were added to a separatory funnel with 25 ml of 1:1 diluted sat NH$_4$Cl/water. The organic phase was collected and washed with an equal volume of brine. The aqueous phase was extracted (2×20 ml EtOAc). The combined organic phase was dried (MgSO$_4$), filtered and concentrated in vacuo. The crude product was purified by preparative tlc: 2 plates; eluted with 2% MeOH/DCM to afford the desired product (106 mg) as a light yellow semi-solid. (M+H)$^+$=376 m/e.

Example 87

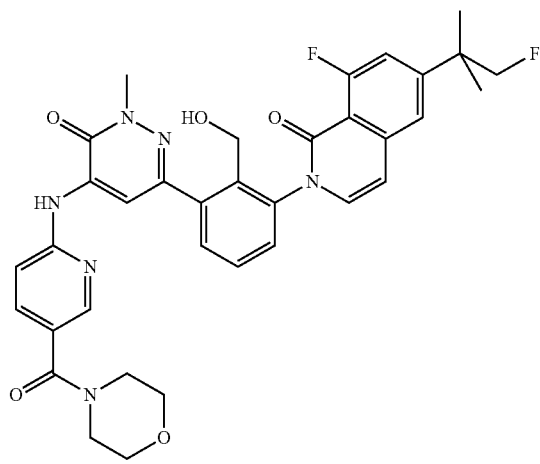 [SMILES: Cn1nc(-c2cccc(-n3ccc4cc(C(C)(C)CF)cc(F)c4c3=O)c2CO)cc(Nc2ccc(C(=O)N3CCOCC3)cn2)c1=O]

Preparation by a procedure similar to Example 15 (steps 11-12), except substituting 2-chloro-6-[8-fluoro-6-(2-fluoro-1,1-dimethyl-ethyl)-1-oxo-1H-isoquinolin-2-yl]-benzaldehyde for 6-chloro-2-methyl-4-(5-morpholine-4-carbonyl)pyridine-2-ylamino)pyridazin-3(2H)-one in step 11, afforded 8-fluoro-6-(2-fluoro-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one (43 mg) as a yellow solid. (M+H)$^+$=657 m/e. $^1$H NMR (300 MHz, CHLOROFORM-d) δ ppm 1.36 (s, 3H) 1.43 (s, 3H) 2.92-3.10 (m, 2H) 3.56-3.80 (m, 8H) 3.91 (s, 4H) 4.38 (d, J=4.15 Hz, 2H) 6.57 (dd, J=7.55, 1.89 Hz, 1H) 6.97-7.14 (m, 2H) 7.25 (dd, J=10.39, 2.83 Hz, 2H) 7.41 (dd, J=7.74, 1.32 Hz, 1H) 7.52-7.70 (m, 2H) 7.77 (dd, J=8.31, 2.27 Hz, 1H) 8.38-8.53 (m, 2H) 8.70 (s, 1H).

Preparation of I-88

Example 88

Step 1. Preparation of
6-Chloro-3-methoxy-4-trimethylsilanyl-pyridazine

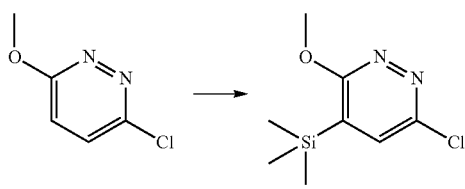

In a 2-necked round bottom flask under argon placed 4.0476 g of distilled diisopropylamine and 60 mL of tetrahydrofuran (Aldrich, anhydrous, no stabilizer). The mixture was cooled to −78° C., then ca 20 mL of 2.0 M butyl lithium in cyclohexane was added. The mixture was set in an ice bath for 20 minutes, then cooled to −78° C. and a solution of 2.8912 g of 3-chloro-6-methoxy-pyridazine and 3.05 mL of chlorotrimethyl silane in 12 mL of tetrahydrofuran was added over 15 minutes. The mixture was stirred for 2 hours (a deep red color formed, then faded to yellow), then quenched by the addition of 10 mL of saturated sodium dihydrogen phosphate solution. The mixture was taken up in 350 mL of ethyl acetate, washed 1×75 mL brine, dried over anhydrous sodium sulfate, filtered and concentrated under reduced pressure.

4.4056 g amber oil which was purified by chromatography on silica gel (silicycle 80 g column, 3.4×19.2 cm (174 mL volume), sample applied in dichloromethane, eluted with dichloromethane-ethyl acetate (199:1) the desired product (3.4 g).

Step 2. Preparation of 6chloro-2-methyl-4-trimethyl-silanyl-2H-pyridazin-3-one and 6-iodo-2-methyl-4-trimethylsilanyl-2H-pyridazin-3-one

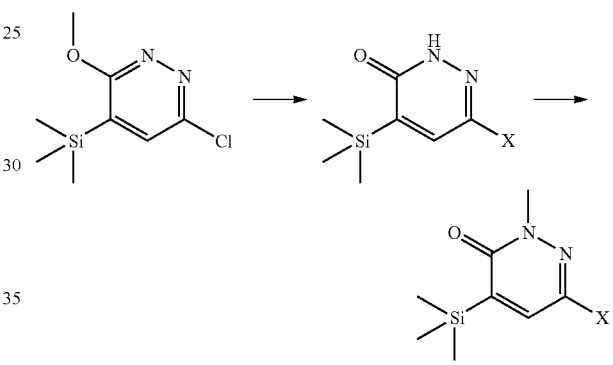

X = Cl, I

In round bottom flask was placed 1.6068 g 6-chloro-3-methoxy-4-trimethylsilanyl-pyridazine and 40 mL of chloroform (Aldrich, anhydrous, amylene inhibitor). The mixture was vacuum flushed 3× argon, then was added 3.33 mL of iodotrimethyl silane in 5 mL of chloroform (reaction turned amber). The flask was set in a bath at 60° C. and stirred. After 2 hours, the mixture was cooled and the reaction mixture was taken up in 450 mL of dichloromethane, washed 1×200 mL brine containing 5 g sodium thiosulfate and 3.6 g of K$_2$HPO$_4$, dried over anhydrous sodium sulfate, filtered and concentrated under reduced pressure. The crude product was purified by chromatographyon (silica gel, Silicycle 40 (2.6×13.3 cm 71 mL vol), sample applied in solvent, eluting with dichloromethane-ethyl acetate (90:10) afforded 2.69 g yellow solid, which consisted of 4:3 mixture of 6-chloro-4-trimethylsilanyl-2H-pyridazin-3-one and 6-iodo-4-trimethylsilanyl-2H-pyridazin-3-one. This mixture was placed in a round bottom flask under argon. To this was added 5.48 g cesium carbonate and 15 mL of dimethylformamide. The mixture was cooled in an ice bath and 2.38 g iodomethane was added over 60 seconds. The cooling bath was removed and the mixture stirred at room temperature. After 90 minutes, the mixture was taken up in 400 mL dichloromethane, washed 3×75 mL water, 1×75 mL brine, dried over anhydrous sodium sulfate, filtered and concentrated under reduced pressure. The crude product was purified on silica gel (Silicycle 40 (2.6×13.3 cm 71 mL vol), sample applied in solvent, eluting with dichloromethane-ethyl acetate (98:2)) to afford 2.53 g of an off white solid as a 6:4 mixture of 6-chloro-2-methyl-4-trimethylsilanyl-2H-pyridazin-3-one and 6-iodo-2-methyl-4-trimethylsilanyl-2H-pyridazin-3-one.

Step 3. Preparation of acetic acid 2-(6-tert-butyl-8-fluoro-1-oxo-1H-phthalazin-2-yl)-6-(1-methyl-6-oxo-5-trimethylsilanyl-1,6-dihydro-pyridazin-3-yl)-benzyl ester

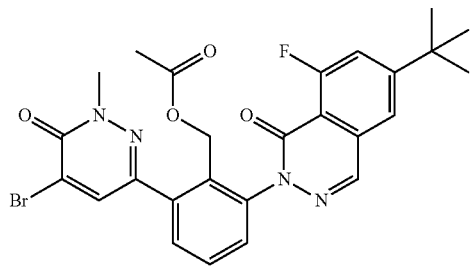

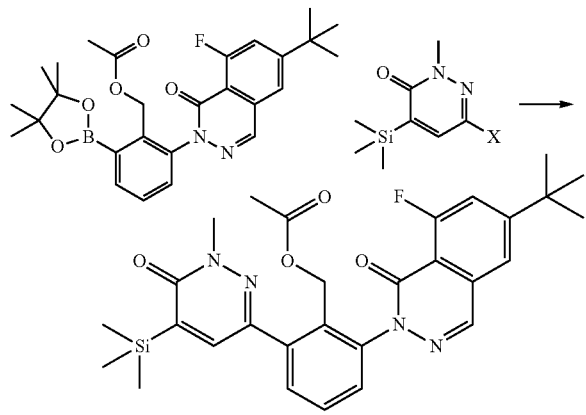

In round bottom flask was placed 3.21 g acetic acid 2-(6-tert-butyl-8-fluoro-1-oxo-1H-phthalazin-2-yl)-6-(4,4,5,5-tetramethyl-[1,3,2]dioxaborolan-2-yl)-benzyl ester, 2.06 g sodium carbonate, 0.68 g bistriphenylphosphine palladium dichloride, and 1.99 g a 6:4 mixture of 6-chloro-2-methyl-4-trimethylsilanyl-2H-pyridazin-3-one and 6-iodo-2-methyl-4-trimethylsilanyl-2H-pyridazin-3-one followed by 130 mL of dioxane (EM DriSolv)-water (10:1). The mixture was vacuum flushed 5× argon, then set in a bath at 95° C. and stirred (mechanical). After 5.5 hours, the mixture was cooled, taken up in 350 mL of ethyl acetate and washed 1×75 mL of brine. The ethyl acetate layer was dried over anhydrous sodium sulfate, filtered and concentrated under reduced pressure. The crude product was purified by chromatography on silica gel (Silicycle 120 g, 3.5×21.5 cm, 207 vol), applied in dichloromethane eluting with CH$_2$Cl$_2$-ethyl acetate (80:20), followed by chromatography on silica gel (Silicycle 120 g, 3.5×21.5 cm, 207 vol), applied in dichloromethane, eluting with dichloromethane-ethyl acetate (80:20) afforded 2.5418 g (71%) of product as a foam.

Step 4. Preparation of acetic acid acetic acid 2-(5-bromo-1-methyl-6-oxo-1,6-dihydro-pyridazin-3-yl)-6-(6-tert-butyl-8-fluoro-1-oxo-1H-phthalazin-2-yl)-benzyl ester

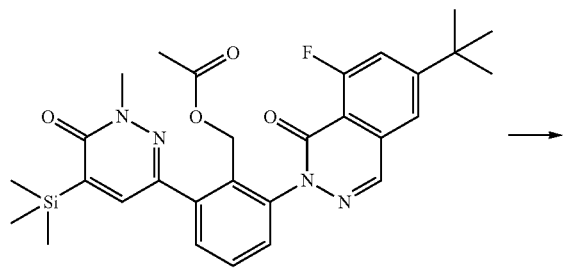

In round bottom flask with reflux condenser was placed 2.54 g acetic acid 2-(6-tert-butyl-8-fluoro-1-oxo-1H-phthalazin-2-yl)-6-(1-methyl-6-oxo-5-trimethylsilanyl-1,6-dihydro-pyridazin-3-yl)-benzyl ester, 5.51 g potassium bromide, 4.55 g potassium acetate, followed by ca 18.4908 g bromine. The mixture warmed on addition of the bromine. The mixture was stirred for 2 minutes at room temperature, then set in a bath at 55° C. and stirred. A stopper was placed lightly in the top of the reflux condenser to contain the bromine vapors. After 70 minutes, the mixture was cooled to room temperature, excess bromine removed under a stream of nitrogen. The mixture was taken up in 500 mL of dichloromethane, washed 1×150 mL brine, containing 12 g sodium bisulfite with some resultant exotherm, dried over anhydrous sodium sulfate, filtered and concentrated under reduced pressure. Purification by chromatography on silica gel (Silicycle 120 g, 3.5×21.5 cm, 207 vol), applied in dichloromethane, eluting with dichloromethane-ethyl acetate (80:20), followed by chromatography on silica gel (Silicycle 120 g, 3.5×21.5 cm, 207 vol), applied in dichloromethane, eluting with dichloromethane-ethyl acetate (80:20) to afford the desired product (1.91 g) as an off white solid.

Step 5. Preparation of acetic acid 6-tert-Butyl-8-fluoro-2-(2-hydroxymethyl-3-{1-methyl-5-[5((1S,4S)-5-methyl-2,5-diaza-bicyclo[2.2.1]hept-2-yl)-pyrazin-2-ylamino]-6-oxo-1,6-dihydro-pyridazin-3-yl}-phenyl)-2H-phthalazin-1-one

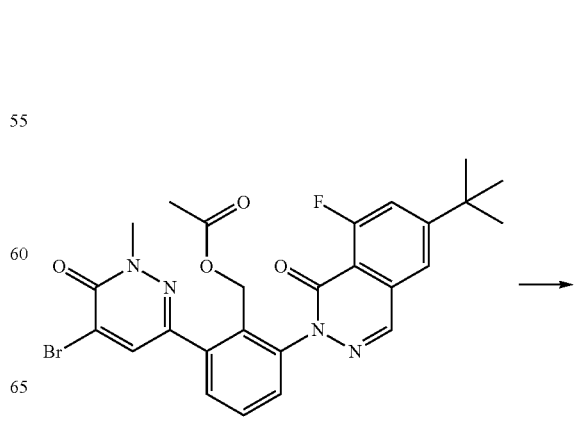

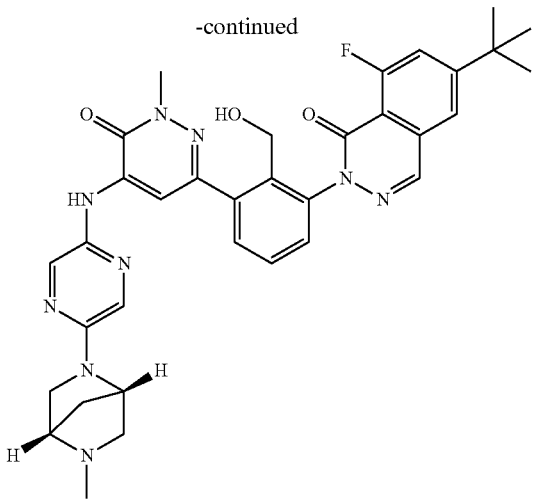

5-((1S,4S)-5-methyl-2,5-diazabicyclo[2.2.1]heptan-2-yl) pyrazin-2-amine (prepared by a similar procedure 4-methyl-3,4,5,6-tetrahydro-2H-[1,2']bipyrazinyl-5'-ylamine in example 34, 50 mg, 292 µmol), 2-(5-bromo-1-methyl-6-oxo-1,6-dihydropyridazin-3-yl)-6-(6-tert-butyl-8-fluoro-1-oxophthala-zin-2(1H)-yl)benzyl acetate (170 mg, 307 µmol), cesium carbonate (286 mg, 877 µmol), xantphos (25 mg, 44 µmol), tris(dibenzylideneacetone)dipalladium (0) (20 mg, 22 µmol) and dioxane (3 mL) were combined in a microwave vial, degassed with argon and heated at 100° C. for 18 h. The crude reaction mixture was filtered through celite, concentrated and purified by chromatography using a gradient of 0% to 25% methanol in DCM. The resulting residue, which was a mixture of acetylated and deacetylated product, was dissolved in methanol. Potassium carbonate (61 mg, 441 µmol) was added and the reaction was heated at 40° C. for 1 hr. Water was added dropwise and the resultant mixture was stirred at room temperature overnight. The solid was collected by filtration. Purification by preparative tlc in 10% methanol in DCM afforded the desired product (17 mg) as a yellow powder. $(M+H)^+=638$ m/e.

$^1$H NMR (300 MHz, DMSO-$d_6$) δ ppm 1.37 (s, 9H) 1.66-1.92 (m, 2H) 2.25 (s, 3H) 2.78 (d, J=8.31 Hz, 1H) 3.41 (d, J=10.20 Hz, 2H) 3.75 (s, 3H) 4.28-4.58 (m, 4H) 7.39-7.55 (m, 3H) 7.68-7.79 (m, 2H) 7.85 (d, J=1.51 Hz, 1H) 8.05 (s, 1H) 8.35 (d, J=1.51 Hz, 1H) 8.49 (d, J=2.27 Hz, 1H) 9.34 (s, 1H).

Preparation of I-89

Example 89

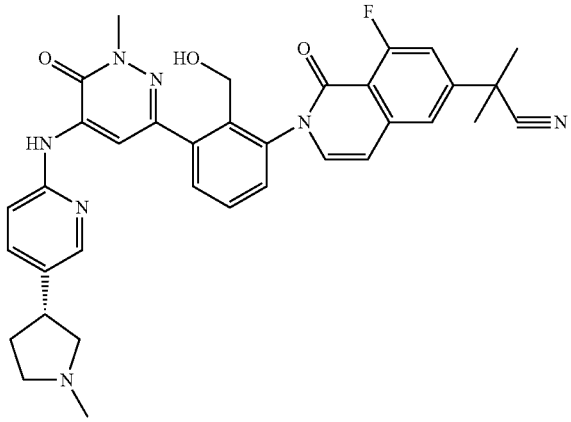 [SMILES: CN1CC[C@H](c2ccc(Nc3cc(-c4cccc(-n5ccc6cc(C(C)(C)C#N)cc(F)c6c5=O)c4CO)nn(C)c3=O)nc2)C1]

2-[8-Fluoro-2-(2-hydroxymethyl-3-{1-methyl-5-[5-((S)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile was prepared using the general procedure described for compound I-15, but substituting 6-chloro-2-methyl-4-[5-((R)-1-methyl-pyrrolidin-3-yl)-pyridin-2-ylamino]-2H-pyridazin-3-one for 6-chloro-2-methyl-4-(5-morpholine-4-carbonyl)pyridine-2-ylamino) pyrid-azin-3(2H)-one in step 11 to provide 32 mg of final product as a light yellow powder.
$(M+H)^+=620$ m/e.

Preparation of I-90

Example 90

Preparation of 6-tert-butyl-8-fluoro-2-(2-hydroxymethyl-3-{1-methyl-6-oxo-5-[1'-(2,2,2-trifluoroethyl)-1',2',3',4',5',6'-hexahydro-[3,4']bipyridinyl-6-ylamino]-1,6-dihydro-pyridazin-3-yl}-phenyl)-2H-phthalazin-1-one

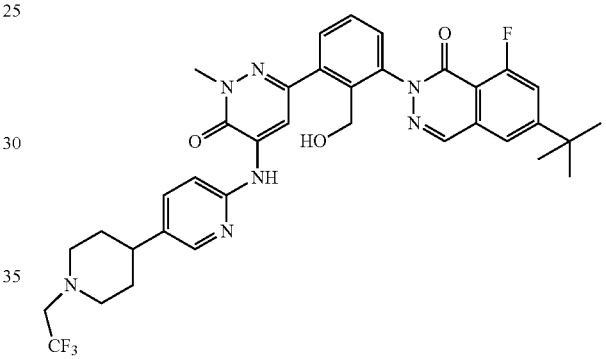

To a solution of 6-tert-butyl-8-fluoro-2-(2-(hydroxymethyl)-3-(1-methyl-6-oxo-5-(5-(piperidin-4-yl)pyridin-2-ylamino)-1,6-dihydropyridazin-3-yl)phenyl)phthalazin-1(2H)-one (10 mg, 16.4 µmol) in DMF (1 ml) was added potassium carbonate (6.8 mg, 49.2 µmol) and 2,2,2-trifluoroethyl trifluoromethanesulfonate (3.81 mg, 2.36 µl, 16.4 µmol) at room temperature. The mixture was stirred for 8 h. at the same temperature. EtOAc was added into the reaction mixture (10 mL) and the mixture was poured into water (10 mL). Organic layer was separated, washed with water (4×5 mL), dried (Na$_2$SO$_4$), and evaporated under vacuum. Crude product was purified by preparative tlc (CH$_2$Cl$_2$:MeOH:NH$_4$OH, 90:9.5:0.5) to give 8 mg of pure product (70% yield): m/z 692 [M+H]$^+$.

Assay Data

Bruton's Tyrosine Kinase (Btk) Inhibition Assay

The assay is a capture of radioactive $^{33}$P phosphorylated product through filtration. The interactions of Btk, biotinylated SH$_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 µm hydrophilic PVDF filter plates (Millipore). Concentrations reported here are final assay concentrations: 10-100 µM compounds in DMSO (Burdick and Jackson), 5-10 nM Btk enzyme (His-tagged, full-length), 30 µM peptide substrate (Biotin-Aca-AAAEEIYGE$_1$-NH$_2$), 100 µM ATP (Sigma), 8 mM imidazole (Sigma, pH 7.2), 8 mM glycerol-2-phosphate (Sigma), 200 µM EGTA (Roche Diagnostics), 1 mM MnCl$_2$ (Sigma), 20 mM MgCl$_2$ (Sigma), 0.1 mg/ml BSA (Sigma), 2 mM DTT (Sigma), 1 µCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 µM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl$_2$, MgCl$_2$, BSA).
2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}$P ATP) and mix with substrate (assay buffer, DTT, ATP, $^{33}$P ATP, peptide substrate) 30° C. for 15 min.
4) To start assay, pre-incubate 10 µL Btk in enzyme buffer (imidazole, glycerol-2-phosphate, BSA) and 10 µL of test compounds for 10 min at RT.
5) Add 30 µL reaction mixture without or with substrate to Btk and compounds.
6) Incubate 50 µL total assay mix for 30 min at 30° C.
7) Transfer 40 µL of assay to 150 µL bead slurry in filter plate to stop reaction.
8) Wash filter plate after 30 min, with following steps
   a. 3×250 µL NaCl
   b. 3×250 µL NaCl containing 1% phosphoric acid
   c. 1×250 µL H$_2$O
9) Dry plate for 1 h at 65° C. or overnight at RT
10) Add 50 µL microscint-20 and count $^{33}$P cpm on scintillation counter.

Calculate percent activity from raw data in cpm percent activity=(sample−*bkg*)/(total activity−*bkg*)×100

Calculate IC$_{50}$ from percent activity, using one-site dose response sigmoidal model $y=A+((B-A)/(1+((x/C)^D)))$ x=cmpd conc, y=% activity, A=min, B=max, C=IC$_{50}$, D=1 (hill slope)

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 µl of each compound dilution is added in duplicate to a 2 ml 96-well V bottom plate (Analytical Sales and Services, #59623-23); 5.5 µl of 10% DMSO in PBS is added to control and no-stimulus wells. HWB (100 µl) is added to each well, and after mixing the plates are incubated at 37 C, 5% CO$_2$, 100% humidity for 30 minutes. Goat F(ab')2 anti-human IgM (Southern Biotech, #2022-14) (10 µl of a 500 µg/ml solution, 50 µg/ml final concentration) is added to each well (except the no-stimulus wells) with mixing and the plates are incubated for an additional 20 hours.

At the end of the 20 hour incubation, samples are incubated with florescent-probe-labeled anti-bodies (15 µl PE Mouse anti-Human CD20, BD Pharmingen, #555623, and/or 20 ul APC Mouse anti-Human CD69, BD Pharmingen #555533) for 30 minutes, at 37 C, 5% CO$_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernantants are removed and pellets are resuspended in 180 µl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Representative compound data for this assay are listed below in Table II.

TABLE II

| Compound | Human Whole Blood (µM) |
| --- | --- |
| I-1 | 0.019 |
| I-2 | 0.014 |
| I-3 | 0.045 |
| I-4 | 0.122 |
| I-5 | 0.025 |
| I-6 | 0.031 |
| I-7 | 0.02 |
| I-8 | 0.02 |
| I-10 | 0.019 |
| I-12 | 0.052 |
| I-13 | 0.009 |
| I-14 | 0.065 |
| I-15 | 0.163 |
| I-16 | 0.026 |
| I-17 | 0.041 |
| I-18 | 0.003 |
| I-19 | 0.007 |
| I-20 | 0.015 |
| I-21 | 0.109 |
| I-22 | 0.033 |
| I-23 | 0.06 |
| I-24 | 0.116 |

TABLE II-continued

| Compound | Human Whole Blood (μM) |
|---|---|
| I-26 | 0.152 |
| I-27 | 0.089 |
| I-28 | 0.006 |
| I-29 | 0.015 |
| I-30 | 0.004 |
| I-31 | 0.032 |
| I-32 | 0.023 |
| I-33 | 0.002 |
| I-34 | 0.125 |
| I-35 | 0.074 |
| I-37 | 0.084 |
| I-38 | 0.012 |
| I-39 | 0.021 |
| I-40 | 0.044 |
| I-41 | 0.015 |
| I-42 | 0.047 |
| I-43 | 0.041 |
| I-44 | 0.014 |
| I-45 | 0.027 |
| I-46 | 0.293 |
| I-47 | 0.076 |
| I-48 | 0.185 |
| I-49 | 0.085 |
| I-50 | 0.086 |
| I-51 | 0.019 |
| I-52 | 0.027 |
| I-53 | 0.039 |
| I-54 | 0.104 |
| I-55 | 0.041 |
| I-56 | 0.017 |
| I-58 | 0.002 |
| I-59 | 0.005 |
| I-60 | 0.004 |
| I-61 | 0.074 |
| I-62 | 0.144 |
| I-63 | 0.189 |
| I-64 | 0.066 |
| I-65 | 0.062 |
| I-66 | 0.023 |
| I-67 | 0.004 |
| I-68 | 0.061 |
| I-69 | 0.018 |
| I-70 | 0.117 |
| I-71 | 0.032 |
| I-72 | 0.056 |
| I-73 | 0.03 |
| I-74 | 0.034 |
| I-75 | 0.18 |
| I-76 | 0.051 |
| I-77 | 0.123 |
| I-78 | 0.084 |
| I-79 | 0.06 |
| I-80 | 0.041 |
| I-81 | 0.123 |
| I-82 | 0.017 |
| I-83 | 0.07 |
| I-84 | 0.242 |
| I-85 | 0.294 |
| I-86 | 0.408 |
| I-87 | 0.455 |
| I-88 | 0.203 |
| I-89 | 0.485 |
| I-90 | 0.34 |

Inhibition of B-Cell Activation

B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 μM FLUO-3AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell $Ca^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring:

1=swelling and/or redness of paw or one digit.

2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 µg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 µl) is determined by Coulter Counter. For differential leukocyte counts, 50-200 µl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I,

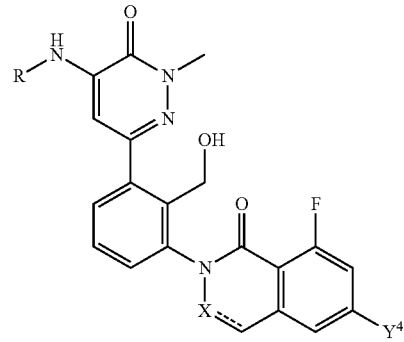

wherein:
= is either a single or double bond;
X is either CH, or $CH_2$;
R is H, $-R^1$, $-R^1-R^2-R^3$, or $-R^1-R^3$, or $-R^2-R^3$;
$R^1$ is aryl, heteroaryl, bicyclic heteroaryl, cycloalkyl, or heterocycloalkyl, each of which is optionally substituted with one or more lower alkyl, hydroxy, hydroxy lower alkyl, lower alkoxy, halo, nitro, amino, amido, cyano, oxo, or lower haloalkyl;
$R^2$ is $-C(=O)$, $-C(=O)O$, $-C(=O)NR^{2'}$, $-NHC(=O)O$, $-C(R^{2'})_2$, $-O$, $-S$, $-C(=NH)NR^{2'}$, or $-S(=O)_2$;
each $R^{2'}$ is independently H or lower alkyl;
$R^3$ is H or $R^4$;
$R^4$ is lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxylamino, carboxy, carbamoyl, carbamate, halo lower alkoxy, heterocycloalkyl, or halo lower alkyl, wherein two lower alkyl groups may together form a ring;
$Y^4$ is $Y^{4a}$, $Y^{4b}$, $Y^{4c}$, or $Y^{4d}$;
$Y^{4a}$ is H or halogen;
$Y^{4b}$ is lower alkyl, optionally substituted with one or more substituents selected from the group consisting of lower haloalkyl, halogen, hydroxy, amino, cyano, and lower alkoxy;
$Y^{4c}$ is lower cycloalkyl, optionally substituted with one or more substituents selected from the group consisting of lower alkyl, lower haloalkyl, halogen, hydroxy, amino, cyano, and lower alkoxy; and
$Y^{4d}$ is amino, optionally substituted with one or more lower alkyl, alkoxy lower alkyl, or hydroxy lower alkyl;
or a pharmaceutically acceptable salt thereof.

2. The compound of claim 1, wherein = is a double bond and X is CH.

3. The compound of claim 1, wherein ⁓ is a single bond and X is CH$_2$.

4. The compound of claim 2, wherein
R is —R$^1$—R$^2$—R$^3$;
R$^1$ is pyridyl;
R$^2$ is —S(=O)$_2$,
R$^3$ is R$^4$; and
R$^4$ is lower alkyl.

5. The compound of claim 2, wherein
R is —R$^1$—R$^2$—R$^3$;
R$^1$ is pyridyl;
R$^2$ is —C(CH$_3$)$_2$;
R$^3$ is R$^4$; and
R$^4$ is lower alkyl amino, lower dialkyl amino, or heterocycloalkyl optionally substituted with one or more lower alkyl.

6. The compound of claim 2, wherein
R is —R$^1$—R$^2$—R$^3$;
R$^1$ is phenyl or pyridyl;
R$^2$ is —C(=O);
R$^3$ is R$^4$; and
R$^4$ is morpholine or piperazine, optionally substituted with one or more lower alkyl.

7. The compound of claim 2, wherein Y$^4$ is tert-butyl.

8. The compound of claim 3, wherein ⁓ is a double bond, X is CH, and Y$^4$ is

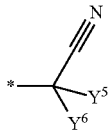

wherein, Y$^5$ and Y$^6$ are independently H, lower alkyl, or lower haloalkyl.

9. The compound of claim 2, wherein Y$^4$ is

wherein, Y$^5$ is H, halogen, lower alkyl or lower haloalkyl.

10. The compound of claim 2, wherein Y$^4$ is

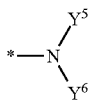

wherein, Y$^5$ and Y$^6$ are independently H or lower alkyl.

11. The compound of claim 7, wherein
R is —R$^1$—R$^3$;
R$^1$ is pyridyl or pyrazolopyrazine;
R$^3$ is R$^4$; and
R$^4$ is optionally substituted lower alkyl, heterocycloalkyl, or alkyl heterocycloalkyl.

12. The compound of claim 7, wherein
R is —R$^1$—R$^2$—R$^3$;
R$^1$ is pyridyl;
R$^2$ is —C(CH$_3$)$_2$;
R$^3$ is R$^4$; and
R$^4$ is lower alkyl amino, lower dialkyl amino, or heterocycloalkyl optionally substituted with one or more lower alkyl.

13. The compound of claim 7, wherein
R is —R$^1$—R$^2$—R$^3$;
R$^1$ is pyridyl;
R$^2$ is —C(=O);
R$^3$ is R$^4$; and
R$^4$ is optionally substituted heterocycloalkyl or bicyclic spiroheterocycloalkyl.

14. The compound of claim 13, wherein R$^4$ is optionally substituted morpholine or piperazine.

15. The compound of claim 1 selected from the group consisting of:
6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide;
2-[8-Fluoro-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-1-oxo-1,2-dihydro-isoquinolin-6-yl]-2-methyl-propionitrile;
6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N,N-dimethyl-nicotinamide;
6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-dimethylamino-ethyl)-nicotinamide;
6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-N-(2-hydroxy-ethyl)-N-methyl-nicotinamide;
1-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridine-3-carbonyl)-azetidine-3-carbonitrile;
2-(8-Fluoro-2-{2-hydroxymethyl-3-[1-methyl-5-(1'-methyl-1',2',3',4',5',6'-hexahydro-[3,4]bipyridinyl-6-ylamino)-6-oxo-1,6-dihydro-pyridazin-3-yl]-phenyl}-1-oxo-1,2-dihydro-isoquinolin-6-yl)-2-methyl-propionitrile;
2-(2-{3-[5-(5-Azetidin-1-ylmethyl-1-methyl-1H-pyrazol-3-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile;
2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2-dihydro-isoquinolin-6-yl]-2-methyl-propionitrile;
2-(8-Fluoro-2-{2-hydroxymethyl-3-[1-methyl-5-(5-methyl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile;
6-(6-{3-[6-(Cyano-dimethyl-methyl)-8-fluoro-1-oxo-1H-isoquinolin-2-yl]-2-hydroxymethyl-phenyl}-2-methyl-3-oxo-2,3-dihydro-pyridazin-4-ylamino)-N,N-dimethyl-nicotinamide;
2-[8-Fluoro-2-(2-hydroxymethyl-3-{1-methyl-5-[5-[((S)-1-methyl-pyrrolidin-2-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile;
2-[8-Fluoro-2-(2-hydroxymethyl-3-{1-methyl-5-[5((S)-1-methyl-pyrrolidin-3-yl)-pyridin-2-ylamino]-6-oxo-1, 6-dihydro-pyridazin-3-yl}-phenyl)-1-oxo-1,2-dihydro-isoquinolin-6-yl]-2-methyl-propionitrile;

2-[2-(3-{5-[5-(2-Azetidin-1-yl-1,1-dimethyl-ethoxy)-pyridin-2-ylamino]-1-methyl-6-oxo-1,6-dihydro-pyridazin-3-yl}-2-hydroxymethyl-phenyl)-8-fluoro-1-oxo-1,2,3,4-tetrahydro-isoquinolin-6-yl]-2-methyl-propionitrile;

2-(8-Fluoro-2-{2-hydroxymethyl-3-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-phenyl}-1-oxo-1,2-dihydro-isoquinolin-6-yl)-2-methyl-propionitrile;

2-(8-Fluoro-2-{2-hydroxymethyl-3-[1-methyl-5-(1'-oxetan-3-yl-1',2',3',4',5',6'-hexahydro-[3,4]bipyridinyl-6-ylamino)-6-oxo-1,6-dihydro-pyridazin-3-yl]-phenyl}-1-oxo-1,2-dihydro-isoquinolin-6-yl)-2-methyl-propionitrile;

6-tert-Butyl-2-{3-[5-(5-ethyl-4,5,6,7-tetrahydro-pyrazolo[1,5-c]pyrazin-2-ylamino)-1-methyl-6-oxo-1,6-dihydro-pyridazin-3-yl]-2-hydroxymethyl-phenyl}-8-fluoro-2H-phthalazin-1-one;

2-(2-{3-[5-(5-Ethyl-4,5,6,7-tetrahydro-pyrazolo[1,5-c]pyrazin-2-ylamino)-1-methyl-6-oxo-1,6-dihydro-pyridazin-3-yl]-2-hydroxymethyl-phenyl}-8-fluoro-1-oxo-1,2-dihydro-isoquinolin-6-yl)-2-methyl-propionitrile;

4-(6-{6-[3-(6-tert-Butyl-8-fluoro-1-oxo-1H-phthalazin-2-yl)-2-hydroxymethyl-phenyl]-2-methyl-3-oxo-2,3-dihydro-pyridazin-4-ylamino}-pyridin-3-yl)-piperazine-1-carboxylic acid ethyl ester;

8-Fluoro-6-(2-fluoro-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one; and 2-[8-Fluoro-2-(2-hydroxymethyl-3-{1-methyl-5-[5-((R)-1-methyl-pyrrolidin-3-yl)-pyridin-2-ylamino]-6-oxo-1,6-dihydro-pyridazin-3-yl}-phenyl)-1-oxo-1,2-dihydro-isoquinolin-6-yl]-2-methyl-propionitrile.

16. A pharmaceutical composition comprising the compound of claim 1.

17. A pharmaceutical composition comprising the compound of claim 1, admixed with at least one pharmaceutically acceptable carrier, excipient or diluent.

18. A method for treating rheumatoid arthritis comprising administering to a patient in need thereof a therapeutically effective amount of the compound of claim 1.

19. A method for treating asthma comprising administering to a patient in need thereof a therapeutically effective amount of the compound of claim 1.

* * * * *